(12) United States Patent
Schariter et al.

(10) Patent No.: US 12,357,575 B2
(45) Date of Patent: *Jul. 15, 2025

(54) METHODS OF MAKING LIPID NANOPARTICLES

(71) Applicant: ModernaTX, Inc., Cambridge, MA (US)

(72) Inventors: Joseph Schariter, Cambridge, MA (US); Kimberly Hassett, Cambridge, MA (US); Mike Smith, Cambridge, MA (US); Orn Almarsson, Cambridge, MA (US); Luis Brito, Cambridge, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/338,485

(22) Filed: Jun. 21, 2023

(65) Prior Publication Data

US 2024/0009131 A1 Jan. 11, 2024

Related U.S. Application Data

(63) Continuation of application No. 16/643,037, filed as application No. PCT/US2018/049251 on Aug. 31, 2018, now Pat. No. 11,744,801.

(Continued)

(51) Int. Cl.
*A61K 47/60* (2017.01)
*A61K 9/127* (2025.01)
(Continued)

(52) U.S. Cl.
CPC .............. *A61K 9/19* (2013.01); *A61K 47/60* (2017.08); *A61K 9/127* (2013.01); *A61K 9/1277* (2013.01); *B82Y 5/00* (2013.01)

(58) Field of Classification Search
None
See application file for complete search history.

(56) References Cited

U.S. PATENT DOCUMENTS

| 4,737,323 A | 4/1988 | Martin et al. |
| 4,857,319 A | 8/1989 | Crowe et al. |

(Continued)

FOREIGN PATENT DOCUMENTS

| AU | 652831 B2 | 9/1994 |
| CN | 101291653 A | 10/2008 |

(Continued)

OTHER PUBLICATIONS

Wei-Yu Chi et al. "Molecular targets and strategies in the development of nucleic acid cancer vaccines: from shared to personalized antigens." Journal of Biomedical Science, vol. 31:94, 2024, pp. 1-26. (Year: 2024).*

(Continued)

*Primary Examiner* — Isaac Shomer
(74) *Attorney, Agent, or Firm* — Clark & Elbing LLP

(57) ABSTRACT

The disclosure features novel methods of producing nucleic acid lipid nanoparticle (LNP) compositions employing a modifying agent after formation of a precursor nucleic acid lipid nanoparticle, the produced compositions thereof, and methods involving the nucleic acid lipid nanoparticles useful in the delivery of therapeutics and/or prophylactics, such as a nucleic acid, to mammalian cells or organs to, for example, to regulate polypeptide, protein, or gene expression.

13 Claims, 61 Drawing Sheets
Specification includes a Sequence Listing.

Related U.S. Application Data

(60) Provisional application No. 62/590,193, filed on Nov. 22, 2017, provisional application No. 62/553,088, filed on Aug. 31, 2017, provisional application No. 62/553,085, filed on Aug. 31, 2017.

(51) Int. Cl.
    *A61K 9/1277*      (2025.01)
    *A61K 9/19*      (2006.01)
    *B82Y 5/00*      (2011.01)

(56) References Cited

U.S. PATENT DOCUMENTS

| | | |
|---|---|---|
| 4,946,683 A | 8/1990 | Forssen |
| 5,049,392 A | 9/1991 | Weiner et al. |
| 5,194,654 A | 3/1993 | Hostetler et al. |
| 5,223,263 A | 6/1993 | Hostetler et al. |
| 5,256,555 A | 10/1993 | Milburn et al. |
| 5,750,114 A | 5/1998 | Burke et al. |
| 6,303,378 B1 | 10/2001 | Bridenbaugh et al. |
| 6,696,038 B1 | 2/2004 | Mahato et al. |
| 7,094,423 B1 | 8/2006 | Maurer et al. |
| 7,371,404 B2 | 5/2008 | Panzner et al. |
| 8,058,069 B2 | 11/2011 | Yaworski et al. |
| 8,158,601 B2 | 4/2012 | Chen et al. |
| 8,420,123 B2 | 4/2013 | Troiano et al. |
| 8,460,696 B2 | 6/2013 | Slobodkin et al. |
| 8,466,122 B2 | 6/2013 | Heyes et al. |
| 8,563,041 B2 | 10/2013 | Grayson et al. |
| 8,569,256 B2 | 10/2013 | Heyes et al. |
| 8,603,499 B2 | 12/2013 | Zale et al. |
| 8,603,500 B2 | 12/2013 | Zale et al. |
| 8,603,501 B2 | 12/2013 | Zale et al. |
| 8,603,534 B2 | 12/2013 | Zale et al. |
| 8,603,535 B2 | 12/2013 | Troiano et al. |
| 8,613,951 B2 | 12/2013 | Zale et al. |
| 8,628,801 B2 | 1/2014 | Garreta et al. |
| 8,642,076 B2 | 2/2014 | Manoharan et al. |
| 8,663,599 B1 | 3/2014 | Sung et al. |
| 8,663,700 B2 | 3/2014 | Troiano et al. |
| 8,691,750 B2 | 4/2014 | Constien et al. |
| 8,691,966 B2 | 4/2014 | Kariko et al. |
| 8,697,098 B2 | 4/2014 | Perumal et al. |
| 8,709,483 B2 | 4/2014 | Farokhzad et al. |
| 8,710,200 B2 | 4/2014 | Schrum et al. |
| 8,734,853 B2 | 5/2014 | Sood et al. |
| 8,754,062 B2 | 6/2014 | De Fougerolles et al. |
| 8,822,663 B2 | 9/2014 | Schrum et al. |
| 8,980,864 B2 | 3/2015 | Hoge et al. |
| 8,999,380 B2 | 4/2015 | Bancel et al. |
| 9,221,891 B2 | 12/2015 | Bancel et al. |
| 9,283,287 B2 | 3/2016 | Chakraborty et al. |
| 9,303,079 B2 | 4/2016 | Chakraborty et al. |
| 9,364,433 B2 | 6/2016 | Andersson et al. |
| 9,464,124 B2 | 10/2016 | Bancel et al. |
| 9,512,456 B2 | 12/2016 | Wang et al. |
| 9,533,047 B2 | 1/2017 | De Fougerolles et al. |
| 9,572,896 B2 | 2/2017 | Bancel et al. |
| 9,597,380 B2 | 3/2017 | Chakraborty et al. |
| 9,693,958 B2 | 7/2017 | Zhu |
| 9,803,199 B2 | 10/2017 | Koizumi et al. |
| 9,868,691 B2 | 1/2018 | Benenato |
| 9,872,900 B2 | 1/2018 | Ciaramella et al. |
| 10,023,626 B2 | 7/2018 | Bolen et al. |
| 10,064,934 B2 | 9/2018 | Ciaramella et al. |
| 10,064,935 B2 | 9/2018 | Ciaramella et al. |
| 10,124,055 B2 | 11/2018 | Ciaramella et al. |
| 10,207,010 B2 | 2/2019 | Besin et al. |
| 10,232,055 B2 | 3/2019 | Kariko et al. |
| 10,273,269 B2 | 4/2019 | Ciaramella |
| 10,286,086 B2 | 5/2019 | Roy et al. |
| 10,323,076 B2 | 6/2019 | Ellsworth et al. |
| 10,385,088 B2 | 8/2019 | Fraley et al. |
| 10,449,244 B2 | 10/2019 | Ciaramella et al. |
| 10,465,190 B1 | 11/2019 | Chen et al. |
| 10,493,143 B2 | 12/2019 | Ciaramella et al. |
| 10,526,629 B2 | 1/2020 | Rabideau et al. |
| 10,653,712 B2 | 5/2020 | Hoge et al. |
| 10,653,767 B2 | 5/2020 | Ciaramella et al. |
| 10,695,419 B2 | 6/2020 | Ciaramella et al. |
| 10,857,105 B2 | 12/2020 | Benenato et al. |
| 10,925,958 B2 | 2/2021 | Ciaramella |
| 11,027,025 B2 | 6/2021 | Hoge et al. |
| 11,045,540 B2 | 6/2021 | Ciaramella |
| 11,103,578 B2 | 8/2021 | Ciaramella et al. |
| 11,351,242 B1 | 6/2022 | Panther et al. |
| 11,384,352 B2 | 7/2022 | Miracco |
| 11,406,703 B2 | 8/2022 | Kramarczyk et al. |
| 11,464,848 B2 | 10/2022 | Ciaramella et al. |
| 11,485,960 B2 | 11/2022 | Dousis et al. |
| 11,497,807 B2 | 11/2022 | Ciaramella et al. |
| 11,744,801 B2 * | 9/2023 | Schariter ............... A61K 9/19 424/450 |
| 11,786,607 B2 * | 10/2023 | Hoge .................. C12N 15/88 424/489 |
| 12,090,235 B2 | 9/2024 | Horhota et al. |
| 2003/0073619 A1 | 4/2003 | Mahato et al. |
| 2003/0092653 A1 | 5/2003 | Kisich et al. |
| 2003/0135040 A1 | 7/2003 | Eritja et al. |
| 2003/0165849 A1 | 9/2003 | Zhang et al. |
| 2004/0132683 A1 | 7/2004 | Felgner et al. |
| 2004/0142474 A1 | 7/2004 | Mahato et al. |
| 2005/0079212 A1 | 4/2005 | Wheeler et al. |
| 2005/0143336 A1 | 6/2005 | Ramesh et al. |
| 2005/0287540 A1 | 12/2005 | Murphy et al. |
| 2006/0008910 A1 | 1/2006 | MacLachlan et al. |
| 2006/0083780 A1 | 4/2006 | Heyes et al. |
| 2007/0252295 A1 | 11/2007 | Panzner et al. |
| 2009/0042825 A1 | 2/2009 | Matar et al. |
| 2009/0042829 A1 | 2/2009 | Matar et al. |
| 2009/0098162 A1 | 4/2009 | Friedman et al. |
| 2010/0068226 A1 | 3/2010 | Taylor et al. |
| 2010/0112042 A1 | 5/2010 | Polisky et al. |
| 2010/0130588 A1 | 5/2010 | Yaworski et al. |
| 2010/0267806 A1 | 10/2010 | Bumcrot et al. |
| 2011/0200582 A1 | 8/2011 | Baryza et al. |
| 2011/0244026 A1 | 10/2011 | Guild et al. |
| 2012/0101148 A1 | 4/2012 | Aking et al. |
| 2012/0177724 A1 | 7/2012 | Irvine et al. |
| 2012/0178702 A1 | 7/2012 | Huang et al. |
| 2012/0201872 A1 * | 8/2012 | Huang ............... A61P 29/00 977/798 |
| 2012/0295832 A1 | 11/2012 | Constien et al. |
| 2013/0017223 A1 | 1/2013 | Hope et al. |
| 2013/0064894 A1 | 3/2013 | Martin et al. |
| 2013/0065942 A1 | 3/2013 | Matar et al. |
| 2013/0090372 A1 | 4/2013 | Budzik et al. |
| 2013/0102034 A1 | 4/2013 | Schrum |
| 2013/0115274 A1 | 5/2013 | Knopov et al. |
| 2013/0116307 A1 | 5/2013 | Heyes et al. |
| 2013/0122054 A1 | 5/2013 | Harashima et al. |
| 2013/0122104 A1 | 5/2013 | Yaworski et al. |
| 2013/0123338 A1 | 5/2013 | Heyes et al. |
| 2013/0129785 A1 | 5/2013 | Manoharan et al. |
| 2013/0150625 A1 | 6/2013 | Budzik et al. |
| 2013/0156845 A1 | 6/2013 | Manoharan et al. |
| 2013/0158021 A1 | 6/2013 | Dong et al. |
| 2013/0164400 A1 | 6/2013 | Knopov et al. |
| 2013/0172406 A1 | 7/2013 | Zale et al. |
| 2013/0178541 A1 | 7/2013 | Stanton et al. |
| 2013/0183244 A1 | 7/2013 | Hanes et al. |
| 2013/0183355 A1 | 7/2013 | Jain et al. |
| 2013/0189351 A1 | 7/2013 | Geall |
| 2013/0195759 A1 | 8/2013 | Mirkin et al. |
| 2013/0195968 A1 | 8/2013 | Geall et al. |
| 2013/0195969 A1 | 8/2013 | Geall et al. |
| 2013/0202684 A1 | 8/2013 | Geall et al. |
| 2013/0236500 A1 | 9/2013 | Zale et al. |
| 2013/0236533 A1 | 9/2013 | Von Andrian et al. |
| 2013/0236968 A1 | 9/2013 | Manoharan et al. |
| 2013/0236974 A1 | 9/2013 | De Fougerolles |
| 2013/0243848 A1 | 9/2013 | Lobovkina et al. |
| 2013/0245103 A1 | 9/2013 | De Fougerolles et al. |

(56) References Cited

U.S. PATENT DOCUMENTS

| | | | |
|---|---|---|---|
| 2013/0245107 A1 | 9/2013 | De Fougerolles et al. |
| 2013/0251766 A1 | 9/2013 | Zale et al. |
| 2013/0251816 A1 | 9/2013 | Zale et al. |
| 2013/0251817 A1 | 9/2013 | Zale et al. |
| 2013/0259923 A1 | 10/2013 | Bancel et al. |
| 2013/0274504 A1 | 10/2013 | Colletti et al. |
| 2013/0274523 A1 | 10/2013 | Bawiec, III et al. |
| 2013/0302432 A1 | 11/2013 | Zale et al. |
| 2013/0330401 A1 | 12/2013 | Payne et al. |
| 2013/0338210 A1 | 12/2013 | Manoharan et al. |
| 2013/0344158 A1 | 12/2013 | Zale et al. |
| 2014/0037573 A1 | 2/2014 | Eliasof et al. |
| 2014/0037660 A1 | 2/2014 | Fotin-Mleczek et al. |
| 2014/0037714 A1 | 2/2014 | Quay et al. |
| 2014/0039032 A1 | 2/2014 | Kuboyama et al. |
| 2014/0044772 A1 | 2/2014 | MacLachlan et al. |
| 2014/0044791 A1 | 2/2014 | Basilion et al. |
| 2014/0045913 A1 | 2/2014 | Kuboyama et al. |
| 2014/0050775 A1 | 2/2014 | Slobodkin et al. |
| 2014/0065228 A1 | 3/2014 | Yaworski et al. |
| 2014/0079774 A1 | 3/2014 | Brinker et al. |
| 2014/0141070 A1 | 5/2014 | Geall et al. |
| 2014/0147432 A1 | 5/2014 | Bancel et al. |
| 2014/0148502 A1 | 5/2014 | Bancel et al. |
| 2014/0161830 A1* | 6/2014 | Anderson ............ C12N 15/111 514/315 |
| 2014/0193482 A1 | 7/2014 | Bancel et al. |
| 2014/0206752 A1 | 7/2014 | Afeyan et al. |
| 2014/0206753 A1 | 7/2014 | Guild et al. |
| 2014/0255472 A1* | 9/2014 | Geall .................... C12N 15/88 514/44 R |
| 2014/0328825 A1 | 11/2014 | Meis et al. |
| 2014/0343139 A1 | 11/2014 | Lippard et al. |
| 2014/0378538 A1 | 12/2014 | Bancel |
| 2015/0030622 A1 | 1/2015 | Marshall et al. |
| 2015/0051268 A1 | 2/2015 | Bancel et al. |
| 2015/0056253 A1 | 2/2015 | Bancel et al. |
| 2015/0064242 A1 | 3/2015 | Heyes et al. |
| 2015/0079121 A1 | 3/2015 | Weiner et al. |
| 2015/0110857 A1 | 4/2015 | DeRosa et al. |
| 2015/0118183 A1 | 4/2015 | Baumhof |
| 2015/0141499 A1 | 5/2015 | Bancel et al. |
| 2015/0307542 A1 | 10/2015 | Roy et al. |
| 2015/0315541 A1 | 11/2015 | Bancel et al. |
| 2015/0376115 A1 | 12/2015 | Ansell et al. |
| 2016/0024140 A1 | 1/2016 | Issa et al. |
| 2016/0024141 A1 | 1/2016 | Issa et al. |
| 2016/0032273 A1 | 2/2016 | Shahrokh et al. |
| 2016/0038612 A1 | 2/2016 | Hoge et al. |
| 2016/0151284 A1 | 6/2016 | Heyes et al. |
| 2016/0243221 A1 | 8/2016 | Hoge et al. |
| 2016/0367638 A1 | 12/2016 | Byers et al. |
| 2016/0376224 A1 | 12/2016 | Du et al. |
| 2017/0043037 A1 | 2/2017 | Kariko et al. |
| 2017/0130255 A1 | 5/2017 | Wang et al. |
| 2017/0202979 A1 | 7/2017 | Chakraborty et al. |
| 2017/0204152 A1 | 7/2017 | Nelson et al. |
| 2017/0210697 A1 | 7/2017 | Benenato et al. |
| 2017/0239371 A1 | 8/2017 | Guild et al. |
| 2018/0000953 A1 | 1/2018 | Almarsson et al. |
| 2018/0002393 A1 | 1/2018 | Bancel et al. |
| 2018/0214537 A1 | 8/2018 | Mutzke et al. |
| 2018/0237849 A1 | 8/2018 | Thompson |
| 2018/0243225 A1 | 8/2018 | Ciaramella |
| 2018/0243230 A1 | 8/2018 | Smith |
| 2018/0256628 A1 | 9/2018 | Hoge et al. |
| 2018/0271795 A1 | 9/2018 | Martini et al. |
| 2018/0271970 A1 | 9/2018 | Ciaramella et al. |
| 2018/0273977 A1 | 9/2018 | Mousavi et al. |
| 2018/0274009 A1 | 9/2018 | Marquardt et al. |
| 2018/0303929 A1 | 10/2018 | Ciaramella et al. |
| 2018/0311336 A1 | 11/2018 | Ciaramella et al. |
| 2018/0311343 A1 | 11/2018 | Huang et al. |
| 2018/0318409 A1 | 11/2018 | Valiante et al. |
| 2018/0369374 A1 | 12/2018 | Frederick et al. |
| 2018/0371047 A1 | 12/2018 | Ticho et al. |
| 2019/0002890 A1 | 1/2019 | Martini et al. |
| 2019/0008938 A1 | 1/2019 | Ciaramella et al. |
| 2019/0022004 A1 | 1/2019 | Kan et al. |
| 2019/0085368 A1 | 3/2019 | Bancel et al. |
| 2019/0175517 A1 | 6/2019 | Martini et al. |
| 2019/0175727 A1 | 6/2019 | Huang et al. |
| 2019/0192646 A1 | 6/2019 | Cohen et al. |
| 2019/0192653 A1 | 6/2019 | Hoge et al. |
| 2019/0216843 A1 | 7/2019 | DeRosa et al. |
| 2019/0241633 A1 | 8/2019 | Fotin-Mleczek et al. |
| 2019/0275170 A1 | 9/2019 | Benenato et al. |
| 2019/0298657 A1 | 10/2019 | Martini et al. |
| 2019/0298658 A1 | 10/2019 | Benenato et al. |
| 2019/0300906 A1 | 10/2019 | Martini et al. |
| 2019/0314292 A1 | 10/2019 | Benenato et al. |
| 2019/0336452 A1 | 11/2019 | Brader |
| 2019/0351040 A1 | 11/2019 | Valiante et al. |
| 2019/0351047 A1 | 11/2019 | Jasny et al. |
| 2019/0382774 A1 | 12/2019 | Hoge et al. |
| 2019/0390181 A1 | 12/2019 | Benenato et al. |
| 2020/0030432 A1 | 1/2020 | Ciaramella et al. |
| 2020/0032274 A1 | 1/2020 | Mauger et al. |
| 2020/0038499 A1 | 2/2020 | Narayanan et al. |
| 2020/0054737 A1 | 2/2020 | Ciaramella et al. |
| 2020/0069599 A1 | 3/2020 | Smith et al. |
| 2020/0069793 A1 | 3/2020 | Ciaramella |
| 2020/0069794 A1 | 3/2020 | Ciaramella et al. |
| 2020/0071689 A1 | 3/2020 | Miracco |
| 2020/0085916 A1 | 3/2020 | Martini et al. |
| 2020/0109420 A1 | 4/2020 | Brito et al. |
| 2020/0129608 A1 | 4/2020 | Ciaramella et al. |
| 2020/0129615 A1 | 4/2020 | Ciaramella et al. |
| 2020/0163878 A1 | 5/2020 | Baumhof et al. |
| 2020/0239869 A1 | 7/2020 | Issa et al. |
| 2020/0254086 A1 | 8/2020 | Hoge et al. |
| 2020/0282047 A1 | 9/2020 | Ciaramella et al. |
| 2020/0306191 A1 | 10/2020 | Schariter et al. |
| 2020/0368162 A1 | 11/2020 | Martini |
| 2021/0046173 A1 | 2/2021 | Ciaramella et al. |
| 2021/0087135 A1 | 3/2021 | Benenato et al. |
| 2021/0145982 A1 | 5/2021 | Hoge et al. |
| 2021/0163919 A1 | 6/2021 | Issa et al. |
| 2021/0187097 A1 | 6/2021 | Ciaramella et al. |
| 2021/0206818 A1 | 7/2021 | Huang et al. |
| 2021/0217484 A1 | 7/2021 | Giessel et al. |
| 2021/0228707 A1 | 7/2021 | Metkar et al. |
| 2021/0268086 A1 | 9/2021 | Zhong et al. |
| 2021/0309976 A1 | 10/2021 | Dousis et al. |
| 2021/0378980 A1 | 12/2021 | Horhota et al. |
| 2022/0031631 A1 | 2/2022 | Almarsson et al. |
| 2022/0047518 A1 | 2/2022 | Hennessy et al. |
| 2022/0054653 A1 | 2/2022 | Martini et al. |
| 2022/0062175 A1 | 3/2022 | Smith et al. |
| 2022/0125899 A1 | 4/2022 | Ashburn et al. |
| 2022/0145381 A1 | 5/2022 | Elich et al. |
| 2022/0236253 A1 | 7/2022 | Hopson |
| 2022/0241399 A1 | 8/2022 | Lusso et al. |
| 2022/0347292 A1 | 11/2022 | Panther et al. |
| 2022/0348900 A1 | 11/2022 | Shamashkin et al. |
| 2022/0349006 A1 | 11/2022 | Amato et al. |
| 2023/0000970 A1 | 1/2023 | Nachbagauer et al. |
| 2023/0277457 A1 | 9/2023 | Shepard et al. |
| 2023/0285297 A1 | 9/2023 | Smith et al. |
| 2024/0335393 A1 | 10/2024 | Smith et al. |
| 2024/0366522 A1 | 11/2024 | Smith et al. |

FOREIGN PATENT DOCUMENTS

| | | |
|---|---|---|
| CN | 102068701 A | 5/2011 |
| CN | 102204920 A | 10/2011 |
| CN | 102813929 A | 12/2012 |
| CN | 104644555 A | 5/2015 |
| CN | 105555757 A | 5/2016 |
| EP | 737750 A2 | 10/1996 |
| EP | 1873180 A1 | 1/2008 |
| EP | 2092064 B1 | 9/2010 |
| EP | 2476430 A1 | 7/2012 |
| EP | 2548960 A1 | 1/2013 |

(56) References Cited

FOREIGN PATENT DOCUMENTS

| | | | |
|---|---|---|---|
| EP | 2620161 A1 | 7/2013 |
| EP | 2073848 B1 | 8/2013 |
| EP | 1404860 B1 | 11/2013 |
| EP | 2732825 A1 | 5/2014 |
| EP | 3269395 A1 | 1/2018 |
| EP | 3452101 A2 | 3/2019 |
| WO | WO-9303709 A1 | 3/1993 |
| WO | WO-9314778 A1 | 8/1993 |
| WO | WO-9617086 A1 | 6/1996 |
| WO | WO-9730064 A1 | 8/1997 |
| WO | WO-9914346 A2 | 3/1999 |
| WO | WO-9952503 A2 | 10/1999 |
| WO | WO-0105373 A1 | 1/2001 |
| WO | WO-03086280 A2 | 10/2003 |
| WO | WO-03097805 A2 | 11/2003 |
| WO | WO-2005034979 A2 | 4/2005 |
| WO | WO-2005118857 A2 | 12/2005 |
| WO | WO-2005120152 A2 | 12/2005 |
| WO | WO-2005121348 A1 | 12/2005 |
| WO | WO-2006044456 A1 | 4/2006 |
| WO | WO-2006044503 A2 | 4/2006 |
| WO | WO-2006044505 A2 | 4/2006 |
| WO | WO-2006044682 A1 | 4/2006 |
| WO | WO-2006058088 A2 | 6/2006 |
| WO | WO-2006063249 A2 | 6/2006 |
| WO | WO-2006065479 A2 | 6/2006 |
| WO | WO-2006065480 A2 | 6/2006 |
| WO | WO-2007069068 A2 | 6/2007 |
| WO | WO-2008014979 A2 | 2/2008 |
| WO | WO-2008042973 A2 | 4/2008 |
| WO | WO-2008068631 A2 | 6/2008 |
| WO | WO-2008077592 A1 | 7/2008 |
| WO | WO-2008103276 A2 | 8/2008 |
| WO | WO-2009024599 A1 | 2/2009 |
| WO | WO-2009068649 A2 | 6/2009 |
| WO | WO-2009095226 A2 | 8/2009 |
| WO | WO-2009120247 A2 | 10/2009 |
| WO | WO-2009127060 A1 | 10/2009 |
| WO | WO-2010033906 A2 | 3/2010 |
| WO | WO-2010042877 A1 | 4/2010 |
| WO | WO-2010045512 A2 | 4/2010 |
| WO | WO-2010053572 A2 | 5/2010 |
| WO | WO-2010054401 A1 | 5/2010 |
| WO | WO-2010054406 A1 | 5/2010 |
| WO | WO-2010088537 A3 | 9/2010 |
| WO | WO-2010111290 A1 | 9/2010 |
| WO | WO-2010129709 A1 | 11/2010 |
| WO | WO-2011026641 A1 | 3/2011 |
| WO | WO-2011062965 A2 | 5/2011 |
| WO | WO-2011068810 A1 | 6/2011 |
| WO | WO-2011071931 A2 | 6/2011 |
| WO | WO-2011119058 A2 | 9/2011 |
| WO | WO-2011120053 A1 | 9/2011 |
| WO | WO-2011127255 A1 | 10/2011 |
| WO | WO-2011140627 A1 | 11/2011 |
| WO | WO-2012006376 A2 | 1/2012 |
| WO | WO-2012006378 A1 | 1/2012 |
| WO | WO-2012030901 A1 | 3/2012 |
| WO | WO-2012031043 A1 | 3/2012 |
| WO | WO-2012031046 A2 | 3/2012 |
| WO | WO-2012045075 A1 | 4/2012 |
| WO | WO-2012094304 A1 | 7/2012 |
| WO | WO-2012099755 A1 | 7/2012 |
| WO | WO-2012112730 A2 | 8/2012 |
| WO | WO-2012129483 A1 | 9/2012 |
| WO | WO-2012135025 A2 | 10/2012 |
| WO | WO-2012149252 A2 | 11/2012 |
| WO | WO-2012149255 A2 | 11/2012 |
| WO | WO-2012149265 A2 | 11/2012 |
| WO | WO-2012149282 A2 | 11/2012 |
| WO | WO-2012149301 A2 | 11/2012 |
| WO | WO-2012149376 A2 | 11/2012 |
| WO | WO-2012149393 A2 | 11/2012 |
| WO | WO-2012152910 A1 | 11/2012 |
| WO | WO-2012153297 A1 | 11/2012 |
| WO | WO-2012153338 A2 | 11/2012 |
| WO | WO-2012159643 A1 | 11/2012 |
| WO | WO-2012166241 A1 | 12/2012 |
| WO | WO-2012168491 A1 | 12/2012 |
| WO | WO-2012170607 A2 | 12/2012 |
| WO | WO-2012170889 A1 | 12/2012 |
| WO | WO-2012170930 A1 | 12/2012 |
| WO | WO-2012170952 A2 | 12/2012 |
| WO | WO-2013006825 A1 | 1/2013 |
| WO | WO-2013006834 A1 | 1/2013 |
| WO | WO-2013006837 A1 | 1/2013 |
| WO | WO-2013006838 A1 | 1/2013 |
| WO | WO-2013006842 A2 | 1/2013 |
| WO | WO-2013012476 A2 | 1/2013 |
| WO | WO-2013032829 A1 | 3/2013 |
| WO | WO-2013033438 A2 | 3/2013 |
| WO | WO-2013033563 A1 | 3/2013 |
| WO | WO-2013033620 A1 | 3/2013 |
| WO | WO-2013049328 A1 | 4/2013 |
| WO | WO-2013052167 A2 | 4/2013 |
| WO | WO-2013056132 A2 | 4/2013 |
| WO | WO-2013057715 A1 | 4/2013 |
| WO | WO-2013059496 A1 | 4/2013 |
| WO | WO-2013059922 A1 | 5/2013 |
| WO | WO-2013063468 A1 | 5/2013 |
| WO | WO-2013064911 A2 | 5/2013 |
| WO | WO-2013066274 A1 | 5/2013 |
| WO | WO-2013066903 A1 | 5/2013 |
| WO | WO-2013067537 A1 | 5/2013 |
| WO | WO-2013070872 A1 | 5/2013 |
| WO | WO-2013072929 A2 | 5/2013 |
| WO | WO-2013082529 A1 | 6/2013 |
| WO | WO-2013086322 A1 | 6/2013 |
| WO | WO-2013086354 A1 | 6/2013 |
| WO | WO-2013086373 A1 | 6/2013 |
| WO | WO-2013086526 A1 | 6/2013 |
| WO | WO-2013087083 A1 | 6/2013 |
| WO | WO-2013087791 A1 | 6/2013 |
| WO | WO-2013090601 A2 | 6/2013 |
| WO | WO-2013093648 A2 | 6/2013 |
| WO | WO-2013112778 A1 | 8/2013 |
| WO | WO-2013112780 A1 | 8/2013 |
| WO | WO-2013113501 A1 | 8/2013 |
| WO | WO-2013113736 A1 | 8/2013 |
| WO | WO-2013135359 A1 | 9/2013 |
| WO | WO-2013138343 A1 | 9/2013 |
| WO | WO-2013138346 A1 | 9/2013 |
| WO | WO-2013143555 A1 | 10/2013 |
| WO | WO-2013143683 A1 | 10/2013 |
| WO | WO-2013143699 A1 | 10/2013 |
| WO | WO-2013148186 A1 | 10/2013 |
| WO | WO-2013148541 A1 | 10/2013 |
| WO | WO-2013149141 A1 | 10/2013 |
| WO | WO-2013151650 A1 | 10/2013 |
| WO | WO-2013151666 A2 | 10/2013 |
| WO | WO-2013151736 A2 | 10/2013 |
| WO | WO-2013154774 A1 | 10/2013 |
| WO | WO-2013155487 A1 | 10/2013 |
| WO | WO-2013155493 A1 | 10/2013 |
| WO | WO-2013158127 A1 | 10/2013 |
| WO | WO-2013158579 A1 | 10/2013 |
| WO | WO-2013166498 A1 | 11/2013 |
| WO | WO-2013173693 A1 | 11/2013 |
| WO | WO-2013174409 A1 | 11/2013 |
| WO | WO-2013177421 A2 | 11/2013 |
| WO | WO-2013185069 A1 | 12/2013 |
| WO | WO-2014008334 A1 | 1/2014 |
| WO | WO-2014024193 A1 | 2/2014 |
| WO | WO-2014025795 A1 | 2/2014 |
| WO | WO-2014026284 A1 | 2/2014 |
| WO | WO-2014028487 A1 | 2/2014 |
| WO | WO-2014028763 A1 | 2/2014 |
| WO | WO-2014042920 A1 | 3/2014 |
| WO | WO-2014043618 A1 | 3/2014 |
| WO | WO-2014047649 A1 | 3/2014 |
| WO | WO-2014052634 A1 | 4/2014 |
| WO | WO-2014053622 A1 | 4/2014 |
| WO | WO-2014053624 A1 | 4/2014 |
| WO | WO-2014053628 A1 | 4/2014 |

(56) References Cited

FOREIGN PATENT DOCUMENTS

| | | |
|---|---|---|
| WO | WO-2014053629 A1 | 4/2014 |
| WO | WO-2014053879 A1 | 4/2014 |
| WO | WO-2014053880 A1 | 4/2014 |
| WO | WO-2014053881 A1 | 4/2014 |
| WO | WO-2014053882 A1 | 4/2014 |
| WO | WO-2014054026 A1 | 4/2014 |
| WO | WO-2014062697 A2 | 4/2014 |
| WO | WO-2014064258 A1 | 5/2014 |
| WO | WO-2014064687 A1 | 5/2014 |
| WO | WO-2014066811 A1 | 5/2014 |
| WO | WO-2014071072 A2 | 5/2014 |
| WO | WO-2014072468 A1 | 5/2014 |
| WO | WO-2014072997 A1 | 5/2014 |
| WO | WO-2014074218 A1 | 5/2014 |
| WO | WO-2014074289 A1 | 5/2014 |
| WO | WO-2014074299 A1 | 5/2014 |
| WO | WO-2014074823 A1 | 5/2014 |
| WO | WO-2014078399 A1 | 5/2014 |
| WO | WO-2014081299 A1 | 5/2014 |
| WO | WO-2014081300 A1 | 5/2014 |
| WO | WO-2014081303 A1 | 5/2014 |
| WO | WO-2014081849 A1 | 5/2014 |
| WO | WO-2014066898 A9 | 6/2014 |
| WO | WO-2014089239 A1 | 6/2014 |
| WO | WO-2014089486 A1 | 6/2014 |
| WO | WO-2014108515 A1 | 7/2014 |
| WO | WO-2014127917 A1 | 8/2014 |
| WO | WO-2014140211 A1 | 9/2014 |
| WO | WO-2014144196 A1 | 9/2014 |
| WO | WO-2014152200 A1 | 9/2014 |
| WO | WO-2014152966 A1 | 9/2014 |
| WO | WO-2014153163 A1 | 9/2014 |
| WO | WO-2014159813 A1 | 10/2014 |
| WO | WO-2014160243 A1 | 10/2014 |
| WO | WO-2014168874 A2 | 10/2014 |
| WO | WO-2014172045 A1 | 10/2014 |
| WO | WO-2014182661 A2 | 11/2014 |
| WO | WO-2014210356 A1 | 12/2014 |
| WO | WO-2015023461 A2 | 2/2015 |
| WO | WO-2015061491 A1 | 4/2015 |
| WO | WO-2015082080 A1 | 6/2015 |
| WO | WO-2015095340 A1 | 6/2015 |
| WO | WO-2015095346 A1 | 6/2015 |
| WO | WO-2015095351 A1 | 6/2015 |
| WO | WO-2015110957 A2 | 7/2015 |
| WO | WO-2015130584 A2 | 9/2015 |
| WO | WO-2015134332 A2 | 9/2015 |
| WO | WO-2015135558 A1 | 9/2015 |
| WO | WO-2015199952 A1 | 12/2015 |
| WO | WO-2016037053 A1 | 3/2016 |
| WO | WO-2016123864 A1 | 8/2016 |
| WO | WO-2016164762 A1 | 10/2016 |
| WO | WO-2016201377 A1 | 12/2016 |
| WO | WO-2017011773 A2 | 1/2017 |
| WO | WO-2017015457 A1 | 1/2017 |
| WO | WO-2017031232 A1 | 2/2017 |
| WO | WO-2017034991 A1 | 3/2017 |
| WO | WO-2017049245 A2 | 3/2017 |
| WO | WO-2017066789 A1 | 4/2017 |
| WO | WO-2017070601 A1 | 4/2017 |
| WO | WO-2017070618 A1 | 4/2017 |
| WO | WO-2017070622 A1 | 4/2017 |
| WO | WO-2017075038 A1 | 5/2017 |
| WO | WO-2017099823 A1 | 6/2017 |
| WO | WO-2017112865 A1 | 6/2017 |
| WO | WO-2017127750 A1 | 7/2017 |
| WO | WO-2017191274 A2 | 11/2017 |
| WO | WO-2017201328 A1 | 11/2017 |
| WO | WO-2017201333 A1 | 11/2017 |
| WO | WO-2017218704 A1 | 12/2017 |
| WO | WO-2017219033 A1 | 12/2017 |
| WO | WO-2018006052 A1 | 1/2018 |
| WO | WO-2018039131 A1 | 3/2018 |
| WO | WO-2018081480 A1 | 5/2018 |
| WO | WO-2018089540 A1 | 5/2018 |
| WO | WO-2018089790 A1 | 5/2018 |
| WO | WO-2018089801 A1 | 5/2018 |
| WO | WO-2018157009 A1 | 8/2018 |
| WO | WO-2018170245 A1 | 9/2018 |
| WO | WO-2018170306 A1 | 9/2018 |
| WO | WO-2018170336 A1 | 9/2018 |
| WO | WO-2018232120 A1 | 12/2018 |
| WO | WO-2018232355 A1 | 12/2018 |
| WO | WO-2018232357 A1 | 12/2018 |
| WO | WO-2019023092 A1 | 1/2019 |
| WO | WO-2019036683 A1 | 2/2019 |
| WO | WO-2019036685 A1 | 2/2019 |
| WO | WO-2019089818 A1 | 5/2019 |
| WO | WO-2019202035 A1 | 10/2019 |
| WO | WO-2019226925 A1 | 11/2019 |
| WO | WO-2020002540 A1 | 1/2020 |
| WO | WO-2020006242 A1 | 1/2020 |
| WO | WO-2020047061 A1 | 3/2020 |
| WO | WO-2020056370 A1 | 3/2020 |
| WO | WO-2020061284 A1 | 3/2020 |
| WO | WO-2020061295 A1 | 3/2020 |
| WO | WO-2020061367 A1 | 3/2020 |
| WO | WO-2020061457 A1 | 3/2020 |
| WO | WO-2020077007 A1 | 4/2020 |
| WO | WO-2020081933 A1 | 4/2020 |
| WO | WO-2020097291 A1 | 5/2020 |
| WO | WO-2020160397 A1 | 8/2020 |
| WO | WO-2020172239 A1 | 8/2020 |
| WO | WO-2020185811 A1 | 9/2020 |
| WO | WO-2020190750 A1 | 9/2020 |
| WO | WO-2020232276 A1 | 11/2020 |
| WO | WO-2020243561 A1 | 12/2020 |
| WO | WO-2021007278 A1 | 1/2021 |
| WO | WO-2021016430 A1 | 1/2021 |
| WO | WO-2021030533 A1 | 2/2021 |
| WO | WO-2021050864 A1 | 3/2021 |
| WO | WO-2021055811 A1 | 3/2021 |
| WO | WO-2021127641 A1 | 6/2021 |
| WO | WO-2021155243 A1 | 8/2021 |
| WO | WO-2021155274 A1 | 8/2021 |
| WO | WO-2021159040 A2 | 8/2021 |
| WO | WO-2021159130 A2 | 8/2021 |
| WO | WO-2021173840 A1 | 9/2021 |
| WO | WO-2021204175 A1 | 10/2021 |
| WO | WO-2021211343 A1 | 10/2021 |
| WO | WO-2021222304 A1 | 11/2021 |
| WO | WO-2021231901 A1 | 11/2021 |
| WO | WO-2021231929 A1 | 11/2021 |
| WO | WO-2021231963 A1 | 11/2021 |
| WO | WO-2021237084 A1 | 11/2021 |
| WO | WO-2021247817 A1 | 12/2021 |
| WO | WO-2022032087 A1 | 2/2022 |
| WO | WO-2022067010 A1 | 3/2022 |
| WO | WO-2022081544 A1 | 4/2022 |
| WO | WO-2022081548 A1 | 4/2022 |
| WO | WO-2022150717 A1 | 7/2022 |
| WO | WO-2022155524 A1 | 7/2022 |
| WO | WO-2022155530 A1 | 7/2022 |
| WO | WO-2022187698 A1 | 9/2022 |
| WO | WO-2022204491 A1 | 9/2022 |
| WO | WO-2022212191 A1 | 10/2022 |
| WO | WO-2022212442 A1 | 10/2022 |
| WO | WO-2022212711 A2 | 10/2022 |
| WO | WO-2022221335 A1 | 10/2022 |
| WO | WO-2022221336 A1 | 10/2022 |
| WO | WO-2022221359 A1 | 10/2022 |
| WO | WO-2022221440 A1 | 10/2022 |
| WO | WO-2022232585 A1 | 11/2022 |
| WO | WO-2022241103 A1 | 11/2022 |
| WO | WO-2022266010 A1 | 12/2022 |
| WO | WO-2022266012 A1 | 12/2022 |
| WO | WO-2022266389 A1 | 12/2022 |
| WO | WO-2023283642 A2 | 1/2023 |
| WO | WO-2023283645 A1 | 1/2023 |
| WO | WO-2023283651 A1 | 1/2023 |
| WO | WO-2023009421 A1 | 2/2023 |
| WO | WO-2023009422 A1 | 2/2023 |

(56) References Cited

OTHER PUBLICATIONS

Fen Wan et al. "Studies on PEG-modified SLNs loading vinorelbine bitartrate (I): Preparation and evaluation in vitro." International Journal of Pharmaceutics, vol. 359, 2008, pp. 104-110. (Year: 2008).*

Thomas Perrier, Patrick Saulnier, Florian Fouchet, Nolwenn Lautram, and Jean-Pierre Benoit. "Post-insertion into Lipid NanoCapsules (LNCs): From experimental aspects to mechanisms." International Journal of Pharmaceutics, vol. 396, 2010, pp. 204-209. (Year: 2010).*

Norbert Pardi et al. "Expression kinetics of nucleoside-modified mRNA delivered in lipid nanoparticles to mice by various routes." Journal of Controlled Release, vol. 217, 2015, pp. 345-351. (Year: 2015).*

Abu Lila et al., Application of polyglycerol coating to plasmid DNA lipoplex for the evasion of the accelerated blood clearance phenomenon in nucleic acid delivery. J Pharm Sci. Feb. 2014;103(2):557-66. doi: 10.1002/jps.23823. Epub Dec. 17, 2013.

Abu Lila et al., Use of polyglycerol (PG), instead of polyethylene glycol (PEG), prevents induction of the accelerated blood clearance phenomenon against long-circulating liposomes upon repeated administration. Int J Pharm. Nov. 1, 2013;456(1):235-42. doi: 10.1016/j.ijpharm.2013.07.059. Epub Aug. 5, 2013.

Adamiak, et al. glycoprotein E [Human alphaherpesvirus 2]. GenBank: ABU45436.1. Pub. Nov. 29, 2007, 1 page.

Adney et al., Efficacy of an Adjuvanted Middle East Respiratory Syndrome Coronavirus Spike Protein Vaccine in Dromedary Camels and Alpacas. Viruses. Mar. 2, 2019;11(3). pii: E212. doi: 10.3390/v11030212.

Agadjanyan, M., Prototype Alzheimer's Disease Vaccine Using the Immunodominant B Cell Type from Beta-Amyloid and Promiscuous T Cell Epitope Pan HLA DR-Binding Peptide, J Immunol, 2005, vol. 174, No. 3, pp. 1580-1586.

Agrawal et al., Immunization with inactivated Middle East Respiratory Syndrome coronavirus vaccine leads to lung immunopathology on challenge with live virus. Hum Vaccin Immunother. Sep. 2016;12(9):2351-6. doi:10.1080/21645515.2016.1177688. Epub Jun. 7, 2016.

Akinc, A., et al., "Targeted Delivery of RNAi Therapeutics with Endogenous and Exogenous Ligand-Based Mechanisms," Molecular Therapy : The Journal of the American Society of Gene Therapy 18(7):1357-1364, Academic Press, United States (2010).

Al Kahlout et al., Comparative Serological Study for the Prevalence of Anti-MERS Coronavirus Antibodies in High- and Low-Risk Groups in Qatar. J Immunol Res. Feb. 18, 2019;2019:1386740. doi: 10.1155/2019/1386740. eCollection 2019.

Aleku, M., et al., Atu027, a liposomal small interfering RNA formulation targeting protein kinase N3, inhibits cancer progression. Cancer Res. 2008; 68: 9788-9798.

Alexander et al., The long view: a selective review of 40 years of Newcastle disease research. Avian Pathol. 2012;41(4):329-35. doi: 10.1080/03079457.2012.697991.

Anderson, D.M. et al., Stability of mRNA/cationic lipid lipoplexes in human and rat cerebrospinal fluid: methods and evidence for nonviral mRNA gene delivery to the central nervous system. Hum Gene Ther. Feb. 10, 2003; 14(3):191-202.

Andreakos et al., Amphoteric liposomes enable systemic antigen-presenting cell-directed delivery of CD40 antisense and are therapeutically effective in experimental arthritis. Arthritis Rheum. Apr. 2009;60(4):994-1005. doi: 10.1002/art.24434.

Andrews-Pfannkoch, C. et al., Hydroxyapatite-mediated separation of double-stranded DNA, single-stranded DNA, and RNA genomes from natural viral assemblages. Appl Environ Microbiol. Aug. 2010;76(15):5039-45. Epub Jun. 11, 2010.

Andries, O., et al., Comparison of the gene transfer efficiency of mRNA/GL67 and pDNA/GL67 complexes in respiratory cells. Mol Pharmaceutics. 2012; 9: 2136-2145.

Ausar et al., High-throughput screening of stabilizers for respiratory syncytial virus: identification of stabilizers and their effects on the conformational thermostability of viral particles. Hum Vaccin. May-Jun. 2007;3(3):94-103. Epub May 15, 2007.
Awasthi et al., Immunization With a Vaccine Combining Herpes Simplex Virus 2 (HSV-2) Glycoprotein C (gC) and gD Subunits Improves the Protection of Dorsal Root Ganglia in Mice and Reduces the Frequency of Recurrent Vaginal Shedding of HSV-2 DNA in Guinea Pigs Compared to Immunization With gD Alone. J Viral. Oct. 2011;85(20):10472-86. doi: 10.1128/JVI.00849-11. Epub Aug. 3, 2011.
Baars, A. et al., A Phase II Study of Active Specific Immunotherapy and 5-FU/Leucovorin as Adjuvant Therapy For Stage III Colon Carcinoma, British Journal of Cancer, 2002, vol. 86, No. 8, pp. 1230-1234.
Badawi et al., Immune Modulating Peptide for the Treatment and Suppression of Multiple Sclerosis. Clin Immunol. Aug. 2012;144(2):127-138. Author manuscript, 22 pages.
Bag, J., Recovery of normal protein synthesis in heat-shocked chicken myotubes by liposome-mediated transfer of mRNAs. Can. J. Biochem. Cell Biol. 1985; 63(3): 231-235.
Balbino, T.A. et al., "Microfluidic devices for continuous production of pDNA/cationic liposome complexes for gene delivery and vaccine therapy," Colloids and Surfaces B: Biointerfaces 111 (2013), pp. 203-210. (Year: 2013).
Beck et al., "Strategies and challenges for the next generation of antibody-drug conjugates," Nature Review Drug Discovery, May 2017, vol. 16, pp. 315-337.
Belliveau et al., "Microfluidic Synthesis of Highly Potent Limit-size Lipid Nanoparticles for In Vivo Delivery of siRNA," Molecular Therapy-Nucleic Acids, 2012, 1, e37, 9 pages.
Betker et al., Nonadditive Effects of Repetitive Administration of Lipoplexes in Immunocompetent Mice. J Pharm Sci. Mar. 2017;106(3):872-881. doi: 10.1016/i.xphs.2016.11.013. Epub Nov. 22, 2016.
Bettinger, T. et al., Peptide-mediated RNA delivery: a novel approach for enhanced transfection of primary and post-mitotic cells. Nucleic Acids Res. Sep. 15, 2001;29(18):3882-91.
Blenke, Intracellular delivery of RNA therapeutics with lipid nanoparticles, publicly available on Jan. 25, 2017, Department of Pharmaceutics, Utrecht Institute for Pharmaceutical Sciences (UIPS), Faculty of Science, University of Utrecht, Netherlands, 164 pages.
Bolhassani A., et al. , Improvement of Different Vaccine Delivery Systems For Cancer Therapy, Molecular Cancer, Jan. 7, 2011;10:3. 20 pages, doi: 10.1186/1476-4598-10-3.
Bonehill, A., et al., Single-step antigen loading and activation of dendritic cells by mRNA electroporation for the purpose of therapeutic vaccination in melanoma patients. Clin Cancer Res. May 2009; 15(10): 3366-3375.
Bonham et al., An assessment of the antisense properties of RNase H-competent and steric-blocking oligomers. Nucleic Acids Res. Apr. 11, 1995; 23(7): 1197-1203.
Borghaei et al., Phase I Dose Escalation, Pharmacokinetic and Pharmacodynamic Study of Naptumomab Estafenatox Alone in Patients With Advanced Cancer and With Docetaxel in Patients With Advanced Non-Small-Cell Lung Cancer. J Clin Oneal. Sep. 1, 2009;27(25):4116-23. doi: 10.1200/JCO.2008.20.2515. Epub Jul. 27, 2009.
Bose et al., Influence of cationic lipid concentration on properties of lipid-polymer hybrid nanospheres for gene delivery. Int J Nanomedicine. Sep. 2, 2015;10:5367-82. doi: 10.2147/IJN.S87120. eCollection 2015.
Bouxsein, N.F., et al., Structure and gene silencing activities of monovalent and pentavalent cationic lipid vectors complexed with siRNA. Biochem. 2007; 46(16): 4785-4792.
Boyer-Diponio et al., Biological function of mutant forms of Jaggedi proteins in Alagille syndrome: inhibitory effect on Notch signaling. Hum Mol Genet. Nov. 15, 2007;16(22):2683-92. Epub Aug. 24, 2007.
Brennan, Ribonucleoside triphosphate concentration-dependent termination of bacteriophage SP0I transcription in vitro by Bacillus subtilis RNA polymerase. Virology. Jun. 1984;135(2):555-60. doi: 10.1016/0042-6822(84)90211-3.

(56) References Cited

OTHER PUBLICATIONS

Brito et al., A cationic nanoemulsion for the delivery of next-generation RNA vaccines. Mol Ther. Dec. 2014;22(12):I-12. doi: 10.1038/mt.2014.133. Epub Jul. 16, 2014.
Brito et al., "Self-amplifying mRNA vaccines," Advances in Genetics, 2014, vol. 89, pp. 179-233.
Brown, Genomes. 2002. 2nd Edition. Oxford:Wiley-Liss. p. 1-20.
Burke et al., Formulation, stability, and delivery of live attenuated vaccines for human use. Crit Rev Ther Drug Carrier Syst. 1999;16(1):1-83.
Buyens et al., "Liposome based systems for systemic siRNA delivery: Stability in blood sets the requirements for optimal carrier design," Journal of Controlled Release, 2012, 158:362-370.
Byoung-Shik et al., Intranasal immunization with plasmid DNA encoding spike protein of SARS-coronavirus/polyethylenimine nanoparticles elicits antigen-specific humoral and cellular immune responses. BMC Immunol. Dec. 31, 2010;11:65. doi: 10.1186/1471-2172-11-65.
Cao et al. 'MDR3/ABCB4 mRNA Therapy for Treating Progressive Familial Intrahepatic Cholestasis 3 (PFIC3)', Abstract No. 768, Molecular Therapy Apr. 22, 2019, vol. 27, No. 4, Suppl 1 pp. 358-359.
Carnahan et al., Epratuzumab, a Humanized Monoclonal Antibody Targeting CD22 Characterization of in Vitro Properties Clin Cancer Res. Sep. 1, 2003;9(10 Pt 2):3982S-90S.
Chamberlain et al., Recurrent lymphomatous meningitis treated with intra-CSF rituximab and liposomal ara-C. J Neurooncol. Feb. 2009;91(3):271-7. doi: 10.1007/s11060-008-9707-1. Epub Sep. 27, 2008.
Chattopadhya Y et al., A chimeric vesiculo/alphavirus is an effective alphavirus vaccine. J Viral. Jan. 2013;87(1):395-402. doi: 10.1128/JVI.01860-12. Epub Oct. 17, 2012.
Chen, D., et al., Rapid discovery of potent siRNA-containing lipid nanoparticles enabled by controlled microfluidic formulation. J Am Chem Soc. 2012; 134: 6948-6951.
Chen et al., Human monoclonal antibodies targeting the haemagglutinin glycoprotein can neutralize H7N9 influenza virus. Nat Commun. Mar. 30, 2015;6:6714. doi: 10.1038/ncomms7714.
Chen et al., "Influence of particle size on the in vivo potency of lipid nanoparticle formulations of siRNA," Journal of Controlled Release, Aug. 10, 2016, pp. 236-244, vol. 235.
Chen et al., Molecular evolution and epidemiology of four serotypes of dengue virus in Thailand from 1973 to 2007. Epidemiol Infect. Feb. 2013;141(2):419-24. doi: 10.1017/S0950268812000908. Epub 2012 Mav 14.
Chudley et al., Harmonisation of short-term in vitro culture for the expansion of antigen-specific CDS(+) T cells with detection by ELISPOT and HLA-multimer staining. Cancer Immunol Immunother. 2014;63(11):1199-1211.
Corazzelli et al., Biweekly rituximab, cyclophosphamide, vincristine, non-pegylated liposome-encapsulated doxorubicin and prednisone (R-COMP-14) in elderly patients with poor-risk diffuse large B-cell lymphoma and moderate to high 'life threat' impact cardiopathy. Br J Haematol. Sep. 2011;154(5):579-89. doi: 10.1111/j.1365-2141.2011.08786.x. Epub Jun. 28, 2011.
Cribbs, David H., Adjuvant-dependent Modulation of Th1 and Th2 Responses to Immunization with beta-amyloid, International Immunology, 2003, vol. 15, No. 4, pp. 505-514.
Crommelin et al., Addressing the Cold Reality of mRNA Vaccine Stability, J Pharm Sci, 2021,110(3), 997-1001, DOI: 10.1016/j.xphs.2020.12.006 (Year: 2021).
Cullis et al., "Lipid Nanoparticle Systems for Enabling Gene Therapies," Molecular Therapy, 2017, 25(7), 1467-1475.
Cun, Dongmei, et al., Preparation and characterization of poly(DL-lactide-co-glycolide) nanoparticles for siRNA delivery. International Journal of Pharmaceutics 390 (2010) 70-75.
Cunnigham, The herpes zoster subunit vaccine. Expert Opin Biol Ther. 2016;16(2):265-71. doi: 10.1517/14712598.2016.1134481.

Dahlman, James E. et al., In vivo endothelial siRNA delivery using polymeric nanoparticles with low molecular weight, Nature Nanotechnology, 2014, No. vol. #, pp. 1-8.
Danaei et al., "Impact of particle Size and Polydispersity Index on the Clinical Applications of Lipidic nanocarrier Systems", Pharmaceutics, 2018, vol. 10, pp. 1-17.
Davtyan, H. et al., Immunogenicity, Efficacy, Safety, and Mechanism of Action of Epitope Vaccine (Lu AF20513) for Alzheimer's Disease: Prelude to a Clinical Trial, The Journal of Neuroscience, Mar. 2013, vol. 33, No. 11, pp. 4923-4934.
Delehanty, James B., Peptides for specific intracellular delivery and targeting of nanoparticles: implications for developing nanoparticle-mediated drug delivery. Ther Deliv. Sep. 2010;1(3):411-433. doi: 10.4155/tde.10.27.
Depledge et al., Deep Sequencing of Distinct Preparations of the Live Attenuated Varicella-Zoster Virus Vaccine Reveals a Conserved Core of Attenuating Single-Nucleotide Polymorphisms. J Viral. Sep. 12, 2016;90(19):8698-704.
Deshayes, S. et al., "Cell-penetrating peptides: tools for intracellular delivery of therapeutics," Cell. Mol. Life Sci., Aug. 2005, 62(16):1839-1849.
Dharap, S.S., et al., Tumor-specific Targeting of an Anticancer Drug Delivery System by LHRH Peptide, PNAS, 2005, vol. 102, No. 36, pp. 12962-12967.
Dickman et al., Ion Pair Reverse-Phase Chromatography: A Versatile Platform for the Analysis of RNA. Chromatography Today. 2011; 22-26.
Diken et al., Current Developments in Actively Personalized Cancer Vaccination with a Focus on RNA as the Drug Format. Prog Tumor Res. 2015;42:44-54. doi: 10.1159/000437184. Epub Sep. 4, 2015. Review.
Dong, Y. et al., Poly(d,1-laclide-co-glycolide)/montmorillonite nanoparticles for oral delivery of anticancer drugs. Biomaterials. Oct. 2005;26(30):6068-76.
Dropulic et al., The challenge of developing a herpes simplex virus 2 vaccine. Expert Rev Vaccines. Dec. 2012; 11(12):1429-40. doi:10.1586/erv.12.129. Author's Manuscript, 21 pages.
Du et al., Recombinant adeno-associated virus expressing the receptor-binding domain of severe acute respiratory syndrome coronavirus S protein elicits neutralizing antibodies: Implication for developing SARS vaccines. Virology. Sep. 15, 2006;353(1):6-16. doi: 10.1016/j.virol.2006.03.049. Epub Jun. 21, 2006.
Du, L. et al., Arginine-rich cell-penetrating peptide dramatically enhances AMO-mediated ATM Aberrant Splicing Correction and Enables Delivery to Brain and Cerebellum, Human Molecular Genetics, 2011, vol. 20, No. 16, pp. 3151-3160.
Durbin et al., RNAs Containing Modified Nucleotides Fail To Trigger RIG-I Conformational Changes for Innate Immune Signaling. mBio. Sep. 20, 2016;7(5):e00833-16. doi: 10.1128/mBio.00833-16.
Easton, LE. et al., Rapid, nondenaturing RNA purification using weak anion-exchange fast performance liquid chromatography. RNA. Mar. 2010;16(3):647-53. Epub Jan. 25, 2010.
El Ouahabi, A., et al., Double long-chain amidine liposome-mediated self replicating RNA transfection. FEBS Letters. Feb. 1996; 380(1-2): 108-112.
Erasmus, "A Nanostructured Lipid Carrier for Delivery of a Replicating Viral RNA Provides Single, Low-Dose Protection against Zika," Molecular Therapy, Oct. 2018, vol. 26, No. 10, pp. 2507-2522.
Espeseth et al., Modified mRNA/lipid nanoparticle-based vaccines expressing respiratory syncytial virus F protein variants are immunogenic and protective in rodent models of RSV infection. NPJ Vaccines. Feb. 14, 20204;5:16. 14 pages doi: 10.1038/s41541-020-0163-z. eCollection 2020.
Ewert et al., Cationic liposome-nucleic acid complexes for gene delivery and silencing: pathways and mechanisms for plasmid DNA and siRNA. Top Curr Chem. 2010;296:191-226. Author's Manuscript, 40 pages.
Ezzat, Kariem et al. PepFect 14, a Novel Cell-penetrating Peptide for Oligonucleotide Deliver in Solution and As Solid Formulation, Nucleic Acids Research, 2011, vol. 39, No. 12, pp. 5284-5298.

(56) References Cited

OTHER PUBLICATIONS

Fable. J, et al., "Surfactants in Consumer Products", Theory, Technology and Application, 1st edition, Jul. 1994, pp. 101-102.
Fang et al., A Novel Cell-Penetrating Peptide Derived from Human Eosinophil Cationic Protein, PLOS One, 2013, vol. 8, Issue 3, e57318 (pp. 1-13).
Felgner, PL Cationic lipid/polynucleotide condensates for in vitro and in vivo polynucleotide delivery—the cytofectins. J. of Liposome Research. 1993; 3(1): 3-16.
Felgner P. L., et al., "Lipofection: A Highly Efficient, Lipid-Mediated DNA-Transfection Procedure," Proceedings of the National Academy of Sciences USA, vol. 84 (21), Nov. 1987, pp. 7413-7417.
Felgner, PL Particulate systems and polymers for in vitro and in vivo delivery of polynucleotides. Adv. Drug Delivery Rev. 1990; 5(3): 163-187.
Fleeton et al., Self-replicative RNA vaccines elicit protection against influenza A virus, respiratory syncytial virus, and a tickborne encephalitis virus. J Infect Dis. May 1, 2001;183(9):1395-8. Epub Mar. 30, 2001.
Freer et al., Varicella-zoster virus infection: natural history, clinical manifestations, immunity and current and future vaccination strategies. New Microbial. Apr. 2018;41(2):95-105. Epub Mar. 2, 2018.
Furie, Richard et al., A Phase III, Randomized, Placebo-Controlled Study of Belimumab, a Monoclonal Antibody That Inhibits B Lymphocyte Stimulator, in Patients With Systemic Lupus Erythematosus, Arthritis & Rheumatism, 2011, vol. 63, No. 12, pp. 3918-3930.
Furuichi, Caps on Eukaryotic mRNAs. eLS. John Wiley & Sons. Jul. 2014. 12 pages.
Gao, X. et al., Nonviral gene delivery: what we know and what is next. AAPS J. Mar. 23, 2007;9(1):E92-104.
Garcia-Manyes., S et al., "Nanomechanics of Lipid Bilayers: Heads or Tails?" Journal of the American Chemical Society, vol. 132, 2010, pp. 12874-12886.
Geall et al., Nonviral delivery of self-amplifying RNA vaccines. Proc Natl Acad Sci U S A. Sep. 4, 2012;109(36):14604-9. doi:10.1073/pnas.1209367109. Epub Aug. 20, 2012.
GENBANK Submission; NIH/NCBI, Accession No. ADG45118.1. Schmidt-Chanasit et al., Jun. 24, 2010. 2 pages.
GENBANK Submission; NIH/NCBI, Accession No. NM_I 72138.2. Zakaria et al., Jan. 13, 2020. 4 pages.
GENBANK Submission; NIH/NCBI, Accession No. YP009137218.1. Davidson. May 16, 2016. 2 Pages.
Genini et al., Serum Antibody Response to the gH/gL/pUL128-131 Five-Protein Complex of Human Cytomegalovirus (HCMV) in Primary and Reactivated HCMV Infections. J Clin Viral. Oct. 2011;52(2):113-8. doi: 10.1016/i.icv.2011.06.018. Eoub Aug. 4, 2011.
Georgopoulos et al., Use of high-performance liquid chromatographic fractionation of large RNA molecules in the assay of group I intron ribozyme activity. J Chromatogr A. Jan. 28, 2000;868(1):109-14.
Giblin, M. et al., Selective Targeting of *E. coli* Heat-stable Enterotoxin Analogs to Human Colon Cancer Cells, Anticancer Research, 2006, vol. 26, pp. 3243-3252.
Giljohann, DA, et al., Gene regulation with polyvalent siRNA-nanoparticle conjugates. J Am Chem Soc. Feb. 2009; 131 (6): 2072-2073.
Gilkeson, G.S. et al., Induction of cross-reactive anti-dsDNA antibodies in preautoimmune NZB/NZW mice by immunization with bacterial DNA. J Clin Invest. Mar. 1995;95(3):1398-402.
Gjetting et al., "A simple protocol for preparation of a liposomal vesicle with encapsulated plasmid DNA that mediate high accumulation and reporter gene activity in tumor tissue," Results in Pharma Sciences, 2011, 1:49-56.
Gjetting et al., In vitro and in vivo effects of polyethylene glycol (PEG)-modified lipid in DOTAP/cholesterol-mediated gene transfection. Int J Nanomedicine. Aug. 9, 2010;5:371-83.

Gluzman et al., Esterification of stearic acid with polyethylene glycols. Zhurnal Prikladnoi Khimii, Maik Nauka: Rossiiskaya Akademiya Nauk. Jan. 1, 1968;41(1):167-170.
Grabbe et al., Translating nanoparticulate-personalized cancer vaccines into clinical applications: case study with RNA-lipoplexes for the treatment of melanoma. Nanomedicine (Lond). Oct. 2016; 11(20):2723-2734.
Hadinoto et al., Lipid-polymer Hybrid Nanoparticles as a New Generation Therapeutic Delivery Platform: A Review. Eur J Pharm Biopharm. Nov. 2013;85(3 Pt A):427-43. doi: 10.1016/j.ejpb.2013.07.002. Epub Jul. 17, 2013.
Hartmaier et al., Genomic analysis of 63,220 tumors reveals insights into tumor uniqueness and targeted cancer immunotherapy strategies. Genome Med. Feb. 24, 2017;9(1):16. doi: 10.1186/s13073-017-0408-2.
Hartmann et al., Handbook of RNA Biochemistry, Second Edition, "Part I RNA Synthesis and Detection." 2014. pp. 1-27.
Hashimoto et al., Relationship between the concentration of anti-polyethylene glycol (PEG) immunoglobulin M (IgM) and the intensity of the accelerated blood clearance (ABC) phenomenon against PEGylated liposomes in mice. Biol Pharm Bull. 2015;38(3):417-24. doi: 10.1248/bpb.b14-00653.
Hassett et al., "Optimization of Lipid Nanoparticles for Intramuscular Administration of mRNA Vaccines", Molecular Therapy: Nucleic Acids, Apr. 2019, vol. 15, 11 pages.
He, K. et al., Synthesis and Separation of Diastereomers of Ribonucleoside 5'-(alpha-P-Borano)triphosphates. J Org Chern. Aug. 21, 1998 ;63(17):5769-5773.
Hecker, Nonviral, cationic lipid-mediated delivery of mRNA. Methods Mol Biol. 2013;969:73-88. doi: 10.1007/978-1-62703-260-5 5.
Hecker, J.G. et al., Non-Viral DNA and mRNA Gene Delivery to the CNS Pre-Operatively for Neuroprotection and Following Neurotrauma. Molecular Therapy. 2004; 9, S258-S258.
Heesch et al., Abstract CT020: MERIT: introducing individualized cancer vaccines for the treatment of TNBC—a phase I trial, [abstract]. In: Proceedings of the 107th Annual Meeting of the American Association for Cancer Research; Apr. 16-20, 2016; New Orleans, LA. Philadelphia (PA): AACR; Cancer Res 2016; 76 (14 Suppl), 5 pages.
Heyes, J. et al. (2005), "Cationic lipid saturation influences intracellular delivery of encapsulated nucleic acids," Journal of Controlled Release, 107:276-287.
Hoarau D et al., Pascal Delmas, Stephanie David, Emmanuelle Roux, and Jean-Christophe Leroux. "Novel Long-Circulating Lipid Nanocapsules." Pharmaceutical Research, vol. 21, No. 10, Oct. 2004, pp. 1783-1789. (Year: 2004).
Hoerr, I. et al., In vivo application of RNA leads to induction of specific cytotoxic T lymphocytes and antibodies. EurJ Immunol. Jan. 2000;30(1): 1-7.
Hope et al., "Production of large unilamellar vesicles by a rapid extrusion procedure: characterization of size distribution, trapped volume and ability to maintain a membrane potential", Biochim Biophys Acta, 1985, 812, 55-65.
Hsu et al., Cationic lipid nanoparticles for therapeutic delivery of siRNA and miRNA to murine liver tumor. Nanomedicine. Nov. 2013;9(8): 1169-80. doi: 10.1016/j.nano.2013.05.007. Epub May 30, 2013.
Huber et al., Analysis of nucleic acids by on-line liquid chromatography—Mass spectrometry (Mass Spectrometry Reviews 2001, 20, pp. 310-343).
Hussein et al., Synthesis, Quantum Chemical Calculations and Properties of Nonionic and Nonionic-Anionic Surfactants Based on Fatty Alkyl Succinate. Journal of Surfactants and Detergents vol. 17, pp. 615-627(2014).
Iden et al., "In vitro and in vivo comparison of immunoliposomes made by conventional coupling techniques with those made by a new post-insertion approach," Biochimica et Biophysica Acta (2001) 1513: 207-216.
Ishida, T et al., "A combinatorial approach to producing sterically stabilized (Stealth) immunoliposomal drugs." FEBS Letters, vol. 460, 1999, pp. 129-133. (Year: 1999).
Ivanovska, N. et al., Immunization with a DNA chimeric molecule encoding a hemagglutinin peptide and a scFv CD21-specific anti-

(56) References Cited

OTHER PUBLICATIONS body fragment induces long-lasting IgM and CTL responses to influenza virus. Vaccine. Mar. 10, 2006;24(11):1830-7. Epub Nov. 2, 2005.

Jachertz, D. et al., Treatment of P815 mastocytoma in DBA/2 mice with RNA. J Immunogen. 1974; 1: 355-362.

Janeway, C. et al., Immunobiology: the immune system in health and disease. Garland Publishing, Inc, London. 1997; 13:12-13:21.

Jayaraman et al., "Maximizing the Potency of siRNA Lipid Nanoparticles for Hepatic Gene Silencing In Vivo," Angew. Chem. Int. Ed. 2012, 51, 8529-8533.

Jeffs et al. (Mar. 2005) "A Scalable, Extrusion-Free Method for Efficient Liposomal Encapsulation of Plasmid DNA" Pharmaceutical Research, vol. 22, No. 3, p. 362-372.

Jia et al., Kinetic mechanism of GTP binding and RNA synthesis during transcription initiation by bacteriophage T7 RNA polymerase. J Biol Chem. Nov. 28, 1997;272(48):30147-53. doi: 10.1074/jbc.272.48.30147.

John et al., Multi-antigenic human cytomegalovirus mRNA vaccines that elicit potent humoral and cell-mediated immunity. Vaccine. Mar. 14, 2018;36(12):1689-1699. doi:10.1016/j.vaccine.2018.01.029. Epub Feb. 15, 2018.

Juliano, R.L., et al., Cell-targeting and cell-penetrating peptides for delivery of therapeutic and imaging agents. Wiley Interdisciplinary Reviews: Nanomedicine and Nanobiotechnology. May/Jun. 2009; 1(3): 324-335.

Kalantari-Dehagi et al., Discovery of Potential Diagnostic and Vaccine Antigens in Herpes Simplex Virus 1 and 2 by Proteome-Wide Antibody Profiling. J Viral. Apr. 2012;86(8):4328-39. doi: 10.1128/JVI.05194-11. Epub Feb. 8, 2012.

Kallen et al., A development that may evolve into a revolution in medicine: mRNA as the basis for novel, nucleotide-based vaccines and drugs. Ther Adv Vaccines. Jan. 2014;2(1):10-31. doi: 10.1177/2051013613508729.

Kallen et al., A novel, disruptive vaccination technology: self-adjuvanted RNActive() vaccines. Hum Vaccin Immunother. Oct. 2013;9(10):2263-76. doi: 10.4161/hv.25181. Epub Jun. 4, 2013. Review.

Kang, Hyunmin, Inhibition of MDR1 Gene Expression by Chimeric HNA Antisense Oligonucleotides, Nucleic Acids Research, 2004, vol. 32, No. 14, pp. 4411-4419.

Kariko et al., Phosphate-enhanced transfection of cationic lipid-complexed mRNA and plasmid DNA. Biochimica et Biophysica Acta. 1998. 1369:320-34.

Kariko et al., "Generating the optimal mRNA for therapy: HPLC purification eliminates immune activation and improves translation of nucleoside-modified, protein-encoding mRNA", Nucleic Acids Research, Oxford University Press, GB, vol. 39, No. 21, Nov. 1, 2011 (Nov. 1, 2011), pp. e142-1.

Kariko, K., et al., In vivo protein expression from mRNA delivered into adult rat brain. J. of Neuroscience Methods. Jan. 2001; 105(1): 77-86.

Kariko K. et al., "Incorporation of pseudouridine into mRNA yields superior nonimmunogenic vector with increased translational capacity and biological stability," Molecular Therapy, Nature Publishing Group, vol. 16 (11):1833-1840 (2008).

Kauffman et al., Efficacy and immunogenicity of unmodified and pseudouridine-modified mRNA delivered systemically with lipid nanoparticles in vivo. Biomaterials. Dec. 2016; 109:78-87. doi: 10.1016/j.biomaterials.2016.09.006. Epub Sep. 25, 2016.

Kauffman et al., "Optimization of Lipid Nanoparticle Formulations for mRNA Delivery in Vivo with Fractional Factorial and Definitive Screening Designs," Nano Letters, 2015, 15(11):7300-7306.

Keown, WA, et al., [41] Methods for Introducing DNA into Mammalian Cells. Methods in Enzymology, 1990, 185:527-37.

Keshwara et al., Rabies-based vaccine induces potent immune responses against Nipah virus. NPJ Vaccines. Apr. 15, 2019;4:15. Erratum in: NPJ Vaccines. May 13, 2019;4:18.

Kingston, 'Preparation of poly (A)+ RNA', Current protocols in molecular biology. 1993;21(1):4.5.1-4.5.3.

Kirchdoerfer et al., "Stabilized coronavirus spikes are resistant to conformational changes induced by receptor recognition or proteolysis.," Scientific Reports, (2018); 8(1):15701. doi: 10.1038/s41598-018-34171-7.

Kirpotin, D.B., et al., Antibody targeting of long-circulating lipidic nanoparticles does not increase tumor localization but does increase internalization in animal models. Cancer Res. 2006; 66: 6732-6740.

Klinman, D.M. et al., DNA vaccines: safety and efficacy issues. Springer Semin Immunopathol. 1997;19(2):245-56.

Knudsen et al., Antisense properties of duplex- and triplex-forming PNAs. Nucleic Acids Res. Feb. 1, 1996; 24(3): 494-500.

Koch, G., et al., Quantitative Studies on the Infectivity of ribonucleic acid from partially purified and highly purified poliovirus preparations. Virology. Mar. 1960; 10(3): 329-343.

Kowalski et al., Delivering the Messenger: Advances in Technologies for Therapeutic mRNA Delivery. Molecular Therapy. Apr. 4, 2019;27(4):710-28.

Kozielski, Kristen L. et al., Bioreducible Cationic Polymer-Based Nanoparticles for Efficient and Environmentally Triggered Cytoplasmic siRNA Delivery to Primary Human Brain Cancer Cells, ACS Nano, 2014, vol. 8, No. 4, pp. 3232-3241.

Krause et al., Prevention of the hemodynamic effects of iopromide-carrying liposomes in rats and pigs. Invest Radiol. Aug. 2000;35(8):493-503.

Kulkarni et al., "Lipid Nanoparticles Enabling Gene Therapies: From Concepts to Clinical Utility," Nucleic Acid Ther., 2018, 28(3): 146-157.

Kumar et al., Shielding of Lipid Nanoparticles for siRNA Delivery: Impact on Physicochemical Properties, Cytokine Induction, and Efficacy. Mol Ther Nucleic Acids. Nov. 18, 2014;3(11):e210. doi: 10.1038/mtna.2014.61.

Kussie, P. H. et al. "A single engineered amino acid substitution changes antibody fine specificity," J Immunol. Jan. 1, 1994; 152(1): 146-52.

Kutchko et al., Transcending the Prediction Paradigm: Novel Applications of SHAPE to RNA Function and Evolution. Wiley Interdiscip Rev RNA. Jan. 2017;8(1):e1374. doi: 10.1002/wrna.1374. Epub Jul. 10, 2016.

Laakkonen et al., Homing Peptides as Targeted Delivery Vehicles, Interactive Biology, 2010, vol. 2, pp. 326-337.

Lai, S.K., et al., Mucus-penetrating nanoparticles for drug and gene delivery to mucosal tissues. Adv Drug Deliv Rev. Feb. 27, 2009; 61(2): 158-171.

Lai, S.K., et al., Rapid transport of large polymeric nanoparticles in fresh undiluted human mucus. PNAS. Jan. 30, 2007; 104(5): 1482-1487.

Leader B., et al., Protein therapeutics: a summary and pharmacological classification. Nat Rev Drug Discov. Jan. 2008; 7(1): 21-39.

Lee et al., Separation and determination of polyethylene glycol fatty acid esters in cosmetics by a reversed-phase HPLC/ELSD. Talanta. Feb. 15, 2008;74(5):1615-20. doi: 10.1016/i.talanta.2007.10.020. Epub Oct. 18, 2007.

Lee, Justin B. et al., Lipid Nanoparticle siRNA Systems for Silencing The Androgen Receptor In Human Prostate Cancer in Vivo, International Journal of Cancer, 2012, vol. 131, pp. 781-790.

Lehto, T., et al., Cell-penetrating peptides for the delivery of nucleic acids. Expert Opin. Drug Deliv. Jul. 2012; 9(7): 823-836.

Leung et al., "Lipid Nanoparticles Containing siRNA Synthesized by Microfluidic Mixing Exhibit an Electron-Dense Nanostructured Core," The Journal of Physical Chemistry C, 2012, 116:18440-18450.

Leung et al., "Microfluidic Mixing: A General Method for Encapsulating macromolecules in Lipid Nanoparticle Systems", The Journal of Physical Chemistry, Jun. 18, 2015, vol. 8, pp. 8698-8706.

Lewandowski, L.J. et al., Separation of the infectious ribonucleic acid of potato spindle tuber virus from double-stranded ribonucleic acid of plant tissue extracts. J Virol. Nov. 1971;8(5):809-12.

Lewis, David, Dynamic Polyconjugates (DPC) Technology: An elegant solution to the siRNA delivery problem. Arrowhead Research Corp (NASDAQ: ARWR). Nov. 2011. 6 pages.

Li et al., Alagille syndrome is caused by mutations in human Jagged1, which encodes a ligand for Notch1. Nat Genet. Jul. 1997;16(3):243-51.

(56) References Cited

OTHER PUBLICATIONS

Li et al., Lipid-based nanoparticles for nucleic acid delivery. Pharm Res. Mar. 2007;24(3):438-49. doi: 10.1007/s11095-006-9180-5.
Li, L. et al., Overcoming obstacles to develop effective and safe siRNA therapeutics. Expert Opin Biol Ther. May 2009; 9(5): 609-19.
Li, L. et al., Preparation and gene delivery of alkaline amino acids-based cationic liposomes. Arch Pharm Res. Jul. 2008;31(7):924-31. Epub Aug. 14, 2008.
Lian, T. et al., Trends and developments in liposome drug delivery systems. J Pharm Sci. Jun. 2001;90(6):667-80.
Liu et al., Nucleic Acid Chemistry in the Organic Phase: From Functionalized Oligonucleotides to DNA Side Chain Polymers, J Am Chem Soc, 2014, 136, 14255-14262, DOI: 10.1021/ja5080486.
Li and Huang, "Targeted Delivery of Antisense Oligodeoxynucleotide and Small Interference RNA into Lung Cancer Cells," Molecular Pharmaceutics, 2006 vol. 3, No. 5, pp. 579-588.
Lo, Albert et al., Hepatocellular Carcinoma Cell-Specific Peptide Ligand for Targeted Drug Delivery, Molecular Cancer Therapeutics, 2008, vol. 7, No. 3, pp. 579-589.
Lopez-Berestein et al., Treatment of systemic fungal infections with liposomalamphotericin B. Arch Intern Med. Nov. 1989;149(11):2533-6.
Lu et al., Bat-to-human: spike features determining 'host jump' of coronaviruses SARS-CoV, MERS-CoV, and beyond. Trends Microbial. Aug. 2015;23(8):468-78. doi: 10.1016/i.tim.2015.06.003. Epub Jul. 21, 2015.
Lu et al., IFNL3 mRNA structure is remodeled by a functional non-coding polymorphism associated with hepatitis C virus clearance. Sci Rep. 2015;5:16037, 14 pages.
Lu, Ruei-Min et al., Targeted Drug Delivery Systems Mediated by a Novel Peptide in Breast Cancer Therapy and Imaging, PLOS One, 2013, vol. 8, Issue 6, e66128, 13 pages.
Luo and Saltzman, "Synthetic DNA delivery systems", Nature Biotechnol. 2000; 18(1): 33-37.
M. Kanapathipillai, et al., Nanoparticle targeting of anti-cancer drugs that alter intracellular signaling or influence the tumor microenvironment, Adv. Drug Deliv. Rev. (2014), pp. 1-12.
MacLachlan, I., "Liposomal Formulations for Nucleic Acid Delivery," Antisense Drug Technologies, Second Edition, Chapter 9, 2007, pp. 237-270.
MacLachlan, Lipid Nanoparticle-mediated delivery of messenger RNA. Presentation. 1st International mRNA Health Conference. Tubingen, Germany. Oct. 24, 2013. http://files.shareholder.com/downloads/ABEA-50QJTB/2628241206x0x699789/47543d12-db34-4e6e-88a9-f3ae5d97b1d2/MacLachlan_mRNA_Conf_2013.pdf. Last accessed Dec. 22, 2016. 32 pages.
Madden et al., Systemic delivery of mRNA therapeutics using lipid nanoparticles (LNP): improved potency for novel LNP and influence of route of administration on protein expression. 2nd International mRNA Health Conference. Nov. 12, 2014. https://acuitastx.com/wp-content/uploads/2015/01/Poster-Second-International-mRNA-Health-Conference.pdf. 1 page.
Magee, W.E. et al., Marked stimulation of lymphocyte-mediated attack on tumor cells by target-directed liposomes containing immune RNA, Cancer Res., 1978, 38(4):1173-6.
Maier, et al., Biodegradable lipids enabling rapidly eliminated lipid nanoparticles for systemic delivery of RNAi therapeutics, Molecular Therapy, Aug. 1, 2013, vol. 21, No. 8, pp. 1570-1578.
Malone, R.W. et al., Cationic liposome-mediated RNA transfection. Proc Natl Acad Sci U S A. Aug. 1989;86 (16):6077-81.
Mar et al., Nucleic acid vaccination strategies against infectious diseases. Expert Opin Drug Deliv. 2015; 12(12):1851-65. doi: 10.1517/17425247.2015.1077559. Epub Sep. 12, 2015.
Marina et al., Dose escalation and pharmacokinetics of pegylated liposomal doxorubicin (Doxil) in children with solid tumors: a pediatric oncology group study. Clin Cancer Res. Feb. 2002;8(2):413-8.
Mas et al., Engineering, Structure and Immunogenicity of the Human Metapneumovirus F Protein in the Postfusion Conformation. PLoS Pathog. Sep. 9, 2016;12(9):e1005859. doi:10.1371/journal.ooat.1005859. eCollection Sep. 2016.
Mateo et al., Vaccines inducing immunity to Lassa virus glycoprotein and nucleoprotein protect macaques after a single shot. Sci Transl Med. Oct. 2, 2019;11(512):eaaw3163. 18 pages doi: 10.1126/scitranslmed.aaw3163.
Maurer, N., et al., Spontaneous entrapment of polynucleotides upon electrostatic interaction with ethanol-destabilized cationic liposomes. Biophys J. May 2001; 80(5): 2310-2326.
McCormack, M., et al., Activation of the T-cell oncogene LM02 after gene therapy for X-linked severe combined immunodeficiency. N Engl J Med. Feb. 2004; 350: 913-922.
MEGAscript Kit Product Manual, Ambion/Invitrogen website: http://lools.invitrogen.com/content/sfs/manuals/ cms_072987.pdf, Publication Date: Oct. 27, 2009 (last accessed Mar. 17, 2013)("Ambion"), Author Life Technologies., 29 pages.
Mellits, K.H. et al., Removal of double-stranded contaminants from RNA transcripts: synthesis of adenovirus VA RNAI from a T7 vector. Nucleic Acids Res. Sep. 25, 1990;18(18):5401-6.
Michel et al., Cationic Nanoliposomes Meet mRNA: Efficient Delivery of Modified mRNA Using Hemocompatible and Stable Vectors for Therapeutic Applications. Mol Ther Nucleic Acids. Sep. 15, 2017;8:459-468. doi: 10.1016/j.omtn.2017.07.013. Epub Jul. 25, 2017.
Middleton et al., Hendra virus vaccine, a one health approach to protecting horse, human, and environmental health. Emerg Infect Dis. Mar. 2014;20(3):372-9. doi: 10.3201/eid2003.131159.
Midoux et al., Lipid-based mRNA vaccine delivery systems. Expert Rev Vaccines. Feb. 2015; 14(2):221-34. doi: 10.1586/14760584.2015.986104. Epub Dec. 26, 2014. Review.
Mishra, N.C. et al., Induction by RNA of inositol independence in Neurospora crassa. Proc. Natl Acad. Sci. U.S.A., 1975, 72(2):642-5.
Mishra, R.K. et al., Improved leishmanicidal effect of phosphorothioate antisense oligonucleotides by LDL-mediated delivery. Biochim Biophys Acta. Nov. 7, 1995;1264(2):229-37.
Morello et al., Immunization With Herpes Simplex Virus 2 (HSV-2) Genes Plus Inactivated HSV-2 Is Highly Protective Against Acute and Recurrent HSV-2 Disease. J Viral. Apr. 2011;85(7):3461-72. doi: 10.1128/JVI.02521-10. Epub Jan. 26, 2011.
Muller, M.R. et al., Transfection of dendritic cells with RNA induces CD4- and COB-mediated T cell immunity against breast carcinomas and reveals the immunodominance of presented T cell epitopes. J Immunol. Jun. 15, 2003;170(12):5892-6.
Nair, S. et al., Soluble proteins delivered to dendritic cells via pH-sensitive liposomes induce primary cytotoxic T lymphocyte responses in vitro. J Exp Med. Feb. 1, 1992; 175(2):609-12.
Nakamura, K. et al., Antigen restricted hybridization between antigen primed macrophage and thymic RNA. Immunol Commun. 1981;10(4-5):367-82.
Nakano et al., The structural stability and catalytic activity of DNA and RNA oligonucleotides in the presence of organic solvents, Biophysical Reviews, 2016, 8, 11-23 DOI: 10.1007/s12551-015-0188-0.
NCT02410733—Evaluation of the Safety and Tolerability of i.v. Administration of a Cancer Vaccine in Patients With Advanced Melanoma (Lipa-MERIT), ClinicalTrials.gov, Jul. 17, 2019, (Online), Viewed online Jan. 2, 2020, URL: https://www.clinicaltrials.gov/ct2/show/record/NCT02410733?term=NCT02410733&draw=2&rank=1 . 9 pages.
Nielsen et al. Toward Personalized Lymphoma Immunotherapy: Identification of Common Driver Mutations Recognized by Patient CDS+ T Cells. Clin Cancer Res. 2016;22(9):2226-2236.
Niu, M.C., et al., Poly(A)-attached RNA as activator in embryonic differentiation. Proc Soc Exp Biol Med. Oct. 1974;147 (1):318-22.
[No Author Listed], NEB RNase H (https://www.neb.com/products/m0297-rnase-h) Downloaded Mar. 30, 2020. 6 pages.
[No Author Listed], Oligotex Handbook, Qiagen, Jun. 2012 [retrieved from internet on Sep. 22, 2020] 104 pages https://www.qiagen.corn/au/resources/resourcedetail?id=f9fa1d98-d54d-47e7-a20b-8b0cb8975009&lang=en.
[No Author Listed] Programme of the 1st International mRNA Health Conference, Germany; Oct. 2013. 32 pages.

(56) References Cited

OTHER PUBLICATIONS

[No Author Listed], User Guide for mMessage mMachine T7 Kit from Ambion. 2012. p. 1-36.
Obeid et al., The impact of solvent selection on the characteristics of niosome nanoparticles prepared by microfluidic mixing, International Journal of Charmaceutics: X, 2023, 5, 100168, 9 pages DOI: 10.1016/j.ijpx.2023.100168.
Oda et al., Mutations in the human Jagged1 gene are responsible for Alagille syndrome. Nat Genet. Jul. 1997;16(3):235-42.
Oja et al., Doxorubicin entrapped within liposome-associated antigens results in a selective inhibition of the antibody response to the linked antigen. Biochim Biophys Acta. Sep. 29, 2000;1468(1-2):31-40.
Okumura, K., et al., Bax mRNA therapy using cationic liposomes for human malignant melanoma. J Gene Med. 2008; 10: 910-917.
Oster, C.G., et al. Comparative study of DNA encapsulation into PLGA microparticles using modified double emulsion methods and spray drying techniques. Journal of Microencapsulation, May 2005; 22(3): 235-244.
Pallesen et al., Immunogenicity and structures of a rationally designed prefusion MERS-CoV spike antigen. Proc Natl Acad Sci US A. Aug. 29, 2017;114(35):E7348-E7357. doi: 10.1073/pnas. 1707304114. Epub Aug. 14, 2017.
Pangburn, Todd et al., Peptide-and Aptamer-Functionalized Nanovectors for Targeted Delivery of Therapeutics, Journal Of Biomedical Engineering, 2009, vol. 131, 20 pages.
Pardi et al., Developing an influenza vaccine using lipid nanoparticle-encapsulated nucleoside-modified mRNA. Eur. J. Immunol. Aug. 2016;46(S1):1232-1233. Abstract 1349.
Pardi et al., "Expression kinetics of nucleoside-modified mRNA delivered in lipid nanoparticles to mice by various routes," Journal of Controlled Release, 217, 2015, 345-351.
Pardi et al., "Nucleoside-modified mRNA vaccines induce potent T follicular helper and germinal center B cell responses," Journal of Experimental Medicine, May 8, 2018, vol. 215, No. 6, pp. 1571-1588.
Parker et al., Targeting of Polyelectrolyte RNA Complexes to Cell Surface Integrins as an Efficient, Cytoplasmic Transfection Mechanism, Journal of Bioactive and Compatible Polymers, Jul. 2002, 17(4), 10 pages.
Patel et al., Arginoplexes: an arginine-anchored nanoliposomal carrier for gene delivery, Journal of Nanoparticle Research, 2014, 16:2345, 10 pages, DOI: doi.org/10.1007/s11051-014-2345-y.
Perouzel E et al., Michael R. Jorgensen, Michael Keller, and Andrew D. Miller. "Synthesis and Formulation of Neoglycolipids for the Functionalization of Liposomes and Lipoplexes." Bioconjugate Chemistry, vol. 14, 2003, pp. 884-898. (Year: 2003).
Perrier et al., "Post-insertion into Lipid NanoCapsules (LNCs): From experimental aspects to mechanisms," International Journal of Pharmaceutics (2010) 396: 204-209.
Petro et al., Herpes simplex type 2 virus deleted in glycoprotein D protects against vaginal, skin and neural disease. Elife. Mar. 10, 2015;4:e06054. 18 pages, doi: 10.7554/eLife.06054.
Petsch et al., Protective efficacy of in vitro synthesized, specific mRNA vaccines against influenza A virus infection. Nat Biotechnol. Dec. 2012;30(12):1210-6. doi: 10.1038/nbt.2436. Epub Nov. 25, 2012.
Phelan, A. et al. (May 1998) "Intercellular Delivery of Functional p53 by the Herpesvirus Protein VP22" Nat. Biotechnol., 16:440-443.
Pollard, C,, et al., Type I IFN counteracts the induction of antigen-specific immune responses by lipid-based delivery of mRNA vaccines. Mol Ther. Jan. 2013; 21(1): 251-259.
Popov et al., Multivalent rituximab lipid nanoparticles as improved lymphoma therapies: indirect mechanisms of action and in vivo activity. nNanomedicine (Lond). Nov. 2011;6(9):1575-91. doi: 10.2217/nnm.11.50. Epub Oct. 20, 2011.
Porteous et al., Evidence for safety and efficacy of DOTAP cationic liposome mediated CFTR gene transfer to the nasal epithelium of patients with cystic fibrosis. Gene Ther. Mar. 1997;4(3):210-8.
Poveda et al., Establishing Preferred Product Characterization for the Evaluation of RNA Vaccine Antigens. Vaccines (Basel). Sep. 27, 2019;7(4):131. doi: 10.3390/vaccines7040131.
PubChem, Ethyl lauroyl arginate, Aug. 9, 2005, 19 pages, retrieved from https://pubchem.ncbi.nlm.nih.gov/compound/188214.
Rajasagi et al., Systematic identification of personal tumor-specific neoantigens in chronic lymphocytic leukemia. Blood. 2014;124(3):453-462.
Ramamoorth et al., Non viral vectors in gene therapy—an overview. J Clin Diagn Res. Jan. 2015; 9(1): GE01-GE06.
Rammensee et al., Cancer Vaccines: Some Basic Considerations. Genomic and Personalized Medicine. 2009;573-589.
Read, M.L., et al., A versatile reducible polycation-based system for efficient delivery of a broad range of nucleic acids. Nucleic Acids Res. 2005; 33(9): e86, 16 pages.
Regberg et al., Applications of Cell-Penetrating Peptides for Tumor Targeting and Future Cancer Therapies. Pharmaceuticals, 2012; 5:991-1007.
Reichmuth, et al., "mRNA Vaccine Delivery Using Lipid Nanoparticles," Therapeutic Delivery (2016), v. 7, No. 5, pp. 319-334.
Riccardi et al., "Dressing up" an Old Drug: An Aminoacyl Lipid for the Functionalization of Ru(III)-Based Anticancer Agents. ACS Biomater. Sci. Eng. 2018, 4, 1, 163-174.
Riley et al., Simple repeat evolution includes dramatic primary sequence changes that conserve folding potential. Biochem Biophys Res Commun. Apr. 13, 2007;355(3):619-25. Epub Feb. 15, 2007.
Rodriguez, PL et al., Minimal "self" peptides that inhibit phagocytic clearance and enhance delivery of nanoparticles. Science. Feb. 22, 2013; 339(6122): 971-975.
Rohloff, C.M., et al., DU ROS Technology delivers peptides and proteins at consistent rate continuously for 3 to 12 months. J Diabetes Sci Technol. May 2008; 2(3): 461-467.
Romano et al., Inter- and intra-host viral diversity in a large seasonal DENV2 outbreak. PLoS One. Aug. 2, 2013;8(8):e70318. 10 pages doi: 10.1371/journal.pone.0070318. Print 2013.
Sabnis et al., "A Novel Amino Lipid Series for mRNA Delivery: Improved Endosomal Escape and Sustained Pharmacology and Safety in Non-human Primates," Molecular Therapy, Jun. 2018, vol. 26, No. 6, pp. 1509-1519.
Sahin et all, Personalized RNA mutanome vaccines mobilize poly-specific therapeutic immunity against cancer. Nature. Jul. 13, 2017;547(7662):222-226. doi: 10.1038/nature23003. Epub Jul. 5, 2017.
Saito, R., et al., Distribution of liposomes into brain and rat brain tumor models by convection-enhanced delivery monitored with magnetic resonance imaging. Cancer Res. Apr. 2004; 64: 2572-2579.
Sakuma, S. et al., Mucoadhesion of polystyrene nanoparticles having surface hydrophilic polymeric chains in the gastrointestinal tract. Int J Pharm. Jan. 25, 1999;177(2):161-72.
Santos et al., "Design of peptide-targeted liposomes containing nucleic acids," Biochimica et Biophysica Acta (2010) 1798: 433-441.
Schirrmacher, V. et al., Intra-pinna anti-tumor vaccination with self-replicating infectious RNA or with DNA encoding a model tumor antigen and a cytokine. Gene Ther. Jul. 2000;7(13):1137-47.
Schleiss, Cyotmegalovirus vaccines under clinical development. J Virus Erad. Oct. 5, 2016;2(4):198-207.
Schmidt et al., Progress in the development of human parainfluenza virus vaccines. Expert Rev Respir Med. Aug. 2011;5(4):515-26. doi: 10.1586/ers.11.32. Author's Manuscript, 20 pages.
Schott, J.W., et al., Viral and non-viral approaches for transient delivery of mRNA and proteins. Current Gene Ther. 2011; 11 (5): 382-398.
Schwendener, Liposomes as vaccine delivery systems: a review of the recent advances. Ther Adv Vaccines. Nov. 2014;2(6):159-82. doi: 10.1177/2051013614541440.
Semple, S.C., et al., "Rational design of cationic lipids for siRNA delivery", Nature Biotechnology, 2010, vol. 28, No. 2, 172-176.
Shah et al., Shingrix for Herpes Zoster: A Review. Skin Therapy Lett. Jul. 2019;24(4):5-7.

(56) References Cited

OTHER PUBLICATIONS

Shea, R.G. et al., Synthesis, hybridization properties and antiviral activity of lipid-oligodeoxynucleotide conjugates. Nucleic Acids Res. Jul. 11, 1990;18(13):3777-83.

Shimizu et al., Transport of PEGylated liposomes from the splenic marginal zone to the follicle in the induction phase of the accelerated blood clearance phenomenon. Immunobiology. May 2013;218(5):725-32. doi: 10.1016/j.imbio.2012.08.274. Epub Aug. 23, 2012.

Shin et al., Recent Advances in RNA Therapeutics and RNA Delivery Systems Based on Nanoparticles. Adv. Therap., Nov. 2018;1(7):1800065. Review.

Shinu et al., Multi-antigenic Human Cytomegalovirus mRNA Vaccines That Elicit Potent Humoral and Cell-Mediated Immunity. Vaccine. Mar. 14, 2018;36(12):1689-1699. doi: 10.1016/j.vaccine. 2018.01.029. Epub Feb. 15, 2018.

Sieber et al., The Definition of Open Reading Frame Revisited. Trends Genet. Mar. 2018;34(3):167-170. doi: 10.1016/j.tig.2017. 12.009. Epub Jan. 30, 2018.

Sigma-Aldrich, "DMG-PEG 2000," retrieved from https://www.sigmaaldrich.com/catalog/product/avanti/880151p?lang=en&region=US on Jan. 4, 2021, 2 pages.

Slater, The purification of poly(a)-containing RNA by affinity chromatography. Methods Mol Biol. 1985;2:117-20. doi: 10.1385/0-89603-064-4:117.

Srivastava, Progressive Familial Intrahepatic Cholestasis. Journal of Clinical and Experimental Hepatology. Mar. 2014;4(1):25-36.

Stanlis et al., Single-strand DNA Aptamers as Probes for Protein Localization in Cells, Journal of Histochemistry & Cytochemistry, 2003, 51(6), 797-808, DOI: 10.1177/002215540305 10061.

Stiles, D.K., et al., Widespread suppression of huntingtin with convection-enhanced delivery of siRNA. Experimental Neurology. Jan. 2012; 233(1): 463-471.

Strobel, I. et al., Human dendritic cells transfected with either RNA or DNA encoding influenza matrix protein M1 differ in their ability to stimulate cytotoxic T lymphocytes. Gene Ther. Dec. 2000; 7(23): 2028-2035.

Sugiyama and Sadzuka, "Character of Liposomes as a Drug Carrier by Modifying Various Polyethyleneglycol-Lipids," Biological and Pharmaceutical Bulletin, 2013, 36(6), pp. 900-906.

Svinarchuk, F.P. et al., Inhibition of HIV proliferation in MT-4 cells by antisense oligonucleotide conjugated to lipophilic groups. Biochimie. 1993;75(1-2):49-54.

Tadin-Strapps, M., et al., "Development of lipoprotein(a) siRNAs for mechanism of action studies in non-human primate models of atherosclerosis", J Cardiovasc Transl Res, 2015, 8(1):44-53.

Taguchi et al., Effect of Repeated Injections of Adenosine Diphosphate-Encapsulated Liposomes Coated with a Fibrinogen-Chain Dodecapeptide Developed as a Synthetic Platelet Substitute on Accelerated Blood Clearance in a Healthy and an Anticancer Drug-Induced Thrombocytopenia Rat Model. J Pharm Sci. Sep. 2015;104(9):3084-91. doi: 10.1002/jps.24418. Epub Mar. 9, 2015.

Taguchi et al., Hemoglobin vesicles, polyethylene glycol (PEG)ylated liposomes developed as a red blood cell substitute, do not induce the accelerated blood clearance phenomenon in mice. Drug Metab Dispos. Nov. 2009;37(11):2197-203. doi: 10.1124/dmd.109. 028852. Epub Aug. 13, 2009.

Tanaka, M. et al., Inhibition of heart transplant injury and graft coronary artery disease after prolonged organ ischemia by selective protein kinase C regulators. J Thorac Cardiovasc Surg. May 2005;129(5):1160-7.

Tang, D.C. et al., Genetic immunization is a simple method for eliciting an immune response. Nature. Mar. 12, 1992;356(6365):152-4.

Tavernier, G. et al., "mRNA as gene therapeutic: How to control protein expression," Journal of Controlled Release, vol. 150 (3):238-247(2011).

Terada et al., Characterization of Lipid Nanoparticles Containing Ionizable Cationic Lipids Using Design-of-Experiments Approach. Langmuir. Jan. 26, 2021;37(3):1120-1128. doi: 10.1021/acs.langmuir. 0c03039. Epub Jan. 13, 2021.

Thess et al., Sequence-engineered mRNA Without Chemical Nucleoside Modifications Enables an Effective Protein Therapy in Large Animals. Mol Ther. Sep. 2015;23(9):1456-64. doi: 10.1038/mt.2015. 103. Epub Jun. 8, 2015.

Torrecilla et al., Lipid Nanoparticles as Carriers for RNAi Against Viral Infections: Current Status and Future Perspectives. Biomed Res Int. 2014;2014:161794. doi: 10.1155/2014/161794. Epub Aug. 12, 2014.

Tracy, M., "Progress in the Development of LNP Delivery for siRNA Advancing LNPs to the Clinic," International Liposome Research Days Meeting, Vancouver, Canada. Aug. 2010, pp. 1-52.

Treat, J. et al., in Liposomes in the Therapy of Infectious Disease and Cancer, Lopez-Berestein and Fidler (eds.), Liss, New York, 1989. 353-65.

Tripathy et al., Long-term expression of erythropoietin in the systemic circulation of mice after intramuscular injection of a plasmid DNA vector, Proc. Natl. Acad. Sci. USA. Oct. 1996; 93:10876-10880.

UNIPROT; NIH/NCBI, Accession No. P06475.1. Swain et al., Jan. 1, 2015. 3 pages.

UNIPROT; NIH/NCBI, Accession No. P06764.1. Hodgman et al., Jan. 7, 2015. 1 page.

Uzgun, S., et al., PEGylation improves nanoparticle formation and transfection efficiency of messenger RNA. Pharm Res. Sep. 2011; 28(9); 2223-2232.

Van Tendeloo V., et al. "Highly efficient gene delivery by mRNA electroporation in human hematopoietic cells: superiority to lipofection and passive pulsing of mRNA and to electroporation of plasmid cDNA for tumor antigen loading of dendritic cells," Blood, vol. 98(1):49-56 (2001).

Viklund et al., Enzymatic synthesis of surfactants based on polyethylene glycol and stearic or 12-hydroxystearic acid. Journal of Molecular Catalysis B Enzymatic 27(2):51-53, Feb. 2004.

Wan et al., Lipid nanoparticle delivery systems for siRNA-based therapeutics. Drug Deliv Transl Res. Feb. 2014;4(1):74-83. doi: 10.1007/s13346-013-0161-z.

Wang et al., Chapter 3: Lipid Nanoparticles for the Delivery of Nucleic Acids. Book: Nanoparticulate Drug Delivery Systems: Strategies, Technologies, and Applications. 2013. 29 pages.

Wang et al., "Delivery of oligonucleotides with lipid nanoparticles," Advanced Drug Delivery Reviews, 2015, 87: 65-80.

Wang et al., "Encapsulating Protein into Preformed Liposomes by Ethanol-Destabilized Method," Artificial Cells, Blood Substitutes, and Technology, 2003, 31(3):303-312.

Wang et al., Enhanced bioavailability and efficiency of curcumin for the treatment of asthma by its formulation in solid lipid nanoparticles. Int J Nanomedicine. 2012;7:3667-77. doi: 10.2147/IJN.S30428. Epub Jul. 17, 2012.

Wang et al., Purification of the messenger ribonucleic acid for the lipoprotein of the *Escherichia coli* outer membrane. Biochemistry. Oct. 2, 1979;18(20):4270-7.

Wang et al., Structural Definition of a Neutralization-sensitive Epitope on the MERS-CoV S1-NTD. Cell Rep. Sep. 24, 2019;28(13):3395-3405.e6. doi: 10.1016/j.celrep.2019.08.052. Author's Manuscript, 29 pages.

Wang Y. et al., "Systemic delivery of modified mRNA encoding herpes simplex virus 1 thymidine kinase for targeted cancer gene therapy", Molecular Therapy, vol. 21(2):358-367 (2012).

Weaver., Molecular Biology. 1999. WCB/McGraw-Hill. Chapter 15:456. 5 pages.

Weilhammer et al., The use of nanolipoprotein particles to enhance the immunostimulatory properties of innate immune agonists against lethal influenza challenge. Biomaterials. Dec. 2013;34(38):10305-18. doi: 10.1016/j.biomaterials.2013.09.038. Epub Sep. 27, 2013.

Weissman et al., HPLC purification of in vitro transcribed long RNA. Methods Mol Biol. 2013;969:43-54. doi: 10.1007/978-1-62703-260-5 3.

WHO Drug Information, International Nonproprietary Names for Pharmaceutical Substances (INN), 1993, vol. 7, No. 4, pp. 1-16.

(56) References Cited

OTHER PUBLICATIONS

Wilson et al., "Real Time Measurement of PEG Shedding from Lipid Nanoparticles in Serum via Spectroscopy," Molecular Pharmaceutics, 2015 12(2):386-392.
Woodward et al., Varicella Virus Vaccine Live: A 22-Year Review of Postmarketing Safety Data. Open Forum Infect Dis. Aug. 1, 2019;6(8):ofz295.
Wrapp et al. "Cryo-EM structure of the 2019-nCoV spike in the prefusion conformation," Science (Mar. 2020) 367:1260-1263.
Wussow et al., Human cytomegalovirus vaccine based on the envelope gH/gL pentamer complex. PLoS Pathog. Nov. 20, 2014;10(11):e1004524, 23 pages. doi: 10.1371/journal.ppat.1004524. eCollection Nov. 2014.
Xu.H, et al., "Enhanced pH-Responsiveness, Cellular Trafficking, Cytotoxicity and Long-circulation of PEGylated Liposomes with Post-insertion Technique Using Gemcitabine as a Model Drug." Pharmaceutical Research, vol. 32, 2015, pp. 2428-2438. (Year: 2015).
Yadav et al., Predicting Immunogenic Tumour Mutations by Combining Mass Spectrometry and Exome Sequencing. Nature. Nov. 27, 2014;515(7528):572-6. doi: 10.1038/nature14001.
Yamamoto et al., Current prospects for mRNA gene delivery, European Journal of Pharmaceutics and Biopharmaceutics 71 (2009) 484-489.
Yang, Xiaoming, et al., Effect of CD44 Binding Peptide Conjugated to an Engineered Inert Matrix on Maintenance of Breast Cancer Stem Cells and Tumorsphere Formation, PLOS One, 2013, vol. 8, Issue 3, pp. 1-15.
Yu, Alice et al, Anti-GD2 Antibody with GM-CSF, Interleukin-2, and Isotretinoin for Neuroblastoma, The New England Journal of Medicine, 2010, vol. 363; No. 14, pp. 1324-1334.
Yuan et al., Cryo-EM structures of MERS-Co V and SARS-Co V spike glycoproteins reveal the dynamic receptor binding domains. Nat Commun. Apr. 10, 2017;8:15092, 9 pages. doi: 10.1038/ncomms15092.
Yuan et al., Human Jagged 1 mutants cause liver defect in Alagille syndrome by overexpression of hepatocyte growth factor. J Mol Biol. Feb. 24, 2006;356(3):559-68. Epub Dec. 20, 2005.
Zhang et al., "Assessing the Heterogeneity Level in Lipid Nanoparticles for siRNA Delivery: Size-Based Separation, Compositional heterogeneity, and Impact of Bioperformance", Molecular Pharmaceutics, vol. 10, 2013, pp. 397-405.
Zhang et al., Personalized cancer vaccines: Targeting the cancer mutanome. Vaccine. Feb. 15, 2017;35(7):1094-1100. doi: 10.1016/j.vaccine.2016.05.073. Epub Jul. 20, 2016. Author's Manuscript, 16 pages.
Zhao et al., A frustrating problem: accelerated blood clearance of PEGylated solid lipid nanoparticles following subcutaneous injection in rats. Eur J Pharm Biopharm. Aug. 2012;81(3):506-13. doi: 10.1016/j.ejpb.2012.04.023. Epub May 11, 2012.
Zhao, Y., et al., "Lipid Nanoparticles for Gene Delivery," Advances in genetics, 2014, vol. 88, pp. 13-36.
Zhigaltsev, I.V., et al., Bottom-Up design and synthesis of limit size lipid nanoparticle systems with aqueous and triglyceride cores using millisecond microfluidic mixing. Langmuir. Feb. 21, 2012; 28(7): 3633-3640.
Zimmermann, E. et al., Electrolyte- and pH-stabilities of aqueous solid lipid nanoparticle (SLN) dispersions in artificial gastrointestinal media. Eur J Pharm Biopharm. Sep. 2001;52(2):203-10.
Zohra, F.T., et al., Drastic effect of nanoapatite particles on liposome-mediated mRNA delivery to mammalian cells. Analytical Biochem. Oct. 2005; 345(1): 164-166.
Zohra, F.T., et al., Effective delivery with enhanced translational activity synergistically accelerates mRNA-based transfection. Biochem Biophys Res Comm. Jun. 2007; 358(1 ): 373-378.
Zou et al., Lipid-mediated delivery of RNA is more efficient than delivery of DNA in non-dividing cells. Int J Pharm. Apr. 15, 2010;389(1-2):232-43. doi: 10.1016/j.ijpharm.2010.01.019. Epub Jan. 18, 2010. Author's Manuscript, 26 pages.
Zou, Li-li et al., Cell-Penetrating Peptide-Mediated Therapeutic Molecule Delivery Into the Central Nervous System, Current Neuropharmacology, 2013, vol. 11, No. 2, pp. 197-208.
Q=V/RT;https://www.cs.montana.edu/webworks/projects/stevesbook/contents/chapters/chapter008/section002/blue/page003.html#:-:text=1.1)%20Flow%20Rate%20Q%20%3D%20V,time%20R%20is%2010%20minutes.; site accesed Jun. 2024 (Year: 2016), 3 pages.
BroadPharm, SM-102 pKa, retrieved from https://broadpharm.com/product/bp-25499, 2022, 6 pages.

* cited by examiner

| Formulation | Size (nm) | PDI | %EE | [mRNA] ug/mL |
|---|---|---|---|---|
| PEG-1 1.5% | 94.3 | 0.16 | 96 | 59 |
| PEG-1 2.0% | 83.2 | 0.19 | 96 | 55 |
| PEG-1 2.5% | 75.3 | 0.18 | 97 | 59 |
| PEG-1 3.0% | 72.7 | 0.19 | 95 | 55 |
| PEG-1 3.5% | 69 | 0.21 | 96 | 61 |
| PEG-1 4% | 65.4 | 0.18 | 95 | 58 |
| 5% | 62.7 | 0.22 | 95 | 58 |

FIG. 11A

| | %EE | | | |
|---|---|---|---|---|
| | 4C (Day 0) | 4C (Day 5) | 1 F-TH | 3 F-TH |
| 1.5% PEG-1 (Citrate)/ Tris/Suc/60Salt/EtOH/D | 71.8 | 81 | 81 | 55 |
| 1.5% PEG-1 (Acetate)/ Tris/Suc/60Salt/EtOH/D | 94.2 | 91 | 89 | 87 |
| 2% PEG-1 (Citrate)/ Tris/Suc/60Salt/EtOH/D | 91.9 | 89 | 88 | 88 |
| 2.5% PEG-1 (Citrate)/ Tris/Suc/60Salt/EtOH/D | 84.2 | 81 | 82 | 83 |
| 3% PEG-1 (Citrate)/ Tris/Suc/60Salt/EtOH/D | 80.5 | 80 | 80 | 77 |
| 3.5% PEG-1 (Citrate)/ Tris/Suc/60Salt/EtOH/D | 66.6 | 69 | 70 | 68 |
| 4.8% PEG-1 (Citrate)/ Tris/Suc/60Salt/EtOH/D | 40.5 | 52 | 54 | 51 |
| PBS | | | | |

FIG. 11B

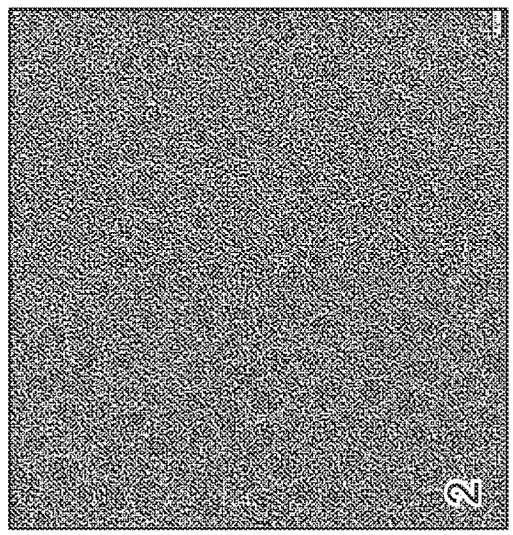
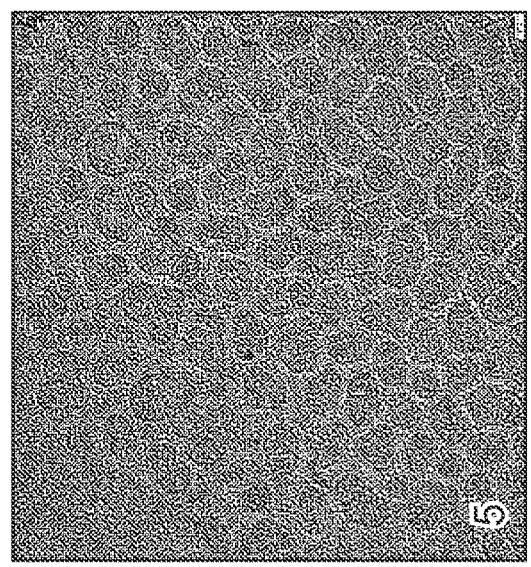
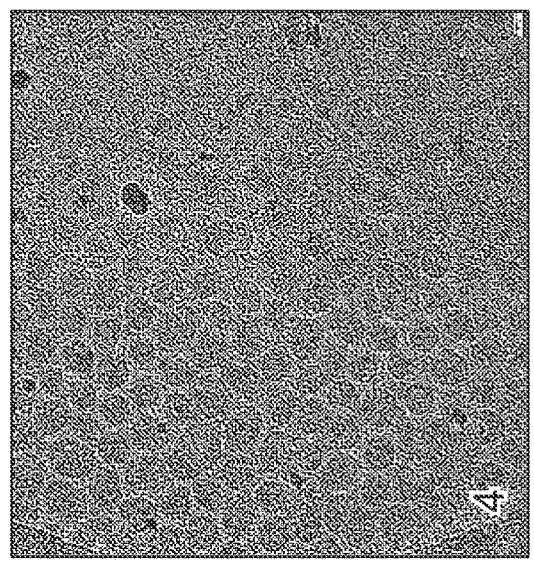
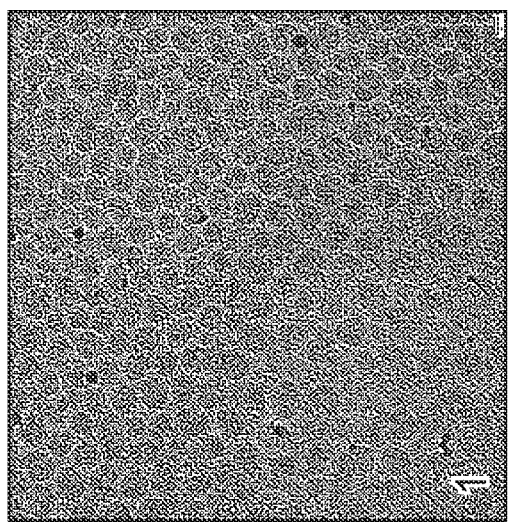
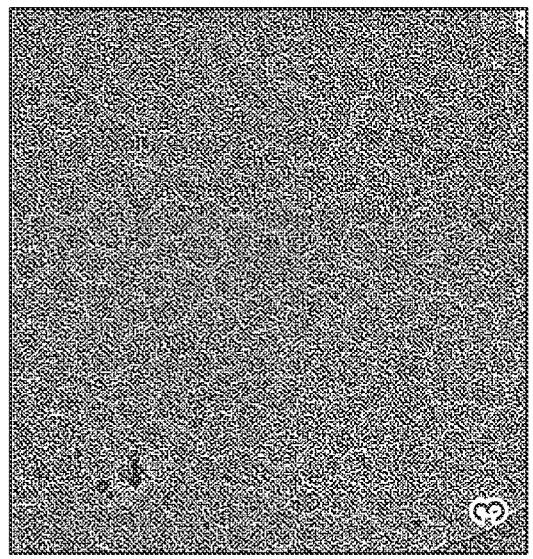
FIG. 20

| Process | Ionizable Lipid: DSPC:Chol:PEG-1 | Final Buffer Composition | IEX mRNA (mg/mL) | Diameter (nm) | PDI (#) | EE % | Lipid:mRNA (g/g) | PEG-1 (mol%) | Ionizable Lipid (mol%) | Chol (mol%) | DSPC (mol%) |
|---|---|---|---|---|---|---|---|---|---|---|---|
| Acetate | 49.8 : 9.8 : 38.3 : 2.0 | 20 mM Tris, 8% Sucrose, 60 mM NaCl, 1.3% EtOH, 1 mM DTPA | 0.77 | 77.4 | 0.195 | 91.8 | 18.8 | 1.8% | 50.4% | 38.7% | 9.1% |
| Acetate - 2.0 mol % Post-Insertion | 50.5 : 10.5 : 39.0 : 0.0 | 20 mM Tris, 8% Sucrose, 60 mM NaCl, 1.3% EtOH, 1 mM DTPA | 0.76 | 104.8 | 0.096 | 96.4 | 19.4 | 1.4% | 49.8% | 39.1% | 9.7% |
| Acetate - 1.5 mol % Post-Insertion | 50.3 : 10.3 : 38.3 : 0.5 | 20 mM Tris, 8% Sucrose, 60 mM NaCl, 1.3% EtOH, 1 mM DTPA | 0.77 | 84.1 | 0.211 | 94.1 | 19.2 | 1.7% | 49.5% | 39.1% | 9.7% |
| Acetate - 1.0 mol % Post-Insertion | 50.2 : 10.2 : 38.7 : 1.0 | 20 mM Tris, 8% Sucrose, 60 mM NaCl, 1.3% EtOH, 1 mM DTPA | 0.77 | 89.9 | 0.229 | 90.4 | 18.2 | 1.7% | 50.1% | 38.9% | 9.3% |
| Acetate - 0.5 mol % Post-Insertion | 50.0 : 10.0 : 38.5 : 1.5 | 20 mM Tris, 8% Sucrose, 60 mM NaCl, 1.3% EtOH, 1 mM DTPA | 0.77 | 84.9 | 0.190 | 90.9 | 17.6 | 1.9% | 50.1% | 38.6% | 9.5% |
| Acetate - 2.0 mol % Final Spike | 50.5 : 10.5 : 39.0 : 0.0 | 20 mM Tris, 8% Sucrose, 60 mM NaCl, 1.3% EtOH, 1 mM DTPA, 2.0 mol% PEG-1 | 0.76 | 155.0 | 0.106 | 86.2 | 17.8 | 2.1% | 49.9% | 38.5% | 9.5% |
| Acetate - 1.5 mol % Final Spike | 50.3 : 10.3 : 38.3 : 0.5 | 20 mM Tris, 8% Sucrose, 60 mM NaCl, 1.3% EtOH, 1 mM DTPA, 1.5 mol% PEG-1 | 0.74 | 98.1 | 0.171 | 91.3 | 18.2 | 2.1% | 49.8% | 38.6% | 9.5% |
| Acetate - 1.0 mol % Final Spike | 50.2 : 10.2 : 38.7 : 1.0 | 20 mM Tris, 8% Sucrose, 60 mM NaCl, 1.3% EtOH, 1 mM DTPA, 1.0 mol% PEG-1 | 0.75 | 88.6 | 0.190 | 91.6 | 18.2 | 2.0% | 50.1% | 38.6% | 9.3% |
| Acetate - 0.5 mol % Final Spike | 50.0 : 10.0 : 38.5 : 1.5 | 20 mM Tris, 8% Sucrose, 60 mM NaCl, 1.3% EtOH, 1 mM DTPA, 1.5 mol% PEG-1 | 0.78 | 89.8 | 0.213 | 88.4 | 17.3 | 2.0% | 50.2% | 38.5% | 9.3% |

FIG. 28

| Batch No. | Process | lipid:DSPC:Chol:PEG1 | Final Buffer Composition | IEX mRNA (mg/mL) | Diameter (nm) | PDI (#) | EE (%) | Lipid:mRNA (g/g) | PEG-1 (mol %) | Ionizable Lipid (mol %) | Chol (mol %) | DSPC (mol %) |
|---|---|---|---|---|---|---|---|---|---|---|---|---|
| 1 | Acetate | 49.8 : 9.8 : 38.3 : 2.0 | 20mM Tris, 8% Sucrose | 81.4 | 0.196 | 91.6 | 18.0 | 81.4 | 1.9% | 49.8% | 38.8% | 9.7% |
| 3 | Acetate - 1.75 mol % Post Add. | 50.5 : 10.5 : 39.0 : 0.25 | 20mM Tris, 8% Sucrose | 119.5 | 0.191 | 85.8 | 17.2 | 119.5 | 1.9% | 49.2% | 38.6% | 10.5% |
| 4 | Acetate - 1.5 mol % Post Add. | 50.3 : 10.3 : 38.3 : 0.5 | 20mM Tris, 8% Sucrose | 117.9 | 0.220 | 88.3 | 17.8 | 117.9 | 1.9% | 49.2% | 38.8% | 10.1% |
| 5 | Acetate - 1.0 mol % Post Add. | 50.2 : 10.2 : 38.7 : 1.0 | 20mM Tris, 8% Sucrose | 97.8 | 0.203 | 91.5 | 18.1 | 97.8 | 1.9% | 49.6% | 39.0% | 9.6% |
| 6 | Acetate - 0.5 mol % Post Add. | 50.0 : 10.0 : 38.5 : 1.5 | 20mM Tris, 8% Sucrose | 91.2 | 0.195 | 90.7 | 17.7 | 91.2 | 1.9% | 49.8% | 38.5% | 9.9% |

FIG. 40

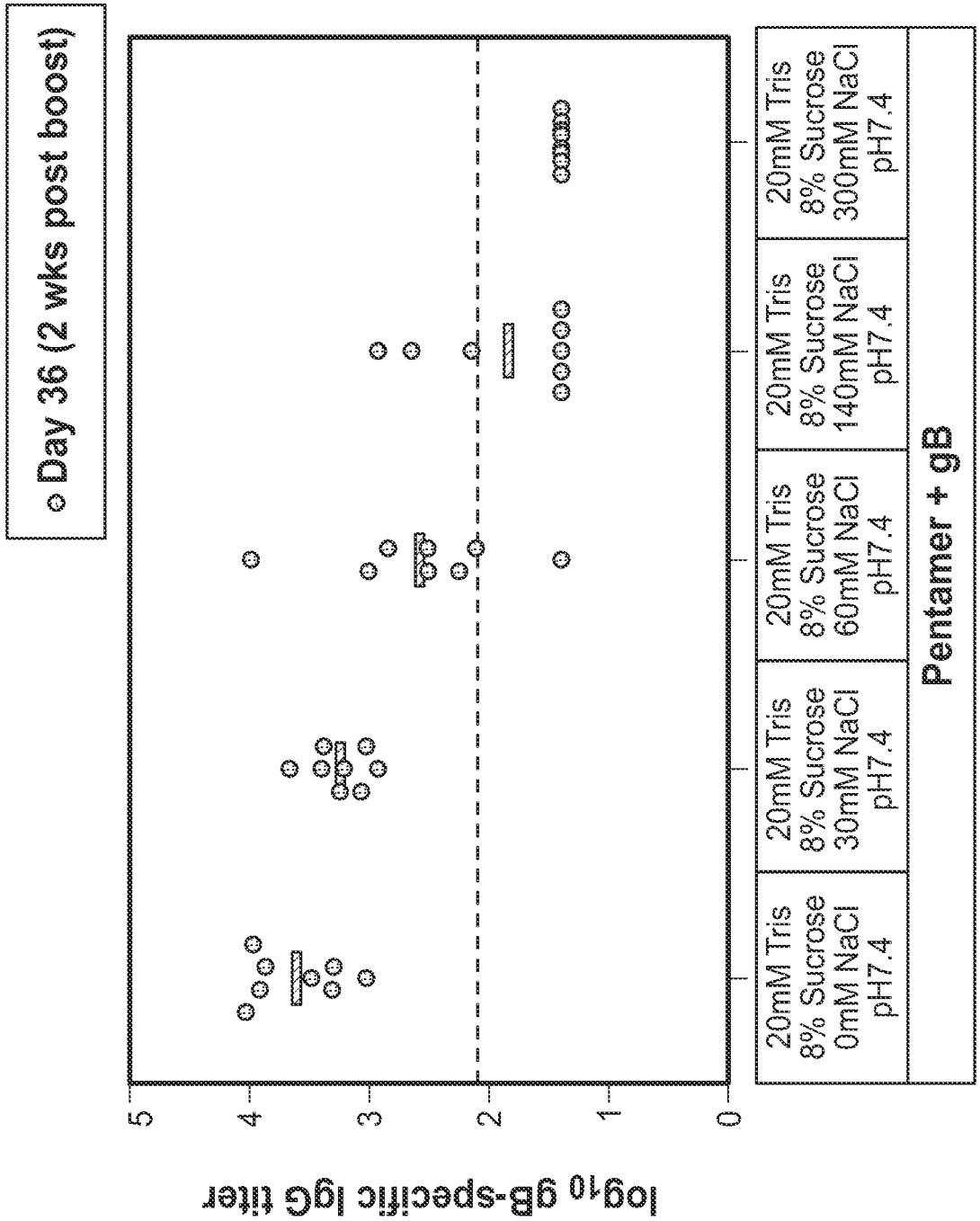

METHODS OF MAKING LIPID NANOPARTICLES

RELATED APPLICATION

This application is a divisional application of U.S. application Ser. No. 16/643,037, filed Feb. 28, 2023, now U.S. Pat. No. 11,744,801, which is a U.S. National Phase application, filed under 35 U.S.C. § 371, of International Application No. PCT/US2018/049251, filed Aug. 31, 2018, which claims priority to, and the benefit of, U.S. provisional application Nos. 62/590,193, filed Nov. 22, 2017; 62/553,088, filed Aug. 31, 2017; and 62/553,085, filed Aug. 31, 2017, the entire contents of each of which are incorporated herein by reference in their entireties.

INCORPORATION-BY-REFERENCE OF SEQUENCE LISTING

The Sequence Listing XML associated with this application is provided electronically in XML file format and is hereby incorporated by reference into the specification. The name of the XML file containing the Sequence Listing XML is "MRNA_039_C01US_SeqList_ST26.xml". The XML file is 3,611 bytes in size, created on Oct. 3, 2024, and is being submitted electronically via USPTO Patent Center.

FIELD OF DISCLOSURE

The present disclosure provides novel methods of producing nucleic acid lipid nanoparticle (LNP) compositions, the produced compositions thereof, and methods involving the nucleic acid lipid nanoparticles to deliver one or more therapeutics and/or prophylactics, such as a nucleic acid, to and/or produce polypeptides in mammalian cells or organs.

BACKGROUND

The effective targeted delivery of biologically active substances such as small molecule drugs, proteins, and nucleic acids represents a continuing medical challenge. In particular, the delivery of nucleic acids to cells is made difficult by the relative instability and low cell permeability of such species. Thus, there exists a need to develop methods and compositions to facilitate the delivery of therapeutics and prophylactics such as nucleic acids to cells.

Lipid-containing nanoparticles or lipid nanoparticles, liposomes, and lipoplexes have proven effective as transport vehicles into cells and/or intracellular compartments for biologically active substances such as small molecule drugs, proteins, and nucleic acids. Though a variety of such lipid-containing nanoparticles have been demonstrated, improvements in safety, efficacy, and specificity are still lacking.

SUMMARY

In some aspects, the present disclosure provides a method of producing a nucleic acid lipid nanoparticle composition, the method comprising: i) mixing a lipid solution comprising an ionizable lipid with a solution comprising a nucleic acid thereby forming a precursor nucleic acid lipid nanoparticle, ii) adding a lipid nanoparticle modifier comprising a modifying agent to the precursor nucleic acid lipid nanoparticle thereby forming a modified nucleic acid lipid nanoparticle, and iii) processing the precursor nucleic acid lipid nanoparticle, the modified nucleic acid lipid nanoparticle, or both thereby forming the nucleic acid lipid nanoparticle composition.

In some embodiments, the precursor nucleic acid lipid nanoparticle is not processed prior to the adding the lipid nanoparticle modifier.

In some embodiments, the precursor nucleic acid lipid nanoparticle is processed prior to the adding the lipid nanoparticle modifier.

In some embodiments, the lipid solution further comprises a first PEG lipid.

In some embodiments, the precursor nucleic acid lipid nanoparticle further comprises a first PEG lipid.

In some embodiments, the lipid solution does not comprise any PEG lipid.

In some embodiments, the precursor nucleic acid lipid nanoparticle does not comprises any PEG lipid.

In some embodiments, the precursor nucleic acid lipid nanoparticle further comprises a phospholipid.

In some embodiments, the precursor nucleic acid lipid nanoparticle further comprises a structural lipid.

In some embodiments, the modifying agent is at least one agent selected from the group consisting of a second PEG lipid and a surfactant.

In some embodiments, the modifying agent is a second PEG lipid.

In some embodiments, the modifying agent is a surfactant.

In some aspects, the present disclosure provides a precursor nucleic acid lipid nanoparticle being prepared by a method disclosed herein.

In some aspects, the present disclosure provides a nucleic acid lipid nanoparticle composition being prepared by a method disclosed herein.

In some aspects, the present disclosure provides a method of characterizing a nucleic acid lipid nanoparticle composition, comprising generating a quantitative value of an amount of the nucleic acid encapsulated in the nucleic acid lipid nanoparticle composition using an ion-exchange (IEX) chromatography assay.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the disclosure will be apparent from the following detailed description and claims.

BRIEF DESCRIPTION OF THE DRAWINGS

FIG. 1A shows the encapsulation efficiency of LNPs prepared by process without post insertion (with 0-3 mol % PEG lipid added during the T-Mix stage). FIG. 1B shows the encapsulation efficiency of LNPs (with a total amount of 3 mol % PEG lipid) prepared by process with post insertion (with 0-3 mol % PEG lipid added during the T-Mix stage and the remaining PED lipid added during post insertion).

FIG. 2A shows particle size change of LNP formulations (with a total amount of 3 mol % PEG lipid; with 0-3 mol % PEG lipid added during the T-Mix stage and the remaining PED lipid added during post insertion) over tangential flow filtration (TFF). FIG. 2B shows particle size of LNP formulations (with a total amount of 0.25-4 mol % PEG lipid; with 0.25 mol % PEG lipid added during the T-Mix stage and the remaining PED lipid added during post insertion) before and upon 1-5 freeze/thaw cycles. FIG. 2C shows particle size of LNP formulations (with a total amount of 2 mol % PEG lipid; prepared by process with and without post insertion or heating) before and upon 1-5 freeze/thaw cycles.

FIG. 3A shows particle size of LNP formulations (with 0-1.5 mol % PEG-1; and with 0-0.1 w/v % Brij S20 surfactant added during post addition) upon 3 freeze/thaw cycles. FIG. 3B shows particle size of LNP formulations (with 0-1.5 mol % PEG-1; and with 0-0.1 w/v % Brij O20 surfactant added during post addition) upon 3 freeze/thaw cycles.

FIG. 4A shows mean expression of LNP formulations (with varied amount of Brij O20 surfactant added during post addition) over 6 hours. FIG. 4B shows mean expression of LNP formulations (with varied amount of Brij O20 surfactant added during post addition) over 24 hours.

FIG. 6A shows the mRNA encapsulation efficiency of LNP formulations with 0-2.5 mol % PEG-2 or PEG-1. FIG. 6B shows the particle size of LNP formulations with 0-2.5 mol % PEG-2 or PEG-1.

FIG. 7A shows the expression of eGFP mRNA LNP formulations with varied amount of PEG-2. FIG. 7B shows the expression of ffLuc mRNA LNP formulations with varied amount of PEG-2 or PEG-1. FIG. 7C shows a comparison of the data shown in FIGS. 7A-7B.

FIGS. 11A-11B are tables showing the mRNA encapsulation of LNP formulations containing ionizable lipid with varied amount of PEG-1.

FIG. 12A summarizes the pentamer specific IgG titer in a viral complex. The figure shows that less PEG in the LNP produces a more immunogenic LNP. FIG. 12B illustrates the dependence of the size of a LNP containing ionizable lipid as a function of storage time on PEG.

FIG. 13A is a histogram of in vitro protein expression for lipid nanoparticles of batches 1-5. FIG. 13B is a histogram of geo mean for lipid nanoparticles of batches 1-5.

FIG. 16 is a histogram showing mRNA encapsulation percent as determined by anion exchange chromatography. FIG. 17 is a histogram showing the average particle size for subvisible particles (>0.8 μm).

FIG. 20 is a series of cryo-electron microscopy images of nanoparticles made by the processes of the disclosure. The numbers 1-5 refer to nanoparticles of batches 1-5 wherein batch 1 is made using the standard process, batches 2 and 4 are made by the post-insertion process, and batches 3 and 5 are made using the post addition process.

FIG. 28 is a table showing varied conditions in preparing LNP formulations.

FIG. 31A shows the particle size of LNP formulations prepared by process with post insertion before and upon 1-10 freeze/thaw cycles. FIG. 31B shows the particle size of LNP formulations prepared by process with post addition before and upon 1-10 freeze/thaw cycles.

FIG. 40 is a table summarizing batches of nanoparticle compositions made with PEG-1 in the post addition process described herein.

FIG. 49A depicts varying encapsulation efficiency based on mRNA formulation buffer conditions. FIG. 49B depicts varying encapsulation efficiency based on mRNA formulation salt concentrations.

FIG. 52A-52F are a set of graphs showing the in vivo immunogenicity (serum Ig titers) for the lipid nanoparticles formed via the processes of the disclosure. FIG. 52A shows the serum IgG titers on day 36 (assayed on pentamer coated plates). FIG. 52B shows the serum IgG titers on day 36 (assayed on gB coated plates). FIG. 52C shows the serum IgG titers on day 21 (assayed on pentamer coated plates). FIG. 52D shows the serum IgG titers on day 21 (assayed on gB coated plates). FIG. 52E shows a comparison of the serum IgG titers on day 21 and day 36 (assayed on pentamer coated plates). FIG. 52F shoes a comparison of the serum IgG titers on day 21 and day 36 (assayed on gB coated plates).

DETAILED DESCRIPTION

Figure 1A:
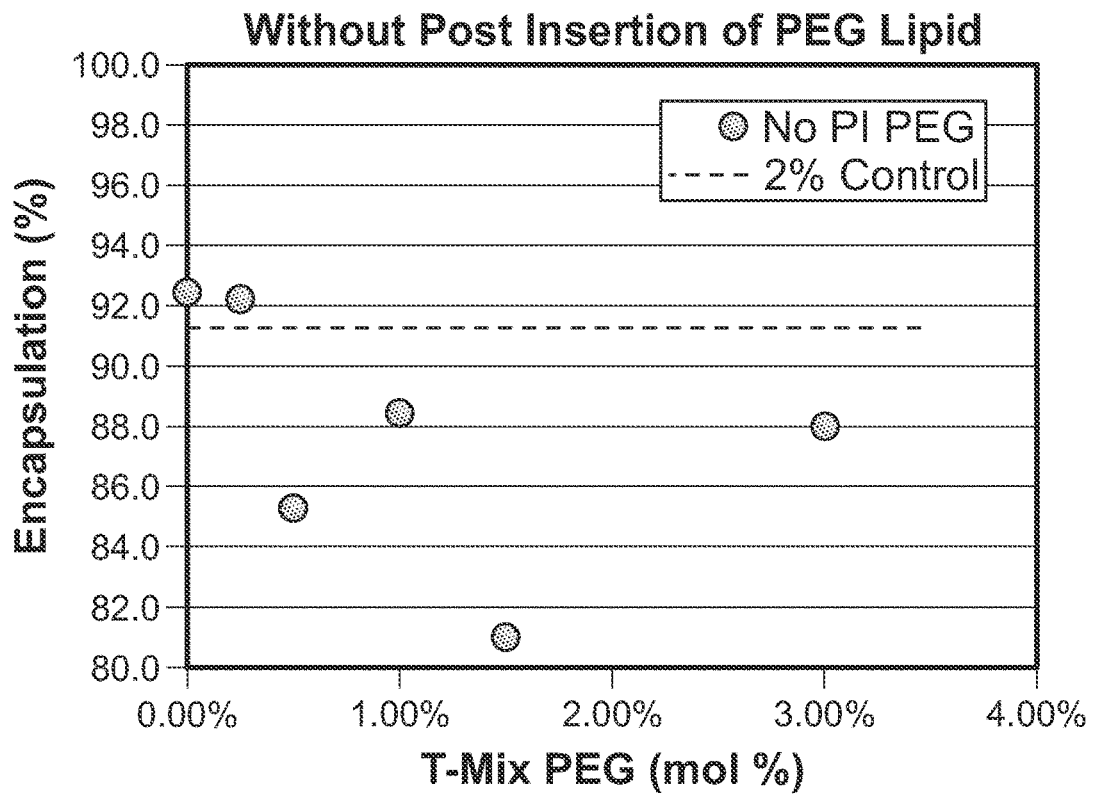
FIGS. 1A-1B are diagrams showing the effect of post insertion on mRNA encapsulation of LNPs.
Figure 1B:
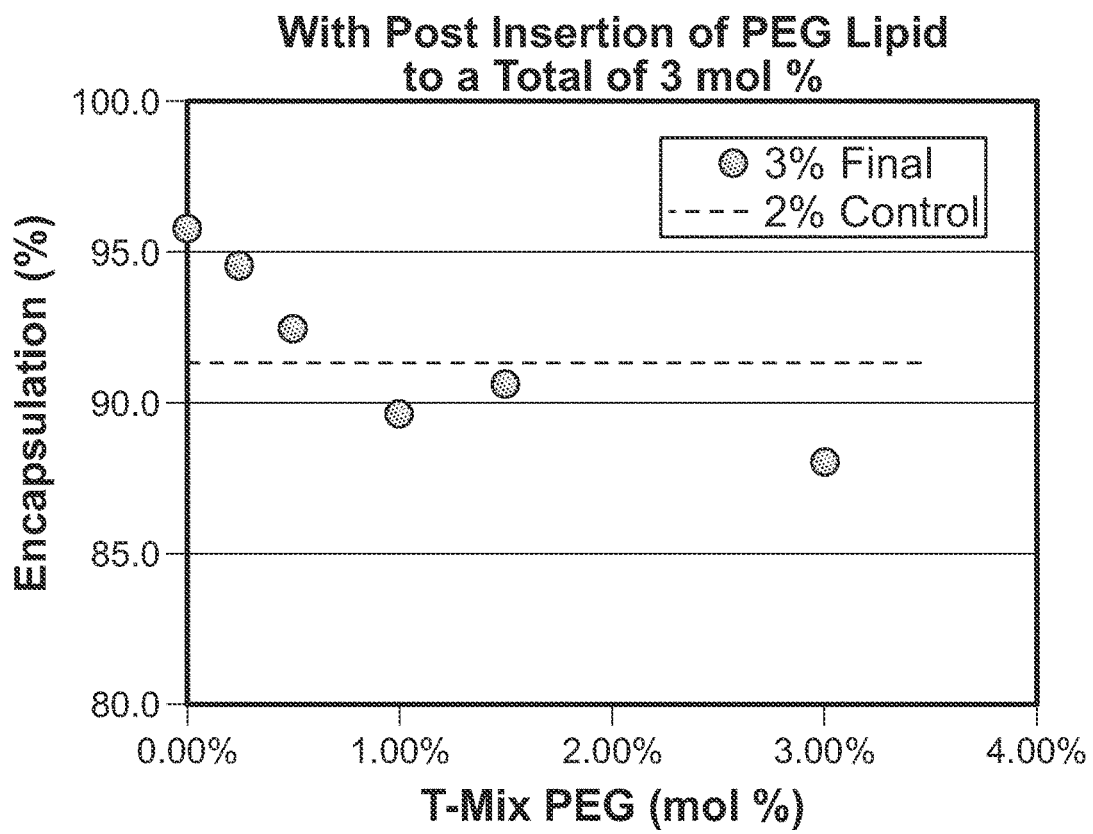
Figure 2A:
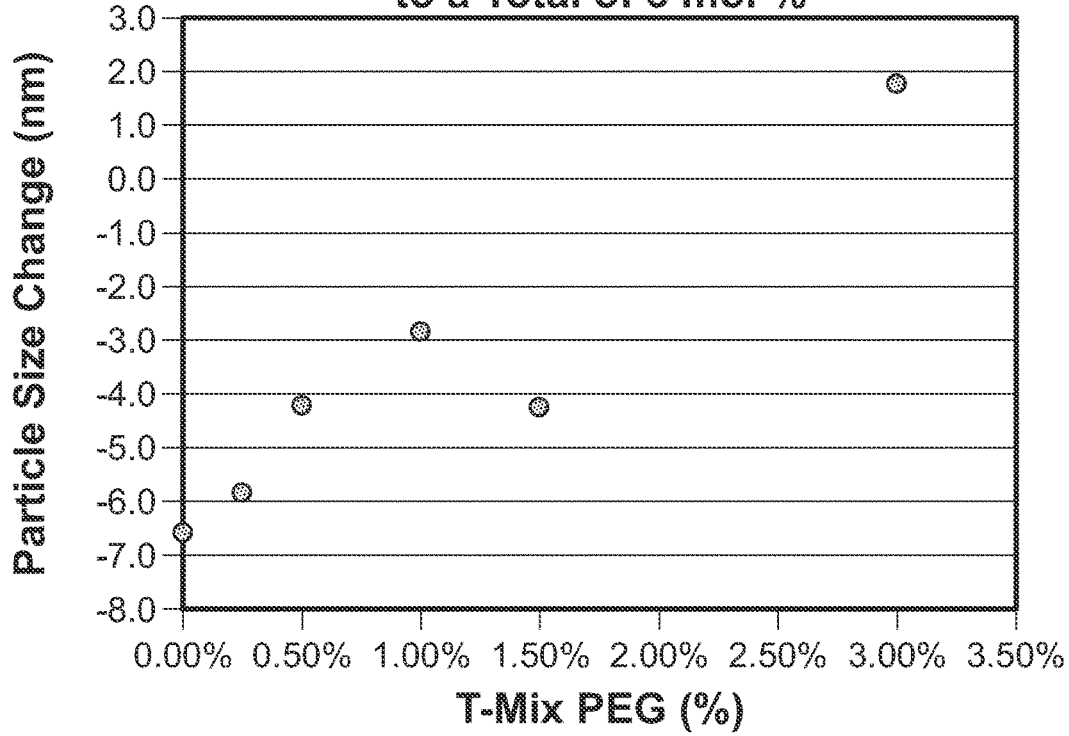
FIGS. 2A-2C are diagrams showing the effect of post insertion on the stability of LNP formulations.
Figure 2B:
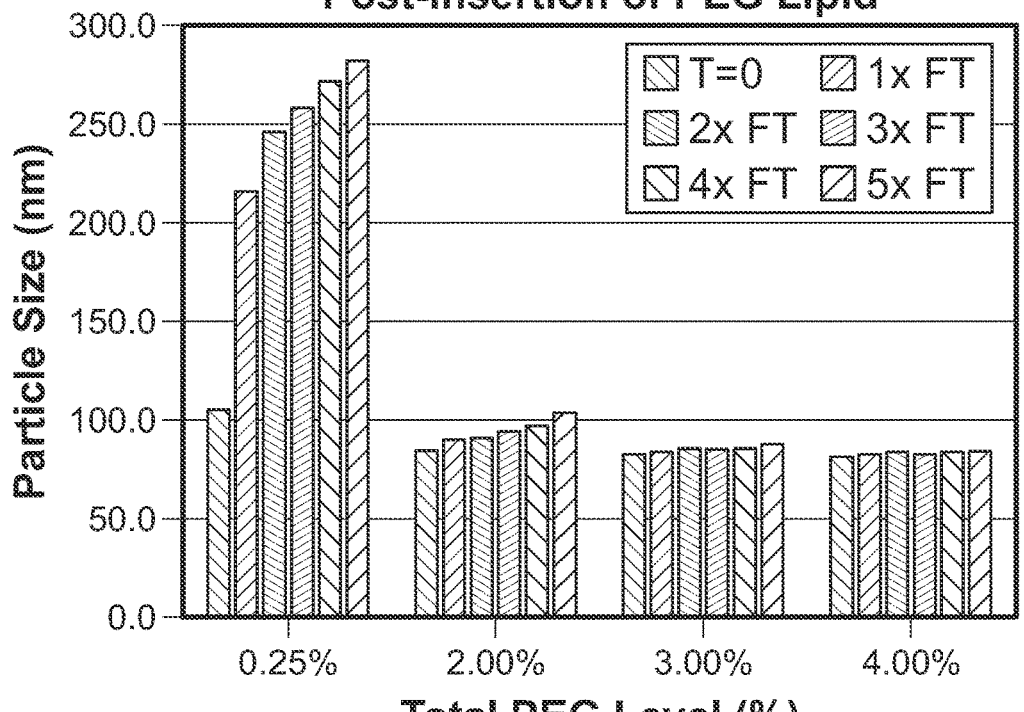
Figure 2C:
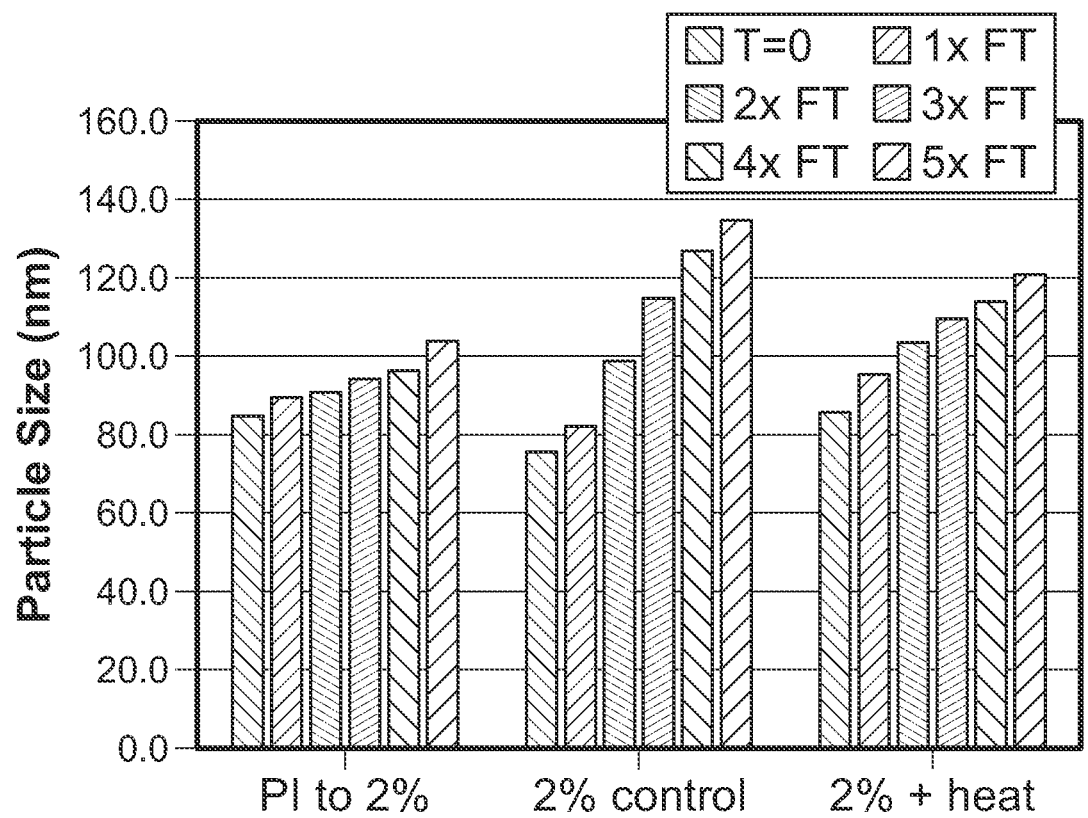
Figure 3A:
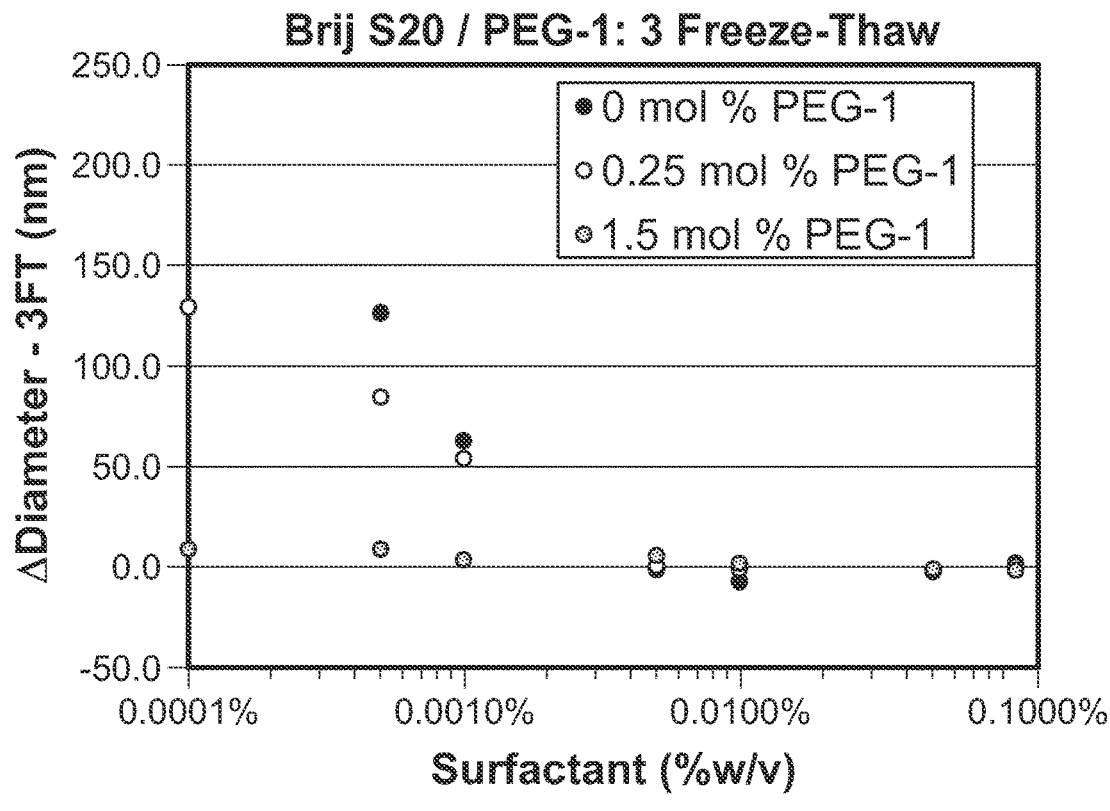
FIGS. 3A-3B are diagrams showing the effect of post addition with surfactant on the stability of LNP formulations.
Figure 3B:
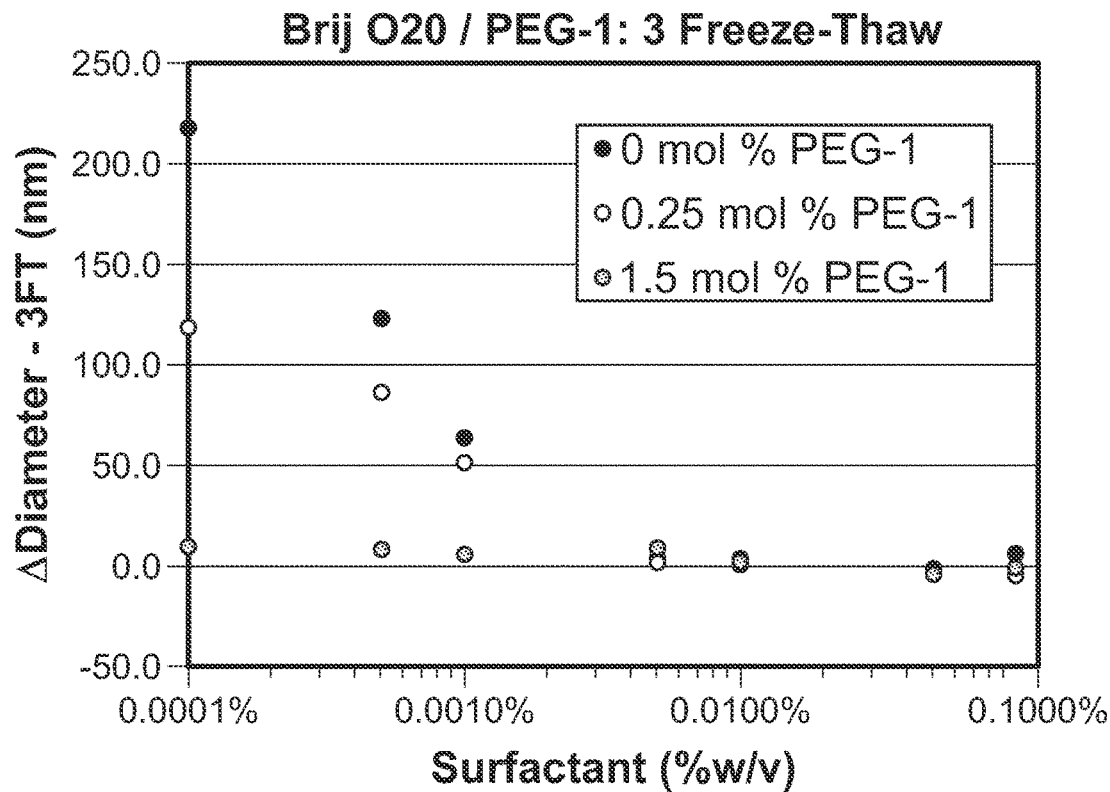
Figure 4A:
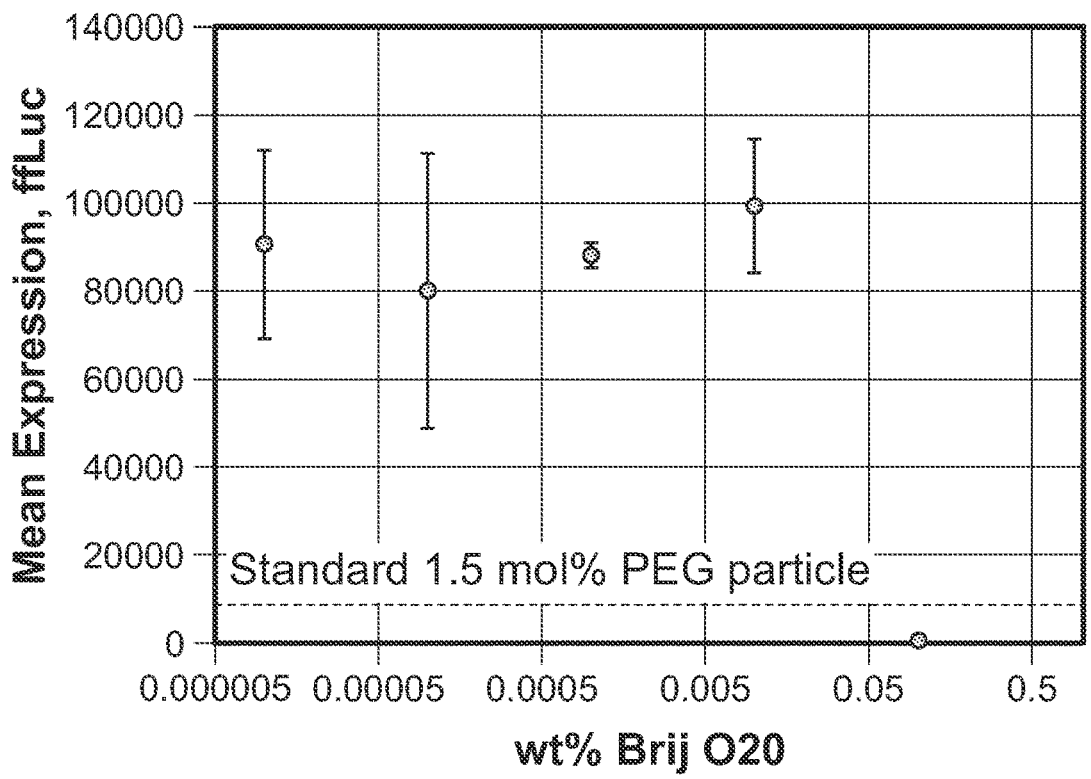
FIGS. 4A-4B are diagrams showing the effect of post addition with surfactant on the expression of LNP formulations.
Figure 4B:
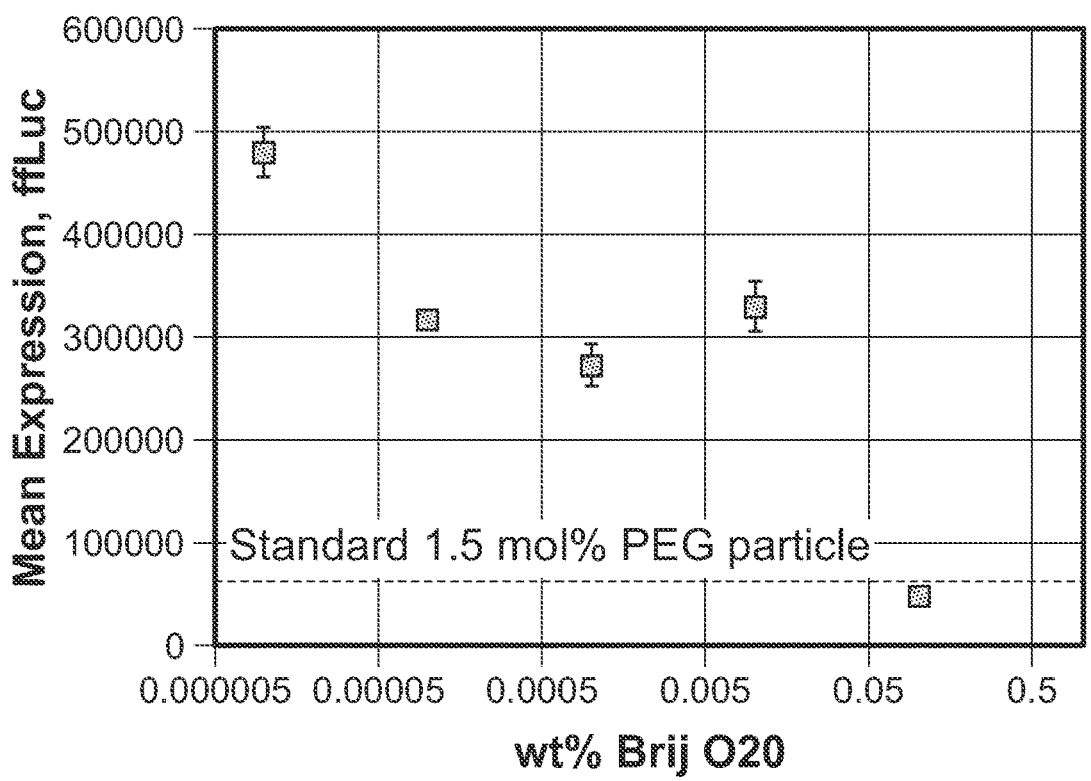
Figure 5A:
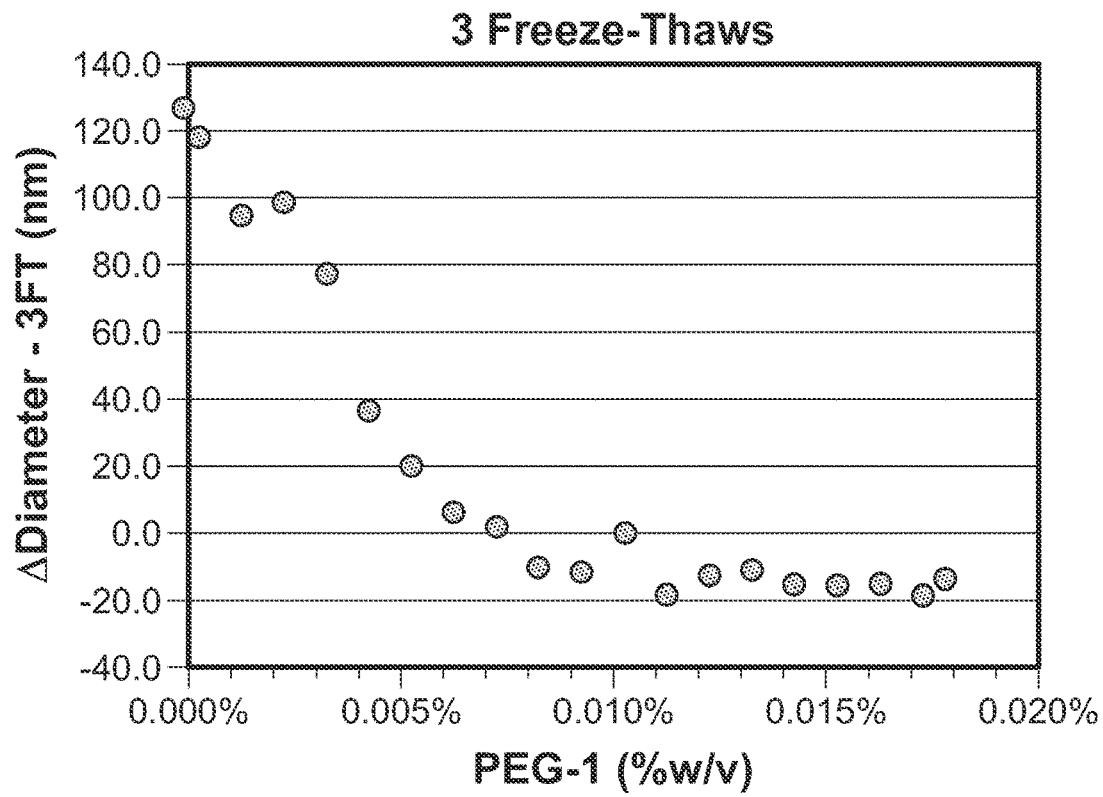
FIGS. 5A-5B are diagrams showing particle size of LNP formulations (with varied amount of PEG-1, presented in w/v % and mol %) upon 3 freeze/thaw cycles.
Figure 5B:
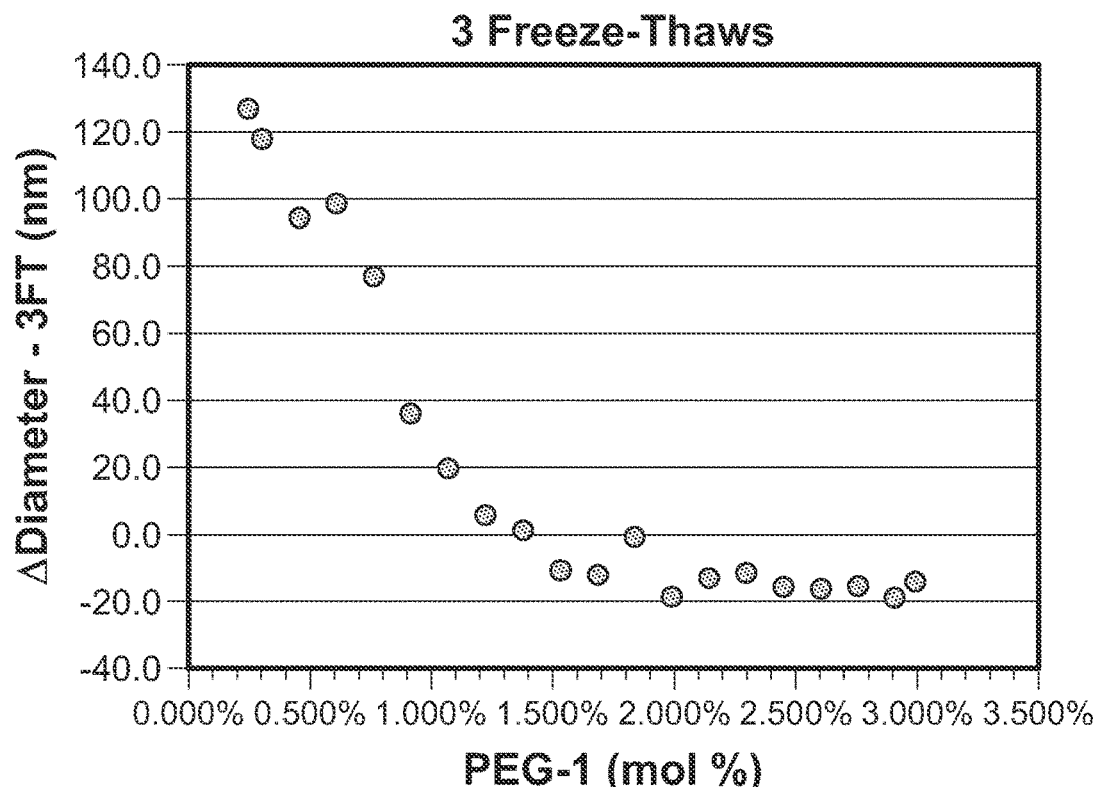
Figure 6A:
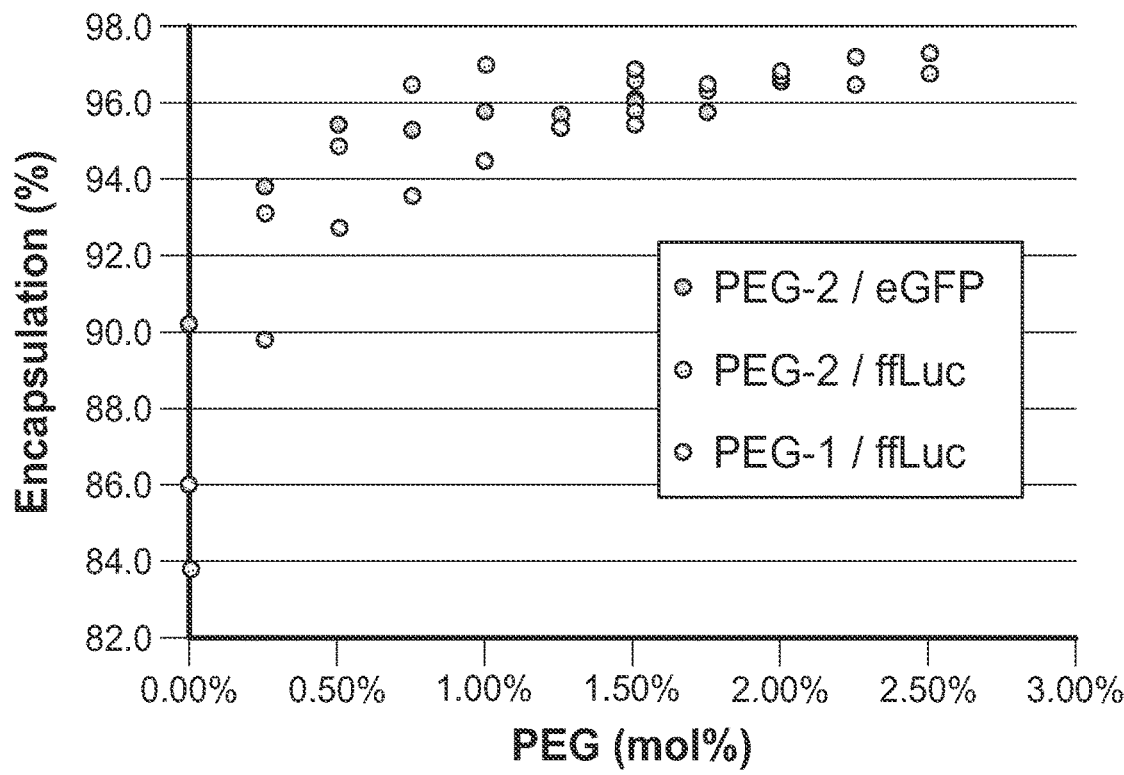
FIGS. 6A-6B are diagrams showing the effect of varied amount of PEG lipids on the LNP formulations.
Figure 6B:
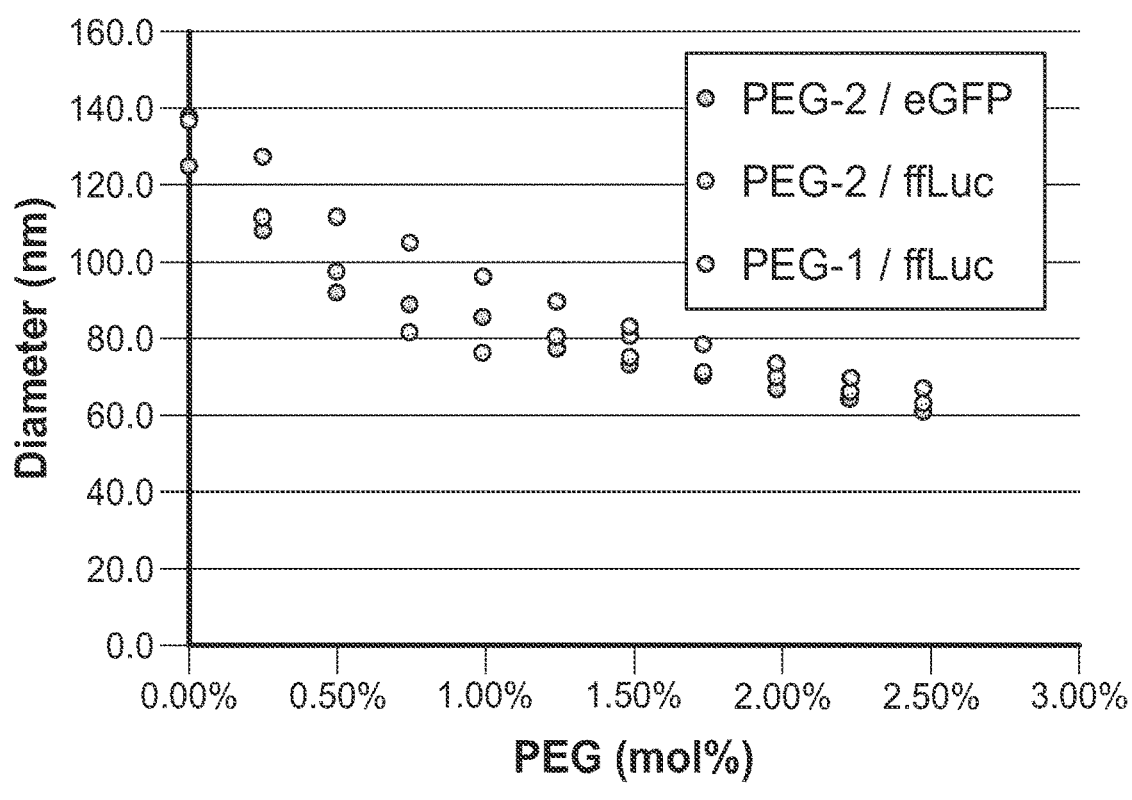
Figure 7A:
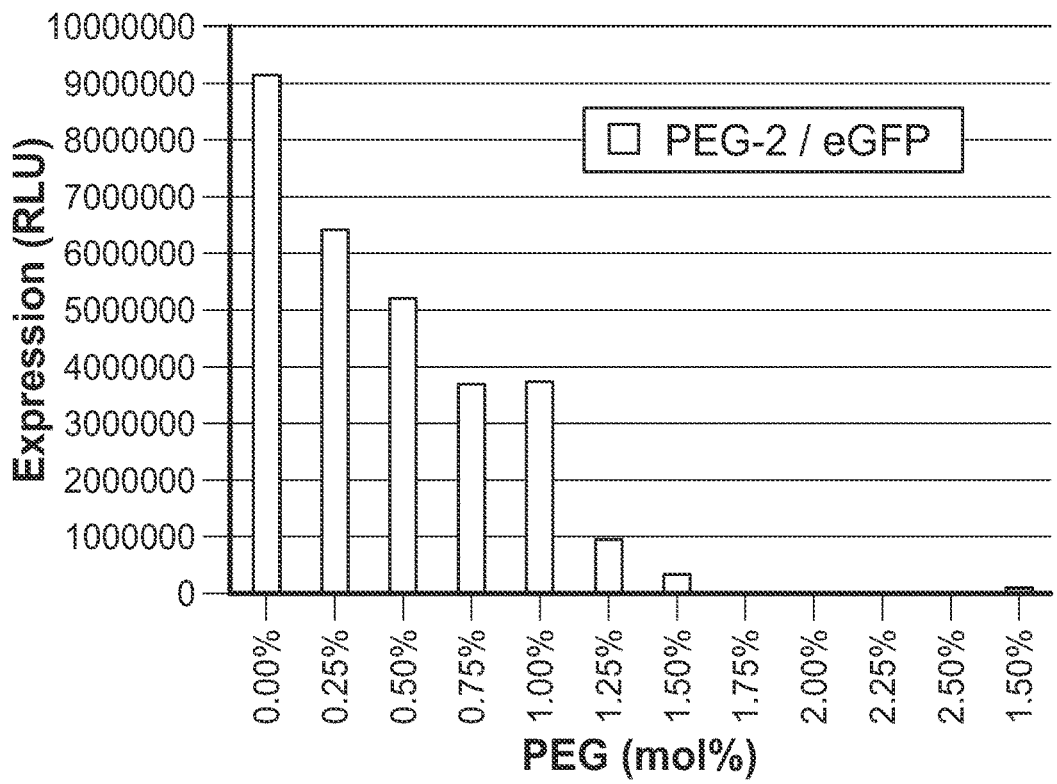
FIGS. 7A-7C are diagrams showing the effect of PEG lipid on the expression of LNP formulations.
Figure 7B:
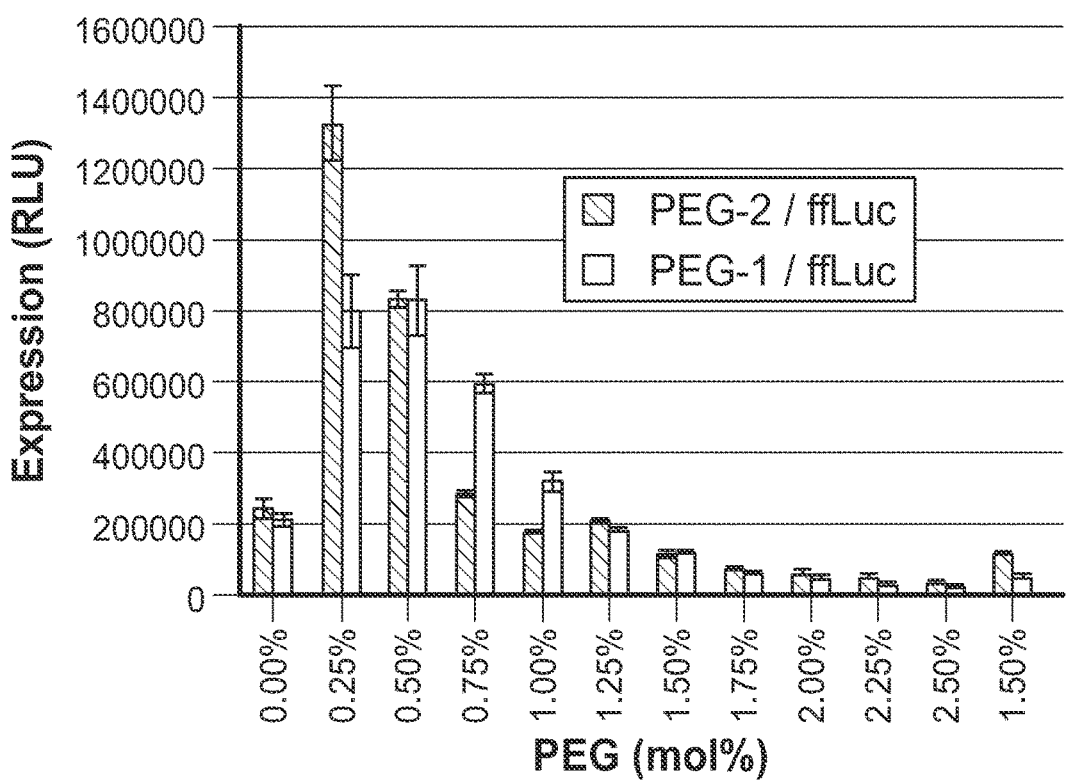
Figure 7C:
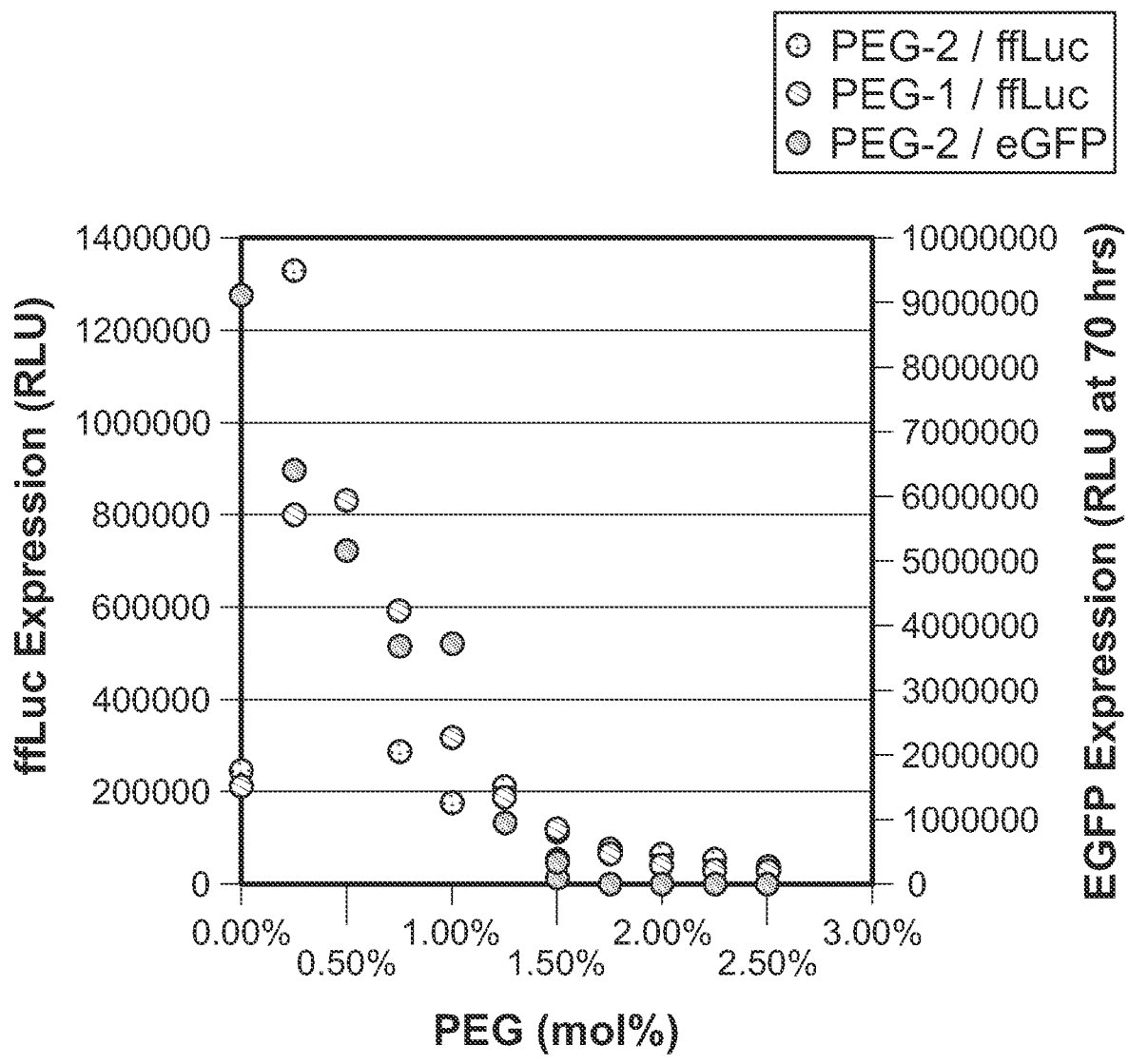
Figure 8:
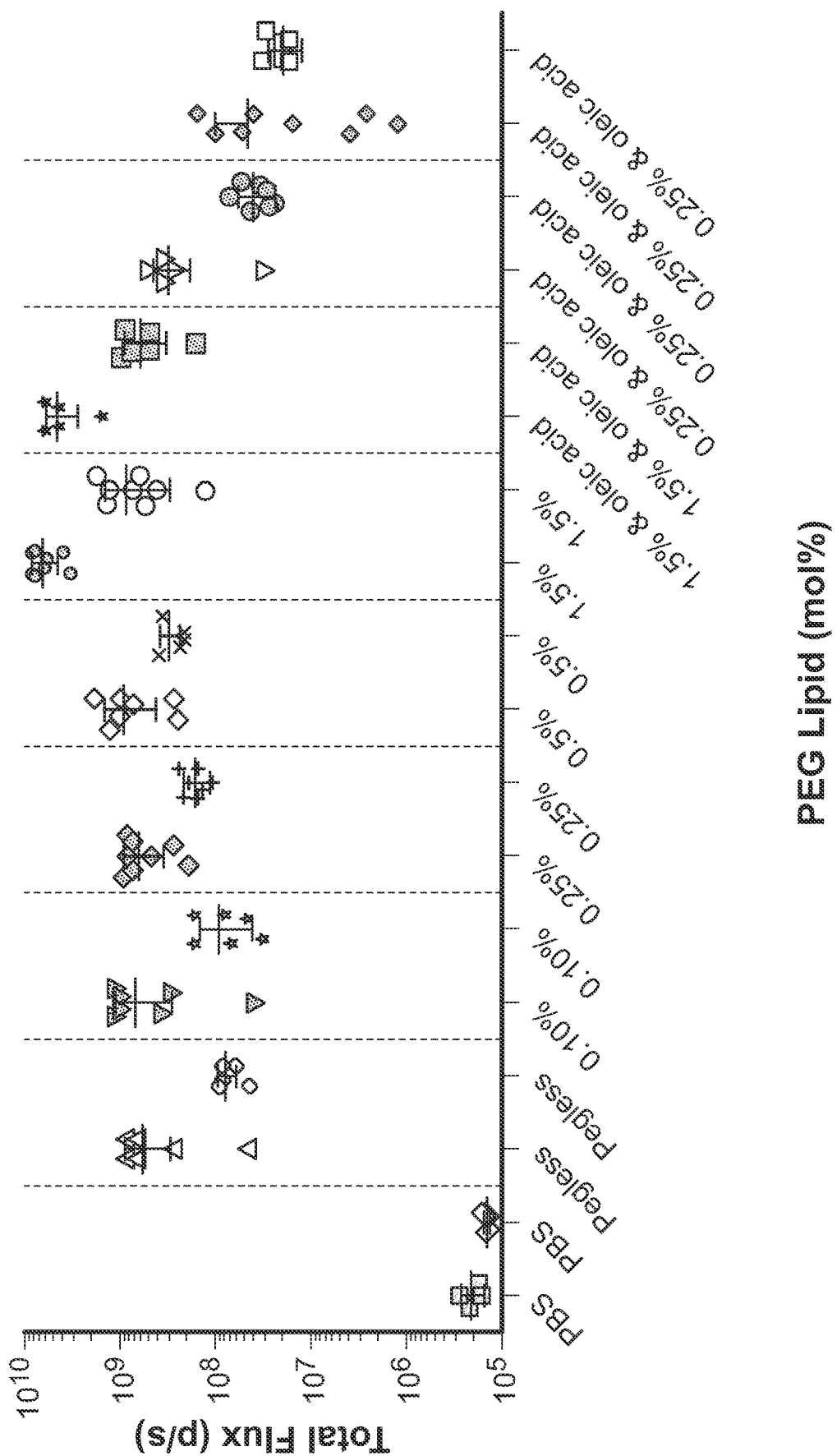
FIG. 8 is a diagram showing the total flux of a multi-dose study in CD-1 mice using LNP formulations containing ionizable lipid and with varied amount of PEG lipid.
Figure 9:
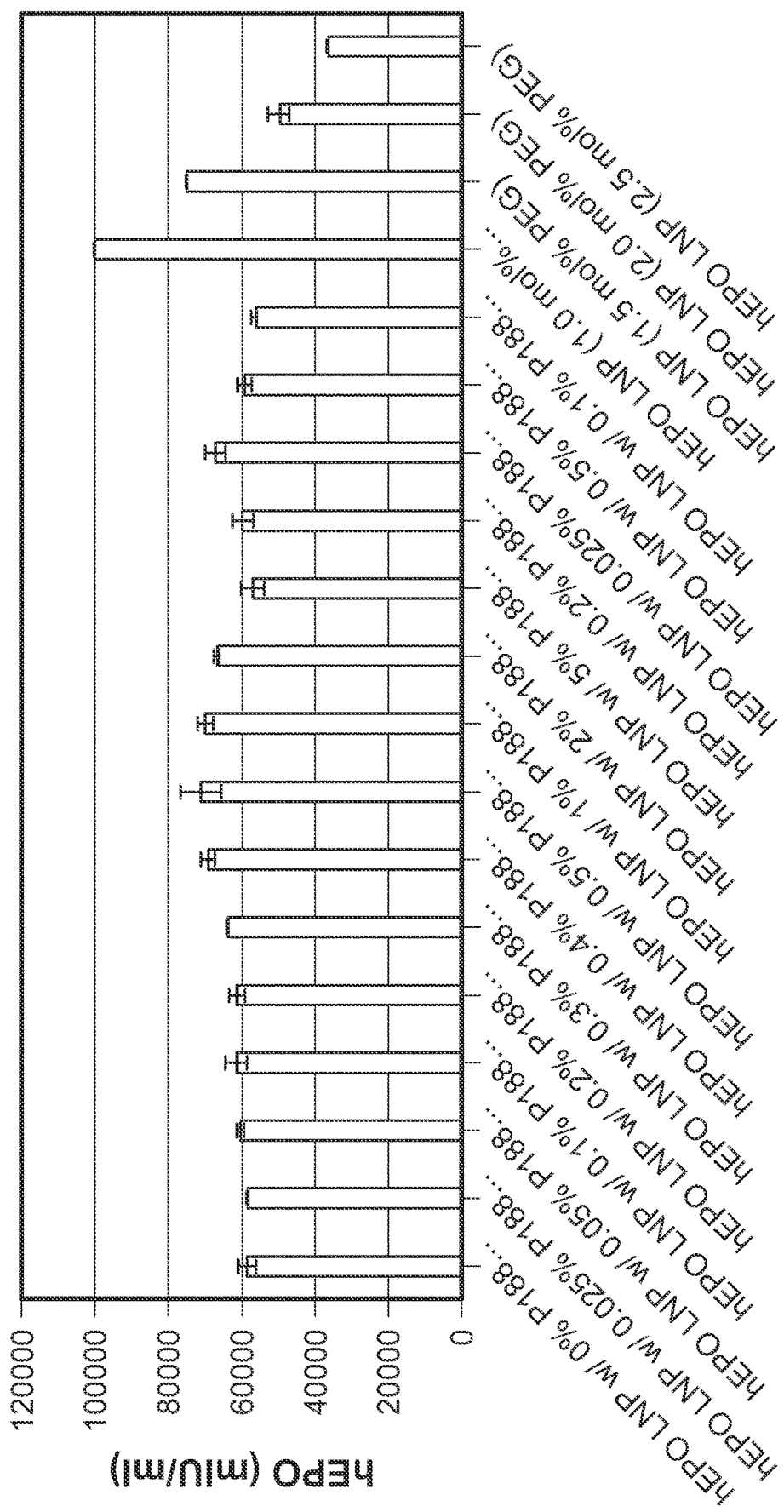
FIG. 9 is a diagram showing the in vitro expression of hEPO mRNA LNP formulations containing ionizable lipid and with varied amount of P188 poloxamer or PEG lipid.
Figure 10:
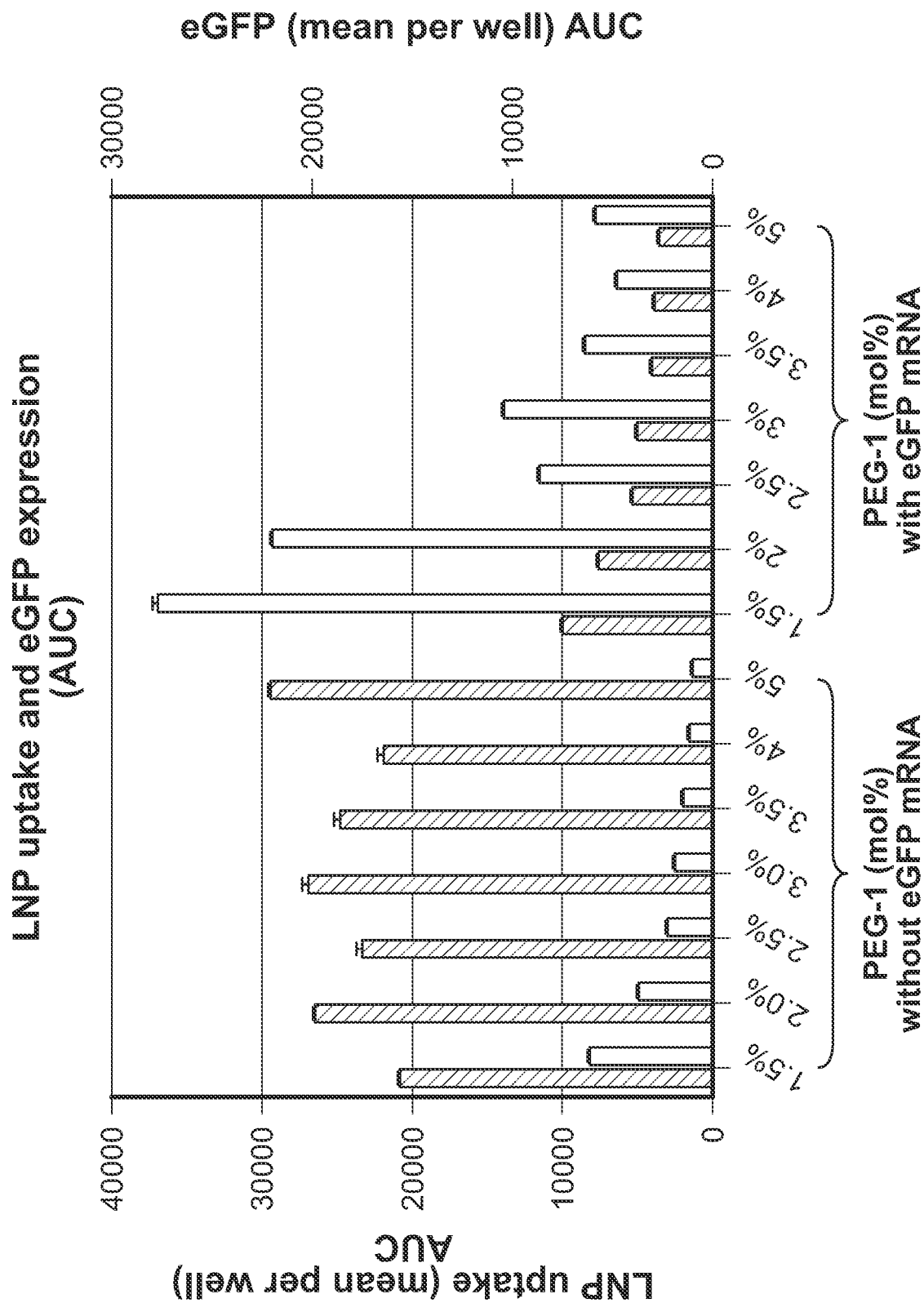
FIG. 10 is a diagram showing the uptake and eGFP mRNA expression of LNP formulations with varied amount of PEG-1.
Figure 12A:
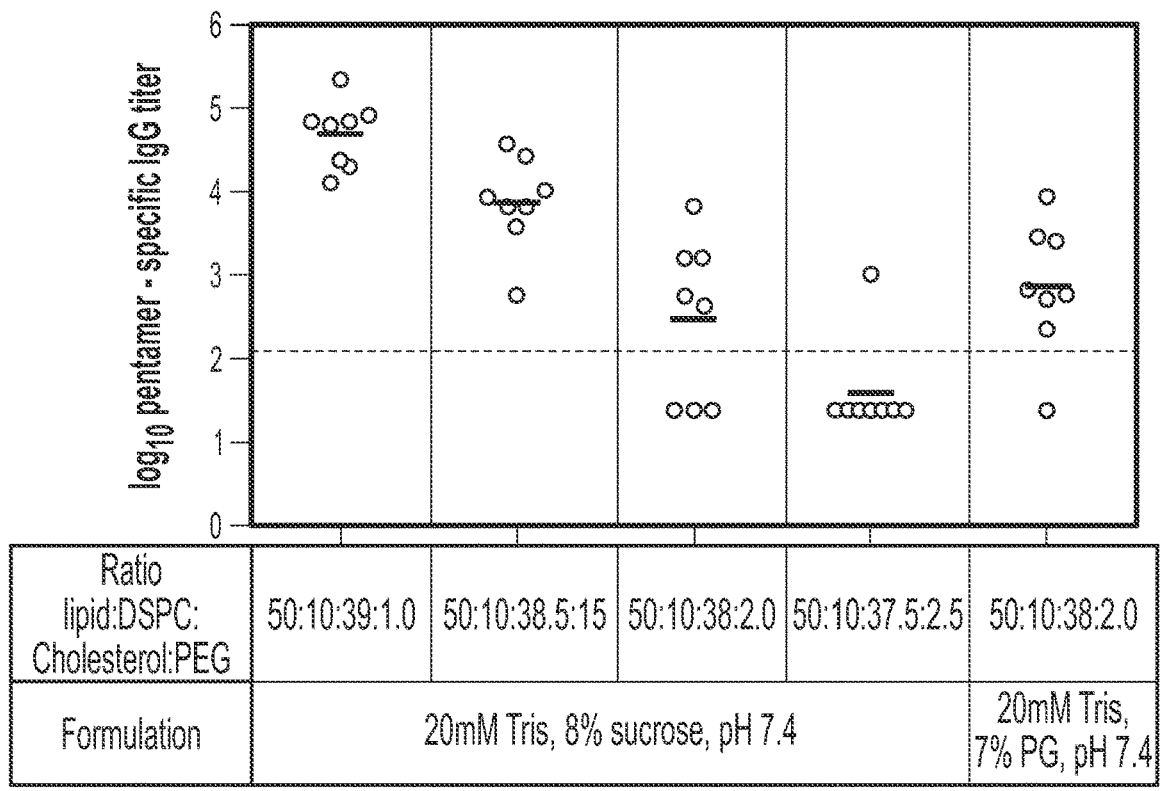
FIGS. 12A-12B are a pair of graphs illustrating the importance of PEG for potency and stability of the nanoparticles (LNP) of the disclosure.
Figure 12B:
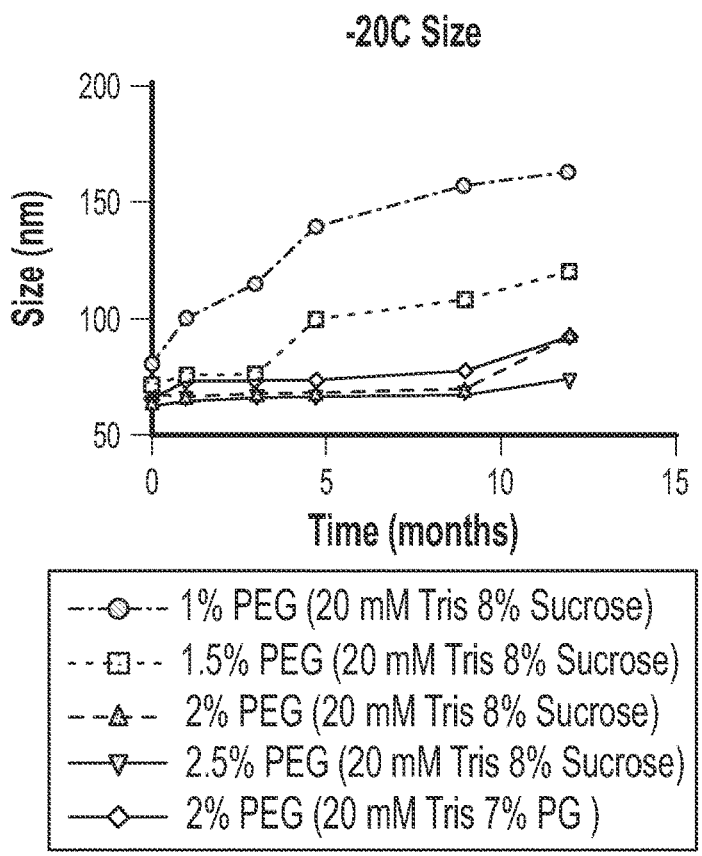
Figure 13A:
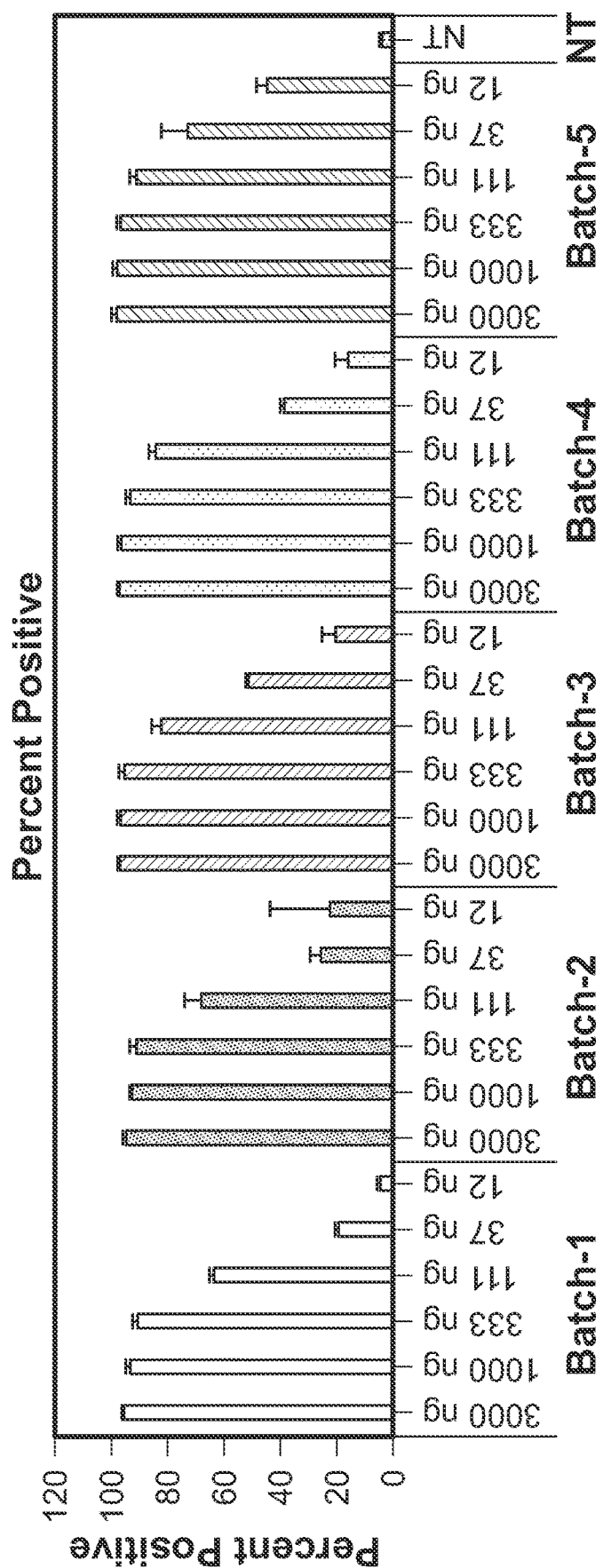
FIGS. 13A-13B are a pair of graphs summarizing in vitro expression on nanoparticles made according to the processes described herein. Batch 1 is made using the standard process. Batches 2 and 4 are made by the post-insertion process, batches 3 and 5 are made using the post addition process.
Figure 13B:
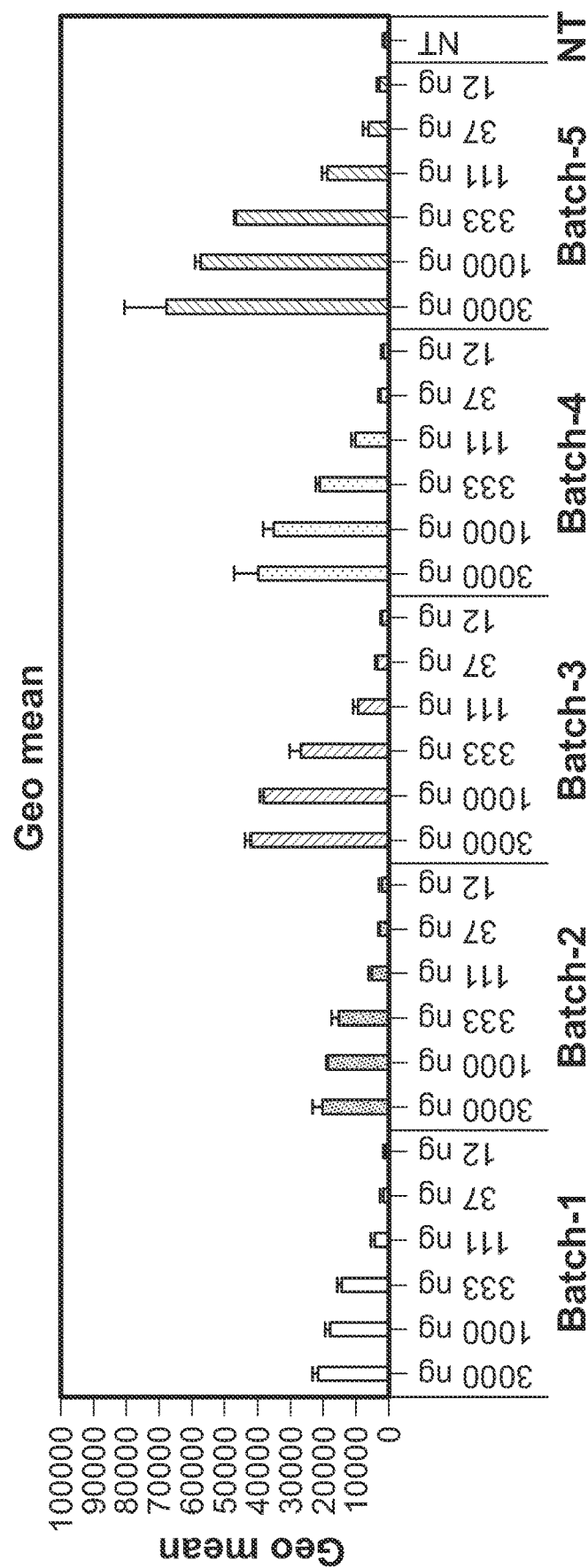
Figure 14:
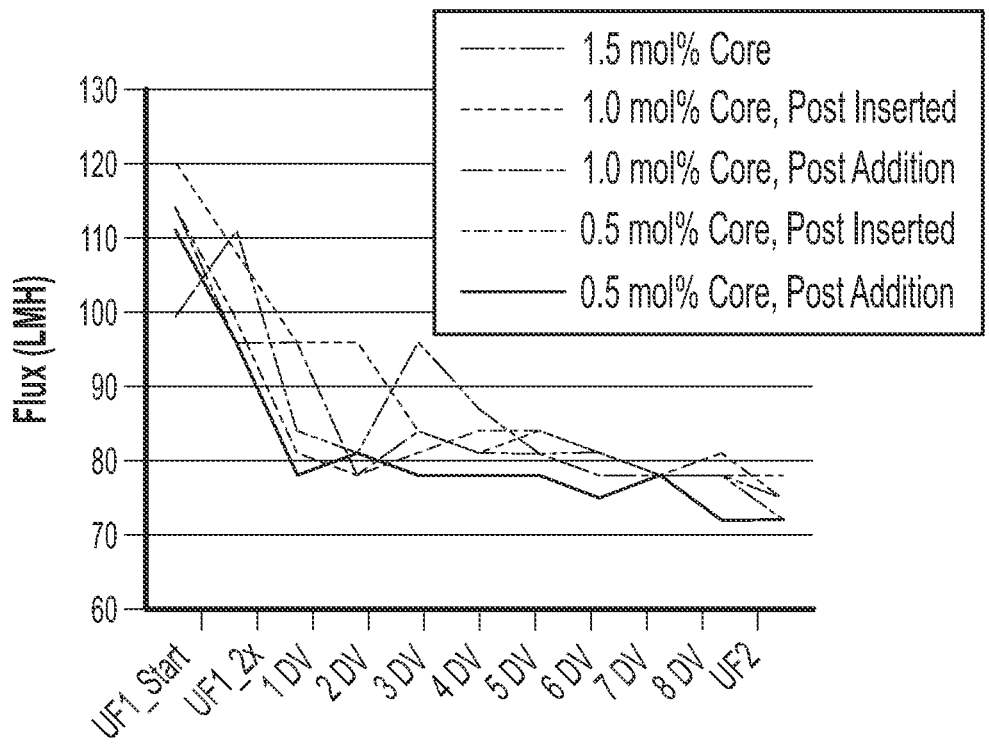
FIG. 14 is a graph of illustrating the performance of nanoparticles made by the processes described herein during tangential flow filtration (TFF).
Figure 15:
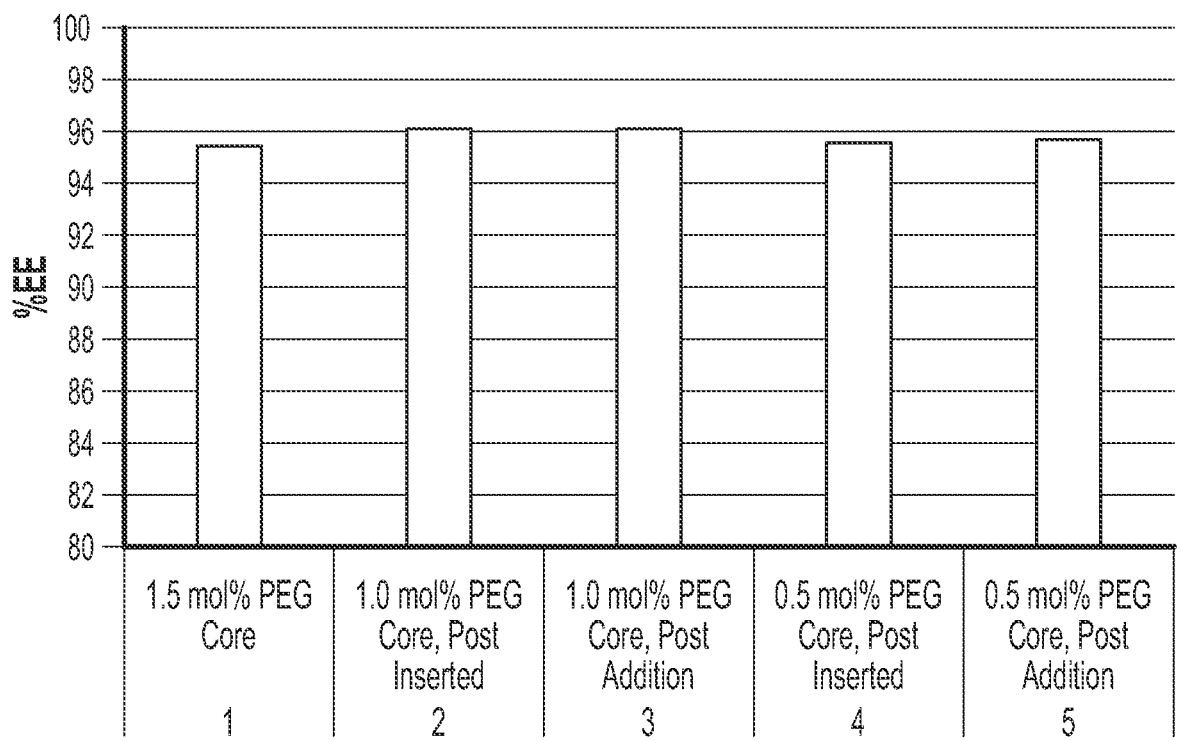
FIG. 15 is a histogram of mRNA encapsulation percent as determined by Ribogreen for lipid nanoparticles formed via the processes disclosed herein.
Figure 16:
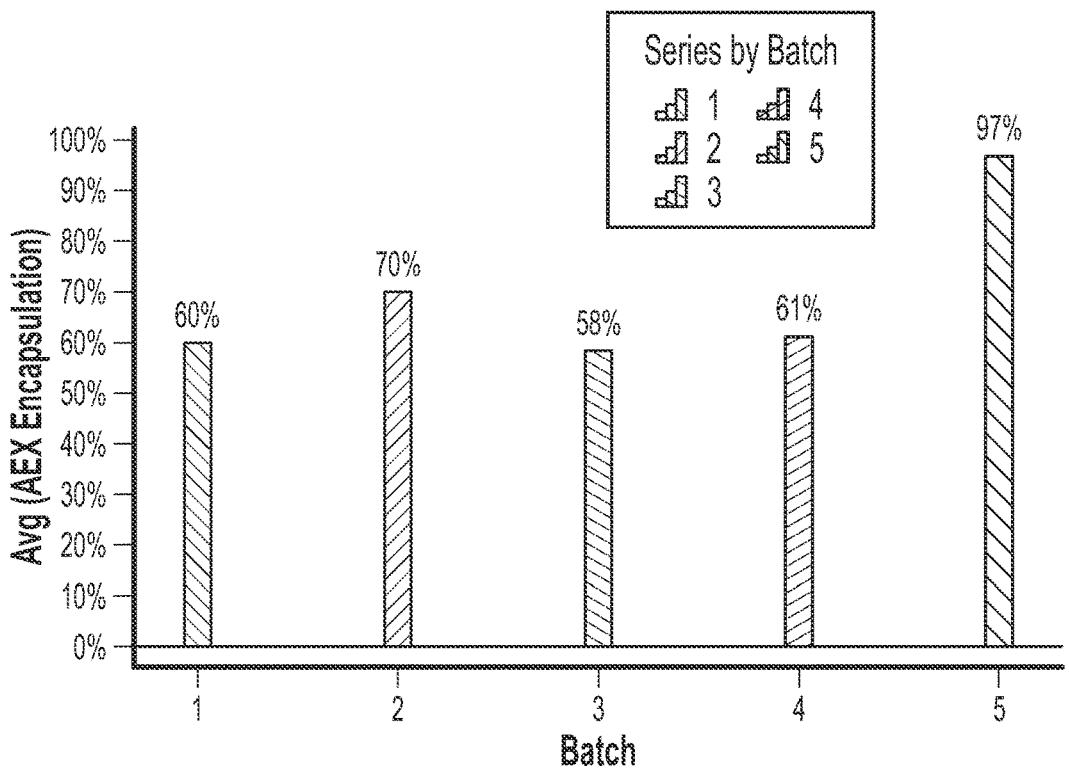
FIGS. 16 and 17 are a pair of histograms illustrating mRNA encapsulation and particle size for lipid nanoparticles formed via the processes described herein. Batch 1 is made using the standard process. Batches 2 and 4 are made by the post-insertion process, batches 3 and 5 are made using the post addition process.

The present disclosure is based, in part, on the discovery that the method of producing the lipid nanoparticle can influence distribution of certain components within the lipid nanoparticles, and that this distribution can influence and/or dictate physical (e.g., stability) and/or biological (e.g. efficacy, intracellular delivery, immunogenicity) properties of the lipid nanoparticles.

In some embodiments, the method of the present disclosure yields compositions comprising lipid nanoparticles having an advantageous distribution of components.

In some embodiments, the method of the present disclosure mitigates an undesired property change from the produced lipid nanoparticle (LNP) formulation.

In some embodiments, the undesired property change caused by a stress upon the LNP formulation or the LNP therein. In some embodiments, the stress is induced during producing, purifying, packing, storing, transporting, and/or using the LNP formulation. In some embodiments, the stress is heat, shear, excessive agitation, membrane concentration polarization (change in charge state), dehydration, freezing stress, drying stress, freeze/thaw stress, and/or nebulization stress. In some embodiments, the stress is induced during freezing or lyophilizing a LNP formulation.

In some embodiments, the undesired property change is a reduction of the physical stability of the LNP formulation. In some embodiments, the undesired property change is an increase of the amount of impurities and/or sub-visible particles, or an increase in the average size of the LNP in the LNP formulation.

In some embodiments, the method of the present disclosure mitigates a reduction of the physical stability (e.g., an increase in the average size of the LNP) from the produced LNP formulation as compared to the LNP formulation produced by a comparable method (e.g., a method without one or more of the steps i), ia), ib), ii), iia), iib), iic), iid), iie), and iif) as disclosed herein (e.g., a method without step ia) and/or step iia))).

In some embodiments, the LNP formulation produced by the method of the present disclosure has an average LNP diameter being about 99% or less, about 98% or less, about 97% or less, about 96% or less, about 95% or less, about 90% or less, about 85% or less, about 80% or less, about 75% or less, about 70% or less, about 65% or less, about 60% or less, about 55% or less, about 50% or less, about 40% or less, about 30% or less, about 20% or less, or about 10% or less as compared to the average LNP diameter of the LNP formulation produced by a comparable method (e.g., a method without one or more of the steps as disclosed herein).

In some embodiments, the undesired property change is a reduction of the chemical stability of the LNP formulation. In some embodiments, the undesired property change is a reduction of the integrity of the nucleic acid (e.g., RNA (e.g., mRNA)) in the LNP formulation.

In some embodiments, the method of the present disclosure mitigates a reduction of the chemical stability (e.g., a reduction of the integrity of the nucleic acid in the LNP formulation) from the produced LNP formulation as compared to the LNP formulation produced by a comparable method (e.g., a method without one or more of the steps as disclosed herein).

In some embodiments, the LNP formulation produced by the method of the present disclosure has an LNP integrity being about the same as the integrity of the LNP used to produce the LNP formulation.

In some embodiments, the LNP formulation produced by the method of the present disclosure has an LNP integrity being lower than the integrity of the LNP used to produce the LNP formulation by about 50% or less, about 40% or less, about 30% or less, about 20% or less, about 15% or less, about 10% or less, about 8% or less, about 6% or less, about 4% or less, about 3% or less, about 2% or less, or about 1% or less.

In some embodiments, the LNP formulation produced by the method of the present disclosure has an LNP integrity higher than the LNP integrity of the LNP formulation produced by a comparable method (e.g., a method without one or more of the steps i), ia), ib), ii), iia), iib), iic), iid), iie), and iif) as disclosed herein (e.g., a method without one or more of the steps as disclosed herein).

In some embodiments, the LNP formulation produced by the method of the present disclosure has an LNP integrity higher than the LNP integrity of the LNP formulation produced by a comparable method by about 5% or more, about 10% or more, about 15% or more, about 20% or more, about 30% or more, about 40% or more, about 50% or more, about 60% or more, about 70% or more, about 80% or more, about 90% or more, about 1 folds or more, about 2 folds or more, about 3 folds or more, about 4 folds or more, about 5 folds or more, about 10 folds or more, about 20 folds or more, about 30 folds or more, about 40 folds or more, about 50 folds or more, about 100 folds or more, about 200 folds or more, about 300 folds or more, about 400 folds or more, about 500 folds or more, about 1000 folds or more, about 2000 folds or more, about 3000 folds or more, about 4000 folds or more, about 5000 folds or more, or about 10000 folds or more.

In some embodiments, the undesired property change is a reduction of the biological property of the LNP formulation. In some embodiments, the undesired property change is a reduction of efficacy, intracellular delivery, and/or immunogenicity of the LNP formulation.

In some embodiments, the LNP formulation produced by the method of the present disclosure has an efficacy, intracellular delivery, and/or immunogenicity being higher than the efficacy, intracellular delivery, and/or immunogenicity of the LNP formulation produced by a comparable method (e.g., a method without one or more of the steps as disclosed herein).

In some embodiments, the LNP formulation produced by the method of the present disclosure has an efficacy, intracellular delivery, and/or immunogenicity being higher than the efficacy, intracellular delivery, and/or immunogenicity of the LNP formulation produced by a comparable method by about 5% or higher, about 10% or more, about 15% or more, about 20% or more, about 30% or more, about 40% or more, about 50% or more, about 60% or more, about 70% or more, about 80% or more, about 90% or more, about 1 folds or more, about 2 folds or more, about 3 folds or more, about 4 folds or more, about 5 folds or more, about 10 folds or more, about 20 folds or more, about 30 folds or more, about 40 folds or more, about 50 folds or more, about 100 folds or more, about 200 folds or more, about 300 folds or more, about 400 folds or more, about 500 folds or more, about 1000 folds or more, about 2000 folds or more, about 3000 folds or more, about 4000 folds or more, about 5000 folds or more, or about 10000 folds or more.

In some embodiments, the LNP formulation produced by the method of the present disclosure exhibits a nucleic acid expression (e.g., the mRNA expression) higher than the nucleic acid expression (e.g., the mRNA expression) of the LNP formulation produced by a comparable method.

In some embodiments, the LNP formulation produced by the method of the present disclosure exhibits a nucleic acid expression (e.g., the mRNA expression) higher than the nucleic acid expression (e.g., the mRNA expression) of the LNP formulation produced by a comparable method by about 5% or higher, about 10% or more, about 15% or more, about 20% or more, about 30% or more, about 40% or more, about 50% or more, about 60% or more, about 70% or more, about 80% or more, about 90% or more, about 1 folds or more, about 2 folds or more, about 3 folds or more, about 4 folds or more, about 5 folds or more, about 10 folds or more, about 20 folds or more, about 30 folds or more, about 40 folds or more, about 50 folds or more, about 100 folds or more, about 200 folds or more, about 300 folds or more, about 400 folds or more, about 500 folds or more, about 1000 folds or more, about 2000 folds or more, about 3000 folds or more, about 4000 folds or more, about 5000 folds or more, or about 10000 folds or more.

Methods of Producing Lipid Nanoparticle (LNP) Compositions and LNP Compositions Produced Thereof The present disclosure provides methods of producing a nucleic acid lipid nanoparticle composition, the method comprising: i) mixing a lipid solution comprising an ionizable lipid with a solution comprising a nucleic acid thereby forming a precursor nucleic acid lipid nanoparticle, ii) adding a lipid nanoparticle modifier comprising a modifying agent to the precursor nucleic acid lipid nanoparticle thereby forming a modified nucleic acid lipid nanoparticle, and iii) processing the precursor nucleic acid lipid nanoparticle, the modified nucleic acid lipid nanoparticle, or both thereby forming the nucleic acid lipid nanoparticle composition.

In some embodiments, the precursor nucleic acid lipid nanoparticle is not processed prior to the adding the lipid nanoparticle modifier. As used herein, this embodiment may be referred to as a "post insertion" method or process.

In some embodiments, the precursor nucleic acid lipid nanoparticle is processed prior to adding the lipid nanoparticle modifier. As used herein, this embodiment may be referred to as a "post addition" method or process.

In some embodiments, the lipid solution further comprises a first PEG lipid.

In some embodiments, the lipid solution does not comprise any PEG lipid.

In some embodiments, the precursor nucleic acid lipid nanoparticle further comprises a first PEG lipid.

In some embodiments, the precursor nucleic acid lipid nanoparticle does not comprise any PEG lipid.

In some embodiments, the modifying agent is at least one selected from the group consisting of a second PEG lipid and a surfactant. In some embodiments, the modifying agent is a second PEG lipid. In some embodiments, the modifying agent is a surfactant.

In some embodiments, the modifying agent is a second PEG lipid. In some embodiments, the first PEG lipid and the second PEG lipid are the same. In some embodiments, the first PEG lipid and the second PEG lipid are not the same.

In some embodiments, the molar ratio of the first PEG lipid to the modifying agent is in a range of about 1:100 to about 1:1, preferably about 1:50 to about 1:1, preferably about 1:25 to about 1:1, preferably about 1:10 to about 1:1. In some embodiments, the modifying agent is a second PEG lipid and the molar ratio of the first PEG lipid to the second PEG lipid is in a range of about 1:100 to about 1:1, preferably about 1:50 to about 1:1, preferably about 1:25 to about 1:1, preferably about 1:10 to about 1:1. In some embodiments, the modifying agent is a surfactant and the molar ratio of the first PEG lipid to the surfactant is in a range of about 1:100 to about 1:1, preferably about 1:50 to about 1:1, preferably about 1:25 to about 1:1, preferably about 1:10 to about 1:1.

The lipid mixture can be solubilized in a water miscible organic solvent, preferably absolute ethanol. In some embodiments, the organic solvent is used in the form in which it is commercially available. In one exemplary embodiment, the mixture of lipids is a mixture of an ionizable lipid and a first PEG lipid are co-solubilized in the organic solvent. In some embodiments, the lipid mixture consists essentially of an ionizable lipid and a PEG lipid, and optionally a phospholipid and/or a structural lipid. Preferred molar ranges are between 30 to 60 mol % ionizable lipid and 0.01 to 10 mol % first PEG lipid, preferably 0.01-5 mol %, preferably 0.01-4 mol %, preferably 0.01-3 mol %, preferably 0.01-2 mol %, preferably 0.01-1 mol %, preferably 0.01-0.8 mol %, preferably 0.01-0.6 mol %, preferably 0.01-0.5 mol %, preferably 0.01-0.25 mol % first PEG lipid. The total concentration of lipid is preferably less than 25 mg/ml, preferably less than 5 mg/ml. The lipid mixture may filtered through membrane, e.g. a 0.45 or 0.2 m filter.

In accordance with the present invention, the lipid mixture may be combined with a nucleic acid solution, preferably in the form of a buffered aqueous solution. The buffered aqueous solution may be a solution in which the buffer has a pH less than the pKa of a protonated lipid in the lipid mixture. Examples of suitable buffers include, but are not limited to, citrate, phosphate, and acetate. A particularly preferred buffer is acetate buffer. Preferred buffers will be in the concentration range of 1-1000 mM of the anion, depending on the chemistry of the nucleic acid being encapsulated, and optimization of buffer concentration may be significant to achieving high loading levels. It may be suitable to add a cryoprotectant, and/or a non-ionic solute, which will balance the osmotic potential across the particle membrane, e.g., when the particles are dialyzed to remove ethanol, increase the pH, or mixed with a pharmaceutically acceptable carrier or diluent. The amount of nucleic acid in buffer is preferably from about 0.01 to 1.0 mg/mL, preferably 0.08 to 0.8 mg/mL At the time of addition of the lipid solution (e.g., ethanol), the temperature of the aqueous nucleic acid solution is 25 to 45° C., preferably 30 to 40° C. In some embodiments, briefly heating the aqueous nucleic acid solution at elevated temperature may be useful, e.g., 1-2 minutes at 65° C. The lipid solution may be added to the aqueous solution either by spraying on the air-water interface, in a narrow stream, or through a liquid-liquid interface between lipid solution delivered through a tube that is submerged in the aqueous nucleic acid solution.

The organic lipid solution may be added by gravity or by a pump delivering the organic lipid solution to the aqueous nucleic acid solution at a controlled rate, preferably a constant rate. In some embodiments, the delivery of the organic lipid is continuous (e.g., by a pump operating under continuous flow). The delivery of the organic lipid solution can be completed in 1 minute to 6 hours, in 1 minute to 100 minutes, or in 1 to 25 minutes. The organic lipid solution may be added through a single spray or stream, through a tube or outlet, or through a multi-outlet system. While the lipid organic solution is added into the nucleic acid aqueous solution, the resulting solution it may be mixed by stirring, shaking, or recirculation. As used herein, "mixing" preferably comprises turbulent mixing ("T-mix"), vortex mixing ("V-mix"), microfluidic mixing, or both. The addition/mixing step results in a final concentration that is 10 to 45% ethanol, preferably 11 to 30% ethanol, more preferably 12.5 to 25% ethanol. Preferably, formation involves either turbulent or microfluidic mixing of solutions to induce precipitation lipids in organic phase with nucleic acid in aqueous phase, or extrusion of an already phase-separated mixture of nucleic acid and lipids through membranes to create LNPs.

In one step of the process a lipid solution comprising a first PEG lipid is mixed with a solution comprising a nucleic acid thereby forming a precursor nucleic acid lipid nanoparticle. In some embodiments, the precursor nucleic provided. In another aspect, precursor lipid nanoparticles are provided. As used herein, a "precursor lipid nanoparticle" refers to a lipid nanoparticle that is a precursor to a lipid nanoparticle, described herein. In some embodiments, a precursor lipid nanoparticle may be formed and/or exist during one or more steps in the particle formulation process. In some embodiments, in which a lipid nanoparticle comprises a PEG molecule, the precursor lipid nanoparticle may comprise a relatively low percentage of PEG molecules (e.g., at least about 0.01 mol % and less than or equal to about 1.0 mol %, at least about 0.05 mol %, at least about 0.1 mol %, at least about 0.2 mol %, at least about 0.3 mol %, at least about 0.4 mol %, at least about 0.5 mol %, at least about 0.6 mol %, at least about 0.7 mol %, or 0.8 mol %).

In some embodiments, all of the nucleic acid in the precursor nucleic acid lipid nanoparticle is associated with the ionizable lipid. In some embodiments, between about 80% and about 100%, between about 85% and about 100%, or between about 90% and about 100% of the nucleic acid in the precursor nucleic acid lipid nanoparticle is associated with the ionizable lipid, preferably about 95% to about 100%, preferably about 98% to about 100%, preferably about 99% to about 100%.

In some embodiments, in which a lipid nanoparticle comprises a PEG molecule, the precursor lipid nanoparticle may have more nucleic acid associated with the ionizable lipid than the PEG molecule. For instance, at least about 50%, at least about 60%, at least about 70%, at least about 80%, or at least about 90% of the nucleic acid in the precursor lipid nanoparticle is associated with the ionizable lipid. In some such cases, less than about 50%, less than about 40%, less than about 30%, less than about 20%, or less than about 10% of the nucleic acid in the precursor lipid nanoparticle is associated with the PEG molecule (e.g., PEG lipid). In some embodiments, a ratio of nucleic acid associated with the ionizable lipid to nucleic acid associated with the PEG lipid in the precursor lipid nanoparticles is at least about 2:1. In some embodiments, a composition comprising precursor lipid nanoparticles may comprise one or more organic solvents (e.g., ethanol). In some embodiments, the nucleic acid lipid nanoparticle composition may be enriched in precursor lipid nanoparticles. For instance, at least about 50% of the lipid nanoparticles in the nucleic acid lipid nanoparticle composition may be precursor lipid nanoparticles.

In some embodiments, the precursor nucleic acid lipid nanoparticle comprises about 30-60 mol % ionizable lipid; about 0-30 mol % phospholipid; about 15-50 mol % structural lipid; and about 0.01-10 mol % the first PEG lipid. In some embodiments, the precursor nucleic acid lipid nanoparticle comprises about 30-60 mol % ionizable lipid; about 0-30 mol % phospholipid; about 15-50 mol % structural lipid; and about 0.01-1 mol % the first PEG lipid. In some embodiments, the precursor nucleic acid lipid nanoparticle comprises about 40-60 mol % ionizable lipid; about 5-15 mol % phospholipid; about 35-45 mol % structural lipid; and about 0.01-10 mol % the first PEG lipid. In some embodiments, the precursor nucleic acid lipid nanoparticle comprises about 40-60 mol % ionizable lipid; about 5-15 mol % phospholipid; about 35-45 mol % structural lipid; and about 0.01-1 mol % the first PEG lipid. In some embodiments, the precursor nucleic acid lipid nanoparticle comprises about 30-60 mol % ionizable lipid; about 0-30 mol % phospholipid; about 15-50 mol % structural lipid; and about 0.01-0.75 mol % the first PEG lipid. In some embodiments, the precursor nucleic acid lipid nanoparticle comprises about 30-60 mol % ionizable lipid; about 0-30 mol % phospholipid; about 15-50 mol % structural lipid; and about 0.01-0.5 mol % the first PEG lipid.

In some embodiments, the processing may involve treating to remove an organic solvent (i.e., ethanol), by dialysis or filtration, preferably by diafiltration. As used herein, "processing" includes steps to purify, pH adjustment, buffer exchange, and/or concentrate LNPs. In some embodiments, the processing comprises a filtration such as a sterile filtration. In a more preferred embodiment, the processing comprises a tangential flow filtration (TFF). While the ethanol is removed, the aqueous solution is converted to a one buffered at a neutral pH, pH 6.5 to 7.8, pH 6.8 to pH 7.5, preferably, pH 7.0 to pH 7.2, for example a phosphate or HEPES buffer. The resulting aqueous solution is preferably sterilized before storage or use, such as, for example by filtration through a 0.22 m filter.

In some embodiments, the processing may comprise a freezing and/or lyophilizing. Lyophilizing steps may be carried out in a suitable glass receptacle, preferably a 1 ml to 10 ml (e.g., 3 ml), cylindrical glass vial. The glass vial should withstand extreme changes in temperatures of less than −40° C. and greater than room temperature in short periods of time, and be cut in a uniform shape. The composition comprising the nucleic acid lipid nanoparticle is added to the vial, preferably in a volume ranging from about 0.1 ml to about 5 ml, from 0.2 ml to about 3 ml, from 0.3 ml to about 1 ml, or from about 0.4 ml to about 0.8 ml (e.g., about 0.5 ml), and preferably with about 9 mg/ml lipid. The step of lyophilizing may comprise freezing the composition at a temperature of greater than about −40° C., or e.g. less than about −30° C., forming a frozen composition; and drying the frozen composition to form the lyophilized composition. The freezing step preferably results in a linear decrease in temperature to the final over about 100 to 180 minutes (e.g., about 130 minutes), preferably at 0.1 to 1° C./minute (e.g., about 0.5° C./minute) from 20 to −40° C. More preferably, sucrose at 5-15% (e.g., 8-12%) may be used, and the drying step is at about 50-150 mTorr, first at a low temperature of about −15 to about −35° C., and thereafter at a higher temperature of room temperature to about 25° C., and is completed in three to seven days. In another embodiment of the present disclosure the drying step is at about 50-100 mTorr, first at a low temperature of about −40° C. to about −20° C., and then at the higher temperature.

In some embodiments, the method may further comprise packing the nucleic acid lipid nanoparticle composition. As used herein, "storage" or "packing" may refer to storing drug product in its final state or in-process storage of LNPs before they are placed into final packaging. Modes of storage and/or packing include, but are not limited to refrigeration in sterile bags, refrigerated or frozen formulations in vials, lyophilized formulations in vials and syringes, etc.

In some embodiments, the nucleic acid lipid nanoparticle comprises about 30-60 mol % ionizable lipid; about 0-40 mol % phospholipid; about 15-50 mol % structural lipid; and about 0.01-20 mol % total amount of the first PEG lipid and the second PEG lipid. In some embodiments, the nucleic acid lipid nanoparticle comprises about 30-60 mol % ionizable lipid; about 0-30 mol % phospholipid; about 15-50 mol % structural lipid; and about 0.5-3.0 mol % total amount of the first PEG lipid and the second PEG lipid. In some embodiments, the nucleic acid lipid nanoparticle comprises about 40-60 mol % ionizable lipid; about 5-15 mol % phospholipid; about 35-45 mol % structural lipid; and about 0.01-20 mol % total amount of the first PEG lipid and the second PEG lipid. In some embodiments, the nucleic acid lipid nanoparticle comprises about 40-60 mol % ionizable lipid; about 5-15 mol % phospholipid; about 35-45 mol % structural lipid; and about 0.5-3 mol % total amount of the first PEG lipid and the second PEG lipid. In some embodiments, the nucleic acid lipid nanoparticle comprises about 30-60 mol % ionizable lipid; about 0-30 mol % phospholipid; about 15-50 mol % structural lipid; and about 0.5-2.5 mol % total amount of the first PEG lipid and the second PEG lipid. In some embodiments, the nucleic acid lipid nanoparticle comprises about 30-60 mol % ionizable lipid; about 0-30 mol % phospholipid; about 15-50 mol % structural lipid; and about 0.5-2.25 mol % total amount of the first PEG lipid and the second PEG lipid.

In some embodiments, the concentration of the non-ionic surfactant in the nucleic acid LNP formulation ranges from about 0.00001% w/v to about 1% w/v, e.g., from about 0.00005% w/v to about 0.5% w/v, or from about 0.0001% w/v to about 0.1% w/v.

In some embodiments, the concentration of the non-ionic surfactant in the nucleic acid LNP formulation ranges from about 0.000001 wt % to about 1 wt %, e.g., from about 0.000002 wt % to about 0.8 wt %, or from about 0.000005 wt % to about 0.5 wt %.

In some embodiments, the concentration of the PEG lipid in the stabilized LNP formulation ranges from about 0.01% by molar to about 50% by molar, e.g., from about 0.05% by molar to about 20% by molar, from about 0.07% by molar to about 10% by molar, from about 0.1% by molar to about 8% by molar, from about 0.2% by molar to about 5% by molar, or from about 0.25% by molar to about 3% by molar.

In some embodiments, the distribution of one or more components in the lipid nanoparticle may be dictated, at least in part, by the process by which the components are assembled. For instance, in some embodiments, the distribution (e.g., accessibility, arrangement) of nucleic acid (e.g., mRNA) within the lipid nanoparticle may be controlled, at least in part, by the formulation process. For example, the formulation process may comprise one or more steps that allow the distribution of mRNA to be tailored, as described in more detail below. For example, the formulation process may use a relatively low weight percentage of certain components (e.g., PEG lipid) during the particle formation step (e.g., nanoprecipitation reaction) and/or add certain lipid nanoparticle components after particle formation.

In some embodiments, regardless of the process used, the distribution of one or more components within the lipid nanoparticle may be influenced, at least in part, by the distribution of another component in the lipid nanoparticle. For instance, the distribution of the nucleic acid within the lipid nanoparticle may be dictated, at least in part, by the distribution of another component in the lipid nanoparticle, such as a molecule comprising polyethylene glycol (also referred to as "PEG molecules"). Without being bound by theory, it is believed that certain distributions of PEG molecules promote certain associations that result in a beneficial mRNA distribution. Regardless of whether the distribution of a molecule comprising PEG (e.g., PEG lipid) influences the distribution of mRNA, certain distributions of molecules comprising polyethylene glycol (e.g., PEG lipid) may result in beneficial properties.

As described herein, in some embodiments, lipid nanoparticles having a certain distribution of molecules comprising polyethylene glycol (e.g., PEG lipid) may have advantageous physical and/or biological properties. In some embodiments, a molecule comprising polyethylene glycol (e.g., PEG lipid) may be distributed, such that a relatively high percentage (e.g., majority) of the molecule comprising polyethylene glycol (e.g., PEG-lipid) is accessible from the surface of the lipid nanoparticle. As used herein, the term "accessible" (also referred to as "surface accessible") with respect to molecules comprising polyethylene glycol (e.g., PEG-lipid) may refer to PEG molecules that are localized at the surface of the lipid nanoparticle and/or PEG molecules that can be readily localized, e.g., through facile reorganization, at the surface of the lipid nanoparticle under certain conditions (e.g., physiological conditions, in serum, in buffer). PEG molecules that are not surface accessible may be referred to as "residual" PEG molecules. In some embodiments, residual PEG molecules may be positioned in one or more interior regions of the lipid nanoparticles. In some embodiments, surface accessible PEG molecules may be positioned within the exterior region of the lipid nanoparticles.

In some embodiments, the surface accessibility of PEG molecules may be determined by one or more assays (e.g., in vitro assay). In general, any suitable in vitro assay may be used. In some embodiments, the shedding of PEG molecules from the lipid nanoparticles as assessed via diffusion-ordered spectroscopy (DOSY) NMR may be used to determine the relative percentage of surface accessible and residual PEG molecules in the lipid nanoparticles and/or a composition. PEG shedding and DOSY NMR is further described in Wilson, S. C.; Baryza, J. L.; Reynolds, A. J.; Bowman, K.; Rajan, S.; et al. (2015). Real Time Measurement of PEG Shedding from Lipid Nanoparticles in Serum via NMR Spectroscopy. *Molecular Pharmaceutics*, 12(2):386-92, which is incorporated by reference in its entirety. In some embodiments, the percentage of surface accessible PEG molecules corresponds to the percentage of PEG molecules shed after a certain period of time (e.g., 6 hours, 24 hours) under certain conditions (e.g., in mouse serum at 25° C.).

In some embodiments, the PEG molecules may be distributed in a manner that produces a relatively short half-life. As used herein, the "half-life" of a molecule comprising polyethylene glycol is the time it takes for 50% of the molecule comprising polyethylene glycol to shed from the surface of the lipid nanoparticle under certain conditions (e.g., in mouse serum at 25° C.) as determined by DOSY NMR. In some embodiments, the lipid nanoparticles may have a shorter half-life than certain comparative lipid nanoparticles.

In some embodiments, the surface accessibility, arrangement, and/or half-life of PEG molecules may correlate to one or more biological and/or physical properties of the lipid nanoparticles. For example, in some embodiments, the surface accessibility, arrangement, and/or half-life of a PEG molecule may correlate with the immunogenicity of the lipid nanoparticles and/or composition. For instance, in some embodiments, a relatively high percentage of surface accessible PEG molecules and/or a relatively short half-life may correspond to low or no immunogenicity. Certain inventive compositions may have a lower immunogenicity than comparative compositions.

In some embodiments, the surface accessibility, arrangement, and/or half-life of PEG molecules may correlate to one or more physical properties of the lipid nanoparticles. For example, a relatively high percentage of surface accessible PEG molecules and/or a relatively short half-life may correspond to higher nucleic acid encapsulation efficiency. As another example, the surface accessibility, arrangement, and/or half-life of PEG molecules may correlate with surface polarization. For instance, in some embodiments, lipid nanoparticles having a relatively high percentage of surface accessible PEG molecules and/or a relatively short half-life may have a relatively low surface polarization (e.g., low surface polarity).

As described herein, in some embodiments, lipid nanoparticles may have a beneficial distribution of one or more components. In some embodiments, a lipid nanoparticle may have a beneficial distribution of two or more components (e.g., three or more components, four or more components, five or more components). For instance, the lipid nanoparticle may have a having a beneficial distribution of nucleic acid and a beneficial distribution of a PEG molecule. In some such cases, the lipid nanoparticle may have at least some (e.g., all) of the advantageous properties associated with the beneficial distribution of each component.

In some embodiments, compositions are provided. The compositions may comprise the lipid nanoparticles described herein. In some embodiments, a composition may comprise a relatively high percentage of the lipid nanoparticles described herein. In some embodiments, the lipid nanoparticles, described herein, may have one or more properties that are superior to other lipid nanoparticles in the formulation. Such a lipid nanoparticle having one or more superior properties to another lipid nanoparticle in the formulation may be referred to as an "enhanced lipid nanoparticle." For example, an enhanced lipid nanoparticle may have more inaccessible mRNA than another lipid nanoparticle (e.g., all other lipid nanoparticles) in a composition. In some instances, an enhanced lipid nanoparticle may have more inaccessible mRNA than accessible mRNA. In certain embodiment, an enhanced lipid nanoparticle may have a relatively high percentage (e.g., at least about 50%, at least about 60%, at least about 70%, at least about 80%, at least about 90%, at least about 95%) of surface accessible PEG molecules. In some embodiments in which the enhanced lipid nanoparticles comprise a relatively high percentage (e.g., at least about 50%, about least about 60%, at least about 70%, about least about 80%, at least about 90%, at least about 95%) of the total lipid nanoparticles in the composition, the composition may be referred to as being enriched in enhanced lipid nanoparticles.

In some embodiments, the lipid nanoparticles and/or composition, described herein, may have a low amount of accessible nucleic acid (e.g., mRNA). For instance, in some embodiments, less than or equal to about 50%, less than or equal to about 45%, less than or equal to about 40%, less than or equal to about 35%, less than or equal to about 30%, less than or equal to about 25%, less than or equal to about 20%, less than or equal to about 15%, less than or equal to about 10%, or less than or equal to about 5% of the total amount of nucleic acid in the lipid nanoparticles and/or a composition is accessible nucleic acid (e.g., mRNA). In some embodiments, lipid nanoparticles and/or a composition may comprise accessible nucleic acid. In some such embodiments, a lipid nanoparticle and/or a composition may comprise at least about 0.01%, at least about 0.05%, at least about 0.1%, at least about 0.5%, at least about 1%, or at least about 2% of accessible nucleic acid. All combinations of the above referenced ranges are possible (e.g., at least about 0.01% and less than or equal to about 50%).

In some embodiments, a lipid nanoparticle and/or composition, described herein, may have a beneficial amount of inaccessible nucleic acid (e.g., mRNA). For instance, in some embodiments, at least about 50%, at least about 55%, at least about 60%, at least about 65%, at least about 70%, at least about 75%, at least about 80%, at least about 85%, less than or equal to about 90%, or at least about 95% of the total amount of nucleic acid in a lipid nanoparticle and/or a composition is inaccessible nucleic acid (e.g., mRNA).

In some embodiments, a lipid nanoparticle and/or composition, described herein, may have a beneficial amount of nucleic acid (e.g., mRNA) positioned in the one or more interior regions of the lipid nanoparticles. For instance, in some embodiments, at least about 30%, at least about 35%, at least about 40%, at least about 45%, at least about 50%, at least about 55%, at least about 60%, at least about 65%, less than or equal to about 70%, at least about 75%, at least about 80%, at least about 85%, less than or equal to about 90%, or at least about 95% of the total amount of nucleic acid in the lipid nanoparticle and/or a composition is positioned in the interior region(s) of the lipid nanoparticles.

In some embodiments, a lipid nanoparticles and/or composition, described herein, may have a beneficial amount of nucleic acid (e.g., mRNA) that is at least partially (e.g., fully) encapsulated. For instance, in some embodiments, at least about 30%, at least about 35%, at least about 40%, at least about 45%, at least about 50%, at least about 55%, at least about 60%, at least about 65%, less than or equal to about 70%, at least about 75%, at least about 80%, at least about 85%, less than or equal to about 90%, or at least about 95% of the total amount of nucleic acid in the lipid nanoparticle and/or a composition is at least partially (e.g., fully) encapsulated. In some embodiments, the percentage of at least partially (e.g., fully) encapsulated nucleic acid may be determined by an in vitro assay (e.g., IEX) as described herein.

In some embodiments, a lipid nanoparticle and/or composition, described herein, may have a beneficial amount of surface accessible PEG molecules (e.g., PEG lipid). For instance, in some embodiments, at least about 50%, at least about 55%, at least about 60%, at least about 65%, at least about 70%, at least about 75%, at least about 80%, at least about 85%, less than or equal to about 90%, or at least about 95% of the total amount of molecules comprising PEG (e.g., PEG lipid) in the lipid nanoparticle and/or composition is surface accessible PEG molecules.

In some embodiments, a lipid nanoparticle and/or composition, described herein, may have a beneficial amount of residual molecules comprising PEG (e.g., PEG lipid). For instance, in some embodiments, less than or equal to about 50%, less than or equal to about 45%, less than or equal to about 40%, less than or equal to about 35%, less than or equal to about 30%, less than or equal to about 25%, less than or equal to about 20%, less than or equal to about 15%, less than or equal to about 10%, or less than or equal to about 5% of the total amount of PEG molecules (e.g., PEG-lipid) in the lipid nanoparticle and/or composition is residual PEG molecules. In some embodiments, a lipid nanoparticle and/or a composition may comprise residual PEG molecules. In some such embodiments, the lipid nanoparticle and/or composition may comprise at least about 0.01%, at least about 0.05%, at least about 0.1%, at least about 0.5%, at least about 1%, or at least about 2% of residual PEG molecules. All combinations of the above referenced ranges are possible (e.g., at least about 0.01% and less than or equal to about 50%). In some embodiments, the lipid nanoparticle and/or composition may not comprise residual PEG molecules.

In some embodiments, a lipid nanoparticle and/or composition, described herein, may have a beneficial amount of PEG molecules (e.g., PEG lipid) positioned in the exterior region of the lipid nanoparticle(s). For instance, in some embodiments, at least about 30%, at least about 35%, at least about 40%, at least about 45%, at least about 50%, at least about 55%, at least about 60%, at least about 65%, less than or equal to about 70%, at least about 75%, at least about 80%, at least about 85%, less than or equal to about 90%, or at least about 95% of the total amount of PEG molecules (e.g., PEG lipid) in the lipid nanoparticle and/or composition is positioned in the exterior region(s) of the lipid nanoparticle(s).

In some embodiments in which the lipid nanoparticles comprise a molecule comprising polyethylene glycol (e.g., PEG-lipid), the half-life of the molecule comprising polyethylene glycol may be relatively short. For instance, the half-life may be less than or equal to about 5 hours, less than or equal to about 4.5 hours, less than or equal to about 4 hours, less than or equal to about 3 hours, less than or equal to about 2.75 hours, less than or equal to about 2.25 hours, less than or equal to about 2.0 hours, less than or equal to about 1.75 hours, less than or equal to about 1.5 hours, less than or equal to about 1.25 hours, less than or equal to about 1.0 hours, less than or equal to about 0.75 hours, or less than or equal to about 0.5 hours. In some instances, the half-life may be at least about 0.01 hours, at least about 0.05 hour, at least about 0.1 hours, at least about 0.5 hours. All combinations of the above-referenced ranges are possible (e.g., at least about 0.01 hours and less than or equal to about 5 hours, at least about 0.01 hours and less than or equal to about 3 hours, at least about 0.5 hours and less than or equal to about 3 hours).

In some embodiments in which a lipid nanoparticle and/or composition comprises a molecule comprising polyethylene glycol (e.g., PEG-lipid), the mole percentage of PEG molecule in the lipid nanoparticle and/or composition may be relatively small. For instance, in some embodiments, the mole percent of PEG molecule(s) in the lipid nanoparticle and/or composition is less than or equal to about 5%, less than or equal to about 4.5%, less than or equal to about 4.0%, less than or equal to about 3.5%, less than or equal to about 3.0%, less than or equal to about 2.5%, less than or equal to about 2.0%, less than or equal to about 1.5%, less than or equal to about 1.0%, or less than or equal to about 0.5%. In some embodiments, a lipid nanoparticle and/or composition may comprise PEG molecule(s). In some such embodiments, lipid nanoparticles and/or a composition may comprise at least about 0.01%, at least about 0.05%, at least about 0.1%, at least about 0.5%, at least about 1%, or at least about 2% of mole percent of PEG molecules. All combinations of the above referenced ranges are possible (e.g., at least about 0.01% and less than or equal to about 5.0%). In some embodiments, the mole percentage of the PEG molecules (e.g., PEG lipid) in the lipid nanoparticle and/or composition may be less than the critical micelle concentration of the PEG molecule (e.g., PEG lipid).

In some embodiments, the molecule comprising polyethylene glycol may be a PEG lipid. In some such embodiments, the PEG lipid may comprise one or more aliphatic groups. In some instances, the PEG lipid may comprise two or more aliphatic groups. It should be understood that the two or more aliphatic groups refer to aliphatic groups that are not within the same aliphatic chain. For example, a carbon atom of the first aliphatic group may not form a direct carbon-carbon covalent bond with a carbon atom of second aliphatic group. That is, the two or more aliphatic groups may be indirectly attached to each other.

Processing LNP Solutions

The term "processing", as used herein, includes one or more steps to purify, pH adjustment, buffer exchange, and/or concentrate LNPs.

In some embodiments, the step of processing the LNP solution comprises:

a) filtering the LNP solution.

In some embodiments, the filtration removes an organic solvent (e.g., ethanol) from the LNP solution. In some embodiments, the processing comprises a filtration such as a sterile filtration. In some embodiments, the processing comprises a tangential flow filtration (TFF). In some embodiments, upon removal of the organic solvent (e.g., ethanol), the LNP solution is converted to a solution buffered at a neutral pH, pH 6.5 to 7.8, pH 6.8 to pH 7.5, preferably, pH 7.0 to pH 7.2 (e.g., a phosphate or HEPES buffer). In some embodiments, the resulting LNP solution is preferably sterilized before storage or use, e.g., by filtration (e.g., through a 0.22 m filter).

In some embodiments, the step of processing the LNP solution further comprises packing the LNP solution.

As used herein, "packing" may refer to storing drug product in its final state or in-process storage of LNPs before they are placed into final packaging. Modes of storage and/or packing include, but are not limited to refrigeration in sterile bags, refrigerated or frozen formulations in vials, lyophilized formulations in vials and syringes, etc.

In some embodiments, the step of packing the LNP solution comprises one or more of the following steps:

b) adding a cryoprotectant to the LNP solution; and c) lyophilizing the LNP solution, thereby forming a lyophilized LNP composition.

d) storing the LNP solution or the lyophilized LNP composition; and adding a reconstituting solution to the LNP solution or the lyophilized LNP composition, thereby forming the LNP formulation.

In some embodiments, the cryoprotectant is added to the LNP solution prior to the lyophilization. In some embodiments, the cryoprotectant comprises one or more cryoprotective agents, and each of the one or more cryoprotective agents is independently a polyol (e.g., a diol or a triol such as propylene glycol (i.e., 1,2-propanediol), 1,3-propanediol, glycerol, (+/−)-2-methyl-2,4-pentanediol, 1,6-hexanediol, 1,2-butanediol, 2,3-butanediol, ethylene glycol, or diethylene glycol), a nondetergent sulfobetaine (e.g., NDSB-201 (3-(1-pyridino)-1-propane sulfonate), an osmolyte (e.g., L-proline or trimethylamine N-oxide dihydrate), a polymer (e.g., polyethylene glycol 200 (PEG 200), PEG 400, PEG 600, PEG 1000, PEG 3350, PEG 4000, PEG 8000, PEG 10000, PEG 20000, polyethylene glycol monomethyl ether 550 (mPEG 550), mPEG 600, mPEG 2000, mPEG 3350, mPEG 4000, mPEG 5000, polyvinylpyrrolidone (e.g., polyvinylpyrrolidone K 15), pentaerythritol propoxylate, or polypropylene glycol P 400), an organic solvent (e.g., dimethyl sulfoxide (DMSO) or ethanol), a sugar (e.g., D-(+)-sucrose, D-sorbitol, trehalose, D-(+)-maltose monohydrate, meso-erythritol, xylitol, myo-inositol, D-(+)-raffinose pentahydrate, D-(+)-trehalose dihydrate, or D-(+)-glucose monohydrate), or a salt (e.g., lithium acetate, lithium chloride, lithium formate, lithium nitrate, lithium sulfate, magnesium acetate, sodium chloride, sodium formate, sodium malonate, sodium nitrate, sodium sulfate, or any hydrate thereof), or any combination thereof. In some embodiments, the cryoprotectant comprises sucrose.

In some embodiments, the lyophilization carried out in a suitable glass receptacle (e.g., a 2, 3, 5, or 10 ml cylindrical glass vial). The glass receptacle preferably withstands extreme changes in temperatures between lower than −40° C. and higher than room temperature in short periods of time, and/or be cut in a uniform shape. In some embodiments, the step of lyophilizing comprises freezing the LNP solution at a temperature lower than about −40° C., thereby forming a frozen LNP solution; and drying the frozen LNP solution to form the lyophilized LNP composition. The freezing step preferably results in a linear decrease in temperature to the final over about 100 to 180 minutes (e.g., about 130 minutes), preferably at 0.1 to 1° C./minute (e.g., about 0.5° C./minute) from 20 to −40° C. More preferably, sucrose at 5-15% (e.g., 8-12%) may be used, and the drying step is performed at a vacuum ranging from about 50 mTorr to about 150 mTorr, preferably, first at a low temperature lower than −10° C. (e.g., from about −35° C. to about −15° C.), lower than −20° C., lower than −30° C., or lower than −40° C., and then at a higher temperature ranging from room temperature to about 25° C., preferably, the drying step is completed in three to seven days. In some embodiments, the drying step is performed at a vacuum ranging from about 50 mTorr to about 100 mTorr, preferably, first at a low temperature below about 0° C., below about −10° C., below about −20° C., or below about −30° C. (e.g., −35° C.), and then at a higher temperature.

In some embodiments, the LNP solution or the lyophilized LNP composition is stored at a temperature of about −40° C., about −35° C., about −30° C., about −25° C., about −20° C., about −15° C., about −10° C., about −5° C., about 0° C., about 5° C., about 10° C., about 15° C., about 20° C., or about 25° C. prior to adding the reconstituting solution.

In some embodiments, the LNP solution or the lyophilized LNP composition is stored at a temperature of ranging from about −40° C. to about 0° C., from about −35° C. to about −5° C., from about −30° C. to about −10° C., from about −25° C. to about −15° C., from about −22° C. to about −18° C., or from about −21° C. to about −19° C. prior to adding the reconstituting solution.

In some embodiments, the LNP solution or the lyophilized LNP composition is stored at a temperature of about −20° C. prior to adding the reconstituting solution.

In some embodiments, the LNP solution or the lyophilized LNP composition is stored at a temperature of ranging from about −15° C. to about 25° C., from about −10° C. to about 20° C., from about −5° C. to about 15° C., from about 0° C. to about 10° C., from about 1° C. to about 9° C., or from about 2° C. to about 8° C. prior to adding the reconstituting solution.

In some embodiments, the LNP solution or the lyophilized LNP composition is stored for about 30 minutes, about 1 hour, about 2 hours, about 4 hours, about 6 hours, about 12 hours, about 1 day, about 2 days, about 3 days, about 4 days, about 5 days, about 6 days, about 1 week, about 2 weeks, about 3 weeks, about 4 weeks, about 1 month, about 2 months, about 3 months, about 4 months, about 6 months, about 9 months, about 1 year, about 2 years, about 3 years, about 4 years, about 5 years, about 6 years, about 7 years about 8 years, about 9 years, or about 10 years prior to adding the reconstituting solution.

In some embodiments, the LNP solution or the lyophilized LNP composition is stored for a time period ranging from about 1 month to about 10 years, from about 3 months to about 8 years, from about 6 months to about 6 years, from about 9 months to about 4 years, from about 1 year to about 3 years, or from about 1.5 years to about 2.5 years prior to adding the reconstituting solution.

In some embodiments, the LNP solution or the lyophilized LNP composition is stored for about 2 years prior to adding the reconstituting solution.

Methods of Stabilizing a LNP Formulation

The present disclosure provides methods of producing a nucleic acid lipid nanoparticle composition.

The present disclosure provides methods of stabilizing a lipid nanoparticle (LNP) formulation upon application of stress, by adding modifying agent to the LNP formulation before or when the stress is applied or during its production.

In some embodiments, the stress includes any stress applied to the formulation when producing, purifying, packing, storing, transporting and using the formulation, such as heat, shear, excessive agitation, membrane concentration polarization (change in charge state), dehydration, freezing stress, drying stress, freeze/thaw stress, nebulization stress, etc. For example, the stress can cause one or more undesired property changes to the formulation, such as an increased amount of impurities, of sub-visible particles, or both, an increase in LNP size, a decrease in encapsulation efficiency, in therapeutic efficacy, or both, and a decrease in tolerability (e.g., an increase in immunogenicity).

In some embodiments, the stress applied is from producing a LNP formulation, for example, from mixing lipid components in an organic solvent (e.g., ethanol) to produce an organic phase, from mixing mRNA into an acidic solution to produce an aqueous phase, from adjusting pH values of the aqueous phase, and/or from mixing the organic phase with the aqueous phase to produce the LNP formulation. For example, each said mixing step can comprise turbulent mixing or microfluidic mixing. For example, before mixing the organic with the aqueous phase, each phase may be purified via, e.g., filtration (such as tangential flow filtration or TFF). For example, the stress applied is from such purification.

In some embodiments, the stress applied is from processing LNPs following LNP formation, e.g., downstream purification and concentration by tangential flow filtration (TFF). For example, during a typical TFF process, the LNP dispersion is exposed to a variety of hydrophobic interfaces, shear forces, and turbulence. For example, during a typical TFF process, molecules larger than the membrane pores (i.e., LNPs) accumulate at the membrane surface to form a gel or concentration-polarized layer. For example, the increased concentration of LNPs serve as a destabilizing stress, promoting inter-molecular interactions that may generate larger particulate species.

In some embodiments, the stress applied is from purification of a LNP formulation. Accordingly, the disclosure also features a method of purifying a lipid nanoparticle (LNP) formulation, comprising filtering a first LNP formulation in the presence of an amphiphilic polymer to obtain a second LNP formulation.

In some embodiments, the stress applied is from freezing or lyophilizing a LNP formulation. Accordingly, the disclosure also features a method of freezing or lyophilizing a lipid nanoparticle (LNP) formulation, comprising freezing or lyophilizing a first LNP formulation in the presence of modifying agent.

For example, the modifying agent is present at a concentration ranging between about 0.025% w/v and about 1% w/v (e.g., about 0.025% w/v, about 0.05% w/v, about 0.1% w/v, about 0.5% w/v, about 1% w/v, about 0.025-0.5% w/v, about 0.05-1% w/v, about 0.1-1% w/v, or about 0.1-0.5% w/v). For example, the modifying agent is present at a concentration ranging between about 0.025% w/w and about 1% w/w (e.g., about 0.025% w/w, about 0.05% w/w, about 0.1% w/w, about 0.5% w/w, about 1% w/w, about 0.025-0.5% w/w, about 0.05-1% w/w, about 0.1-1% w/w, or about 0.1-0.5% w/w).

For example, the modifying agent is present at a concentration ranging between about 0.025% w/v and about 1% w/v (e.g., about 0.025% w/v, about 0.05% w/v, about 0.1% w/v, about 0.5% w/v, about 1% w/v, about 0.025-0.5% w/v, about 0.05-1% w/v, about 0.1-1% w/v, or about 0.1-0.5% w/v). For example, the modifying agent is present at a concentration ranging between about 0.025% w/w and about 1% w/w (e.g., about 0.025% w/w, about 0.05% w/w, about 0.1% w/w, about 0.5% w/w, about 1% w/w, about 0.025-0.5% w/w, about 0.05-1% w/w, about 0.1-1% w/w, or about 0.1-0.5% w/w).

For example, the third amphiphilic polymer is present at a concentration ranging between about 0.1% w/v and about 3% w/v (e.g., about 0.1% w/v, about 0.5% w/v, about 1% w/v, about 2% w/v, about 2.5% w/v, about 0.1-2.5% w/v, about 0.1-1% w/v, about 0.1-0.5% w/v, or about 0.1-0.4% w/v). For example, the third amphiphilic polymer is present at a concentration ranging between about 0.1% w/w and about 3% w/w (e.g., about 0.1% w/w, about 0.5% w/w, about 1% w/w, about 2% w/w, about 2.5% w/w, about 0.1-2.5% w/w, about 0.1-1% w/w, about 0.1-0.5% w/w, or about 0.1-0.4% w/w).

For example, the fourth amphiphilic polymer is present at a concentration ranging between about 0.1% w/v and about 3% w/v (e.g., about 0.1% w/v, about 0.5% w/v, about 1% w/v, about 2% w/v, about 0.1-2.5% w/v, about 0.1-1% w/v, about 0.1-0.5% w/v, or about 0.1-0.4% w/v). For example, the fourth amphiphilic polymer is present at a concentration ranging between about 0.1% w/w and about 3% w/w (e.g., about 0.1% w/w, about 0.5% w/w, about 1% w/w, about 2% w/w, about 2.5% w/w, about 0.1-2.5% w/w, about 0.1-1% w/w, about 0.1-0.5% w/w, or about 0.1-0.4% w/w).

For example, the weight ratio between the modifying agent and the nucleic acid is about 0.025:1 to about 100:1.

For example, the modifying agent is added such that the weight ratio between the modifying agent and the LNP is about 0.0004:1 to about 100:1 (e.g., about 0.001:1 to about 10:1, about 0.001:1 to about 5:1, about 0.001:1 to about 0.1:1, about 0.005 to about 0.4:1, or about 0.5:1 to about 4:1, about 0.05:1 to about 5:1, about 0.1:1 to about 5:1 or about 0.05:1 to about 2.5:1, about 1:1 to about 50:1, about 2:1 to about 50:1 or about 1:1 to about 25:1).

Methods of Characterizing LNP Compositions

In some embodiments, the accessibility of the nucleic acid in a LNP composition comprising LNPs may be determined by one or more assays (e.g., in vitro assay). In general, any suitable in vitro assay may be used. Suitable assays are able to distinguish between different encapsulation states of the nucleic acid and/or association states of the nucleic acid with components of the lipid nanoparticle. For example, the accessibility of a nucleic acid may be determined by an ion-exchange chromatography (IEX) assay. In certain embodiments, as described in more detail below, certain conventional assays may not be suitable for determining the accessibility of a nucleic acid. For instance, in some embodiments, a Ribogreen assay is not suitable for determining the accessibility of a nucleic acid (e.g., mRNA). In some embodiments, the in vitro assay may be used to generate a quantitative value of the amount of accessible or inaccessible nucleic acids (e.g., mRNA) in the lipid nanoparticles or composition. For example, an ion-exchange chromatography (IEX) assay may be used to generate a quantitative value of the amount of accessible or inaccessible mRNA in a composition comprising lipid nanoparticles. In general, the amount of inaccessible or accessible nucleic acids may be determined for the total composition and/or a fraction of the composition (e.g., fraction comprising certain lipid nanoparticles).

In some embodiments, the accessibility of the nucleic acid within the lipid nanoparticle may correlate to one or more biological properties of the lipid nanoparticle. In certain embodiments, the accessibility of the nucleic acid within the lipid nanoparticle may correlate with protein expression levels and/or the efficacy of intracellular nucleic acid delivery. For instance, in some embodiments, a relatively high percentage of inaccessible nucleic acid, and accordingly a relatively low percentage of accessible nucleic acid, may produce high levels of protein expression (e.g., in vitro, in vivo). In such cases, a composition having a low percentage of accessible mRNA may have a higher level of mRNA expression than a comparative composition having a higher percentage of accessible mRNA.

In some aspects, the present disclosure provides a method of characterizing a LNP composition (e.g., the LNP composition prepared by a method of the present disclosure) using a chromatography assay.

In some embodiments, a quantitative value of an amount of the nucleic acid (e.g., mRNA) encapsulated in the LNP composition is measured using the chromatography assay.

In some embodiments, the chromatography assay is an ion-exchange (IEX) chromatography assay.

In some embodiments, at least about 50%, at least about 55%, at least about 60%, at least about 65%, at least about 70%, at least about 75%, at least about 80%, at least about 85%, at least about 95%, or at least about 95% of the LNPs in the LNP composition have mRNA encapsulated therein, as determined by the ion-exchange chromatography (IEX) assay.

An ion exchange (IEX) chromatography method was developed to accurately determine encapsulation efficiency for mRNAs encapsulated in ionizable-lipid-based LNPs, produced according to routine T-mix methodologies (Example 4) or V-mix methodologies. IEX chromatography can be used to separate bound versus free mRNA. IEX Screening method separates free mRNA from LNP's when there is a gradient change from low to high salt concentration. LNP elutes in the void (peak 1) and mRNA elutes when gradient changes from low to high salt concentration (peak 2, termed "accessible mRNA").

Without being bound in theory, it is believed that within a population of LNPs (e.g., LNPs encapsulating mRNA), mRNA can exist in a variety of different encapsulation states, including, for example, fully encapsulated, surface-associated, loosely encapsulated (or other physical states). Art-recognized methods for determining nucleic acid encapsulation efficiency, in particular, the routinely-used Ribogreen assay, fails to differentiate between such physical states (e.g., does not discern important differences in structural characteristics and contexts). To exemplify the utility of the IEX method of the invention, a LNP sample population can be subjected to an art-recognized separation technique, for example, size-exclusion chromatography (SEC). This fractionates particles based on size. Fractions can be subjected, for example, to a biological assay, e.g., in vitro protein expression assay. Fractions can likewise be subjected to determination of encapsulation efficiency according to the IEX methods of the invention.

Ionizable Lipids

The present disclosure provides ionizable lipids, preferably including a central amine moiety and at least one biodegradable group. The lipids described herein may be advantageously used in lipid nanoparticles for the delivery of therapeutics and/or prophylactics, such as a nucleic acid, to mammalian cells or organs.

In embodiments, the ionizable lipids of the present disclosure may be one or more of compounds of Formula (IL-1):

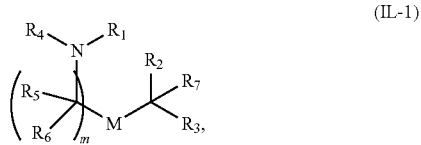
(IL-1)

or their N-oxides, or salts or isomers thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of hydrogen, a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, —N(R)R$_8$, N(R)S(O)$_2$R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H; M and M' are independently selected from —C(O)O—, —OC(O)—, —OC(O)-M"—C(O)O—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group, in which M" is a bond, $C_{1-13}$ alkyl or $C_{2-13}$ alkenyl;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-15}$ alkyl and $C_{3-15}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13; and wherein when $R_4$ is —(CH$_2$)$_n$Q, —(CH$_2$)$_n$CHQR, —CHQR, or —CQ(R)$_2$, then (i) Q is not —N(R)$_2$ when n is 1, 2, 3, 4 or 5, or (ii) Q is not 5, 6, or 7-membered heterocycloalkyl when n is 1 or 2.

In some embodiments, a subset of compounds of Formula (IL-I) includes those of Formula (IL-IA):

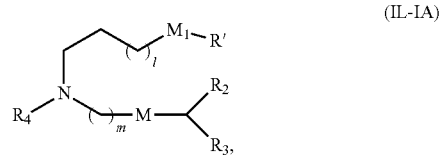
(IL-IA)

or its N-oxide, or a salt or isomer thereof, wherein 1 is selected from 1, 2, 3, 4, and 5; m is selected from 5, 6, 7, 8, and 9; $M_1$ is a bond or M'; $R_4$ is hydrogen, unsubstituted $C_{1-3}$ alkyl, or —(CH$_2$)$_n$Q, in which Q is OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl or heterocycloalkyl; M and M' are independently selected from —C(O)O—, —OC(O)—, —OC(O)-M"—C(O)O—, —C(O)N(R')—, —P(O)(OR')O—, —S—S—, an aryl group, and a heteroaryl group, and $R_2$ and $R_3$ are independently selected from the group consisting of H, $C_{1-14}$ alkyl, and $C_{2-14}$ alkenyl. In some embodiments, m is 5, 7, or 9. In some embodiments, Q is OH, —NHC(S)N(R)$_2$, or —NHC(O)N(R)$_2$. In some embodiments, Q is —N(R)C(O)R, or —N(R)S(O)$_2$R.

In some embodiments, a subset of compounds of Formula (I) includes those of Formula (IL-IB):

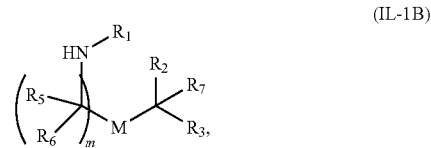
(IL-1B)

or its N-oxide, or a salt or isomer thereof, in which all variables are as defined herein. In some embodiments, m is selected from 5, 6, 7, 8, and 9; $R_4$ is hydrogen, unsubstituted $C_{1-3}$ alkyl, or —$(CH_2)_n$Q, in which Q is —OH, —NHC(S)N(R)$_2$, —NHC(O)N(R)$_2$, —N(R)C(O)R, —N(R)S(O)$_2$R, —N(R)R8, —NHC(=NR$_9$)N(R)$_2$, —NHC(=CHR$_9$)N(R)$_2$, —OC(O)N(R)$_2$, —N(R)C(O)OR, heteroaryl or heterocycloalkyl; M and M' are independently selected from —C(O)O—, —OC(O)—, —OC(O)-M"—C(O)O—, —C(O)N(R')—, —P(O)(OR')O—, —S—S—, an aryl group, and a heteroaryl group, and $R^2$ and $R_3$ are independently selected from the group consisting of H, $C_{1-14}$ alkyl, and $C_{2-14}$ alkenyl. In some embodiments, m is 5, 7, or 9. In some embodiments, Q is OH, —NHC(S)N(R)$_2$, or —NHC(O)N(R)$_2$. In some embodiments, Q is —N(R)C(O)R, or —N(R)S(O)$_2$R.

In some embodiments, a subset of compounds of Formula (IL-I) includes those of Formula (IL-II):

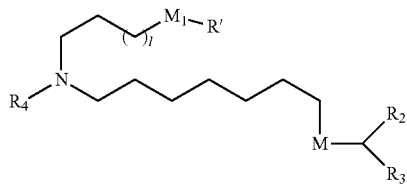

(IL-II)

or its N-oxide, or a slat or isomer thereof, wherein 1 is selected from 1, 2, 3, 4 and 5; M1 is a bond or M'; $R_4$ is hydrogen, unsubstituted $C_{1-3}$ alkyl, or —$(CH_2)_n$Q, in which n is 2, 3, or 4, and Q is —OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl or heterocycloalkyl; M and M' are independently selected from —C(O)O—, —OC(O)—, —OC(O)-M"—C(O)O—, —C(O)N(R')—, —P(O)(OR')O—, —S—S—, an aryl group, and a heteroaryl group, and $R^2$ and $R^3$ are independently selected from the group consisting of H, $C_{1-14}$ alkyl, and $C_{2-14}$ alkenyl.

In one embodiment, the compounds of Formula (IL-I) are of Formula (IL-IIa):

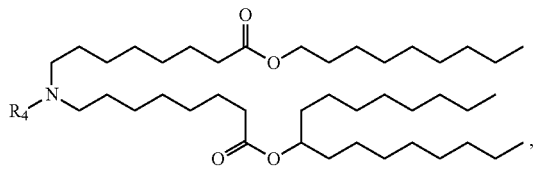

(IL-IIa)

or their N-oxides, or salts or isomers thereof, wherein $R_4$ is as described herein.

In another embodiment, the compounds of Formula (IL-I) are of Formula (IL-IIb):

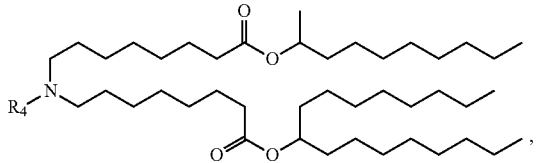

(IL-IIb)

or their N-oxides, or salts or isomers thereof, wherein $R_4$ is as described herein.

In another embodiment, the compounds of Formula (IL-I) are of Formula (IL-IIc) or (IL-IIe):

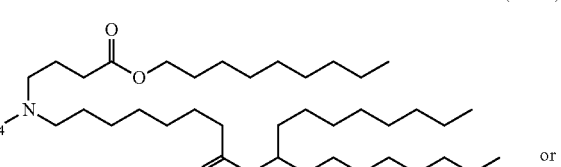

(IL-IIc)

or

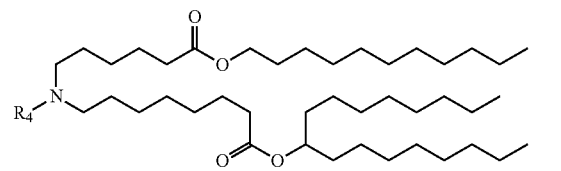

(IL-IIe)

or their N-oxides, or salts or isomers thereof, wherein $R_4$ is as described herein.

In another embodiment, the compounds of Formula (IL-I) are of Formula (IL-IIf):

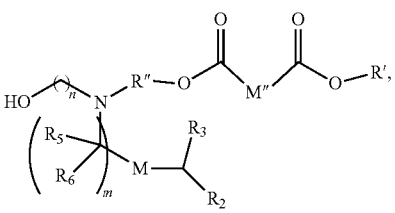

(IL-IIf)

or their N-oxides, or salts or isomers thereof, wherein M is —C(O)O— or —OC(O)—, M" is $C_{1-6}$ alkyl or $C_{2-6}$ alkenyl, $R_2$ and $R_3$ are independently selected from the group consisting of $C_{5-14}$ alkyl and $C_{5-14}$ alkenyl, and n is selected from 2, 3, and 4.

In a further embodiment, the compounds of Formula (IL-I) are of Formula (IL-IId):

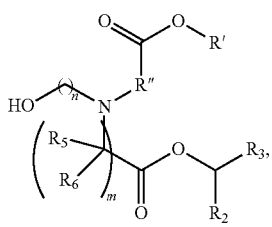
(IL-IId)

or their N-oxides, or salts or isomers thereof, wherein n is 2, 3, or 4; and m, R', R", and $R_2$ through $R_6$ are as described herein. In some embodiments, each of $R_2$ and $R_3$ may be independently selected from the group consisting of $C_{5-14}$ alky and $C_{5-14}$ alkenyl.

In some embodiments, the compounds of Formula (IL-I) are of Formula (IL-IIg):

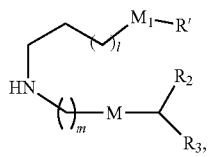
(IL-IIg)

or their N-oxides, or salts or isomers thereof, wherein 1 is selected from 1, 2, 3, 4, and 5; m is selected from 5, 6, 7, 8, and 9; $M_1$ is a bond or M'; M and M' are independently selected from from —C(O)O—, —OC(O)—, —OC(O)-M"-C(O)O—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl. In some embodiments, M" is $C_{1-6}$ alkyl (e.g., $C_{1-4}$ alkyl) or $C_{2-6}$ alkenyl (e.g. $C_{2-4}$ alkenyl). In some embodiments, $R_2$ and $R_3$ are independently selected from the group consisting of $C_{5-14}$ alkyl and $C_{5-14}$ alkenyl.

In some embodiments, the ionizable lipids are one or more of the compounds described in U.S. Application Nos. 62/220,091, 62/252,316, 62/253,433, 62/266,460, 62/333,557, 62/382,740, 62/393,940, 62/471,937, 62/471,949, 62/475,140, and 62/475,166, and PCT Application No. PCT/US2016/052352.

In some embodiments, the ionizable lipids are selected from Compounds 1-280 described in U.S. Application No. 62/475,166.

In some embodiments, the ionizable lipid is

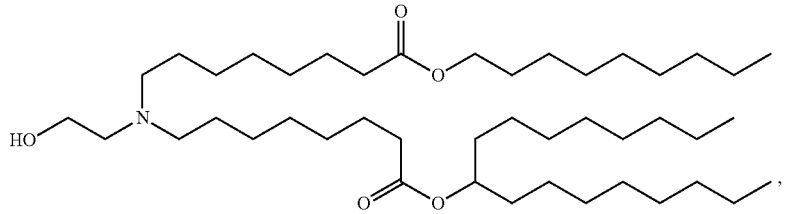 [SMILES: CCCCCCCCCOC(=O)CCCCCCCN(CCO)CCCCCCCC(=O)OC(CCCCCCCC)CCCCCCCC]

or a salt thereof.

In some embodiments, the ionizable lipid is

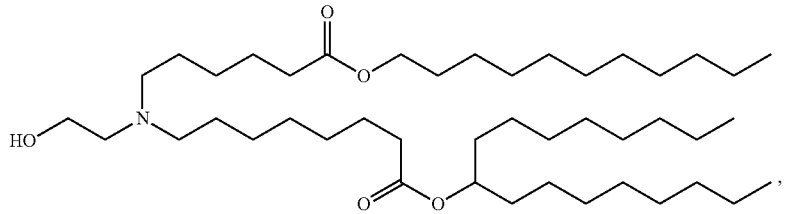 [SMILES: CCCCCCCCCCCOC(=O)CCCCCN(CCO)CCCCCCCC(=O)OC(CCCCCCCC)CCCCCCCC]

or a salt thereof.

In some embodiments, the ionizable lipid is

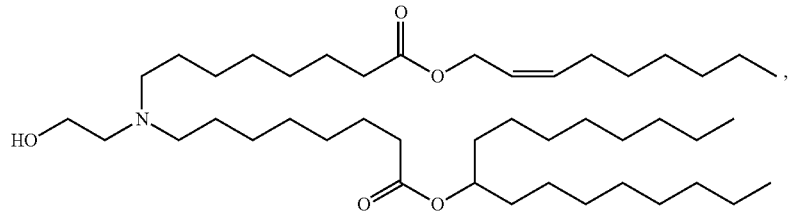 [SMILES: CCCCCC/C=C\COC(=O)CCCCCCCN(CCO)CCCCCCCC(=O)OC(CCCCCCCC)CCCCCCCC]

or a salt thereof.

In some embodiments, the ionizable lipid is

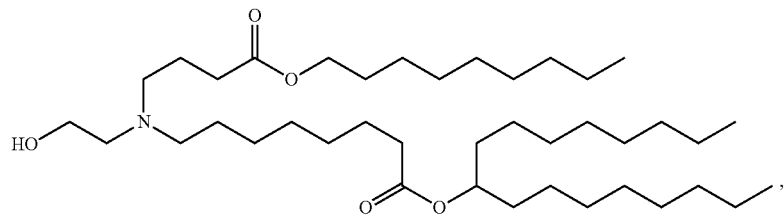 [SMILES: CCCCCCCCCOC(=O)CCCN(CCO)CCCCCCCC(=O)OC(CCCCCCCC)CCCCCCCC]

or a salt thereof.

In some embodiments, the ionizable lipids of the present disclosure may be one or more of compounds of formula (IL-III):

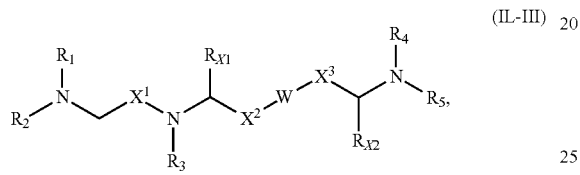

or salts or isomers thereof, wherein,
W is

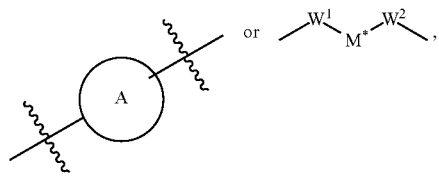

t is 1 or 2;
$A_1$ and $A_2$ are each independently selected from CH or N;
Z is $CH_2$ or absent wherein when Z is $CH_2$, the dashed lines (1) and (2) each represent a single bond; and when Z is absent, the dashed lines (1) and (2) are both absent;
$R_1$, $R_2$, $R_3$, $R_4$, and $R_5$ are independently selected from the group consisting of $C_{5-20}$ alkyl, $C_{5-20}$ alkenyl, —R"MR', —R*YR", —YR", and —R*OR";
$R_{X1}$ and $R_{X2}$ are each independently H or $C_{1-3}$ alkyl;
each M is independently selected from the group consisting of —C(O)O—, —OC(O)—, —OC(O)O—, —C(O)N(R')—, —N(R')C(O)—, —C(O)—, —C(S)—, —C(S)S—, —SC(S)—, —CH(OH)—, —P(O)(OR')O—, —S(O)$_2$—, —C(O)S—, —SC(O)—, an aryl group, and a heteroaryl group;
M* is $C_1$-$C_6$ alkyl,
$W^1$ and $W^2$ are each independently selected from the group consisting of —O— and —N($R_6$)—;
each $R_6$ is independently selected from the group consisting of H and $C_{1-5}$ alkyl;
$X^1$, $X^2$, and $X^3$ are independently selected from the group consisting of a bond, —$CH_2$—, —$(CH_2)_2$—, —CHR—, —CHY—, —C(O)—, —C(O)O—, —OC(O)—, —$(CH_2)_n$—C(O)—, —C(O)—$(CH_2)_n$—, —$(CH_2)_n$—C(O)O—, —OC(O)—$(CH_2)_n$—, —$(CH_2)_n$—OC(O)—, —C(O)O—$(CH_2)_n$—, —CH(OH)—, —C(S)—, and —CH(SH)—;
each Y is independently a $C_{3-6}$ carbocycle;
each R* is independently selected from the group consisting of $C_{1-12}$ alkyl and $C_{2-12}$ alkenyl;
each R is independently selected from the group consisting of $C_{1-3}$ alkyl and a $C_{3-6}$ carbocycle;
each R' is independently selected from the group consisting of $C_{1-12}$ alkyl, $C_{2-12}$ alkenyl, and H;
each R" is independently selected from the group consisting of $C_{3-12}$ alkyl, $C_{3-12}$ alkenyl and —R*MR'; and
n is an integer from 1-6;
wherein when ring A is

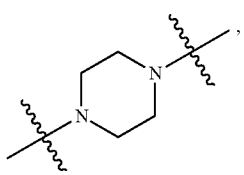 [SMILES: *N1CCN(*)CC1]

then
i) at least one of $X^1$, $X^2$, and $X^3$ is not —$CH_2$—; and/or
ii) at least one of $R_1$, $R_2$, $R_3$, $R_4$, and $R_5$ is —R"MR'.

In some embodiments, the compound is of any of formulae (IL-IIIa1)-(IL-IIIa8):

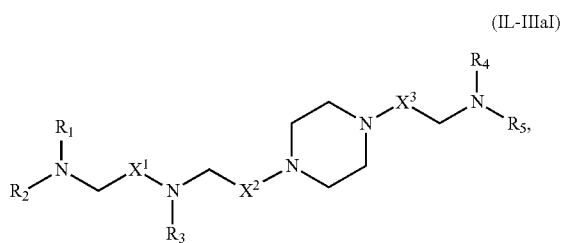

(IL-IIIa1)

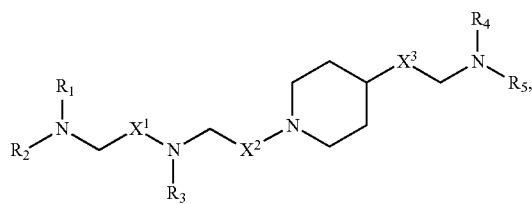
(IL-IIIa2)

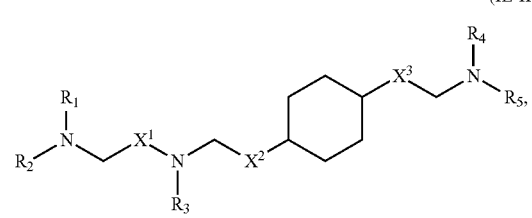
(IL-IIIa3)

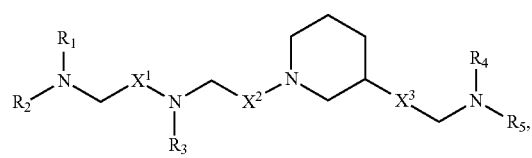
(IL-IIIa4)

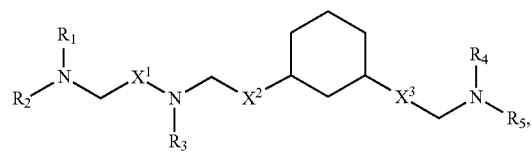
(IL-IIIa5)

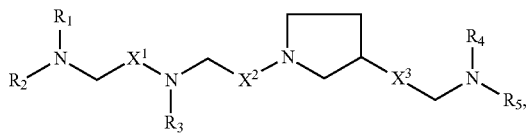
(IL-IIIa6)

(IL-IIIa7)

(IL-IIIa8)

In some embodiments, the ionizable lipids are one or more of the compounds described in U.S. Application Nos. 62/271,146, 62/338,474, 62/413,345, and 62/519,826, and PCT Application No. PCT/US2016/068300.

In some embodiments, the ionizable lipids are selected from Compound 1-156 described in U.S. Application No. 62/519,826.

In some embodiments, the ionizable lipids are selected from Compounds 1-16, 42-66, 68-76, and 78-156 described in U.S. Application No. 62/519,826.

In some embodiments, the ionizable lipid is

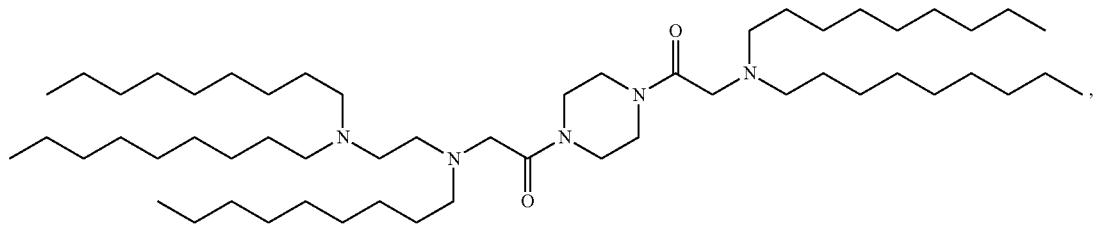 [SMILES: CCCCCCCCCN(CCCCCCCCC)CCN(CCCCCCCCC)CC(=O)N1CCN(C(=O)CN(CCCCCCCCC)CCCCCCCCC)CC1]

or a salt thereof.

The central amine moiety of a lipid according to Formula (IL-1), (IL-IA), (IL-IB), (IL-II), (IL-IIa), (IL-IIb), (IL-IIc), (IL-IId), (IL-IIe), (IL-IIf), (IL-IIg), (IL-III), (IL-IIIa1), (IL-IIIa2), (IL-IIIa3), (IL-IIIa4), (IL-IIIa5), (IL-IIIa6), (IL-IIIa7), or (IL-IIIa8) may be protonated at a physiological pH. Thus, a lipid may have a positive or partial positive charge at physiological pH. Such lipids may be referred to as cationic or ionizable (amino)lipids. Lipids may also be zwitterionic, i.e., neutral molecules having both a positive and a negative charge.

In some embodiments, the ionizable lipid is selected from the group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraazaoctatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)-[1,3]-dioxolane (DLin-KC2-DMA), 1,2-dioleyloxy-N,N-dimethylaminopropane (DODMA), 2-({8-[(3β)-cholest-5-en-3-yloxy]octyl}oxy)-N,N-dimethyl-3-[(9Z,12Z)-octadeca-9,12-dien-1-yl oxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)), and (2S)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)).

Polyethylene Glycol (PEG) Lipids

As used herein, the term "PEG lipid" refers to polyethylene glycol (PEG)-modified lipids. Non-limiting examples of PEG lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. In some embodiments, a PEG lipid can be PEG-c-DOMG, PEG-DMG, PEG-DLPE, PEG-DMPE, PEG-DPPC, or a PEG-DSPE lipid.

In some embodiments, the PEG lipid includes, but are not limited to, 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA).

In one embodiment, the PEG lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

In some embodiments, the lipid moiety of the PEG lipids includes those having lengths of from about $C_{14}$ to about $C_{22}$, preferably from about $C_{14}$ to about $C_{16}$. In some embodiments, a PEG moiety, for example an mPEG-NH$_2$, has a size of about 1000, 2000, 5000, 10,000, 15,000 or 20,000 daltons. In one embodiment, the PEG lipid is PEG$_{2k}$-DMG.

In one embodiment, the lipid nanoparticles described herein can comprise a PEG lipid which is a non-diffusible PEG. Non-limiting examples of non-diffusible PEGs include PEG-DSG and PEG-DSPE.

PEG lipids are known in the art, such as those described in U.S. Pat. No. 8,158,601 and International Publ. No. WO 2015/130584 A2, which are incorporated herein by reference in their entirety.

In general, some of the other lipid components (e.g., PEG lipids) of various formulae, described herein may be synthesized as described International Patent Application No. PCT/US2016/000129, filed Dec. 10, 2016, entitled "Compositions and Methods for Delivery of Therapeutic Agents," which is incorporated by reference in its entirety.

The lipid component of a lipid nanoparticle composition may include one or more molecules comprising polyethylene glycol, such as PEG or PEG-modified lipids. Such species may be alternately referred to as PEGylated lipids. A PEG lipid is a lipid modified with polyethylene glycol. A PEG lipid may be selected from the non-limiting group including PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. In some embodiments, a PEG lipid may be PEG-c-DOMG, PEG-DMG, PEG-DLPE, PEG-DMPE, PEG-DPPC, or a PEG-DSPE lipid.

In one embodiment, PEG lipids useful in the present invention can be PEGylated lipids described in International Publication No. WO2012099755, the contents of which is herein incorporated by reference in its entirety. Any of these exemplary PEG lipids described herein may be modified to comprise a hydroxyl group on the PEG chain. In some embodiments, the PEG lipid is a PEG-OH lipid. As generally defined herein, a "PEG-OH lipid" (also referred to herein as "hydroxy-PEGylated lipid") is a PEGylated lipid having one or more hydroxyl (—OH) groups on the lipid. In some embodiments, the PEG-OH lipid includes one or more hydroxyl groups on the PEG chain. In some embodiments, a PEG-OH or hydroxy-PEGylated lipid comprises an —OH group at the terminus of the PEG chain. Each possibility represents a separate embodiment of the present invention.

In some embodiments, a PEG lipid useful in the present invention is a compound of Formula (PL-I). Provided herein are compounds of Formula (PL-I):

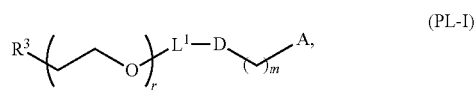

(PL-I)

or salts thereof, wherein:

$R_3$ is —OR$^O$;

$R^O$ is hydrogen, optionally substituted alkyl, or an oxygen protecting group;

r is an integer between 1 and 100, inclusive;

$L^1$ is optionally substituted $C_{1-10}$ alkylene, wherein at least one methylene of the optionally substituted $C_{1-10}$ alkylene is independently replaced with optionally substituted carbocyclylene, optionally substituted heterocyclylene, optionally substituted arylene, optionally substituted heteroarylene, O, N($R^N$), S, C(O), C(O)N($R^N$), NR$^N$C(O) C(O)O, OC(O), OC(O)O, OC(O)N($R^N$), NR$^N$C(O)O, or NR$^N$C(O)N($R^N$);

D is a moiety obtained by click chemistry or a moiety cleavable under physiological conditions;

m is 0, 1, 2, 3, 4, 5, 6, 7, 8, 9, or 10;

A is of the formula:

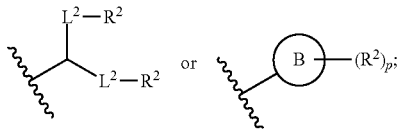

each instance of $L^2$ is independently a bond or optionally substituted $C_{1-6}$ alkylene, wherein one methylene unit of the optionally substituted $C_{1-6}$ alkylene is optionally replaced with O, N($R^N$), S, C(O), C(O)N($R^N$), $NR^NC$(O), C(O)O, OC(O), OC(O)O, OC(O)N($R^N$), $NR^N$C(O)O or $NR^N$C(O)N($R^N$);

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, N($R^N$), O, S, C(O), C(O)N($R^N$), $NR^N$C(O), $NR^N$C(O)N($R^N$) C(O)O, OC(O), —OC(O)O, OC(O)N($R^N$), $NR^N$C(O)O, C(O)S, SC(O), C(=$NR^N$), C(=$NR^N$)N($R^N$), $NR^N$C(=$NR^N$) $NR^N$C(=$NR^N$)N($R^N$), C(S), C(S)N($R^N$), $NR^N$C(S), $NR^N$C(S)N($R^N$) S(O), OS(O), S(O)O, —OS(O)O, OS(O)$_2$, S(O)$_2$O, OS(O)$_2$O, N($R_N$)S(O), S(O)N($R_N$), N($R_N$)S(O)N($R_N$), OS(O)N($R_N$) N($R_N$)S(O)O, S(O)$_2$, N($R_N$)S(O)$_2$, S(O)$_2$N($R_N$), N($R_N$)S(O)$_2$N($R_N$), OS(O)$_2$N($R_N$), or —N($R^N$)S(O)$_2$O;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2.

In some embodiments, the compound of Formula (PL-I) is a PEG-OH lipid (i.e., $R^3$ is —$OR^O$, and $R^O$ is hydrogen). In some embodiments, the compound of Formula (PL-I) is of Formula (PL-I-OH):

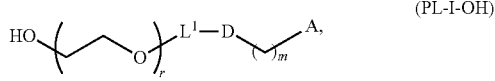

(PL-I-OH)

or a salt thereof.

In some embodiments, a PEG lipid useful in the present invention is a PEGylated fatty acid. In some embodiments, a PEG lipid useful in the present invention is a compound of Formula (PL-II). Provided herein are compounds of Formula (PL-II):

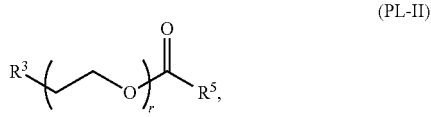

(PL-II)

or a salt thereof, wherein:

$R^3$ is-$OR^O$;

$R^O$ is hydrogen, optionally substituted alkyl or an oxygen protecting group;

r is an integer between 1 and 100;

$R^5$ is optionally substituted $C_{10-40}$ alkyl, optionally substituted $C_{10-40}$ alkenyl, or optionally substituted $C_{10-40}$ alkynyl; and optionally one or more methylene groups of $R^5$ are replaced with optionally substituted carbocyclylene, optionally substituted heterocyclylene, optionally substituted arylene, optionally substituted heteroarylene, N($R^N$), O, S, C(O), C(O)N($R^N$), —$NR^N$C(O), $NR^N$C(O)N($R^N$), C(O)O, OC(O), OC(O)O, OC(O)N($R^N$), NC(O)O C(O)S, SC(O), C(=$NR^N$), C(=$NR^N$)N($R^N$), $NR^N$C(=$NR^N$), $NR^N$C(=$NR^N$)N($R^N$), C(S), C(S)N($R^N$), $NR^N$C(S), —$NR^N$C(S)N($R^N$), S(O), OS(O), S(O)O, OS(O)O, OS(O)$_2$, S(O)$_2$O, OS(O)$_2$O, N($R^N$)S(O), —S(O)N($R^N$), N($R^N$)S(O)N($R^N$), OS(O)N($R^N$), N($R^N$)S(O)O, S(O)$_2$, N($R^N$)S(O)$_2$, S(O)$_2$N($R^N$), —N($R^N$)S(O)$_2$N($R^N$), OS(O)$_2$N($R^N$), or N($R^N$)S(O)$_2$O; and each instance of $R^N$ is independently hydrogen, optionally substituted alkyl, or a nitrogen protecting group.

In some embodiments, the compound of Formula (PL-II) is of Formula (PL-II-OH):

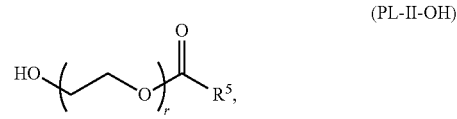

(PL-II-OH)

or a salt thereof, wherein:

r is an integer between 1 and 100;

$R^5$ is optionally substituted $C_{10-40}$ alkyl, optionally substituted $C_{10-40}$ alkenyl, or optionally substituted $C_{10-40}$ alkynyl; and optionally one or more methylene groups of $R^5$ are replaced with optionally substituted carbocyclylene, optionally substituted heterocyclylene, optionally substituted arylene, optionally substituted heteroarylene, N($R^N$), O, S, C(O), C(O)N($R^N$), —$NR^N$C(O), $NR^N$C(O)N($R^N$), C(O)O, OC(O), OC(O)O, OC(O)N($R^N$), $NR^N$C(O)O, C(O)S, SC(O), C(=$NR^N$), C(=$NR^N$)N($R^N$), $NR^N$C(=$NR^N$), $NR^N$C(=$NR^N$)N($R^N$), C(S), C(S)N($R^N$), $NR^N$C(S), —$NR^N$C(S)N($R^N$), S(O), OS(O), S(O)O, OS(O)O, OS(O)$_2$, S(O)$_2$O, OS(O)$_2$O, N($R_N$)S(O), —S(O)N($R^N$), N($R^N$)S(O)N($R^N$), OS(O)N($R^N$), N($R^N$)S(O)O, S(O)$_2$, N($R^N$)S(O)$_2$, S(O)$_2$N($R^N$), —N($R^N$)S(O)$_2$N($R^N$), OS(O)$_2$N($R^N$), or N($R^N$)S(O)$_2$O; and each instance of $R^N$ is independently hydrogen, optionally substituted alkyl, or a nitrogen protecting group.

In some embodiments, r is an integer between 10 to 80, between 20 to 70, between 30 to 60, or between 40 to 50.

In some embodiments, r is 45.

In some embodiments, $R^5$ is $C_{17}$ alkyl

In some embodiments, the compound of Formula (PL-II) is:

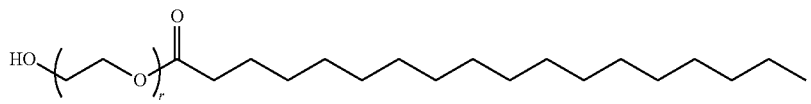

or a salt thereof.

In some embodiments, the compound of Formula (PL-II) is

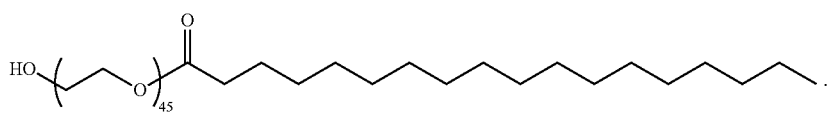

In some aspects, the lipid composition of the pharmaceutical compositions described herein does not comprise a PEG lipid.

In some embodiments, the PEG lipid is any one of the PEG lipids described in U.S. Application No. 62/520,530. In some embodiments, the PEG lipid is a compound of Formula (PL-III):

(PL-III)

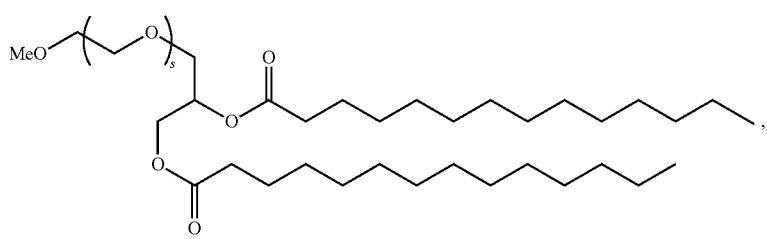

or a salt or isomer thereof, wherein s is an integer between 1 and 100.

In some embodiments, the PEG lipid is a compound of the following formula:

(PEG-2)

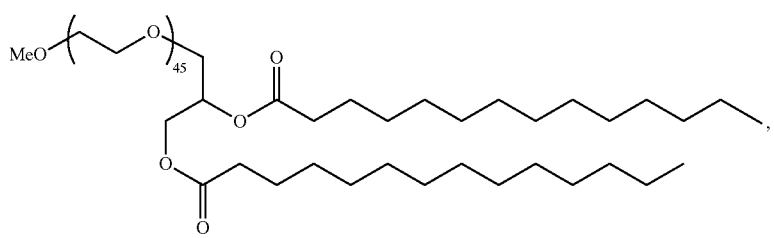

or a salt or isomer thereof.

Surfactants

In some embodiments, the modifying agent is a surfactant.

In some embodiments, the surfactant is an amphiphilic polymer.

For example, the amphiphilic polymer is a block copolymer.

For example, the amphiphilic polymer is a lyoprotectant.

For example, amphiphilic polymer has a critical micelle concentration (CMC) of less than $2\times10^{-4}$ M in water at about 30° C. and atmospheric pressure.

(PEG-1)

For example, amphiphilic polymer has a critical micelle concentration (CMC) ranging between about $0.1\times10^{-4}$ M and about $1.3\times10^{-4}$ M in water at about 30° C. and atmospheric pressure.

For example, the concentration of the amphiphilic polymer ranges between about its CMC and about 30 times of CMC (e.g., up to about 25 times, about 20 times, about 15 times, about 10 times, about 5 times, or about 3 times of its CMC) in the formulation, e.g., prior to freezing or lyophilization.

For example, the amphiphilic polymer is selected from poloxamers (Pluronic®), poloxamines (Tetronic®), polyoxyethylene glycol sorbitan alkyl esters (polysorbates) and polyvinyl pyrrolidones (PVPs).

For example, the amphiphilic polymer is a poloxamer. For example, the amphiphilic polymer is of the following structure:

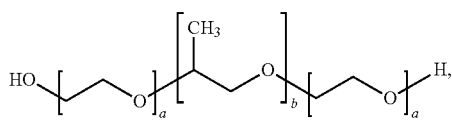

wherein a is an integer between 10 and 150 and b is an integer between 20 and 60. For example, a is about 12 and b is about 20, or a is about 80 and b is about 27, or a is about 64 and b is about 37, or a is about 141 and b is about 44, or a is about 101 and b is about 56.

For example, the amphiphilic polymer is P124, P188, P237, P338, or P407.

For example, the amphiphilic polymer is P188 (e.g., Poloxamer 188, CAS Number 9003-11-6, also known as Kolliphor P188).

For example, the amphiphilic polymer is a poloxamine, e.g., tetronic 304 or tetronic 904.

For example, the amphiphilic polymer is a polyvinylpyrrolidone (PVP), such as PVP with molecular weight of 3 kDa, 10 kDa, or 29 kDa.

For example, the amphiphilic polymer is a polysorbate, such as PS 20.

In some embodiments, the surfactant is a non-ionic surfactant.

In some embodiments, the LNP modifying agent comprises a surfactant. In some embodiments, the surfactant is an amphiphilic polymer. In some embodiments, the surfactant is a non-ionic surfactant.

For example, the non-ionic surfactant is selected from the group consisting of polyethylene glycol ether (Brij), poloxamer, polysorbate, sorbitan, and derivatives thereof.

For example, the polyethylene glycol ether is a compound of Formula (S-1):

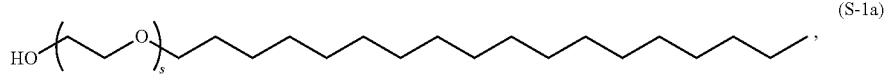

or a salt or isomer thereof, wherein:
t is an integer between 1 and 100;
$R^{1BRIJ}$ independently is $C_{10-40}$ alkyl, $C_{10-40}$ alkenyl, or $C_{10-40}$ alkynyl; and optionally one or more methylene groups of $R^{5PEG}$ are independently replaced with $C_{3-10}$ carbocyclylene, 4 to 10 membered heterocyclylene, $C_{6-10}$ arylene, 4 to 10 membered heteroarylene, —N($R^N$)—, —O—, —S—, —C(O)—, —C(O)N($R^N$)—, —$NR^NC(O)$—, —$NR^NC(O)N(R_N)$—, —C(O)O—, —OC(O)—, —OC(O)O—, —OC(O)N($R^N$)—, —$NR^NC(O)O$—, —C(O)S—, —SC(O)—, —C(=$NR^N$)—, —C(=$NR^N$)N($R^N$)—, —$NR^NC(=NR^N)$—, —$NR^NC(=NR^N)N(R^N)$—, —C(S)—, —C(S)N($R^N$)—, —$NR^NC(S)$—, —$NR^NC(S)N(R^N)$—, —S(O)—, —OS(O)—, —S(O)O—, —OS(O)O—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N($R^N$)S(O)O—, —S(O)$_2$—, —N($R^N$)S(O)$_2$—, —S(O)$_2$N($R^N$)—, —N($R^N$)S(O)$_2$N($R^N$)—, —OS(O)$_2$N($R^N$)—, or —N($R^N$)S(O)$_2$O—; and
each instance of $R^N$ is independently hydrogen, $C_{1-6}$ alkyl, or a nitrogen protecting group In some embodiment, $R^{1BRIJ}$ is $C_{18}$ alkyl. For example, the polyethylene glycol ether is a compound of Formula (S-1a):

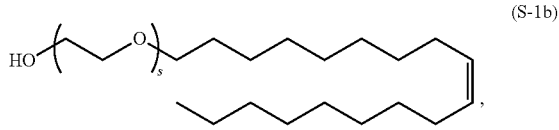

or a salt or isomer thereof, wherein s is an integer between 1 and 100.

In some embodiments, $R^{1BRIJ}$ is $C_{18}$ alkenyl. For example, the polyethylene glycol ether is a compound of Formula (S-1b):

(S-1b)

or a salt or isomer thereof, wherein s is an integer between 1 and 100.

In some embodiments, the poloxamer is selected from the group consisting of poloxamer 101, poloxamer 105, poloxamer 108, poloxamer 122, poloxamer 123, poloxamer 124, poloxamer 181, poloxamer 182, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 304, poloxamer 331, poloxamer 333, poloxamer 334, poloxamer 335, poloxamer 338, poloxamer 401, poloxamer 402, poloxamer 403, and poloxamer 407.

In some embodiments, the surfactant is Tween® 20, Tween® 40, Tween®, 60, or Tween® 80.

In some embodiments, the surfactant is Span® 20, Span® 40, Span® 60, Span® 65, Span® 80, or Span® 85.

In some embodiments, the surfactant is Brij® C10, Brij® S10, Brij® 58, Brij® S100, Brij® 010, Brij® 020, Brij® S20, Brij® 58, Brij® 93.

In some embodiments, the surfactant is PVP 10 k or PVP 40 k.

In some embodiments, the concentration of the non-ionic surfactant in the nucleic acid LNP composition ranges from about 0.00001% w/v to about 1% w/v, e.g., from about 0.00005% w/v to about 0.5% w/v, or from about 0.0001% w/v to about 0.1% w/v.

In some embodiments, the concentration of the non-ionic surfactant in the nucleic acid LNP formulation ranges from about 0.000001 wt % to about 1 wt %, e.g., from about 0.000002 wt % to about 0.8 wt %, or from about 0.000005 wt % to about 0.5 wt %.

In some embodiments, the concentration of the PEG lipid in the nucleic acid LNP formulation ranges from about 0.01% by molar to about 50% by molar, e.g., from about 0.05% by molar to about 20% by molar, from about 0.07% by molar to about 10% by molar, from about 0.1% by molar to about 8% by molar, from about 0.2% by molar to about 5% by molar, or from about 0.25% by molar to about 3% by molar.

Structural Lipids

As used herein, the term "structural lipid" refers to sterols and also to lipids containing sterol moieties.

Incorporation of structural lipids in the lipid nanoparticle may help mitigate aggregation of other lipids in the particle. Structural lipids can be selected from the group including but not limited to, cholesterol, fecosterol, sitosterol, ergosterol, campesterol, stigmasterol, brassicasterol, tomatidine, tomatine, ursolic acid, alpha-tocopherol, hopanoids, phytosterols, steroids, and mixtures thereof. In some embodiments, the structural lipid is a mixture of two or more components each independently selected from cholesterol, fecosterol, sitosterol, ergosterol, campesterol, stigmasterol, brassicasterol, tomatidine, tomatine, ursolic acid, alpha-tocopherol, hopanoids, phytosterols, and steroids. In some embodiments, the structural lipid is a sterol. In some embodiments, the structural lipid is a mixture of two or more sterols. As defined herein, "sterols" are a subgroup of steroids consisting of steroid alcohols. In some embodiments, the structural lipid is a steroid. In some embodiments, the structural lipid is cholesterol. In some embodiments, the structural lipid is an analog of cholesterol. In some embodiments, the structural lipid is alpha-tocopherol.

In some embodiments, the structural lipids may be one or more structural lipids described in U.S. Application No. 62/520,530.

Phospholipids

Phospholipids may assemble into one or more lipid bilayers. In general, phospholipids comprise a phospholipid moiety and one or more fatty acid moieties.

A phospholipid moiety can be selected, for example, from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin.

A fatty acid moiety can be selected, for example, from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

Particular phospholipids can facilitate fusion to a membrane. In some embodiments, a cationic phospholipid can interact with one or more negatively charged phospholipids of a membrane (e.g., a cellular or intracellular membrane). Fusion of a phospholipid to a membrane can allow one or more elements (e.g., a therapeutic agent) of a lipid-containing composition (e.g., LNPs) to pass through the membrane permitting, e.g., delivery of the one or more elements to a target tissue.

Non-natural phospholipid species including natural species with modifications and substitutions including branching, oxidation, cyclization, and alkynes are also contemplated. In some embodiments, a phospholipid can be functionalized with or cross-linked to one or more alkynes (e.g., an alkenyl group in which one or more double bonds is replaced with a triple bond). Under appropriate reaction conditions, an alkyne group can undergo a copper-catalyzed cycloaddition upon exposure to an azide. Such reactions can be useful in functionalizing a lipid bilayer of a nanoparticle composition to facilitate membrane permeation or cellular recognition or in conjugating a nanoparticle composition to a useful component such as a targeting or imaging moiety (e.g., a dye).

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin.

In some embodiments, a phospholipid useful or potentially useful in the present invention is an analog or variant of DSPC. In some embodiments, a phospholipid useful or potentially useful in the present invention is a compound of Formula (PL-I):

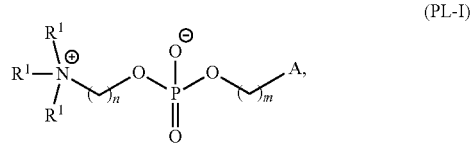

(PL-I)

or a salt thereof, wherein:

each $R^1$ is independently optionally substituted alkyl; or optionally two $R^1$ are joined together with the intervening atoms to form optionally substituted monocyclic carbocyclyl or optionally substituted monocyclic heterocyclyl; or optionally three $R^1$ are joined together with the intervening atoms to form optionally substituted bicyclic carbocyclyl or optionally substitute bicyclic heterocyclyl;

n is 1, 2, 3, 4, 5, 6, 7, 8, 9, or 10;

m is 0, 1, 2, 3, 4, 5, 6, 7, 8, 9, or 10;

A is of the formula:

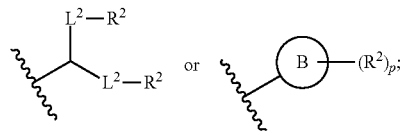

each instance of $L^2$ is independently a bond or optionally substituted $C_{1-6}$ alkylene, wherein one methylene unit of the optionally substituted $C_{1-6}$ alkylene is optionally replaced with —O—, —N($R^N$)—, —S—, —C(O)—, —C(O)N($R^N$)—, —$NR^NC(O)$—, —C(O)O—, —OC(O)O—, —OC(O)N($R^N$)—, —$NR^NC(O)O$—, or —$NR^NC(O)N(R^N)$—;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —$NR^NC(O)$—, —$NR^NC(O)N(R^N)$—, —C(O)O—, —OC(O)—, —OC(O)O—, —OC(O)N($R^N$)—, —$NR^NC(O)O$—, —C(O)S—, —SC(O)—, —C(=$NR^N$)—, —C(=$NR^N$)N($R^N$)—, —$NR^NC(=NR^N)$—, —$NR^NC(=NR^N)N(R^N)$—, —C(S)—, —C(S)N($R^N$)—, —$NR^NC(S)$—, —$NR^NC(S)N(R^N)$—, —S(O)—, —OS(O)—, —S(O)O—, —OS(O)O—, —OS(O)$_2$—, —S(O)$_2$O—, —OS(O)$_2$O—, —N(R$^N$)S(O)—, —S(O)N(R$^N$)—, —N(R$^N$)S(O)N(R$^N$)—, —OS(O)N(R$^N$)—, —N(R$^N$)S(O)O—, —S(O)$_2$—, —N(R$^N$)S(O)$_2$—, —S(O)$_2$N(R$^N$)—, —N(R$^N$)S(O)$_2$N(R$^N$)—, —OS(O)$_2$N(R$^N$)—, or —N(R$^N$)S(O)$_2$O—;

each instance of R$^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2;

provided that the compound is not of the formula:

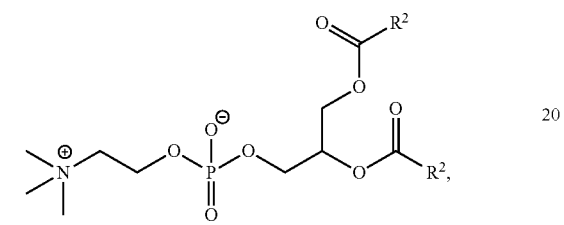

wherein each instance of R$^2$ is independently unsubstituted alkyl, unsubstituted alkenyl, or unsubstituted alkynyl.

In some embodiments, the phospholipids may be one or more of the phospholipids described in U.S. Application No. 62/520,530.

In some embodiments, the phospholipids may be selected from the non-limiting group consisting of 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), and sphingomyelin. In some embodiments, a LNP includes DSPC. In some embodiments, a LNP includes DOPE. In some embodiments, a LNP includes both DSPC and DOPE.

i) Phospholipid Head Modifications

In some embodiments, a phospholipid useful or potentially useful in the present invention comprises a modified phospholipid head (e.g., a modified choline group). In some embodiments, a phospholipid with a modified head is DSPC, or analog thereof, with a modified quaternary amine. In some embodiments, in embodiments of Formula (PL-I), at least one of R$^1$ is not methyl. In some embodiments, at least one of R$^1$ is not hydrogen or methyl. In some embodiments, the compound of Formula (PL-I) is one of the following formulae:

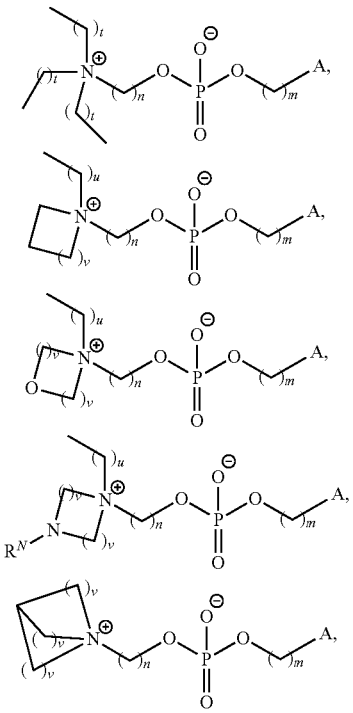

or a salt thereof, wherein:
each t is independently 1, 2, 3, 4, 5, 6, 7, 8, 9, or 10;
each u is independently 0, 1, 2, 3, 4, 5, 6, 7, 8, 9, or 10; and
each v is independently 1, 2, or 3.

In some embodiments, a compound of Formula (PL-I) is of Formula (PL-I-a):

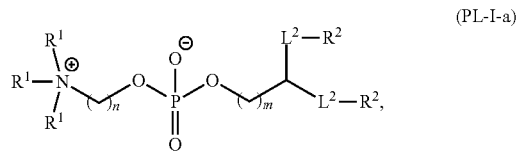

(PL-I-a)

or a salt thereof.

In some embodiments, a phospholipid useful or potentially useful in the present invention comprises a cyclic moiety in place of the glyceride moiety. In some embodiments, a phospholipid useful in the present invention is DSPC, or analog thereof, with a cyclic moiety in place of the glyceride moiety. In some embodiments, the compound of Formula (PL-I) is of Formula (PL-I-b):

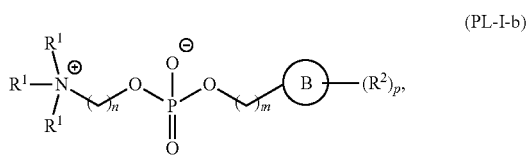

(PL-I-b)

or a salt thereof.

ii) Phospholipid Tail Modifications

In some embodiments, a phospholipid useful or potentially useful in the present invention comprises a modified tail. In some embodiments, a phospholipid useful or potentially useful in the present invention is DSPC, or analog thereof, with a modified tail. As described herein, a "modified tail" may be a tail with shorter or longer aliphatic chains, aliphatic chains with branching introduced, aliphatic chains with substituents introduced, aliphatic chains wherein one or more methylenes are replaced by cyclic or heteroatom groups, or any combination thereof. In some embodiments, In some embodiments, the compound of (PL-I) is of Formula (PL-I-a), or a salt thereof, wherein at least one instance of $R^2$ is each instance of $R^2$ is optionally substituted $C_{1-30}$ alkyl, wherein one or more methylene units of $R^2$ are independently replaced with optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —N$R^N$C(O)—, —N$R^N$C(O)N($R^N$)—, —C(O)O—, —OC(O)—, —OC(O)O—, —OC(O)N($R^N$)—, —N$R^N$C(O)O—, —C(O)S—, —SC(O)—, —C(=N$R^N$)—, —C(=N$R^N$)N($R^N$)—, —N$R^N$C(=N$R^N$)—, —N$R^N$C(=N$R^N$)N($R^N$)—, —C(S)—, —C(S)N($R^N$)—, —N$R^N$C(S)—, —N$R^N$C(S)N($R^N$)—, —S(O)—, —OS(O)—, —S(O)O—, —OS(O)O—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N($R^N$)S(O)O—, —S(O)$_2$—, —N($R^N$)S(O)$_2$—, —S(O)$_2$N($R^N$)—, —N($R^N$)S(O)$_2$N($R^N$)—, —OS(O)$_2$N($R^N$)—, or —N($R^N$)S(O)$_2$O—.

In some embodiments, the compound of Formula (PL-I) is of Formula (PL-I-c):

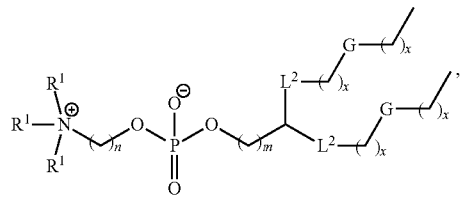

(PL-I-c)

or a salt thereof, wherein:
each x is independently an integer between 0-30, inclusive; and each instance is G is independently selected from the group consisting of optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —N$R^N$C(O)—, —N$R^N$C(O)N($R^N$)—, —C(O)O—, —OC(O)—, —OC(O)O—, —OC(O)N($R^N$)—, —N$R^N$C(O)O—, —C(O)S—, —SC(O)—, —C(=N$R^N$)—, —C(=N$R^N$)N($R^N$)—, —N$R^N$C(=N$R^N$)—, —N$R^N$C(=N$R^N$)N($R^N$)—, —C(S)—, —C(S)N($R^N$)—, —N$R^N$C(S)—, —N$R^N$C(S)N($R^N$)—, —S(O)—, —OS(O)—, —S(O)O—, —OS(O)O—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N($R^N$)S(O)O—, —S(O)$_2$—, —N($R^N$)S(O)$_2$—, —S(O)$_2$N($R^N$)—, —N($R^N$)S(O)$_2$N($R^N$)—, —OS(O)$_2$N($R^N$)—, or —N($R^N$)S(O)$_2$O—. Each possibility represents a separate embodiment of the present invention.

In some embodiments, a phospholipid useful or potentially useful in the present invention comprises a modified phosphocholine moiety, wherein the alkyl chain linking the quaternary amine to the phosphoryl group is not ethylene (e.g., n is not 2). Therefore, in some embodiments, a phospholipid useful or potentially useful in the present invention is a compound of Formula (PL-I), wherein n is 1, 3, 4, 5, 6, 7, 8, 9, or 10. In some embodiments, a compound of Formula (PL-I) is of one of the following formulae:

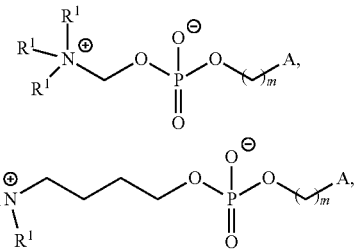

or a salt thereof.

Alternative Lipids

In some embodiments, an alternative lipid is used in place of a phospholipid of the present disclosure. Non-limiting examples of such alternative lipids include the following:

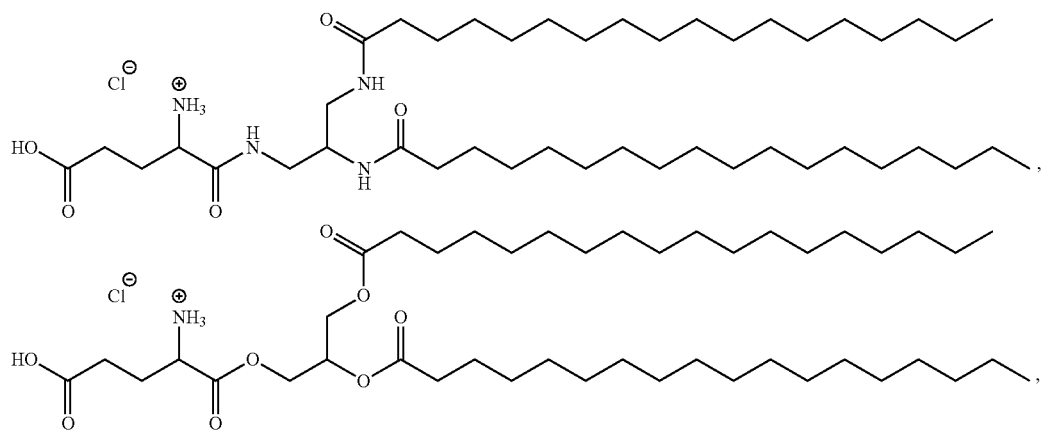

-continued

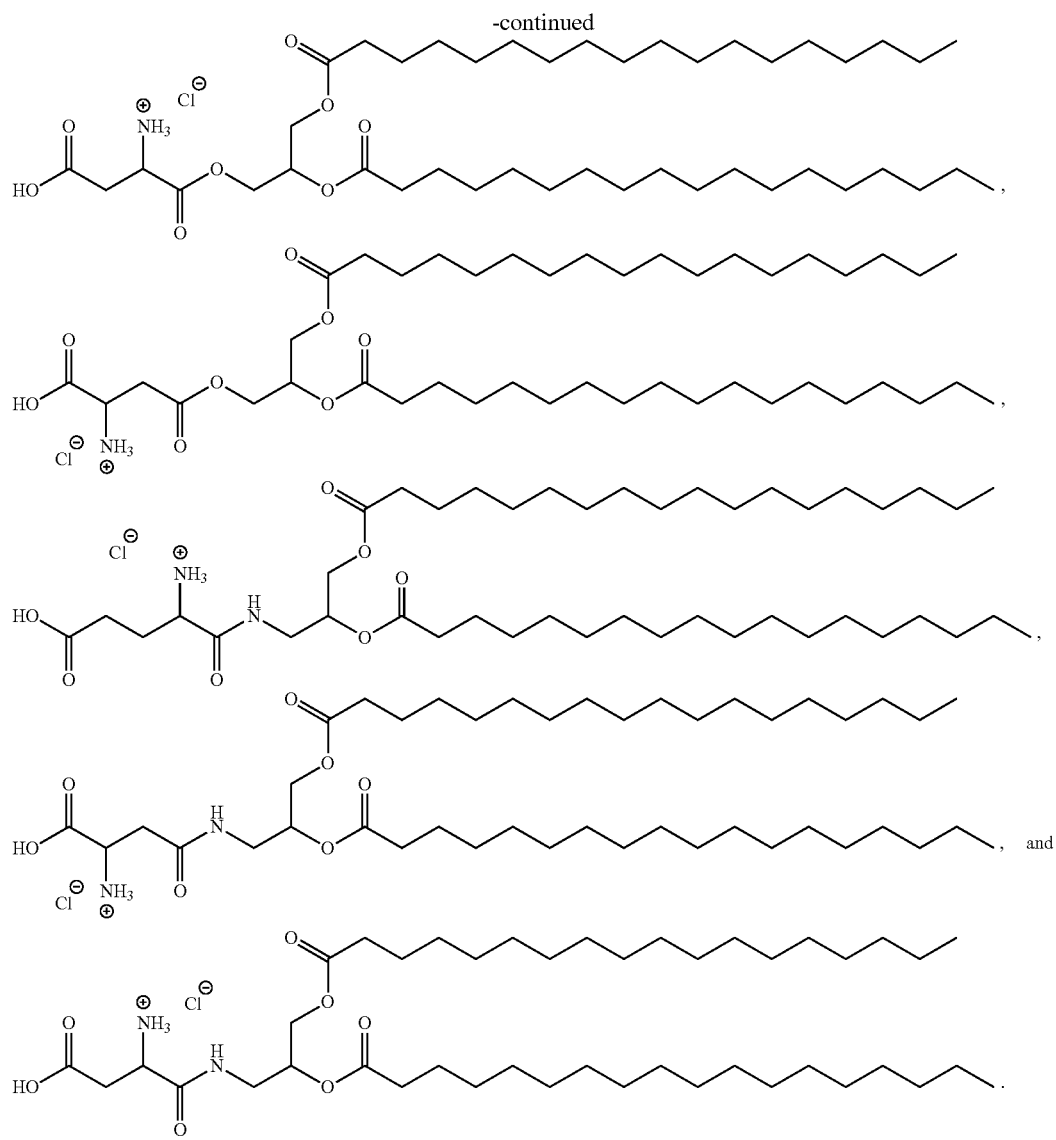

Adjuvants

In some embodiments, a LNP that includes one or more lipids described herein may further include one or more adjuvants, e.g., Glucopyranosyl Lipid Adjuvant (GLA), CpG oligodeoxynucleotides (e.g., Class A or B), poly(I:C), aluminum hydroxide, and Pam3CSK4.

Therapeutic Agents

Lipid nanoparticles may include one or more therapeutics and/or prophylactics, such as a nucleic acid. The disclosure features methods of delivering a therapeutic and/or prophylactic, such as a nucleic acid to a mammalian cell or organ, producing a polypeptide of interest in a mammalian cell, and treating a disease or disorder in a mammal in need thereof comprising administering to a mammal and/or contacting a mammalian cell with a LNP including a therapeutic and/or prophylactic, such as a nucleic acid.

Therapeutics and/or prophylactics include biologically active substances and are alternately referred to as "active agents". A therapeutic and/or prophylactic may be a substance that, once delivered to a cell or organ, brings about a desirable change in the cell, organ, or other bodily tissue or system. Such species may be useful in the treatment of one or more diseases, disorders, or conditions. In some embodiments, a therapeutic and/or prophylactic is a small molecule drug useful in the treatment of a particular disease, disorder, or condition. Examples of drugs useful in the lipid nanoparticles include, but are not limited to, antineoplastic agents (e.g., vincristine, doxorubicin, mitoxantrone, camptothecin, cisplatin, bleomycin, cyclophosphamide, methotrexate, and streptozotocin), antitumor agents (e.g., actinomycin D, vincristine, vinblastine, cytosine arabinoside, anthracyclines, alkylating agents, platinum compounds, antimetabolites, and nucleoside analogs, such as methotrexate and purine and pyrimidine analogs), anti-infective agents, local anesthetics (e.g., dibucaine and chlorpromazine), beta-adrenergic blockers (e.g., propranolol, timolol, and labetalol), antihypertensive agents (e.g., clonidine and hydralazine), anti-depressants (e.g., imipramine, amitriptyline, and doxepin), anti-conversants (e.g., phenytoin), antihistamines (e.g., diphenhydramine, chlorpheniramine, and promethazine), antibiotic/antibacterial agents (e.g., gentamycin, ciprofloxacin, and cefoxitin), antifungal agents (e.g., miconazole, terconazole, econazole, isoconazole, butaconazole, clotrimazole, itraconazole, nystatin, naftifine, and amphotericin B), antiparasitic agents, hormones, hormone antagonists, immunomodulators, neurotransmitter antagonists, antiglaucoma agents, vitamins, narcotics, and imaging agents.

In some embodiments, a therapeutic and/or prophylactic is a cytotoxin, a radioactive ion, a chemotherapeutic, a vaccine, a compound that elicits an immune response, and/or another therapeutic and/or prophylactic. A cytotoxin or cytotoxic agent includes any agent that may be detrimental to cells. Examples include, but are not limited to, taxol, cytochalasin B, gramicidin D, ethidium bromide, emetine, mitomycin, etoposide, teniposide, vincristine, vinblastine, colchicine, doxorubicin, daunorubicin, dihydroxyanthracinedione, mitoxantrone, mithramycin, actinomycin D, 1-dehydrotestosterone, glucocorticoids, procaine, teracaine, lidocaine, propranolol, puromycin, maytansinoids, e.g., maytansinol, rachelmycin (CC-1065), and analogs or homologs thereof. Radioactive ions include, but are not limited to iodine (e.g., iodine 125 or iodine 131), strontium 89, phosphorous, palladium, cesium, iridium, phosphate, cobalt, yttrium 90, samarium 153, and praseodymium. Vaccines include compounds and preparations that are capable of providing immunity against one or more conditions related to infectious diseases such as influenza, measles, human papillomavirus (HPV), rabies, meningitis, whooping cough, tetanus, plague, hepatitis, and tuberculosis and can include mRNAs encoding infectious disease derived antigens and/or epitopes. Vaccines also include compounds and preparations that direct an immune response against cancer cells and can include mRNAs encoding tumor cell derived antigens, epitopes, and/or neoepitopes. Compounds eliciting immune responses may include, but are not limited to, vaccines, corticosteroids (e.g., dexamethasone), and other species.

In other embodiments, a therapeutic and/or prophylactic is a protein. Therapeutic proteins useful in the nanoparticles in the disclosure include, but are not limited to, gentamycin, amikacin, insulin, erythropoietin (EPO), granulocyte-colony stimulating factor (G-CSF), granulocyte-macrophage colony stimulating factor (GM-CSF), Factor VIR, luteinizing hormone-releasing hormone (LHRH) analogs, interferons, heparin, Hepatitis B surface antigen, typhoid vaccine, and cholera vaccine. In some embodiments, a vaccine and/or a compound capable of eliciting an immune response is administered intramuscularly via a composition including a compound according to Formula (IL-I), (IL-IA), (IL-IB), (IL-II), (IL-IIa), (IL-IIb), (IL-IIc), (IL-IId), (IL-IIe), (IL-IIf), (IL-IIg), (IL-III), (IL-IIIa1), (IL-IIIa2), (IL-IIIa3), (IL-IIIa4), (IL-IIIa5), (IL-IIIa6), (IL-IIIa7), or (IL-IIIa8) (e.g., Compound 3, 18, 20, 26, or 29). Other therapeutics and/or prophylactics include, but are not limited to, antimetabolites (e.g., methotrexate, 6-mercaptopurine, 6-thioguanine, cytarabine, 5-fluorouracil dacarbazine), alkylating agents (e.g., mechlorethamine, thiotepa chlorambucil, rachelmycin (CC-1065), melphalan, carmustine (BSNU), lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

Polynucleotides and Nucleic Acids

In some embodiments, a therapeutic agent is a polynucleotide or nucleic acid (e.g., ribonucleic acid or deoxyribonucleic acid). The term "polynucleotide", in its broadest sense, includes any compound and/or substance that is or can be incorporated into an oligonucleotide chain. Exemplary polynucleotides for use in accordance with the present disclosure include, but are not limited to, one or more of deoxyribonucleic acid (DNA), ribonucleic acid (RNA) including messenger RNA (mRNA), hybrids thereof, RNAi-inducing agents, RNAi agents, siRNAs, shRNAs, miRNAs, antisense RNAs, ribozymes, catalytic DNA, RNAs that induce triple helix formation, aptamers, vectors, etc. In some embodiments, a therapeutic and/or prophylactic is an RNA. RNAs useful in the compositions and methods described herein can be selected from the group consisting of, but are not limited to, shortmers, antagomirs, antisense, ribozymes, small interfering RNA (siRNA), asymmetrical interfering RNA (aiRNA), microRNA (miRNA), Dicer-substrate RNA (dsRNA), small hairpin RNA (shRNA), transfer RNA (tRNA), messenger RNA (mRNA), and mixtures thereof. In some embodiments, the RNA is an mRNA.

In some embodiments, a therapeutic and/or prophylactic is an mRNA. An mRNA may encode any polypeptide of interest, including any naturally or non-naturally occurring or otherwise modified polypeptide. A polypeptide encoded by an mRNA may be of any size and my have any secondary structure or activity. In some embodiments, a polypeptide encoded by an mRNA may have a therapeutic effect when expressed in a cell.

In other embodiments, a therapeutic and/or prophylactic is an siRNA. An siRNA may be capable of selectively knocking down or down regulating expression of a gene of interest. For example, an siRNA could be selected to silence a gene associated with a particular disease, disorder, or condition upon administration to a subject in need thereof of a LNP including the siRNA. An siRNA may comprise a sequence that is complementary to an mRNA sequence that encodes a gene or protein of interest. In some embodiments, the siRNA may be an immunomodulatory siRNA.

In some embodiments, a therapeutic and/or prophylactic is an shRNA or a vector or plasmid encoding the same. An shRNA may be produced inside a target cell upon delivery of an appropriate construct to the nucleus. Constructs and mechanisms relating to shRNA are well known in the relevant arts.

Nucleic acids and polynucleotides useful in the disclosure typically include a first region of linked nucleosides encoding a polypeptide of interest (e.g., a coding region), a first flanking region located at the 5'-terminus of the first region (e.g., a 5'-UTR), a second flanking region located at the 3'-terminus of the first region (e.g., a 3'-UTR) at least one 5'-cap region, and a 3'-stabilizing region. In some embodiments, a nucleic acid or polynucleotide further includes a poly-A region or a Kozak sequence (e.g., in the 5'-UTR). In some cases, polynucleotides may contain one or more intronic nucleotide sequences capable of being excised from the polynucleotide. In some embodiments, a polynucleotide or nucleic acid (e.g., an mRNA) may include a 5' cap structure, a chain terminating nucleotide, a stem loop, a polyA sequence, and/or a polyadenylation signal. Any one of the regions of a nucleic acid may include one or more alternative components (e.g., an alternative nucleoside). For example, the 3'-stabilizing region may contain an alternative nucleoside such as an L-nucleoside, an inverted thymidine, or a 2'-O-methyl nucleoside and/or the coding region, 5-UTR, 3'-UTR, or cap region may include an alternative nucleoside such as a 5-substituted uridine (e.g., 5-methoxyuridine), a 1-substituted pseudouridine (e.g., 1-methyl-pseudouridine), and/or a 5-substituted cytidine (e.g., 5-methyl-cytidine).

Generally, the shortest length of a polynucleotide can be the length of the polynucleotide sequence that is sufficient to encode for a dipeptide. In another embodiment, the length of the polynucleotide sequence is sufficient to encode for a tripeptide. In another embodiment, the length of the polynucleotide sequence is sufficient to encode for a tetrapeptide. In another embodiment, the length of the polynucleotide sequence is sufficient to encode for a pentapeptide. In another embodiment, the length of the polynucleotide sequence is sufficient to encode for a hexapeptide. In another embodiment, the length of the polynucleotide sequence is sufficient to encode for a heptapeptide. In another embodiment, the length of the polynucleotide sequence is sufficient to encode for an octapeptide. In another embodiment, the length of the polynucleotide sequence is sufficient to encode for a nonapeptide. In another embodiment, the length of the polynucleotide sequence is sufficient to encode for a decapeptide.

Examples of dipeptides that the alternative polynucleotide sequences can encode for include, but are not limited to, carnosine and anserine.

In some cases, a polynucleotide is greater than 30 nucleotides in length. In another embodiment, the polynucleotide molecule is greater than 35 nucleotides in length. In another embodiment, the length is at least 40 nucleotides. In another embodiment, the length is at least 45 nucleotides. In another embodiment, the length is at least 50 nucleotides. In another embodiment, the length is at least 55 nucleotides. In another embodiment, the length is at least 60 nucleotides. In another embodiment, the length is at least 80 nucleotides. In another embodiments, the length is at least 90 nucleotides. In another embodiment, the length is at least 100 nucleotides. In another embodiment, the length is at least 120 nucleotides. In another embodiment, the length is at least 140 nucleotides. In another embodiment, the length is at least 160 nucleotides. In another embodiment, the length is at least 180 nucleotides. In another embodiment, the length is at least 200 nucleotides. In another embodiment, the length is at least 250 nucleotides. In another embodiment, the length is at least 300 nucleotides. In another embodiment, the length is at least 350 nucleotides. In another embodiment, the length is at least 400 nucleotides. In another embodiment, the length is at least 450 nucleotides. In another embodiment, the length is at least 500 nucleotides. In another embodiment, the length is at least 600 nucleotides. In another embodiment, the length is at least 700 nucleotides. In another embodiment, the length is at least 800 nucleotides. In another embodiment, the length is at least 900 nucleotides. In another embodiment, the length is at least 1000 nucleotides. In another embodiment, the length is at least 1100 nucleotides. In another embodiment, the length is at least 1200 nucleotides. In another embodiment, the length is at least 1300 nucleotides. In another embodiment, the length is at least 1400 nucleotides. In another embodiment, the length is at least 1500 nucleotides. In another embodiment, the length is at least 1600 nucleotides. In another embodiment, the length is at least 1800 nucleotides. In another embodiment, the length is at least 2000 nucleotides. In another embodiment, the length is at least 2500 nucleotides. In another embodiment, the length is at least 3000 nucleotides. In another embodiment, the length is at least 4000 nucleotides. In another embodiment, the length is at least 5000 nucleotides, or greater than 5000 nucleotides.

Nucleic acids and polynucleotides may include one or more naturally occurring components, including any of the canonical nucleotides A (adenosine), G (guanosine), C (cytosine), U (uridine), or T (thymidine). In some embodiments, all or substantially all of the nucleotides comprising (a) the 5'-UTR, (b) the open reading frame (ORF), (c) the 3'-UTR, (d) the poly A tail, and any combination of (a, b, c, or d above) comprise naturally occurring canonical nucleotides A (adenosine), G (guanosine), C (cytosine), U (uridine), or T (thymidine).

Nucleic acids and polynucleotides may include one or more alternative components, as described herein, which impart useful properties including increased stability and/or the lack of a substantial induction of the innate immune response of a cell into which the polynucleotide is introduce. For example, an alternative polynucleotide or nucleic acid exhibits reduced degradation in a cell into which the polynucleotide or nucleic acid is introduced, relative to a corresponding unaltered polynucleotide or nucleic acid. These alternative species may enhance the efficiency of protein production, intracellular retention of the polynucleotides, and/or viability of contacted cells, as well as possess reduced immunogenicity.

Polynucleotides and nucleic acids may be naturally or non-naturally occurring. Polynucleotides and nucleic acids may include one or more modified (e.g., altered or alternative) nucleobases, nucleosides, nucleotides, or combinations thereof. The nucleic acids and polynucleotides useful in a LNP can include any useful modification or alteration, such as to the nucleobase, the sugar, or the internucleoside linkage (e.g., to a linking phosphate, to a phosphodiester linkage, to the phosphodiester backbone). In some embodiments, alterations (e.g., one or more alterations) are present in each of the nucleobase, the sugar, and the internucleoside linkage. Alterations according to the present disclosure may be alterations of ribonucleic acids (RNAs) to deoxyribonucleic acids (DNAs), e.g., the substitution of the 2'-OH of the ribofuranosyl ring to 2'-H, threose nucleic acids (TNAs), glycol nucleic acids (GNAs), peptide nucleic acids (PNAs), locked nucleic acids (LNAs), or hybrids thereof. Additional alterations are described herein.

Polynucleotides and nucleic acids may or may not be uniformly altered along the entire length of the molecule. For example, one or more or all types of nucleotide (e.g., purine or pyrimidine, or any one or more or all of A, G, U, C) may or may not be uniformly altered in a polynucleotide or nucleic acid, or in a given predetermined sequence region thereof. In some instances, all nucleotides X in a polynucleotide (or in a given sequence region thereof) are altered, wherein X may be any one of nucleotides A, G, U, C, or any one of the combinations A+G, A+U, A+C, G+U, G+C, U+C, A+G+U, A+G+C, G+U+C, or A+G+U+C.

Different sugar alterations and/or internucleoside linkages (e.g., backbone structures) may exist at various positions in a polynucleotide. One of ordinary skill in the art will appreciate that the nucleotide analogs or other alteration(s) may be located at any position(s) of a polynucleotide such that the function of the polynucleotide is not substantially decreased. An alteration may also be a 5'- or 3'-terminal alteration. In some embodiments, the polynucleotide includes an alteration at the 3'-terminus. The polynucleotide may contain from about 1% to about 100% alternative nucleotides (either in relation to overall nucleotide content, or in relation to one or more types of nucleotide, i.e., any one or more of A, G, U, or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100% from 90% to 95%, from 90% to 100%, and from 95% to 100%). It will be understood that any remaining percentage is accounted for by the presence of a canonical nucleotide (e.g., A, G, U, or C).

Polynucleotides may contain at a minimum zero and at a maximum 100% alternative nucleotides, or any intervening percentages, such as at least 5% alternative nucleotides, at least 10% alternative nucleotides, at least 25% alternative nucleotides, at least 50% alternative nucleotides, at least 80% alternative nucleotides, or at least 90% alternative nucleotides. For example, polynucleotides may contain an alternative pyrimidine such as an alternative uracil or cytosine. In some embodiments, at least 5%, at least 10%, at least 25%, at least 50%, at least 80%, at least 90% or 100% of the uracil in a polynucleotide is replaced with an alternative uracil (e.g., a 5-substituted uracil). The alternative uracil can be replaced by a compound having a single unique structure, or can be replaced by a plurality of compounds having different structures (e.g., 2, 3, 4 or more unique structures). In some instances, at least 5%, at least 10%, at least 25%, at least 50%, at least 80%, at least 90% or 100% of the cytosine in the polynucleotide is replaced with an alternative cytosine (e.g., a 5-substituted cytosine). The alternative cytosine can be replaced by a compound having a single unique structure, or can be replaced by a plurality of compounds having different structures (e.g., 2, 3, 4 or more unique structures).

In some instances, nucleic acids do not substantially induce an innate immune response of a cell into which the polynucleotide (e.g., mRNA) is introduced. Features of an induced innate immune response include 1) increased expression of pro-inflammatory cytokines, 2) activation of intracellular PRRs (RIG-I, MDA5, etc.), and/or 3) termination or reduction in protein translation.

The nucleic acids can optionally include other agents (e.g., RNAi-inducing agents, RNAi agents, siRNAs, shRNAs, miRNAs, antisense RNAs, ribozymes, catalytic DNA, tRNA, RNAs that induce triple helix formation, aptamers, vectors). In some embodiments, the nucleic acids may include one or more messenger RNAs (mRNAs) having one or more alternative nucleoside or nucleotides (i.e., alternative mRNA molecules).

In some embodiments, a nucleic acid (e.g., mRNA) molecule, formula, composition or method associated therewith comprises one or more polynucleotides comprising features as described in WO2002/098443, WO2003/051401, WO2008/052770, WO2009127230, WO2006122828, WO2008/083949, WO2010088927, WO2010/037539, WO2004/004743, WO2005/016376, WO2006/024518, WO2007/095976, WO2008/014979, WO2008/077592, WO2009/030481, WO2009/095226, WO2011069586, WO2011026641, WO2011/144358, WO2012019780, WO2012013326, WO2012089338, WO2012113513, WO2012116811, WO2012116810, WO2013113502, WO2013113501, WO2013113736, WO2013143698, WO2013143699, WO2013143700, WO2013/120626, WO2013120627, WO2013120628, WO2013120629, WO2013174409, WO2014127917, WO2015/024669, WO2015/024668, WO2015/024667, WO2015/024665, WO2015/024666, WO2015/024664, WO2015101415, WO2015101414, WO2015024667, WO2015062738, WO2015101416, all of which are incorporated by reference herein.

Nucleobase Alternatives

The alternative nucleosides and nucleotides can include an alternative nucleobase. A nucleobase of a nucleic acid is an organic base such as a purine or pyrimidine or a derivative thereof. A nucleobase may be a canonical base (e.g., adenine, guanine, uracil, thymine, and cytosine). These nucleobases can be altered or wholly replaced to provide polynucleotide molecules having enhanced properties, e.g., increased stability such as resistance to nucleases. Non-canonical or modified bases may include, for example, one or more substitutions or modifications including, but not limited to, alkyl, aryl, halo, oxo, hydroxyl, alkyloxy, and/or thio substitutions; one or more fused or open rings; oxidation; and/or reduction.

Alternative nucleotide base pairing encompasses not only the standard adenine-thymine, adenine-uracil, or guanine-cytosine base pairs, but also base pairs formed between nucleotides and/or alternative nucleotides including non-standard or alternative bases, wherein the arrangement of hydrogen bond donors and hydrogen bond acceptors permits hydrogen bonding between a non-standard base and a standard base or between two complementary non-standard base structures. One example of such non-standard base pairing is the base pairing between the alternative nucleotide inosine and adenine, cytosine, or uracil.

In some embodiments, the nucleobase is an alternative uracil. Exemplary nucleobases and nucleosides having an alternative uracil include, but are not limited to, pseudouridine (ψ, pyridin-4-one ribonucleoside, 5-aza-uracil, 6-aza-uracil, 2-thio-5-aza-uracil, 2-thio-uracil ($s^2U$), 4-thio-uracil ($s^4U$), 4-thio-pseudouridine, 2-thio-pseudouridine, 5-hydroxy-uracil ($ho^5U$), 5-aminoallyl-uracil, 5-halo-uracil (e.g., 5-iodo-uracil or 5-bromo-uracil), 3-methyl-uracil ($m^3U$), 5-methoxy-uracil ($mo^5U$), uracil 5-oxyacetic acid ($cmo^5U$), uracil 5-oxyacetic acid methyl ester ($mcmo^5U$), 5-carboxymethyl-uracil ($cm^5U$), 1-carboxymethyl-pseudouridine, 5-carboxyhydroxymethyl-uracil ($chm^5U$), 5-carboxyhydroxymethyl-uracil methyl ester ($mchm^5U$), 5-methoxycarbonylmethyl-uracil ($mcm^5U$), 5-methoxycarbonylmethyl-2-thio-uracil ($mcm^5s^2U$), 5-aminomethyl-2-thio-uracil ($nm^5s^2U$), 5-methylaminomethyl-uracil ($mnm^5U$), 5-methylaminomethyl-2-thio-uracil ($mnm^5s^2U$), 5-methylaminomethyl-2-seleno-uracil ($mnm^5se^2U$), 5-carbamoylmethyl-uracil ($ncm^5U$), 5-carboxymethylaminomethyl-uracil ($cmnm^5U$), 5-carboxymethylaminomethyl-2-thio-uracil ($cmnm^5s^2U$), 5-propynyl-uracil, 1-propynyl-pseudouracil, 5-taurinomethyl-uracil ($τm^5U$), 1-taurinomethyl-pseudouridine, 5-taurinomethyl-2-thio-uracil($τm^5s^2U$), 1-taurinomethyl-4-thio-pseudouridine, 5-methyl-uracil ($m^5U$, i.e., having the nucleobase deoxythymine), 1-methyl-pseudouridine ($m^1ψ$), 5-methyl-2-thio-uracil ($m^5s^2U$), 1-methyl-4-thio-pseudouridine ($m^1s^4ψ$), 4-thio-1-methyl-pseudouridine, 3-methyl-pseudouridine ($m^3ψ$), 2-thio-1-methyl-pseudouridine, 1-methyl-1-deaza-pseudouridine, 2-thio-1-methyl-1-deaza-pseudouridine, dihydrouracil (D), dihydropseudouridine, 5,6-dihydrouracil, 5-methyl-dihydrouracil ($m^5D$), 2-thio-dihydrouracil, 2-thio-dihydropseudouridine, 2-methoxy-uracil, 2-methoxy-4-thio-uracil, 4-methoxy-pseudouridine, 4-methoxy-2-thio-pseudouridine, N1-methyl-pseudouridine, 3-(3-amino-3-carboxypropyl)uracil ($acp^3U$), 1-methyl-3-(3-amino-3-carboxypropyl)pseudouridine ($acp^3 ψ$), 5-(isopentenylaminomethyl)uracil ($inm^5U$), 5-(isopentenylaminomethyl)-2-thio-uracil ($inm^5s^2U$), 5,2'-O-dimethyluridine (m5Um), 2-thio-2'-O-methyl-uridine (s2Um), 5-methoxycarbonylmethyl-2'-O-methyl-uridine (mcm5Um), 5-carbamoylmethyl-2'-O-methyl-uridine (ncm5Um), 5-carboxymethylaminomethyl-2'-O-methyl-uridine (cmnm5Um), 3,2'-O-dimethyl-uridine (m3Um), and 5-(isopentenylaminomethyl)-2'-O-methyl-uridine (inm5Um), 1-thio-uracil, deoxythymidine, 5-(2-carbomethoxyvinyl)-uracil, 5-(carbamoylhydroxymethyl)-uracil, 5-carbamoylmethyl-2-thio-uracil, 5-carboxymethyl-2-thio-uracil, 5-cyanomethyl-uracil, 5-methoxy-2-thio-uracil, and 5-[3-(1-E-propenylamino)]uracil.

In some embodiments, the nucleobase is an alternative cytosine. Exemplary nucleobases and nucleosides having an alternative cytosine include, but are not limited to, 5-aza-cytosine, 6-aza-cytosine, pseudoisocytidine, 3-methyl-cytosine (m3C), N4-acetyl-cytosine (ac4C), 5-formyl-cytosine (f5C), N4-methyl-cytosine (m4C), 5-methyl-cytosine (m5C), 5-halo-cytosine (e.g., 5-iodo-cytosine), 5-hydroxymethyl-cytosine (hm5C), 1-methyl-pseudoisocytidine, pyrrolo-cytosine, pyrrolo-pseudoisocytidine, 2-thio-cytosine (s2C), 2-thio-5-methyl-cytosine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytosine, 2-methoxy-5-methyl-cytosine, 4-methoxy-pseudoisocytidine, 4-methoxy-1-methyl-pseudoisocytidine, lysidine (k2C), 5,2'-O-dimethyl-cytidine (m5Cm), N4-acetyl-2'-O-methyl-cytidine (ac4Cm), N4,2'-O-dimethyl-cytidine (m4Cm), 5-formyl-2'-O-methyl-cytidine (f5Cm), N4,N4,2'-O-trimethyl-cytidine (m42Cm), 1-thio-cytosine, 5-hydroxy-cytosine, 5-(3-azidopropyl)-cytosine, and 5-(2-azidoethyl)-cytosine.

In some embodiments, the nucleobase is an alternative adenine. Exemplary nucleobases and nucleosides having an alternative adenine include, but are not limited to, 2-amino-purine, 2,6-diaminopurine, 2-amino-6-halo-purine (e.g., 2-amino-6-chloro-purine), 6-halo-purine (e.g., 6-chloro-purine), 2-amino-6-methyl-purine, 8-azido-adenine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenine (m1A), 2-methyl-adenine (m2A), N6-methyl-adenine (m6A), 2-methylthio-N6-methyl-adenine (ms2m6A), N6-isopentenyl-adenine (i6A), 2-methylthio-N6-isopentenyl-adenine (ms2i6A), N6-(cis-hydroxyisopentenyl)adenine (io6A), 2-methylthio-N6-(cis-hydroxyisopentenyl)adenine (ms2io6A), N6-glycinylcarbamoyl-adenine (g6A), N6-threonylcarbamoyl-adenine (t6A), N6-methyl-N6-threonylcarbamoyl-adenine (m6t6A), 2-methylthio-N6-threonyl-carbamoyl-adenine (ms2g6A), N6,N6-dimethyl-adenine (m62A), N6-hydroxynorvalylcarbamoyl-adenine (hn6A), 2-methylthio-N6-hydroxynorvalylcarbamoyl-adenine (ms2hn6A), N6-acetyl-adenine (ac6A), 7-methyl-adenine, 2-methylthio-adenine, 2-methoxy-adenine, N6,2'-O-dimethyl-adenosine (m6Am), N6,N6,2'-O-trimethyl-adenosine (m62Am), 1,2'-O-dimethyl-adenosine (m1Am), 2-amino-N6-methyl-purine, 1-thio-adenine, 8-azido-adenine, N6-(19-amino-pentaoxanonadecyl)-adenine, 2,8-dimethyl-adenine, N6-formyl-adenine, and N6-hydroxymethyl-adenine.

In some embodiments, the nucleobase is an alternative guanine. Exemplary nucleobases and nucleosides having an alternative guanine include, but are not limited to, inosine (I), 1-methyl-inosine (m1I), wyosine (imG), methylwyosine (mimG), 4-demethyl-wyosine (imG-14), isowyosine (imG2), wybutosine (yW), peroxywybutosine (o2yW), hydroxywybutosine (OHyW), undermodified hydroxywybutosine (OHyW*), 7-deaza-guanine, queuosine (Q), epoxyqueuosine (oQ), galactosyl-queuosine (galQ), mannosyl-queuosine (manQ), 7-cyano-7-deaza-guanine (preQ0), 7-aminomethyl-7-deaza-guanine (preQ1), archaeosine (G+), 7-deaza-8-aza-guanine, 6-thio-guanine, 6-thio-7-deaza-guanine, 6-thio-7-deaza-8-aza-guanine, 7-methyl-guanine (m7G), 6-thio-7-methyl-guanine, 7-methyl-inosine, 6-methoxy-guanine, 1-methyl-guanine (m1G), N2-methyl-guanine (m2G), N2,N2-dimethyl-guanine (m22G), N2,7-dimethyl-guanine (m2,7G), N2, N2,7-dimethyl-guanine (m2,2,7G), 8-oxo-guanine, 7-methyl-8-oxo-guanine, 1-methyl-6-thio-guanine, N2-methyl-6-thio-guanine, N2,N2-dimethyl-6-thio-guanine, N2-methyl-2'-O-methyl-guanosine (m2Gm), N2,N2-dimethyl-2'-O-methyl-guanosine (m22Gm), 1-methyl-2'-O-methyl-guanosine (m1Gm), N2,7-dimethyl-2'-O-methyl-guanosine (m2,7Gm), 2'-O-methyl-inosine (Im), 1,2'-O-dimethyl-inosine (m1Im), 1-thio-guanine, and O-6-methyl-guanine.

The alternative nucleobase of a nucleotide can be independently a purine, a pyrimidine, a purine or pyrimidine analog. For example, the nucleobase can be an alternative to adenine, cytosine, guanine, uracil, or hypoxanthine. In another embodiment, the nucleobase can also include, for example, naturally-occurring and synthetic derivatives of a base, including, but not limited to, pyrazolo[3,4-d]pyrimidines, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-propynyl uracil and cytosine, 6-azo uracil, cytosine and thymine, 5-uracil (pseudouracil), 4-thiouracil, 8-halo (e.g., 8-bromo), 8-amino, 8-thiol, 8-thioalkyl, 8-hydroxy and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, deazaguanine, 7-deazaguanine, 3-deazaguanine, deazaadenine, 7-deazaadenine, 3-deazaadenine, pyrazolo[3,4-d]pyrimidine, imidazo[1,5-a]1,3,5 triazinones, 9-deazapurines, imidazo[4,5-d]pyrazines, thiazolo[4,5-d]pyrimidines, pyrazin-2-ones, 1,2,4-triazine, pyridazine; or 1,3,5 triazine. When the nucleotides are depicted using the shorthand A, G, C, T or U, each letter refers to the representative base and/or derivatives thereof, e.g., A includes adenine or adenine analogs, e.g., 7-deaza adenine).

Alterations on the Sugar

Nucleosides include a sugar molecule (e.g., a 5-carbon or 6-carbon sugar, such as pentose, ribose, arabinose, xylose, glucose, galactose, or a deoxy derivative thereof) in combination with a nucleobase, while nucleotides are nucleosides containing a nucleoside and a phosphate group or alternative group (e.g., boranophosphate, thiophosphate, selenophosphate, phosphonate, alkyl group, amidate, and glycerol). A nucleoside or nucleotide may be a canonical species, e.g., a nucleoside or nucleotide including a canonical nucleobase, sugar, and, in the case of nucleotides, a phosphate group, or may be an alternative nucleoside or nucleotide including one or more alternative components. For example, alternative nucleosides and nucleotides can be altered on the sugar of the nucleoside or nucleotide. In some embodiments, the alternative nucleosides or nucleotides include the structure:

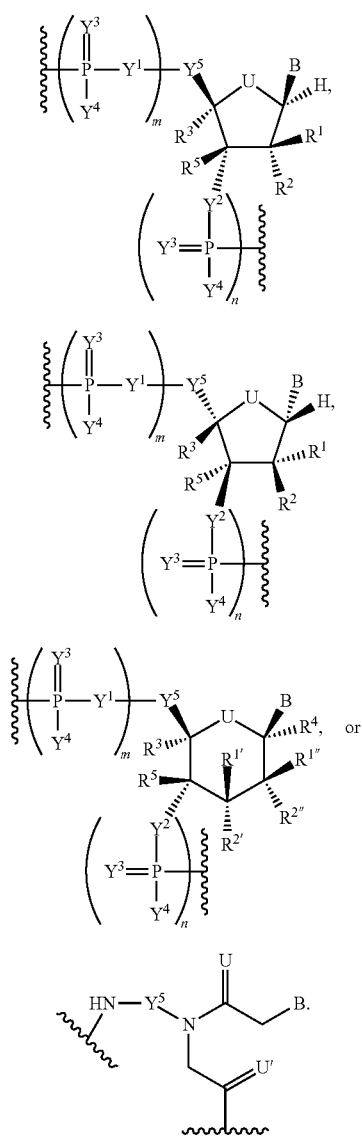

Formula IV

Formula V

Formula VI

Formula VII

In each of the Formulae IV, V, VI and VII,
each of m and n is independently, an integer from 0 to 5,
each of U and U' independently, is O, S, $N(R^U)_{nu}$, or $C(R^U)_{nu}$, wherein nu is an integer from 0 to 2 and each $R^U$ is, independently, H, halo, or optionally substituted alkyl;
each of $R^{1'}$, $R^{2'}$, $R^{1''}$, $R^{2''}$, $R^1$, $R^2$, $R^3$, $R^4$, and $R^5$ is, independently, if present, H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, optionally substituted aminoalkynyl, or absent; wherein the combination of $R_3$ with one or more of $R^{1'}$, $R^{1''}$, $R^{2'}$, $R^{2''}$, or $R^5$ (e.g., the combination of $R^{1'}$ and $R^3$, the combination of $R^{1''}$ and $R^3$, the combination of $R^{2'}$ and $R^3$, the combination of $R^{2''}$ and $R^3$, or the combination of $R^5$ and $R^3$) can join together to form optionally substituted alkylene or optionally substituted heteroalkylene and, taken together with the carbons to which they are attached, provide an optionally substituted heterocyclyl (e.g., a bicyclic, tricyclic, or tetracyclic heterocyclyl); wherein the combination of $R^5$ with one or more of $R^{1'}$, $R^{1''}$, $R^{2'}$, or $R^{2''}$ (e.g., the combination of $R^{1'}$ and $R^5$, the combination of $R^{1''}$ and $R^5$, the combination of $R^{2'}$ and $R^5$, or the combination of $R^{2''}$ and $R^5$) can join together to form optionally substituted alkylene or optionally substituted heteroalkylene and, taken together with the carbons to which they are attached, provide an optionally substituted heterocyclyl (e.g., a bicyclic, tricyclic, or tetracyclic heterocyclyl); and wherein the combination of $R^5$ and one or more of $R^{1'}$, $R^{1''}$, $R^{2'}$, $R^{2''}$, $R^3$, or $R^5$ can join together to form optionally substituted alkylene or optionally substituted heteroalkylene and, taken together with the carbons to which they are attached, provide an optionally substituted heterocyclyl (e.g., a bicyclic, tricyclic, or tetracyclic heterocyclyl); each of m' and m'' is, independently, an integer from 0 to 3 (e.g., from 0 to 2, from 0 to 1, from 1 to 3, or from 1 to 2);
each of $Y^1$, $Y^2$, and $Y^3$, is, independently, O, S, Se, $-NR^{N1}-$, optionally substituted alkylene, or optionally substituted heteroalkylene, wherein $R^{N1}$ is H, optionally substituted alkyl, optionally substituted alkenyl, optionally substituted alkynyl, optionally substituted aryl, or absent;
each $Y^4$ is, independently, H, hydroxy, thiol, boranyl, optionally substituted alkyl, optionally substituted alkenyl, optionally substituted alkynyl, optionally substituted alkoxy, optionally substituted alkenyloxy, optionally substituted alkynyloxy, optionally substituted thioalkoxy, optionally substituted alkoxyalkoxy, or optionally substituted amino;
each $Y^5$ is, independently, O, S, Se, optionally substituted alkylene (e.g., methylene), or optionally substituted heteroalkylene; and
B is a nucleobase, either modified or unmodified.

In some embodiments, the 2'-hydroxy group (OH) can be modified or replaced with a number of different substituents. Exemplary substitutions at the 2'-position include, but are not limited to, H, azido, halo (e.g., fluoro), optionally substituted $C_{1-6}$ alkyl (e.g., methyl); optionally substituted $C_{1-6}$ alkoxy (e.g., methoxy or ethoxy); optionally substituted $C_{6-10}$ aryloxy; optionally substituted $C_{3-8}$ cycloalkyl; optionally substituted $C_{6-10}$ aryl-$C_{1-6}$ alkoxy, optionally substituted $C_{1-12}$ (heterocyclyl)oxy; a sugar (e.g., ribose, pentose, or any described herein); a polyethyleneglycol (PEG), $-O(CH_2CH_2O)_nCH_2CH_2OR$, where R is H or optionally substituted alkyl, and n is an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20); "locked" nucleic acids (LNA) in which the 2'-hydroxy is connected by a $C_{1-6}$ alkylene or $C_{1-6}$ heteroalkylene bridge to the 4'-carbon of the same ribose sugar, where exemplary bridges included methylene, propylene, ether, or amino bridges; aminoalkyl, as defined herein; aminoalkoxy, as defined herein; amino as defined herein; and amino acid, as defined herein.

Generally, RNA includes the sugar group ribose, which is a 5-membered ring having an oxygen. Exemplary, non-limiting alternative nucleotides include replacement of the oxygen in ribose (e.g., with S, Se, or alkylene, such as methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for anhydrohexitol, altritol, mannitol, cyclohexanyl, cyclohexenyl, and morpholino (that also has a phosphoramidate backbone)); multicyclic forms (e.g., tricyclo and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with α-L-threofuranosyl-(3'→2')), and peptide nucleic acid (PNA, where 2-amino-ethyl-glycine linkages replace the ribose and phosphodiester backbone).

In some embodiments, the sugar group contains one or more carbons that possess the opposite stereochemical configuration of the corresponding carbon in ribose. Thus, a polynucleotide molecule can include nucleotides containing, e.g., arabinose or L-ribose, as the sugar.

In some embodiments, the polynucleotide includes at least one nucleoside wherein the sugar is L-ribose, 2'-O-methyl-ribose, 2'-fluoro-ribose, arabinose, hexitol, an LNA, or a PNA.

Alterations on the Internucleoside Linkage

Alternative nucleotides can be altered on the internucleoside linkage (e.g., phosphate backbone). Herein, in the context of the polynucleotide backbone, the phrases "phosphate" and "phosphodiester" are used interchangeably. Backbone phosphate groups can be altered by replacing one or more of the oxygen atoms with a different substituent.

The alternative nucleotides can include the wholesale replacement of an unaltered phosphate moiety with another internucleoside linkage as described herein. Examples of alternative phosphate groups include, but are not limited to, phosphorothioate, phosphoroselenates, boranophosphates, boranophosphate esters, hydrogen phosphonates, phosphoramidates, phosphorodiamidates, alkyl or aryl phosphonates, and phosphotriesters. Phosphorodithioates have both non-linking oxygens replaced by sulfur. The phosphate linker can also be altered by the replacement of a linking oxygen with nitrogen (bridged phosphoramidates), sulfur (bridged phosphorothioates), and carbon (bridged methylene-phosphonates).

The alternative nucleosides and nucleotides can include the replacement of one or more of the non-bridging oxygens with a borane moiety ($BH_3$), sulfur (thio), methyl, ethyl, and/or methoxy. As a non-limiting example, two non-bridging oxygens at the same position (e.g., the alpha (α), beta (β) or gamma (γ) position) can be replaced with a sulfur (thio) and a methoxy.

The replacement of one or more of the oxygen atoms at the α position of the phosphate moiety (e.g., α-thio phosphate) is provided to confer stability (such as against exonucleases and endonucleases) to RNA and DNA through the unnatural phosphorothioate backbone linkages. Phosphorothioate DNA and RNA have increased nuclease resistance and subsequently a longer half-life in a cellular environment.

Other internucleoside linkages that may be employed according to the present disclosure, including internucleoside linkages which do not contain a phosphorous atom, are described herein.

Internal Ribosome Entry Sites

Polynucleotides may contain an internal ribosome entry site (IRES). An IRES may act as the sole ribosome binding site, or may serve as one of multiple ribosome binding sites of an mRNA. A polynucleotide containing more than one functional ribosome binding site may encode several peptides or polypeptides that are translated independently by the ribosomes (e.g., multicistronic mRNA). When polynucleotides are provided with an IRES, further optionally provided is a second translatable region. Examples of IRES sequences that can be used according to the present disclosure include without limitation, those from picornaviruses (e.g., FMDV), pest viruses (CFFV), polio viruses (PV), encephalomyocarditis viruses (ECMV), foot-and-mouth disease viruses (FMDV), hepatitis C viruses (HCV), classical swine fever viruses (CSFV), murine leukemia virus (MLV), simian immune deficiency viruses (SIV) or cricket paralysis viruses (CrPV).

5'-Cap Structure

A polynucleotide (e.g., an mRNA) may include a 5'-cap structure. The 5'-cap structure of a polynucleotide is involved in nuclear export and increasing polynucleotide stability and binds the mRNA Cap Binding Protein (CBP), which is responsible for polynucleotide stability in the cell and translation competency through the association of CBP with poly-A binding protein to form the mature cyclic mRNA species. The cap further assists the removal of 5'-proximal introns removal during mRNA splicing.

Endogenous polynucleotide molecules may be 5'-end capped generating a 5'-ppp-5'-triphosphate linkage between a terminal guanosine cap residue and the 5'-terminal transcribed sense nucleotide of the polynucleotide. This 5'-guanylate cap may then be methylated to generate an N7-methyl-guanylate residue. The ribose sugars of the terminal and/or anteterminal transcribed nucleotides of the 5' end of the polynucleotide may optionally also be 2'-O-methylated. 5'-decapping through hydrolysis and cleavage of the guanylate cap structure may target a polynucleotide molecule, such as an mRNA molecule, for degradation.

Alterations to polynucleotides may generate a non-hydrolyzable cap structure preventing decapping and thus increasing polynucleotide half-life. Because cap structure hydrolysis requires cleavage of 5'-ppp-5' phosphorodiester linkages, alternative nucleotides may be used during the capping reaction. For example, a Vaccinia Capping Enzyme from New England Biolabs (Ipswich, MA) may be used with α-thio-guanosine nucleotides according to the manufacturer's instructions to create a phosphorothioate linkage in the 5'-ppp-5' cap. Additional alternative guanosine nucleotides may be used such as α-methyl-phosphonate and selenophosphate nucleotides.

Additional alterations include, but are not limited to, 2'-O-methylation of the ribose sugars of 5'-terminal and/or 5'-anteterminal nucleotides of the polynucleotide (as mentioned above) on the 2'-hydroxy group of the sugar. Multiple distinct 5'-cap structures can be used to generate the 5'-cap of a polynucleotide, such as an mRNA molecule.

5'-Cap structures include those described in International Patent Publication Nos. WO2008127688, WO 2008016473, and WO 2011015347, the cap structures of each of which are incorporated herein by reference.

Cap analogs, which herein are also referred to as synthetic cap analogs, chemical caps, chemical cap analogs, or structural or functional cap analogs, differ from natural (i.e., endogenous, wild-type, or physiological) 5'-caps in their chemical structure, while retaining cap function. Cap analogs may be chemically (i.e., non-enzymatically) or enzymatically synthesized and/linked to a polynucleotide.

For example, the Anti-Reverse Cap Analog (ARCA) cap contains two guanosines linked by a 5'-5'-triphosphate group, wherein one guanosine contains an N7-methyl group as well as a 3'-O-methyl group (i.e., N7,3'-O-dimethylguanosine-5'-triphosphate-5'-guanosine, m⁷G-3'mppp-G, which may equivalently be designated 3' O-Me-m7G(5')ppp (5')G). The 3'-O atom of the other, unaltered, guanosine becomes linked to the 5'-terminal nucleotide of the capped polynucleotide (e.g., an mRNA). The N7- and 3'-O-methylated guanosine provides the terminal moiety of the capped polynucleotide (e.g., mRNA).

Another exemplary cap is mCAP, which is similar to ARCA but has a 2'-O-methyl group on guanosine (i.e., N7,2'-O-dimethyl-guanosine-5'-triphosphate-5'-guanosine, m⁷Gm-ppp-G).

A cap may be a dinucleotide cap analog. As a non-limiting example, the dinucleotide cap analog may be modified at different phosphate positions with a boranophosphate group or a phophoroselenoate group such as the dinucleotide cap analogs described in U.S. Pat. No. 8,519,110, the cap structures of which are herein incorporated by reference.

Alternatively, a cap analog may be a N7-(4-chlorophenoxyethyl) substituted dinucleotide cap analog known in the art and/or described herein. Non-limiting examples of N7-(4-chlorophenoxyethyl) substituted dinucleotide cap analogs include a N7-(4-chlorophenoxyethyl)-G(5')ppp(5')G and a N7-(4-chlorophenoxyethyl)-m3'-OG(5')ppp(5')G cap analog (see, e.g., the various cap analogs and the methods of synthesizing cap analogs described in Kore et al. Bioorganic & Medicinal Chemistry 2013 21:4570-4574; the cap structures of which are herein incorporated by reference). In other instances, a cap analog useful in the polynucleotides of the present disclosure is a 4-chloro/bromophenoxyethyl analog.

While cap analogs allow for the concomitant capping of a polynucleotide in an in vitro transcription reaction, up to 20% of transcripts remain uncapped. This, as well as the structural differences of a cap analog from endogenous 5'-cap structures of polynucleotides produced by the endogenous, cellular transcription machinery, may lead to reduced translational competency and reduced cellular stability.

Alternative polynucleotides may also be capped post-transcriptionally, using enzymes, in order to generate more authentic 5'-cap structures. As used herein, the phrase "more authentic" refers to a feature that closely mirrors or mimics, either structurally or functionally, an endogenous or wild type feature. That is, a "more authentic" feature is better representative of an endogenous, wild-type, natural or physiological cellular function, and/or structure as compared to synthetic features or analogs of the prior art, or which outperforms the corresponding endogenous, wild-type, natural, or physiological feature in one or more respects. Non-limiting examples of more authentic 5'-cap structures useful in the polynucleotides of the present disclosure are those which, among other things, have enhanced binding of cap binding proteins, increased half-life, reduced susceptibility to 5'-endonucleases, and/or reduced 5'-decapping, as compared to synthetic 5'-cap structures known in the art (or to a wild-type, natural or physiological 5'-cap structure). For example, recombinant Vaccinia Virus Capping Enzyme and recombinant 2'-O-methyltransferase enzyme can create a canonical 5'-5'-triphosphate linkage between the 5'-terminal nucleotide of a polynucleotide and a guanosine cap nucleotide wherein the cap guanosine contains an N7-methylation and the 5'-terminal nucleotide of the polynucleotide contains a 2'-O-methyl. Such a structure is termed the Cap1 structure. This cap results in a higher translational-competency, cellular stability, and a reduced activation of cellular pro-inflammatory cytokines, as compared, e.g., to other 5' cap analog structures known in the art. Other exemplary cap structures include 7mG(5')ppp(5')N,pN2p (Cap 0), 7mG(5')ppp(5')NlmpNp (Cap 1), 7mG(5')-ppp(5')NlmpN2mp (Cap 2), and m(7)Gpppm(3)(6,6,2')Apm(2')Apm(2')Cpm(2)(3,2') Up (Cap 4).

Because the alternative polynucleotides may be capped post-transcriptionally, and because this process is more efficient, nearly 100% of the alternative polynucleotides may be capped. This is in contrast to ~80% when a cap analog is linked to a polynucleotide in the course of an in vitro transcription reaction.

5'-terminal caps may include endogenous caps or cap analogs. A 5'-terminal cap may include a guanosine analog. Useful guanosine analogs include inosine, N1-methyl-guanosine, 2'-fluoro-guanosine, 7-deaza-guanosine, 8-oxo-guanosine, 2-amino-guanosine, LNA-guanosine, and 2-azido-guanosine.

In some cases, a polynucleotide contains a modified 5'-cap. A modification on the 5'-cap may increase the stability of polynucleotide, increase the half-life of the polynucleotide, and could increase the polynucleotide translational efficiency. The modified 5'-cap may include, but is not limited to, one or more of the following modifications: modification at the 2'- and/or 3'-position of a capped guanosine triphosphate (GTP), a replacement of the sugar ring oxygen (that produced the carbocyclic ring) with a methylene moiety ($CH_2$), a modification at the triphosphate bridge moiety of the cap structure, or a modification at the nucleobase (G) moiety.

5'-UTRs

A 5'-UTR may be provided as a flanking region to polynucleotides (e.g., mRNAs). A 5'-UTR may be homologous or heterologous to the coding region found in a polynucleotide. Multiple 5'-UTRs may be included in the flanking region and may be the same or of different sequences. Any portion of the flanking regions, including none, may be codon optimized and any may independently contain one or more different structural or chemical alterations, before and/or after codon optimization.

Shown in Table 21 in U.S. Provisional Application No. 61/775,509, and in Table 21 and in Table 22 in U.S. Provisional Application No. 61/829,372, of which are incorporated herein by reference, is a listing of the start and stop site of alternative polynucleotides (e.g., mRNA). In Table 21 each 5'-UTR (5'-UTR-005 to 5'-UTR 68511) is identified by its start and stop site relative to its native or wild type (homologous) transcript (ENST; the identifier used in the ENSEMBL database).

To alter one or more properties of a polynucleotide (e.g., mRNA), 5'-UTRs which are heterologous to the coding region of an alternative polynucleotide (e.g., mRNA) may be engineered. The polynucleotides (e.g., mRNA) may then be administered to cells, tissue or organisms and outcomes such as protein level, localization, and/or half-life may be measured to evaluate the beneficial effects the heterologous 5'-UTR may have on the alternative polynucleotides (mRNA). Variants of the 5'-UTRs may be utilized wherein one or more nucleotides are added or removed to the termini, including A, T, C or G. 5'-UTRs may also be codon-optimized, or altered in any manner described herein.

5'-UTRs, 3'-UTRs, and translation enhancer elements (TEEs)

The 5'-UTR of a polynucleotides (e.g., mRNA) may include at least one translation enhancer element. The term "translational enhancer element" refers to sequences that increase the amount of polypeptide or protein produced from a polynucleotide. As a non-limiting example, the TEE may be located between the transcription promoter and the start codon. The polynucleotides (e.g., mRNA) with at least one TEE in the 5'-UTR may include a cap at the 5'-UTR. Further, at least one TEE may be located in the 5'-UTR of polynucleotides (e.g., mRNA) undergoing cap-dependent or cap-independent translation.

In one aspect, TEEs are conserved elements in the UTR which can promote translational activity of a polynucleotide such as, but not limited to, cap-dependent or cap-independent translation. The conservation of these sequences has been previously shown by Panek et al. (Nucleic Acids Research, 2013, 1-10) across 14 species including humans.

In one non-limiting example, the TEEs known may be in the 5'-leader of the Gtx homeodomain protein (Chappell et al., Proc. Natl. Acad. Sci. USA 101:9590-9594, 2004, the TEEs of which are incorporated herein by reference).

In another non-limiting example, TEEs are disclosed in US Patent Publication Nos. 2009/0226470 and 2013/0177581, International Patent Publication Nos. WO2009/075886, WO2012/009644, and WO1999/024595, U.S. Pat. Nos. 6,310,197, and 6,849,405, the TEE sequences of each of which are incorporated herein by reference.

In yet another non-limiting example, the TEE may be an internal ribosome entry site (IRES), HCV-IRES or an IRES element such as, but not limited to, those described in U.S. Pat. No. 7,468,275, US Patent Publication Nos. 2007/0048776 and 2011/0124100 and International Patent Publication Nos. WO2007/025008 and WO2001/055369, the IRES sequences of each of which are incorporated herein by reference. The IRES elements may include, but are not limited to, the Gtx sequences (e.g., Gtx9-nt, Gtx8-nt, Gtx7-nt) described by Chappell et al. (Proc. Natl. Acad. Sci. USA 101:9590-9594, 2004) and Zhou et al. (PNAS 102:6273-6278, 2005) and in US Patent Publication Nos. 2007/0048776 and 2011/0124100 and International Patent Publication No. WO2007/025008, the IRES sequences of each of which are incorporated herein by reference.

"Translational enhancer polynucleotides" are polynucleotides which include one or more of the specific TEE exemplified herein and/or disclosed in the art (see e.g., U.S. Pat. Nos. 6,310,197, 6,849,405, 7,456,273, 7,183,395, U.S. Patent Publication Nos. 20090/226470, 2007/0048776, 2011/0124100, 2009/0093049, 2013/0177581, International Patent Publication Nos. WO2009/075886, WO2007/025008, WO2012/009644, WO2001/055371 WO1999/024595, and European Patent Nos. 2610341 and 2610340; the TEE sequences of each of which are incorporated herein by reference) or their variants, homologs or functional derivatives. One or multiple copies of a specific TEE can be present in a polynucleotide (e.g., mRNA). The TEEs in the translational enhancer polynucleotides can be organized in one or more sequence segments. A sequence segment can harbor one or more of the specific TEEs exemplified herein, with each TEE being present in one or more copies. When multiple sequence segments are present in a translational enhancer polynucleotide, they can be homogenous or heterogeneous. Thus, the multiple sequence segments in a translational enhancer polynucleotide can harbor identical or different types of the specific TEEs exemplified herein, identical or different number of copies of each of the specific TEEs, and/or identical or different organization of the TEEs within each sequence segment.

A polynucleotide (e.g., mRNA) may include at least one TEE that is described in International Patent Publication Nos. WO1999/024595, WO2012/009644, WO2009/075886, WO2007/025008, WO1999/024595, European Patent Publication Nos. 2610341 and 2610340, U.S. Pat. Nos. 6,310, 197, 6,849,405, 7,456,273, 7,183,395, and US Patent Publication Nos. 2009/0226470, 2011/0124100, 2007/0048776, 2009/0093049, and 2013/0177581 the TEE sequences of each of which are incorporated herein by reference. The TEE may be located in the 5'-UTR of the polynucleotides (e.g., mRNA).

A polynucleotide (e.g., mRNA) may include at least one TEE that has at least 50%, at least 55%, at least 60%, at least 65%, at least 70%, at least 75%, at least 80%, at least 85%, at least 90%, at least 95% or at least 99% identity with the TEEs described in US Patent Publication Nos. 2009/0226470, 2007/0048776, 2013/0177581 and 2011/0124100, International Patent Publication Nos. WO1999/024595, WO2012/009644, WO2009/075886 and WO2007/025008, European Patent Publication Nos. 2610341 and 2610340, U.S. Pat. Nos. 6,310,197, 6,849,405, 7,456,273, 7,183,395, the TEE sequences of each of which are incorporated herein by reference.

The 5'-UTR of a polynucleotide (e.g., mRNA) may include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18 at least 19, at least 20, at least 21, at least 22, at least 23, at least 24, at least 25, at least 30, at least 35, at least 40, at least 45, at least 50, at least 55 or more than 60 TEE sequences. The TEE sequences in the 5'-UTR of a polynucleotide (e.g., mRNA) may be the same or different TEE sequences. The TEE sequences may be in a pattern such as ABABAB, AABBAABBAABB, or ABCABCABC, or variants thereof, repeated once, twice, or more than three times. In these patterns, each letter, A, B, or C represent a different TEE sequence at the nucleotide level.

In some cases, the 5'-UTR may include a spacer to separate two TEE sequences. As a non-limiting example, the spacer may be a 15 nucleotide spacer and/or other spacers known in the art. As another non-limiting example, the 5'-UTR may include a TEE sequence-spacer module repeated at least once, at least twice, at least 3 times, at least 4 times, at least 5 times, at least 6 times, at least 7 times, at least 8 times, at least 9 times, or more than 9 times in the 5'-UTR.

In other instances, the spacer separating two TEE sequences may include other sequences known in the art which may regulate the translation of the polynucleotides (e.g., mRNA) of the present disclosure such as, but not limited to, miR sequences (e.g., miR binding sites and miR seeds). As a non-limiting example, each spacer used to separate two TEE sequences may include a different miR sequence or component of a miR sequence (e.g., miR seed sequence).

In some instances, the TEE in the 5'-UTR of a polynucleotide (e.g., mRNA) may include at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% or more than 99% of the TEE sequences disclosed in US Patent Publication Nos. 2009/0226470, 2007/0048776, 2013/0177581 and 2011/0124100, International Patent Publication Nos. WO1999/024595, WO2012/009644, WO2009/075886 and WO2007/025008, European Patent Publication Nos. 2610341 and 2610340, and U.S. Pat. Nos. 6,310,197, 6,849,405, 7,456,273, and 7,183,395 the TEE sequences of each of which are incorporated herein by reference. In another embodiment, the TEE in the 5'-UTR of the polynucleotides (e.g., mRNA) of the present disclosure may include a 5-30 nucleotide fragment, a 5-25 nucleotide fragment, a 5-20 nucleotide fragment, a 5-15 nucleotide fragment, a 5-10 nucleotide fragment of the TEE sequences disclosed in US Patent Publication Nos. 2009/0226470, 2007/0048776, 2013/0177581 and 2011/0124100, International Patent Publication Nos. WO1999/024595, WO2012/009644, WO2009/075886 and WO2007/025008, European Patent Publication Nos. 2610341 and 2610340, and U.S. Pat. Nos. 6,310,197, 6,849,405, 7,456,273, and 7,183,395; the TEE sequences of each of which are incorporated herein by reference.

In certain cases, the TEE in the 5'-UTR of the polynucleotides (e.g., mRNA) of the present disclosure may include at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% or more than 99% of the TEE sequences disclosed in Chappell et al. (Proc. Natl. Acad. Sci. USA 101:9590-9594, 2004) and Zhou et al. (PNAS 102: 6273-6278, 2005), in Supplemental Table 1 and in Supplemental Table 2 disclosed by Wellensiek et al (Genome-wide profiling of human cap-independent translation-enhancing elements, Nature Methods, 2013; DOI:10.1038/NMETH.2522); the TEE sequences of each of which are herein incorporated by reference. In another embodiment, the TEE in the 5'-UTR of the polynucleotides (e.g., mRNA) of the present disclosure may include a 5-30 nucleotide fragment, a 5-25 nucleotide fragment, a 5-20 nucleotide fragment, a 5-15 nucleotide fragment, a 5-10 nucleotide fragment of the TEE sequences disclosed in Chappell et al. (Proc. Natl. Acad. Sci. USA 101:9590-9594, 2004) and Zhou et al. (PNAS 102:6273-6278, 2005), in Supplemental Table 1 and in Supplemental Table 2 disclosed by Wellensiek et al (Genome-wide profiling of human cap-independent translation-enhancing elements, Nature Methods, 2013; DOI:10.1038/NMETH.2522); the TEE sequences of each of which is incorporated herein by reference.

In some cases, the TEE used in the 5'-UTR of a polynucleotide (e.g., mRNA) is an IRES sequence such as, but not limited to, those described in U.S. Pat. No. 7,468,275 and International Patent Publication No. WO2001/055369, the TEE sequences of each of which are incorporated herein by reference.

In some instances, the TEEs used in the 5'-UTR of a polynucleotide (e.g., mRNA) may be identified by the methods described in US Patent Publication Nos. 2007/0048776 and 2011/0124100 and International Patent Publication Nos. WO2007/025008 and WO2012/009644, the methods of each of which are incorporated herein by reference.

In some cases, the TEEs used in the 5'-UTR of a polynucleotide (e.g., mRNA) of the present disclosure may be a transcription regulatory element described in U.S. Pat. Nos. 7,456,273 and 7,183,395, US Patent Publication No. 2009/0093049, and International Publication No. WO2001/055371, the TEE sequences of each of which is incorporated herein by reference. The transcription regulatory elements may be identified by methods known in the art, such as, but not limited to, the methods described in U.S. Pat. Nos. 7,456,273 and 7,183,395, US Patent Publication No. 2009/0093049, and International Publication No. WO2001/055371, the methods of each of which is incorporated herein by reference.

In yet other instances, the TEE used in the 5'-UTR of a polynucleotide (e.g., mRNA) is a polynucleotide or portion thereof as described in U.S. Pat. Nos. 7,456,273 and 7,183,395, US Patent Publication No. 2009/0093049, and International Publication No. WO2001/055371, the TEE sequences of each of which are incorporated herein by reference.

The 5'-UTR including at least one TEE described herein may be incorporated in a monocistronic sequence such as, but not limited to, a vector system or a polynucleotide vector. As a non-limiting example, the vector systems and polynucleotide vectors may include those described in U.S. Pat. Nos. 7,456,273 and 7,183,395, US Patent Publication Nos. 2007/0048776, 2009/0093049 and 2011/0124100, and International Patent Publication Nos. WO2007/025008 and WO2001/055371, the TEE sequences of each of which are incorporated herein by reference.

The TEEs described herein may be located in the 5'-UTR and/or the 3'-UTR of the polynucleotides (e.g., mRNA). The TEEs located in the 3'-UTR may be the same and/or different than the TEEs located in and/or described for incorporation in the 5'-UTR.

In some cases, the 3'-UTR of a polynucleotide (e.g., mRNA) may include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18 at least 19, at least 20, at least 21, at least 22, at least 23, at least 24, at least 25, at least 30, at least 35, at least 40, at least 45, at least 50, at least 55 or more than 60 TEE sequences. The TEE sequences in the 3'-UTR of the polynucleotides (e.g., mRNA) of the present disclosure may be the same or different TEE sequences. The TEE sequences may be in a pattern such as ABABAB, AABBAABBAABB, or ABCABCABC, or variants thereof, repeated once, twice, or more than three times. In these patterns, each letter, A, B, or C represent a different TEE sequence at the nucleotide level.

In one instance, the 3'-UTR may include a spacer to separate two TEE sequences. As a non-limiting example, the spacer may be a 15 nucleotide spacer and/or other spacers known in the art. As another non-limiting example, the 3'-UTR may include a TEE sequence-spacer module repeated at least once, at least twice, at least 3 times, at least 4 times, at least 5 times, at least 6 times, at least 7 times, at least 8 times, at least 9 times, or more than 9 times in the 3'-UTR.

In other cases, the spacer separating two TEE sequences may include other sequences known in the art which may regulate the translation of the polynucleotides (e.g., mRNA) of the present disclosure such as, but not limited to, miR sequences described herein (e.g., miR binding sites and miR seeds). As a non-limiting example, each spacer used to separate two TEE sequences may include a different miR sequence or component of a miR sequence (e.g., miR seed sequence).

In some embodiments, a polyribonucleotide of the disclosure comprises a miR and/or TEE sequence. In some embodiments, the incorporation of a miR sequence and/or a TEE sequence into a polyribonucleotide of the disclosure can change the shape of the stem loop region, which can increase and/or decrease translation. See e.g., Kedde et al., Nature Cell Biology 2010 12(10):1014-20, herein incorporated by reference in its entirety).

Sensor Sequences and MicroRNA (miRNA) Binding Sites

Sensor sequences include, for example, microRNA (miRNA) binding sites, transcription factor binding sites, structured mRNA sequences and/or motifs, artificial binding sites engineered to act as pseudo-receptors for endogenous nucleic acid binding molecules, and combinations thereof. Non-limiting examples of sensor sequences are described in U.S. Publication 2014/0200261, the contents of which are incorporated herein by reference in their entirety.

In some embodiments, a polyribonucleotide (e.g., a ribonucleic acid (RNA), e.g., a messenger RNA (mRNA)) of the disclosure comprising an open reading frame (ORF) encoding a polypeptide further comprises a sensor sequence. In some embodiments, the sensor sequence is a miRNA binding site.

A miRNA is a 19-25 nucleotide long noncoding RNA that binds to a polyribonucleotide and down-regulates gene expression either by reducing stability or by inhibiting translation of the polyribonucleotide. A miRNA sequence comprises a "seed" region, i.e., a sequence in the region of positions 2-8 of the mature miRNA. A miRNA seed can comprise positions 2-8 or 2-7 of the mature miRNA. In some embodiments, a miRNA seed can comprise 7 nucleotides (e.g., nucleotides 2-8 of the mature miRNA), wherein the seed-complementary site in the corresponding miRNA binding site is flanked by an adenosine (A) opposed to miRNA position 1. In some embodiments, a miRNA seed can comprise 6 nucleotides (e.g., nucleotides 2-7 of the mature miRNA), wherein the seed-complementary site in the corresponding miRNA binding site is flanked by an adenosine (A) opposed to miRNA position 1. See, for example, Grimson A, Farh K K, Johnston W K, Garrett-Engele P, Lim L P, Bartel D P; Mol Cell. 2007 Jul. 6; 27(1):91-105. miRNA profiling of the target cells or tissues can be conducted to determine the presence or absence of miRNA in the cells or tissues. In some embodiments, a polyribonucleotide (e.g., a ribonucleic acid (RNA), e.g., a messenger RNA (mRNA)) of the disclosure comprises one or more microRNA target sequences, microRNA sequences, or microRNA seeds. Such sequences can correspond to any known microRNA such as those taught in US Publication US2005/0261218 and US Publication US2005/0059005, the contents of each of which are incorporated herein by reference in their entirety.

As used herein, the term "microRNA (miRNA or miR) binding site" refers to a sequence within a polyribonucleotide, e.g., within a DNA or within an RNA transcript, including in the 5'UTR and/or 3'UTR, that has sufficient complementarity to all or a region of a miRNA to interact with, associate with or bind to the miRNA. In some embodiments, a polyribonucleotide of the disclosure comprising an ORF encoding a polypeptide further comprises a miRNA binding site. In exemplary embodiments, a 5'UTR and/or 3'UTR of the polyribonucleotide (e.g., a ribonucleic acid (RNA), e.g., a messenger RNA (mRNA)) comprises a miRNA binding site.

A miRNA binding site having sufficient complementarity to a miRNA refers to a degree of complementarity sufficient to facilitate miRNA-mediated regulation of a polyribonucleotide, e.g., miRNA-mediated translational repression or degradation of the polyribonucleotide. In exemplary aspects of the disclosure, a miRNA binding site having sufficient complementarity to the miRNA refers to a degree of complementarity sufficient to facilitate miRNA-mediated degradation of the polyribonucleotide, e.g., miRNA-guided RNA-induced silencing complex (RISC)-mediated cleavage of mRNA. The miRNA binding site can have complementarity to, for example, a 19-25 nucleotide miRNA sequence, to a 19-23 nucleotide miRNA sequence, or to a 22-nucleotide miRNA sequence. A miRNA binding site can be complementary to only a portion of a miRNA, e.g., to a portion less than 1, 2, 3, or 4 nucleotides of the full length of a naturally-occurring miRNA sequence. Full or complete complementarity (e.g., full complementarity or complete complementarity over all or a significant portion of the length of a naturally-occurring miRNA) is preferred when the desired regulation is mRNA degradation.

In some embodiments, a miRNA binding site includes a sequence that has complementarity (e.g., partial or complete complementarity) with a miRNA seed sequence. In some embodiments, the miRNA binding site includes a sequence that has complete complementarity with a miRNA seed sequence. In some embodiments, a miRNA binding site includes a sequence that has complementarity (e.g., partial or complete complementarity) with a miRNA sequence. In some embodiments, the miRNA binding site includes a sequence that has complete complementarity with a miRNA sequence. In some embodiments, a miRNA binding site has complete complementarity with a miRNA sequence but for 1, 2, or 3 nucleotide substitutions, terminal additions, and/or truncations.

In some embodiments, the miRNA binding site is the same length as the corresponding miRNA. In other embodiments, the miRNA binding site is one, two, three, four, five, six, seven, eight, nine, ten, eleven or twelve nucleotide(s) shorter than the corresponding miRNA at the 5' terminus, the 3' terminus, or both. In still other embodiments, the microRNA binding site is two nucleotides shorter than the corresponding microRNA at the 5' terminus, the 3' terminus, or both. The miRNA binding sites that are shorter than the corresponding miRNAs are still capable of degrading the mRNA incorporating one or more of the miRNA binding sites or preventing the mRNA from translation.

In some embodiments, the miRNA binding site binds to the corresponding mature miRNA that is part of an active RISC containing Dicer. In another embodiment, binding of the miRNA binding site to the corresponding miRNA in RISC degrades the mRNA containing the miRNA binding site or prevents the mRNA from being translated. In some embodiments, the miRNA binding site has sufficient complementarity to miRNA so that a RISC complex comprising the miRNA cleaves the polyribonucleotide comprising the miRNA binding site. In other embodiments, the miRNA binding site has imperfect complementarity so that a RISC complex comprising the miRNA induces instability in the polyribonucleotide comprising the miRNA binding site. In another embodiment, the miRNA binding site has imperfect complementarity so that a RISC complex comprising the miRNA represses transcription of the polyribonucleotide comprising the miRNA binding site.

In some embodiments, the miRNA binding site has one, two, three, four, five, six, seven, eight, nine, ten, eleven or twelve mismatch(es) from the corresponding miRNA.

In some embodiments, the miRNA binding site has at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one contiguous nucleotides complementary to at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one, respectively, contiguous nucleotides of the corresponding miRNA.

By engineering one or more miRNA binding sites into a polyribonucleotide of the disclosure, the polyribonucleotide can be targeted for degradation or reduced translation, provided the miRNA in question is available. This can reduce off-target effects upon delivery of the polyribonucleotide. For example, if a polyribonucleotide of the disclosure is not intended to be delivered to a tissue or cell but ends up there, then a miRNA abundant in the tissue or cell can inhibit the expression of the gene of interest if one or multiple binding sites of the miRNA are engineered into the 5'UTR and/or 3'UTR of the polyribonucleotide.

Conversely, miRNA binding sites can be removed from polyribonucleotide sequences in which they naturally occur in order to increase protein expression in specific tissues. For example, a binding site for a specific miRNA can be removed from a polyribonucleotide to improve protein expression in tissues or cells containing the miRNA.

In some embodiments, a polyribonucleotide of the disclosure can include at least one miRNA-binding site in the 5'UTR and/or 3'UTR in order to direct cytotoxic or cytoprotective mRNA therapeutics to specific cells such as, but not limited to, normal and/or cancerous cells. In another embodiment, a polyribonucleotide of the disclosure can include two, three, four, five, six, seven, eight, nine, ten, or more miRNA-binding sites in the 5'-UTR and/or 3'-UTR in order to direct cytotoxic or cytoprotective mRNA therapeutics to specific cells such as, but not limited to, normal and/or cancerous cells.

Regulation of expression in multiple tissues can be accomplished through introduction or removal of one or more miRNA binding sites. The decision whether to remove or insert a miRNA binding site can be made based on miRNA expression patterns and/or their profiling in diseases. Identification of miRNAs, miRNA binding sites, and their expression patterns and role in biology have been reported (e.g., Bonauer et al., Curr Drug Targets 2010 11:943-949; Anand and Cheresh Curr Opin Hematol 2011 18:171-176; Contreras and Rao Leukemia 2012 26:404-413 (2011 Dec. 20. doi: 10.1038/leu.2011.356); Bartel Cell 2009 136:215-233; Landgraf et al, Cell, 2007 129:1401-1414; Gentner and Naldini, Tissue Antigens. 2012 80:393-403 and all references therein; each of which is incorporated herein by reference in its entirety).

miRNAs and miRNA binding sites can correspond to any known sequence, including non-limiting examples described in U.S. Publication Nos. 2014/0200261, 2005/0261218, and 2005/0059005, each of which are incorporated herein by reference in their entirety.

Examples of tissues where miRNA are known to regulate mRNA, and thereby protein expression, include, but are not limited to, liver (miR-122), muscle (miR-133, miR-206, miR-208), endothelial cells (miR-17-92, miR-126), myeloid cells (miR-142-3p, miR-142-5p, miR-16, miR-21, miR-223, miR-24, miR-27), adipose tissue (let-7, miR-30c), heart (miR-1d, miR-149), kidney (miR-192, miR-194, miR-204), and lung epithelial cells (let-7, miR-133, miR-126).

Specifically, miRNAs are known to be differentially expressed in immune cells (also called hematopoietic cells), such as antigen presenting cells (APCs) (e.g., dendritic cells and macrophages), macrophages, monocytes, B lymphocytes, T lymphocytes, granulocytes, natural killer cells, etc. Immune cell specific miRNAs are involved in immunogenicity, autoimmunity, the immune-response to infection, inflammation, as well as unwanted immune response after gene therapy and tissue/organ transplantation. Immune cells specific miRNAs also regulate many aspects of development, proliferation, differentiation and apoptosis of hematopoietic cells (immune cells). For example, miR-142 and miR-146 are exclusively expressed in immune cells, particularly abundant in myeloid dendritic cells. It has been demonstrated that the immune response to a polyribonucleotide can be shut-off by adding miR-142 binding sites to the 3'-UTR of the polyribonucleotide, enabling more stable gene transfer in tissues and cells. miR-142 efficiently degrades exogenous polyribonucleotides in antigen presenting cells and suppresses cytotoxic elimination of transduced cells (e.g., Annoni A et al., blood, 2009, 114, 5152-5161; Brown B D, et al., Nat med. 2006, 12(5), 585-591; Brown B D, et al., blood, 2007, 110(13): 4144-4152, each of which is incorporated herein by reference in its entirety).

An antigen-mediated immune response can refer to an immune response triggered by foreign antigens, which, when entering an organism, are processed by the antigen presenting cells and displayed on the surface of the antigen presenting cells. T cells can recognize the presented antigen and induce a cytotoxic elimination of cells that express the antigen.

Introducing a miR-142 binding site into the 5'UTR and/or 3'UTR of a polyribonucleotide of the disclosure can selectively repress gene expression in antigen presenting cells through miR-142 mediated degradation, limiting antigen presentation in antigen presenting cells (e.g., dendritic cells) and thereby preventing antigen-mediated immune response after the delivery of the polyribonucleotide. The polyribonucleotide is then stably expressed in target tissues or cells without triggering cytotoxic elimination.

In some embodiments, binding sites for miRNAs that are known to be expressed in immune cells, antigen presenting cells, can be engineered into a polyribonucleotide of the disclosure to suppress the expression of the polyribonucleotide in antigen presenting cells through miRNA mediated RNA degradation, subduing the antigen-mediated immune response. Expression of the polyribonucleotide is maintained in non-immune cells where the immune cell specific miRNAs are not expressed. For example, in some embodiments, to prevent an immunogenic reaction against a liver specific protein, any miR-122 binding site can be removed and a miR-142 (and/or mirR-146) binding site can be engineered into the 5'UTR and/or 3'UTR of a polyribonucleotide of the disclosure.

To further drive the selective degradation and suppression in APCs and macrophage, a polyribonucleotide of the disclosure can include a further negative regulatory element in the 5'UTR and/or 3'UTR, either alone or in combination with miR-142 and/or miR-146 binding sites. As a non-limiting example, the further negative regulatory element is a Constitutive Decay Element (CDE).

Immune cell specific miRNAs include, but are not limited to, hsa-let-7a-2-3p, hsa-let-7a-3p, hsa-7a-5p, hsa-let-7c, hsa-let-7e-3p, hsa-let-7e-5p, hsa-let-7g-3p, hsa-let-7g-5p, hsa-let-7i-3p, hsa-let-7i-5p, miR-10a-3p, miR-10a-5p, miR-1184, hsa-let-7f-1-3p, hsa-let-7f-2-5p, hsa-let-7f-5p, miR-125b-1-3p, miR-125b-2-3p, miR-125b-5p, miR-1279, miR-130a-3p, miR-130a-5p, miR-132-3p, miR-132-5p, miR-142-3p, miR-142-5p, miR-143-3p, miR-143-5p, miR-146a-3p, miR-146a-5p, miR-146b-3p, miR-146b-5p, miR-147a, miR-147b, miR-148a-5p, miR-148a-3p, miR-150-3p, miR-150-5p, miR-151b, miR-155-3p, miR-155-5p, miR-15a-3p, miR-15a-5p, miR-15b-5p, miR-15b-3p, miR-16-1-3p, miR-16-2-3p, miR-16-5p, miR-17-5p, miR-181a-3p, miR-181a-5p, miR-181a-2-3p, miR-182-3p, miR-182-5p, miR-197-3p, miR-197-5p, miR-21-5p, miR-21-3p, miR-214-3p, miR-214-5p, miR-223-3p, miR-223-5p, miR-221-3p, miR-221-5p, miR-23b-3p, miR-23b-5p, miR-24-1-5p, miR-24-2-5p, miR-24-3p, miR-26a-1-3p, miR-26a-2-3p, miR-26a-5p, miR-26b-3p, miR-26b-5p, miR-27a-3p, miR-27a-5p, miR-27b-3p, miR-27b-5p, miR-28-3p, miR-28-5p, miR-2909, miR-29a-3p, miR-29a-5p, miR-29b-1-5p, miR-29b-2-5p, miR-29c-3p, miR-29c-5p, miR-30e-3p, miR-30e-5p, miR-331-5p, miR-339-3p, miR-339-5p, miR-345-3p, miR-345-

5p, miR-346, miR-34a-3p, miR-34a-5p, miR-363-3p, miR-363-5p, miR-372, miR-377-3p, miR-377-5p, miR-493-3p, miR-493-5p, miR-542, miR-548b-5p, miR548c-5p, miR-548i, miR-548j, miR-548n, miR-574-3p, miR-598, miR-718, miR-935, miR-99a-3p, miR-99a-5p, miR-99b-3p, and miR-99b-5p. Furthermore, novel miRNAs can be identified in immune cell through micro-array hybridization and microtome analysis (e.g., Jima D D et al, Blood, 2010, 116:e118-e127; Vaz C et al., BMC Genomics, 2010, 11,288, the content of each of which is incorporated herein by reference in its entirety.)

miRNAs that are known to be expressed in the liver include, but are not limited to, miR-107, miR-122-3p, miR-122-5p, miR-1228-3p, miR-1228-5p, miR-1249, miR-129-5p, miR-1303, miR-151a-3p, miR-151a-5p, miR-152, miR-194-3p, miR-194-5p, miR-199a-3p, miR-199a-5p, miR-199b-3p, miR-199b-5p, miR-296-5p, miR-557, miR-581, miR-939-3p, and miR-939-5p. miRNA binding sites from any liver specific miRNA can be introduced to or removed from a polyribonucleotide of the disclosure to regulate expression of the polyribonucleotide in the liver. Liver specific miRNA binding sites can be engineered alone or further in combination with immune cell (e.g., APC) miRNA binding sites in a polyribonucleotide of the disclosure.

miRNAs that are known to be expressed in the lung include, but are not limited to, let-7a-2-3p, let-7a-3p, let-7a-5p, miR-126-3p, miR-126-5p, miR-127-3p, miR-127-5p, miR-130a-3p, miR-130a-5p, miR-130b-3p, miR-130b-5p, miR-133a, miR-133b, miR-134, miR-18a-3p, miR-18a-5p, miR-18b-3p, miR-18b-5p, miR-24-1-5p, miR-24-2-5p, miR-24-3p, miR-296-3p, miR-296-5p, miR-32-3p, miR-337-3p, miR-337-5p, miR-381-3p, and miR-381-5p. MiRNA binding sites from any lung specific miRNA can be introduced to or removed from a polyribonucleotide of the disclosure to regulate expression of the polyribonucleotide in the lung. Lung specific miRNA binding sites can be engineered alone or further in combination with immune cell (e.g., APC) miRNA binding sites in a polyribonucleotide of the disclosure.

miRNAs that are known to be expressed in the heart include, but are not limited to, miR-1, miR-133a, miR-133b, miR-149-3p, miR-149-5p, miR-186-3p, miR-186-5p, miR-208a, miR-208b, miR-210, miR-296-3p, miR-320, miR-451a, miR-451b, miR-499a-3p, miR-499a-5p, miR-499b-3p, miR-499b-5p, miR-744-3p, miR-744-5p, miR-92b-3p, and miR-92b-5p. MiRNA binding sites from any heart specific microRNA can be introduced to or removed from a polyribonucleotide of the disclosure to regulate expression of the polyribonucleotide in the heart. Heart specific miRNA binding sites can be engineered alone or further in combination with immune cell (e.g., APC) miRNA binding sites in a polyribonucleotide of the disclosure.

miRNAs that are known to be expressed in the nervous system include, but are not limited to, miR-124-5p, miR-125a-3p, miR-125a-5p, miR-125b-1-3p, miR-125b-2-3p, miR-125b-5p, miR-1271-3p, miR-1271-5p, miR-128, miR-132-5p, miR-135a-3p, miR-135a-5p, miR-135b-3p, miR-135b-5p, miR-137, miR-139-5p, miR-139-3p, miR-149-3p, miR-149-5p, miR-153, miR-181c-3p, miR-181c-5p, miR-183-3p, miR-183-5p, miR-190a, miR-190b, miR-212-3p, miR-212-5p, miR-219-1-3p, miR-219-2-3p, miR-23a-3p, miR-23a-5p, miR-30a-5p, miR-30b-3p, miR-30b-5p, miR-30c-1-3p, miR-30c-2-3p, miR-30c-5p, miR-30d-3p, miR-30d-5p, miR-329, miR-342-3p, miR-3665, miR-3666, miR-380-3p, miR-380-5p, miR-383, miR-410, miR-425-3p, miR-425-5p, miR-454-3p, miR-454-5p, miR-483, miR-510, miR-516a-3p, miR-548b-5p, miR-548c-5p, miR-571, miR-7-1-3p, miR-7-2-3p, miR-7-5p, miR-802, miR-922, miR-9-3p, and miR-9-5p. MiRNAs enriched in the nervous system further include those specifically expressed in neurons, including, but not limited to, miR-132-3p, miR-132-3p, miR-148b-3p, miR-148b-5p, miR-151a-3p, miR-151a-5p, miR-212-3p, miR-212-5p, miR-320b, miR-320e, miR-323a-3p, miR-323a-5p, miR-324-5p, miR-325, miR-326, miR-328, miR-922 and those specifically expressed in glial cells, including, but not limited to, miR-1250, miR-219-1-3p, miR-219-2-3p, miR-219-5p, miR-23a-3p, miR-23a-5p, miR-3065-3p, miR-3065-5p, miR-30e-3p, miR-30e-5p, miR-32-5p, miR-338-5p, and miR-657. MiRNA binding sites from any CNS specific miRNA can be introduced to or removed from a polyribonucleotide of the disclosure to regulate expression of the polyribonucleotide in the nervous system. Nervous system specific miRNA binding sites can be engineered alone or further in combination with immune cell (e.g., APC) miRNA binding sites in a polyribonucleotide of the disclosure.

miRNAs that are known to be expressed in the pancreas include, but are not limited to, miR-105-3p, miR-105-5p, miR-184, miR-195-3p, miR-195-5p, miR-196a-3p, miR-196a-5p, miR-214-3p, miR-214-5p, miR-216a-3p, miR-216a-5p, miR-30a-3p, miR-33a-3p, miR-33a-5p, miR-375, miR-7-1-3p, miR-7-2-3p, miR-493-3p, miR-493-5p, and miR-944. MiRNA binding sites from any pancreas specific miRNA can be introduced to or removed from a polyribonucleotide of the disclosure to regulate expression of the polyribonucleotide in the pancreas. Pancreas specific miRNA binding sites can be engineered alone or further in combination with immune cell (e.g., APC) miRNA binding sites in a polyribonucleotide of the disclosure.

miRNAs that are known to be expressed in the kidney include, but are not limited to, miR-122-3p, miR-145-5p, miR-17-5p, miR-192-3p, miR-192-5p, miR-194-3p, miR-194-5p, miR-20a-3p, miR-20a-5p, miR-204-3p, miR-204-5p, miR-210, miR-216a-3p, miR-216a-5p, miR-296-3p, miR-30a-3p, miR-30a-5p, miR-30b-3p, miR-30b-5p, miR-30c-1-3p, miR-30c-2-3p, miR30c-5p, miR-324-3p, miR-335-3p, miR-335-5p, miR-363-3p, miR-363-5p, and miR-562. MiRNA binding sites from any kidney specific miRNA can be introduced to or removed from a polyribonucleotide of the disclosure to regulate expression of the polyribonucleotide in the kidney. Kidney specific miRNA binding sites can be engineered alone or further in combination with immune cell (e.g., APC) miRNA binding sites in a polyribonucleotide of the disclosure.

miRNAs that are known to be expressed in the muscle include, but are not limited to, let-7g-3p, let-7g-5p, miR-1, miR-1286, miR-133a, miR-133b, miR-140-3p, miR-143-3p, miR-143-5p, miR-145-3p, miR-145-5p, miR-188-3p, miR-188-5p, miR-206, miR-208a, miR-208b, miR-25-3p, and miR-25-5p. MiRNA binding sites from any muscle specific miRNA can be introduced to or removed from a polyribonucleotide of the disclosure to regulate expression of the polyribonucleotide in the muscle. Muscle specific miRNA binding sites can be engineered alone or further in combination with immune cell (e.g., APC) miRNA binding sites in a polyribonucleotide of the disclosure.

miRNAs are also differentially expressed in different types of cells, such as, but not limited to, endothelial cells, epithelial cells, and adipocytes.

miRNAs that are known to be expressed in endothelial cells include, but are not limited to, let-7b-3p, let-7b-5p, miR-100-3p, miR-100-5p, miR-101-3p, miR-101-5p, miR-126-3p, miR-126-5p, miR-1236-3p, miR-1236-5p, miR- 130a-3p, miR-130a-5p, miR-17-5p, miR-17-3p, miR-18a-3p, miR-18a-5p, miR-19a-3p, miR-19a-5p, miR-19b-1-5p, miR-19b-2-5p, miR-19b-3p, miR-20a-3p, miR-20a-5p, miR-217, miR-210, miR-21-3p, miR-21-5p, miR-221-3p, miR-221-5p, miR-222-3p, miR-222-5p, miR-23a-3p, miR-23a-5p, miR-296-5p, miR-361-3p, miR-361-5p, miR-421, miR-424-3p, miR-424-5p, miR-513a-5p, miR-92a-1-5p, miR-92a-2-5p, miR-92a-3p, miR-92b-3p, and miR-92b-5p. Many novel miRNAs are discovered in endothelial cells from deep-sequencing analysis (e.g., Voellenkle C et al., RNA, 2012, 18, 472-484, herein incorporated by reference in its entirety). MiRNA binding sites from any endothelial cell specific miRNA can be introduced to or removed from a polyribonucleotide of the disclosure to regulate expression of the polyribonucleotide in the endothelial cells.

miRNAs that are known to be expressed in epithelial cells include, but are not limited to, let-7b-3p, let-7b-5p, miR-1246, miR-200a-3p, miR-200a-5p, miR-200b-3p, miR-200b-5p, miR-200c-3p, miR-200c-5p, miR-338-3p, miR-429, miR-451a, miR-451b, miR-494, miR-802 and miR-34a, miR-34b-5p, miR-34c-5p, miR-449a, miR-449b-3p, miR-449b-5p specific in respiratory ciliated epithelial cells, let-7 family, miR-133a, miR-133b, miR-126 specific in lung epithelial cells, miR-382-3p, miR-382-5p specific in renal epithelial cells, and miR-762 specific in corneal epithelial cells. MiRNA binding sites from any epithelial cell specific miRNA can be introduced to or removed from a polyribonucleotide of the disclosure to regulate expression of the polyribonucleotide in the epithelial cells.

In addition, a large group of miRNAs are enriched in embryonic stem cells, controlling stem cell self-renewal as well as the development and/or differentiation of various cell lineages, such as neural cells, cardiac, hematopoietic cells, skin cells, osteogenic cells and muscle cells (e.g., Kuppusamy K T et al., Curr. Mol Med, 2013, 13(5), 757-764; Vidigal J A and Ventura A, Semin Cancer Biol. 2012, 22(5-6), 428-436; Goff L A et al., PLoS One, 2009, 4:e7192; Morin R D et al., Genome Res, 2008, 18, 610-621; Yoo J K et al., Stem Cells Dev. 2012, 21(11), 2049-2057, each of which is herein incorporated by reference in its entirety). MiRNAs abundant in embryonic stem cells include, but are not limited to, let-7a-2-3p, let-a-3p, let-7a-5p, let7d-3p, let-7d-5p, miR-103a-2-3p, miR-103a-5p, miR-106b-3p, miR-106b-5p, miR-1246, miR-1275, miR-138-1-3p, miR-138-2-3p, miR-138-5p, miR-154-3p, miR-154-5p, miR-200c-3p, miR-200c-5p, miR-290, miR-301a-3p, miR-301a-5p, miR-302a-3p, miR-302a-5p, miR-302b-3p, miR-302b-5p, miR-302c-3p, miR-302c-5p, miR-302d-3p, miR-302d-5p, miR-302e, miR-367-3p, miR-367-5p, miR-369-3p, miR-369-5p, miR-370, miR-371, miR-373, miR-380-5p, miR-423-3p, miR-423-5p, miR-486-5p, miR-520c-3p, miR-548e, miR-548f, miR-548g-3p, miR-548g-5p, miR-548i, miR-548k, miR-548l, miR-548m, miR-548n, miR-548o-3p, miR-548o-5p, miR-548p, miR-664a-3p, miR-664a-5p, miR-664b-3p, miR-664b-5p, miR-766-3p, miR-766-5p, miR-885-3p, miR-885-5p, miR-93-3p, miR-93-5p, miR-941, miR-96-3p, miR-96-5p, miR-99b-3p and miR-99b-5p. Many predicted novel miRNAs are discovered by deep sequencing in human embryonic stem cells (e.g., Morin R D et al., Genome Res, 2008, 18, 610-621; Goff L A et al., PLoS One, 2009, 4:e7192; Bar M et al., Stem cells, 2008, 26, 2496-2505, the content of each of which is incorporated herein by reference in its entirety).

In some embodiments, the binding sites of embryonic stem cell specific miRNAs can be included in or removed from the 3'UTR of a polyribonucleotide of the disclosure to modulate the development and/or differentiation of embryonic stem cells, to inhibit the senescence of stem cells in a degenerative condition (e.g., degenerative diseases), or to stimulate the senescence and apoptosis of stem cells in a disease condition (e.g., cancer stem cells).

Many miRNA expression studies are conducted to profile the differential expression of miRNAs in various cancer cells/tissues and other diseases. Some miRNAs are abnormally over-expressed in certain cancer cells and others are under-expressed. For example, miRNAs are differentially expressed in cancer cells (WO2008/154098, US2013/0059015, US2013/0042333, WO2011/157294); cancer stem cells (US2012/0053224); pancreatic cancers and diseases (US2009/0131348, US2011/0171646, US2010/0286232, U.S. Pat. No. 8,389,210); asthma and inflammation (U.S. Pat. No. 8,415,096); prostate cancer (US2013/0053264); hepatocellular carcinoma (WO2012/151212, US2012/0329672, WO2008/054828, U.S. Pat. No. 8,252,538); lung cancer cells (WO2011/076143, WO2013/033640, WO2009/070653, US2010/0323357); cutaneous T cell lymphoma (WO2013/011378); colorectal cancer cells (WO2011/0281756, WO2011/076142); cancer positive lymph nodes (WO2009/100430, US2009/0263803); nasopharyngeal carcinoma (EP2112235); chronic obstructive pulmonary disease (US2012/0264626, US2013/0053263); thyroid cancer (WO2013/066678); ovarian cancer cells (US2012/0309645, WO2011/095623); breast cancer cells (WO2008/154098, WO2007/081740, US2012/0214699), leukemia and lymphoma (WO2008/073915, US2009/0092974, US2012/0316081, US2012/0283310, WO2010/018563, the content of each of which is incorporated herein by reference in its entirety.)

As a non-limiting example, miRNA binding sites for miRNAs that are over-expressed in certain cancer and/or tumor cells can be removed from the 3'UTR of a polyribonucleotide of the disclosure, restoring the expression suppressed by the over-expressed miRNAs in cancer cells, thus ameliorating the corresponsive biological function, for instance, transcription stimulation and/or repression, cell cycle arrest, apoptosis and cell death. Normal cells and tissues, wherein miRNAs expression is not up-regulated, will remain unaffected.

MiRNA can also regulate complex biological processes such as angiogenesis (e.g., miR-132) (Anand and Cheresh Curr Opin Hematol 2011 18:171-176). In the polyribonucleotides of the disclosure, miRNA binding sites that are involved in such processes can be removed or introduced, in order to tailor the expression of the polyribonucleotides to biologically relevant cell types or relevant biological processes. In this context, the polyribonucleotides of the disclosure are defined as auxotrophic polyribonucleotides.

Stem Loops

Polynucleotides (e.g., mRNAs) may include a stem loop such as, but not limited to, a histone stem loop. The stem loop may be a nucleotide sequence that is about 25 or about 26 nucleotides in length such as, but not limited to, those as described in International Patent Publication No. WO2013/103659, which is incorporated herein by reference. The histone stem loop may be located 3'-relative to the coding region (e.g., at the 3'-terminus of the coding region). As a non-limiting example, the stem loop may be located at the 3'-end of a polynucleotide described herein. In some cases, a polynucleotide (e.g., an mRNA) includes more than one stem loop (e.g., two stem loops). Examples of stem loop sequences are described in International Patent Publication Nos. WO2012/019780 and WO201502667, the stem loop sequences of which are herein incorporated by reference. In some instances, a polynucleotide includes the stem loop sequence

CAAAGGCTCTTTTCAGAGCCACCA. (SEQ ID NO: 1)

In others, a polynucleotide includes the stem loop sequence

CAAAGGCUCUUUUCAGAGCCACCA. (SEQ ID NO: 2)

A stem loop may be located in a second terminal region of a polynucleotide. As a non-limiting example, the stem loop may be located within an untranslated region (e.g., 3'-UTR) in a second terminal region.

In some cases, a polynucleotide such as, but not limited to mRNA, which includes the histone stem loop may be stabilized by the addition of a 3'-stabilizing region (e.g., a 3'-stabilizing region including at least one chain terminating nucleoside). Not wishing to be bound by theory, the addition of at least one chain terminating nucleoside may slow the degradation of a polynucleotide and thus can increase the half-life of the polynucleotide.

In other cases, a polynucleotide such as, but not limited to mRNA, which includes the histone stem loop may be stabilized by an alteration to the 3'-region of the polynucleotide that can prevent and/or inhibit the addition of oligo(U) (see e.g., International Patent Publication No. WO2013/103659).

In yet other cases, a polynucleotide such as, but not limited to mRNA, which includes the histone stem loop may be stabilized by the addition of an oligonucleotide that terminates in a 3'-deoxynucleoside, 2',3'-dideoxynucleoside 3'-O-methylnucleosides, 3'-O-ethylnucleosides, 3'-arabinosides, and other alternative nucleosides known in the art and/or described herein.

In some instances, the polynucleotides of the present disclosure may include a histone stem loop, a poly-A region, and/or a 5'-cap structure. The histone stem loop may be before and/or after the poly-A region. The polynucleotides including the histone stem loop and a poly-A region sequence may include a chain terminating nucleoside described herein.

In other instances, the polynucleotides of the present disclosure may include a histone stem loop and a 5'-cap structure. The 5'-cap structure may include, but is not limited to, those described herein and/or known in the art.

In some cases, the conserved stem loop region may include a miR sequence described herein. As a non-limiting example, the stem loop region may include the seed sequence of a miR sequence described herein. In another non-limiting example, the stem loop region may include a miR-122 seed sequence.

In certain instances, the conserved stem loop region may include a miR sequence described herein and may also include a TEE sequence.

In some cases, the incorporation of a miR sequence and/or a TEE sequence changes the shape of the stem loop region which may increase and/or decrease translation. (See, e.g., Kedde et al. A Pumilio-induced RNA structure switch in p27-3'UTR controls miR-221 and miR-22 accessibility. Nature Cell Biology. 2010, herein incorporated by reference in its entirety).

Polynucleotides may include at least one histone stem-loop and a poly-A region or polyadenylation signal. Non-limiting examples of polynucleotide sequences encoding for at least one histone stem-loop and a poly-A region or a polyadenylation signal are described in International Patent Publication No. WO2013/120497, WO2013/120629, WO2013/120500, WO2013/120627, WO2013/120498, WO2013/120626, WO2013/120499 and WO2013/120628, the sequences of each of which are incorporated herein by reference. In certain cases, the polynucleotide encoding for a histone stem loop and a poly-A region or a polyadenylation signal may code for a pathogen antigen or fragment thereof such as the polynucleotide sequences described in International Patent Publication No WO2013/120499 and WO2013/120628, the sequences of both of which are incorporated herein by reference. In other cases, the polynucleotide encoding for a histone stem loop and a poly-A region or a polyadenylation signal may code for a therapeutic protein such as the polynucleotide sequences described in International Patent Publication No WO2013/120497 and WO2013/120629, the sequences of both of which are incorporated herein by reference. In some cases, the polynucleotide encoding for a histone stem loop and a poly-A region or a polyadenylation signal may code for a tumor antigen or fragment thereof such as the polynucleotide sequences described in International Patent Publication No WO2013/120500 and WO2013/120627, the sequences of both of which are incorporated herein by reference. In other cases, the polynucleotide encoding for a histone stem loop and a poly-A region or a polyadenylation signal may code for an allergenic antigen or an autoimmune self-antigen such as the polynucleotide sequences described in International Patent Publication No WO2013/120498 and WO2013/120626, the sequences of both of which are incorporated herein by reference.

Poly-A Regions

A polynucleotide or nucleic acid (e.g., an mRNA) may include a polyA sequence and/or polyadenylation signal. A polyA sequence may be comprised entirely or mostly of adenine nucleotides or analogs or derivatives thereof. A polyA sequence may be a tail located adjacent to a 3' untranslated region of a nucleic acid.

During RNA processing, a long chain of adenosine nucleotides (poly-A region) is normally added to messenger RNA (mRNA) molecules to increase the stability of the molecule. Immediately after transcription, the 3'-end of the transcript is cleaved to free a 3'-hydroxy. Then poly-A polymerase adds a chain of adenosine nucleotides to the RNA. The process, called polyadenylation, adds a poly-A region that is between 100 and 250 residues long.

Unique poly-A region lengths may provide certain advantages to the alternative polynucleotides of the present disclosure.

Generally, the length of a poly-A region of the present disclosure is at least 30 nucleotides in length. In another embodiment, the poly-A region is at least 35 nucleotides in length. In another embodiment, the length is at least 40 nucleotides. In another embodiment, the length is at least 45 nucleotides. In another embodiment, the length is at least 55 nucleotides. In another embodiment, the length is at least 60 nucleotides. In another embodiment, the length is at least 70 nucleotides. In another embodiment, the length is at least 80 nucleotides. In another embodiment, the length is at least 90 nucleotides. In another embodiment, the length is at least 100 nucleotides. In another embodiment, the length is at least 120 nucleotides. In another embodiment, the length is at least 140 nucleotides. In another embodiment, the length is at least 160 nucleotides. In another embodiment, the length is at least 180 nucleotides. In another embodiment, the length is at least 200 nucleotides. In another embodiment, the length is at least 250 nucleotides. In another embodiment, the length is at least 300 nucleotides. In another embodiment, the length is at least 350 nucleotides. In another embodiment, the length is at least 400 nucleotides. In another embodiment, the length is at least 450 nucleotides. In another embodiment, the length is at least 500 nucleotides. In another embodiment, the length is at least 600 nucleotides. In another embodiment, the length is at least 700 nucleotides. In another embodiment, the length is at least 800 nucleotides. In another embodiment, the length is at least 900 nucleotides. In another embodiment, the length is at least 1000 nucleotides. In another embodiment, the length is at least 1100 nucleotides. In another embodiment, the length is at least 1200 nucleotides. In another embodiment, the length is at least 1300 nucleotides. In another embodiment, the length is at least 1400 nucleotides. In another embodiment, the length is at least 1500 nucleotides. In another embodiment, the length is at least 1600 nucleotides. In another embodiment, the length is at least 1700 nucleotides. In another embodiment, the length is at least 1800 nucleotides. In another embodiment, the length is at least 1900 nucleotides. In another embodiment, the length is at least 2000 nucleotides. In another embodiment, the length is at least 2500 nucleotides. In another embodiment, the length is at least 3000 nucleotides.

In some instances, the poly-A region may be 80 nucleotides, 120 nucleotides, 160 nucleotides in length on an alternative polynucleotide molecule described herein.

In other instances, the poly-A region may be 20, 40, 80, 100, 120, 140 or 160 nucleotides in length on an alternative polynucleotide molecule described herein.

In some cases, the poly-A region is designed relative to the length of the overall alternative polynucleotide. This design may be based on the length of the coding region of the alternative polynucleotide, the length of a particular feature or region of the alternative polynucleotide (such as mRNA), or based on the length of the ultimate product expressed from the alternative polynucleotide. When relative to any feature of the alternative polynucleotide (e.g., other than the mRNA portion which includes the poly-A region) the poly-A region may be 10, 20, 30, 40, 50, 60, 70, 80, 90 or 100% greater in length than the additional feature. The poly-A region may also be designed as a fraction of the alternative polynucleotide to which it belongs. In this context, the poly-A region may be 10, 20, 30, 40, 50, 60, 70, 80, or 90% more of the total length of the construct or the total length of the construct minus the poly-A region.

In certain cases, engineered binding sites and/or the conjugation of polynucleotides (e.g., mRNA) for poly-A binding protein may be used to enhance expression. The engineered binding sites may be sensor sequences which can operate as binding sites for ligands of the local microenvironment of the polynucleotides (e.g., mRNA). As a non-limiting example, the polynucleotides (e.g., mRNA) may include at least one engineered binding site to alter the binding affinity of poly-A binding protein (PABP) and analogs thereof. The incorporation of at least one engineered binding site may increase the binding affinity of the PABP and analogs thereof.

Additionally, multiple distinct polynucleotides (e.g., mRNA) may be linked together to the PABP (poly-A binding protein) through the 3'-end using alternative nucleotides at the 3'-terminus of the poly-A region. Transfection experiments can be conducted in relevant cell lines at and protein production can be assayed by ELISA at 12 hours, 24 hours, 48 hours, 72 hours, and day 7 post-transfection. As a non-limiting example, the transfection experiments may be used to evaluate the effect on PABP or analogs thereof binding affinity as a result of the addition of at least one engineered binding site.

In certain cases, a poly-A region may be used to modulate translation initiation. While not wishing to be bound by theory, the poly-A region recruits PABP which in turn can interact with translation initiation complex and thus may be essential for protein synthesis.

In some cases, a poly-A region may also be used in the present disclosure to protect against 3'-5'-exonuclease digestion.

In some instances, a polynucleotide (e.g., mRNA) may include a polyA-G Quartet. The G-quartet is a cyclic hydrogen bonded array of four guanosine nucleotides that can be formed by G-rich sequences in both DNA and RNA. In this embodiment, the G-quartet is incorporated at the end of the poly-A region. The resultant polynucleotides (e.g., mRNA) may be assayed for stability, protein production and other parameters including half-life at various time points. It has been discovered that the polyA-G quartet results in protein production equivalent to at least 75% of that seen using a poly-A region of 120 nucleotides alone.

In some cases, a polynucleotide (e.g., mRNA) may include a poly-A region and may be stabilized by the addition of a 3'-stabilizing region. The polynucleotides (e.g., mRNA) with a poly-A region may further include a 5'-cap structure.

In other cases, a polynucleotide (e.g., mRNA) may include a poly-A-G Quartet. The polynucleotides (e.g., mRNA) with a poly-A-G Quartet may further include a 5'-cap structure.

In some cases, the 3'-stabilizing region which may be used to stabilize a polynucleotide (e.g., mRNA) including a poly-A region or poly-A-G Quartet may be, but is not limited to, those described in International Patent Publication No. WO2013/103659, the poly-A regions and poly-A-G Quartets of which are incorporated herein by reference. In other cases, the 3'-stabilizing region which may be used with the present disclosure include a chain termination nucleoside such as 3'-deoxyadenosine (cordycepin), 3'-deoxyuridine, 3'-deoxycytosine, 3'-deoxyguanosine, 3'-deoxythymine, 2',3'-dideoxynucleosides, such as 2',3'-dideoxyadenosine, 2',3'-dideoxyuridine, 2',3'-dideoxycytosine, 2',3'-dideoxyguanosine, 2',3'-dideoxythymine, a 2'-deoxynucleoside, or an O-methylnucleoside.

In other cases, a polynucleotide such as, but not limited to mRNA, which includes a polyA region or a poly-A-G Quartet may be stabilized by an alteration to the 3'-region of the polynucleotide that can prevent and/or inhibit the addition of oligio(U) (see e.g., International Patent Publication No. WO2013/103659).

In yet other instances, a polynucleotide such as, but not limited to mRNA, which includes a poly-A region or a poly-A-G Quartet may be stabilized by the addition of an oligonucleotide that terminates in a 3'-deoxynucleoside, 2',3'-dideoxynucleoside 3'-O-methylnucleosides, 3'-O-ethylnucleosides, 3'-arabinosides, and other alternative nucleosides known in the art and/or described herein.

Chain Terminating Nucleosides

A nucleic acid may include a chain terminating nucleoside. For example, a chain terminating nucleoside may include those nucleosides deoxygenated at the 2' and/or 3' positions of their sugar group. Such species may include 3'-deoxyadenosine (cordycepin), 3'-deoxyuridine, 3'-deoxycytosine, 3'-deoxyguanosine, 3'-deoxythymine, and 2',3'-dideoxynucleosides, such as 2',3'-dideoxyadenosine, 2',3'-dideoxyuridine, 2',3'-dideoxycytosine, 2',3'-dideoxyguanosine, and 2',3'-dideoxythymine.

Genome Editing Techniques

In some embodiments, the nucleic acid is suitable for a genome editing technique.

In some embodiments, the genome editing technique is clustered regularly interspaced short palindromic repeats (CRISPR) or transcription activator-like effector nuclease (TALEN).

In some embodiments, the nucleic acid is at least one nucleic acid suitable for a genome editing technique selected from the group consisting of a CRISPR RNA (crRNA), a trans-activating crRNA (tracrRNA), a single guide RNA (sgRNA), and a DNA repair template.

Other Components

A LNP may include one or more components in addition to those described in the preceding sections. For example, a LNP may include one or more small hydrophobic molecules such as a vitamin (e.g., vitamin A or vitamin E) or a sterol.

Lipid nanoparticles may also include one or more permeability enhancer molecules, carbohydrates, polymers, surface altering agents, or other components. A permeability enhancer molecule may be a molecule described by U.S. patent application publication No. 2005/0222064, for example. Carbohydrates may include simple sugars (e.g., glucose) and polysaccharides (e.g., glycogen and derivatives and analogs thereof).

A polymer may be included in and/or used to encapsulate or partially encapsulate a LNP. A polymer may be biodegradable and/or biocompatible. A polymer may be selected from, but is not limited to, polyamines, polyethers, polyamides, polyesters, polycarbamates, polyureas, polycarbonates, polystyrenes, polyimides, polysulfones, polyurethanes, polyacetylenes, polyethylenes, polyethyleneimines, polyisocyanates, polyacrylates, polymethacrylates, polyacrylonitriles, and polyarylates. For example, a polymer may include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacrylate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone (PVP), polysiloxanes, polystyrene, polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, poloxamines, poly(ortho) esters, poly(butyric acid), poly(valeric acid), poly(lactide-co-caprolactone), trimethylene carbonate, poly(N-acryloylmorpholine) (PAcM), poly(2-methyl-2-oxazoline) (PMOX), poly(2-ethyl-2-oxazoline) (PEOZ), and polyglycerol.

Surface altering agents may include, but are not limited to, anionic proteins (e.g., bovine serum albumin), surfactants (e.g., cationic surfactants such as dimethyldioctadecyl-ammonium bromide), sugars or sugar derivatives (e.g., cyclodextrin), nucleic acids, polymers (e.g., heparin, polyethylene glycol, and poloxamer), mucolytic agents (e.g., acetylcysteine, mugwort, bromelain, papain, clerodendrum, bromhexine, carbocisteine, eprazinone, mesna, ambroxol, sobrerol, domiodol, letosteine, stepronin, tiopronin, gelsolin, thymosin 04, dornase alfa, neltenexine, and erdosteine), and DNases (e.g., rhDNase). A surface altering agent may be disposed within a nanoparticle and/or on the surface of a LNP (e.g., by coating, adsorption, covalent linkage, or other process).

A LNP may also comprise one or more functionalized lipids. For example, a lipid may be functionalized with an alkyne group that, when exposed to an azide under appropriate reaction conditions, may undergo a cycloaddition reaction. In particular, a lipid bilayer may be functionalized in this fashion with one or more groups useful in facilitating membrane permeation, cellular recognition, or imaging. The surface of a LNP may also be conjugated with one or more useful antibodies. Functional groups and conjugates useful in targeted cell delivery, imaging, and membrane permeation are well known in the art.

In addition to these components, lipid nanoparticles may include any substance useful in pharmaceutical compositions. For example, the lipid nanoparticle may include one or more pharmaceutically acceptable excipients or accessory ingredients such as, but not limited to, one or more solvents, dispersion media, diluents, dispersion aids, suspension aids, granulating aids, disintegrants, fillers, glidants, liquid vehicles, binders, surface active agents, isotonic agents, thickening or emulsifying agents, buffering agents, lubricating agents, oils, preservatives, and other species. Excipients such as waxes, butters, coloring agents, coating agents, flavorings, and perfuming agents may also be included. Pharmaceutically acceptable excipients are well known in the art (see for example Remington's *The Science and Practice of Pharmacy*, 21$^{st}$ Edition, A. R. Gennaro; Lippincott, Williams & Wilkins, Baltimore, M D, 2006).

Examples of diluents may include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and/or combinations thereof. Granulating and dispersing agents may be selected from the non-limiting list consisting of potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM®), sodium lauryl sulfate, quaternary ammonium compounds, and/or combinations thereof.

Surface active agents and/or emulsifiers may include, but are not limited to, natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite [aluminum silicate] and VEEGUM® [magnesium aluminum silicate]), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate [TWEEN®20], polyoxyethylene sorbitan [TWEEN® 60], polyoxyethylene sorbitan monooleate [TWEEN®80], sorbitan monopalmitate [SPAN®40], sorbitan monostearate [SPAN®60], sorbitan tristearate [SPAN®65], glyceryl monooleate, sorbitan monooleate [SPAN®80]), polyoxyethylene esters (e.g., polyoxyethylene monostearate [MYRJ® 45], polyoxyethylene hydrogenated castor oil, polyethoxylated castor oil, polyoxymethylene stearate, and SOLUTOL®), sucrose fatty acid esters, polyethylene glycol fatty acid esters (e.g., CREMOPHOR®), polyoxyethylene ethers, (e.g., polyoxyethylene lauryl ether [BRIJ® 30]), poly(vinylpyrrolidone), diethylene glycol monolaurate, triethanolamine oleate, sodium oleate, potassium oleate, ethyl oleate, oleic acid, ethyl laurate, sodium lauryl sulfate, PLURONIC®F 68, POLOXAMER® 188, cetrimonium bromide, cetylpyridinium chloride, benzalkonium chloride, docusate sodium, and/or combinations thereof.

A binding agent may be starch (e.g., cornstarch and starch paste); gelatin; sugars (e.g., sucrose, glucose, dextrose, dextrin, molasses, lactose, lactitol, mannitol); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUM®), and larch arabogalactan); alginates; polyethylene oxide; polyethylene glycol; inorganic calcium salts; silicic acid; polymethacrylates; waxes; water; alcohol; and combinations thereof, or any other suitable binding agent.

Examples of preservatives may include, but are not limited to, antioxidants, chelating agents, antimicrobial preservatives, antifungal preservatives, alcohol preservatives, acidic preservatives, and/or other preservatives. Examples of antioxidants include, but are not limited to, alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Examples of chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Examples of antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Examples of antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Examples of alcohol preservatives include, but are not limited to, ethanol, polyethylene glycol, benzyl alcohol, phenol, phenolic compounds, bisphenol, chlorobutanol, hydroxybenzoate, and/or phenylethyl alcohol. Examples of acidic preservatives include, but are not limited to, vitamin A, vitamin C, vitamin E, beta-carotene, citric acid, acetic acid, dehydroascorbic acid, ascorbic acid, sorbic acid, and/or phytic acid. Other preservatives include, but are not limited to, tocopherol, tocopherol acetate, deteroxime mesylate, cetrimide, butylated hydroxyanisole (BHA), butylated hydroxytoluene (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL® 115, GERMABEN®II, NEOLONE™, KATHON™, and/or EUXYL®.

Examples of buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, d-gluconic acid, calcium glycerophosphate, calcium lactate, calcium lactobionate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, amino-sulfonate buffers (e.g., HEPES), magnesium hydroxide, aluminum hydroxide, alginic acid, pyrogen-free water, isotonic saline, Ringer's solution, ethyl alcohol, and/or combinations thereof. Lubricating agents may selected from the non-limiting group consisting of magnesium stearate, calcium stearate, stearic acid, silica, talc, malt, glyceryl behenate, hydrogenated vegetable oils, polyethylene glycol, sodium benzoate, sodium acetate, sodium chloride, leucine, magnesium lauryl sulfate, sodium lauryl sulfate, and combinations thereof.

Examples of oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils as well as butyl stearate, caprylic triglyceride, capric triglyceride, cyclomethicone, diethyl sebacate, dimethicone 360, simethicone, isopropyl myristate, mineral oil, octyldodecanol, oleyl alcohol, silicone oil, and/or combinations thereof.

Formulations

The formulation of the disclosure includes at least one lipid nanoparticle component. Lipid nanoparticles may include a lipid component and one or more additional components, such as a therapeutic and/or prophylactic, such as a nucleic acid. A LNP may be designed for one or more specific applications or targets. The elements of a LNP may be selected based on a particular application or target, and/or based on the efficacy, toxicity, expense, ease of use, availability, or other feature of one or more elements. Similarly, the particular formulation of a LNP may be selected for a particular application or target according to, for example, the efficacy and toxicity of particular combinations of elements. The efficacy and tolerability of a LNP formulation may be affected by the stability of the formulation.

In some embodiments, the weight ratio between the modifying agent and the LNP is about 0.0004:1 to about 100:1 (e.g., about 0.001:1 to about 10:1, about 0.001:1 to about 5:1, about 0.001:1 to about 0.1:1, about 0.005 to about 0.4:1, or about 0.5:1 to about 4:1, about 0.05:1 to about 5:1, about 0.1:1 to about 5:1 or about 0.05:1 to about 2.5:1, about 1:1 to about 50:1, about 2:1 to about 50:1 or about 1:1 to about 25:1).

The lipid component of a LNP may include, for example, a lipid according to Formula (I), (IA), (II), (IIa), (IIb), (IIc), (IId) or (IIe), a phospholipid (such as an unsaturated lipid, e.g., DOPE or DSPC), a PEG lipid, and a structural lipid. The lipid component of a LNP may include, for example, a lipid according to Formula (I), (IA), (II), (IIa), (IIb), (IIc), (IId) or (IIe), a phospholipid (such as an unsaturated lipid, e.g., DOPE or DSPC), and a structural lipid. The elements of the lipid component may be provided in specific fractions.

In some embodiments, the lipid component of a LNP includes a lipid according to Formula (I), (IA), (II), (IIa), (IIb), (IIc), (IId) or (IIe), a phospholipid, a PEG lipid, and a structural lipid. In some embodiments, the lipid component of the lipid nanoparticle includes about 30 mol % to about 60 mol % compound of Formula (I), (IA), (II), (IIa), (IIb), (IIc), (IId) or (IIe), about 0 mol % to about 30 mol % phospholipid, about 18.5 mol % to about 48.5 mol % structural lipid, and about 0 mol % to about 10 mol % of PEG lipid, provided that the total mol % does not exceed 100%. In some embodiments, the lipid component of the lipid nanoparticle includes about 35 mol % to about 55 mol % compound of Formula (I), (IA), (II), (IIa), (IIb), (IIc), (IId) or (IIe), about 5 mol % to about 25 mol % phospholipid, about 30 mol % to about 40 mol % structural lipid, and about 0 mol % to about 10 mol % of PEG lipid. In a particular embodiment, the lipid component includes about 50 mol % said compound, about 10 mol % phospholipid, about 38.5 mol % structural lipid, and about 1.5 mol % of PEG lipid. In another particular embodiment, the lipid component includes about 40 mol % said compound, about 20 mol % phospholipid, about 38.5 mol % structural lipid, and about 1.5 mol % of PEG lipid. In some embodiments, the phospholipid may be DOPE or DSPC. In other embodiments, the PEG lipid may be PEG-DMG and/or the structural lipid may be cholesterol.

Lipid nanoparticles may be designed for one or more specific applications or targets. For example, a LNP may be designed to deliver a therapeutic and/or prophylactic such as an RNA to a particular cell, tissue, organ, or system or group thereof in a mammal's body. Physiochemical properties of lipid nanoparticles may be altered in order to increase selectivity for particular bodily targets. For instance, particle sizes may be adjusted based on the fenestration sizes of different organs. The therapeutic and/or prophylactic included in a LNP may also be selected based on the desired delivery target or targets. For example, a therapeutic and/or prophylactic may be selected for a particular indication, condition, disease, or disorder and/or for delivery to a particular cell, tissue, organ, or system or group thereof (e.g., localized or specific delivery). In some embodiments, a LNP may include an mRNA encoding a polypeptide of interest capable of being translated within a cell to produce the polypeptide of interest. Such a composition may be designed to be specifically delivered to a particular organ. In some embodiments, a composition may be designed to be specifically delivered to a mammalian liver.

The amount of a therapeutic and/or prophylactic in a LNP may depend on the size, composition, desired target and/or application, or other properties of the lipid nanoparticle as well as on the properties of the therapeutic and/or prophylactic. For example, the amount of an RNA useful in a LNP may depend on the size, sequence, and other characteristics of the RNA. The relative amounts of a therapeutic and/or prophylactic and other elements (e.g., lipids) in a LNP may also vary. In some embodiments, the wt/wt ratio of the lipid component to a therapeutic and/or prophylactic, such as a nucleic acid, in a LNP may be from about 5:1 to about 60:1, such as 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, 50:1, and 60:1. For example, the wt/wt ratio of the lipid component to a therapeutic and/or prophylactic may be from about 10:1 to about 40:1. In some embodiments, the wt/wt ratio is about 20:1. The amount of a therapeutic and/or prophylactic in a LNP may, for example, be measured using absorption spectroscopy (e.g., ultraviolet-visible spectroscopy).

In some embodiments, a LNP includes one or more RNAs, and the one or more RNAs, lipids, and amounts thereof may be selected to provide a specific N:P ratio. The N:P ratio of the composition refers to the molar ratio of nitrogen atoms in one or more lipids to the number of phosphate groups in an RNA. In general, a lower N:P ratio is preferred. The one or more RNA, lipids, and amounts thereof may be selected to provide an N:P ratio from about 2:1 to about 30:1, such as 2:1, 3:1, 4:1, 5:1, 6:1, 7:1, 8:1, 9:1, 10:1, 12:1, 14:1, 16:1, 18:1, 20:1, 22:1, 24:1, 26:1, 28:1, or 30:1. In some embodiments, the N:P ratio may be from about 2:1 to about 8:1. In other embodiments, the N:P ratio is from about 5:1 to about 8:1. For example, the N:P ratio may be about 5.0:1, about 5.5:1, about 5.67:1, about 6.0:1, about 6.5:1, or about 7.0:1. For example, the N:P ratio may be about 5.67:1.

In some embodiments, the formulation including a LNP may further includes a salt, such as a chloride salt.

In some embodiments, the formulation including a LNP may further includes a sugar such as a disaccharide. In some embodiments, the formulation further includes a sugar but not a salt, such as a chloride salt.

Physical Properties

The characteristics of a LNP may depend on the components thereof. For example, a LNP including cholesterol as a structural lipid may have different characteristics than a LNP that includes a different structural lipid. Similarly, the characteristics of a LNP may depend on the absolute or relative amounts of its components. For instance, a LNP including a higher molar fraction of a phospholipid may have different characteristics than a LNP including a lower molar fraction of a phospholipid. Characteristics may also vary depending on the method and conditions of preparation of the lipid nanoparticle.

Lipid nanoparticles may be characterized by a variety of methods. For example, microscopy (e.g., transmission electron microscopy or scanning electron microscopy) may be used to examine the morphology and size distribution of a LNP. Dynamic light scattering or potentiometry (e.g., potentiometric titrations) may be used to measure zeta potentials. Dynamic light scattering may also be utilized to determine particle sizes. Instruments such as the Zetasizer Nano ZS (Malvern Instruments Ltd, Malvern, Worcestershire, UK) may also be used to measure multiple characteristics of a LNP, such as particle size, polydispersity index, and zeta potential.

The mean size of a LNP may be between 10s of nm and 100s of nm, e.g., measured by dynamic light scattering (DLS). For example, the mean size may be from about 40 nm to about 150 nm, such as about 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm. In some embodiments, the mean size of a LNP may be from about 50 nm to about 100 nm, from about 50 nm to about 90 nm, from about 50 nm to about 80 nm, from about 50 nm to about 70 nm, from about 50 nm to about 60 nm, from about 60 nm to about 100 nm, from about 60 nm to about 90 nm, from about 60 nm to about 80 nm, from about 60 nm to about 70 nm, from about 70 nm to about 100 nm, from about 70 nm to about 90 nm, from about 70 nm to about 80 nm, from about 80 nm to about 100 nm, from about 80 nm to about 90 nm, or from about 90 nm to about 100 nm. In some embodiments, the mean size of a LNP may be from about 70 nm to about 100 nm. In a particular embodiment, the mean size may be about 80 nm. In other embodiments, the mean size may be about 100 nm.

A LNP may be relatively homogenous. A polydispersity index may be used to indicate the homogeneity of a LNP, e.g., the particle size distribution of the lipid nanoparticles. A small (e.g., less than 0.3) polydispersity index generally indicates a narrow particle size distribution. A LNP may have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a LNP may be from about 0.10 to about 0.20.

The zeta potential of a LNP may be used to indicate the electrokinetic potential of the composition. For example, the zeta potential may describe the surface charge of a LNP. Lipid nanoparticles with relatively low charges, positive or negative, are generally desirable, as more highly charged species may interact undesirably with cells, tissues, and other elements in the body. In some embodiments, the zeta potential of a LNP may be from about −10 mV to about +20 mV, from about −10 mV to about +15 mV, from about −10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

The efficiency of encapsulation of a therapeutic and/or prophylactic, such as a nucleic acid describes the amount of therapeutic and/or prophylactic that is encapsulated or otherwise associated with a LNP after preparation, relative to the initial amount provided. The encapsulation efficiency is desirably high (e.g., close to 100%). The encapsulation efficiency may be measured, for example, by comparing the amount of therapeutic and/or prophylactic in a solution containing the lipid nanoparticle before and after breaking up the lipid nanoparticle with one or more organic solvents or detergents. Fluorescence may be used to measure the amount of free therapeutic and/or prophylactic (e.g., RNA) in a solution. For the lipid nanoparticles described herein, the encapsulation efficiency of a therapeutic and/or prophylactic may be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency may be at least 80%. In some embodiments, the encapsulation efficiency may be at least 90%.

A LNP may optionally comprise one or more coatings. For example, a LNP may be formulated in a capsule, film, or tablet having a coating. A capsule, film, or tablet including a composition described herein may have any useful size, tensile strength, hardness, or density.

Pharmaceutical Compositions

Formulations comprising lipid nanoparticles may be formulated in whole or in part as pharmaceutical compositions. Pharmaceutical compositions may include one or more lipid nanoparticles. For example, a pharmaceutical composition may include one or more lipid nanoparticles including one or more different therapeutics and/or prophylactics. Pharmaceutical compositions may further include one or more pharmaceutically acceptable excipients or accessory ingredients such as those described herein. General guidelines for the formulation and manufacture of pharmaceutical compositions and agents are available, for example, in Remington's *The Science and Practice of Pharmacy*, 21$^{st}$ Edition, A. R. Gennaro; Lippincott, Williams & Wilkins, Baltimore, MD, 2006. Conventional excipients and accessory ingredients may be used in any pharmaceutical composition, except insofar as any conventional excipient or accessory ingredient may be incompatible with one or more components of a LNP in the formulation of the disclosure. An excipient or accessory ingredient may be incompatible with a component of a LNP of the formulation if its combination with the component or LNP may result in any undesirable biological effect or otherwise deleterious effect.

In some embodiments, one or more excipients or accessory ingredients may make up greater than 50% of the total mass or volume of a pharmaceutical composition including a LNP. For example, the one or more excipients or accessory ingredients may make up 50%, 60%, 70%, 80%, 90%, or more of a pharmaceutical convention. In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Relative amounts of the one or more lipid nanoparticles, the one or more pharmaceutically acceptable excipients, and/or any additional ingredients in a pharmaceutical composition in accordance with the present disclosure will vary, depending upon the identity, size, and/or condition of the subject treated and further depending upon the route by which the composition is to be administered. By way of example, a pharmaceutical composition may comprise between 0.1% and 100% (wt/wt) of one or more lipid nanoparticles. As another example, a pharmaceutical composition may comprise between 0.1% and 15% (wt/vol) of one or more amphiphilic polymers (e.g., 0.5%, 1%, 2.5%, 5%, 10%, or 12.5% w/v).

In some embodiments, the lipid nanoparticles and/or pharmaceutical compositions of the disclosure are refrigerated or frozen for storage and/or shipment (e.g., being stored at a temperature of 4° C. or lower, such as a temperature between about −150° C. and about 0° C. or between about −80° C. and about −20° C. (e.g., about −5° C., −10° C., −15° C., −20° C., −25° C., −30° C., −40° C., −50° C., −60° C., −70° C., −80° C., −90° C., −130° C. or −150° C.). For example, the pharmaceutical composition comprising one or more lipid nanoparticles is a solution or solid (e.g., via lyophilization) that is refrigerated for storage and/or shipment at, for example, about −20° C., −30° C., −40° C., −50° C., −60° C., −70° C., or −80° C. In some embodiments, the disclosure also relates to a method of increasing stability of the lipid nanoparticles and by storing the lipid nanoparticles and/or pharmaceutical compositions thereof at a temperature of 4° C. or lower, such as a temperature between about −150° C. and about 0° C. or between about −80° C. and about −20° C., e.g., about −5° C., −10° C., −15° C., −20° C., −25° C., −30° C., −40° C., −50° C., −60° C., −70° C., −80° C., −90° C., −130° C. or −150° C.).

Lipid nanoparticles and/or pharmaceutical compositions including one or more lipid nanoparticles may be administered to any patient or subject, including those patients or subjects that may benefit from a therapeutic effect provided by the delivery of a therapeutic and/or prophylactic to one or more particular cells, tissues, organs, or systems or groups thereof, such as the renal system. Although the descriptions provided herein of lipid nanoparticles and pharmaceutical compositions including lipid nanoparticles are principally directed to compositions which are suitable for administration to humans, it will be understood by the skilled artisan that such compositions are generally suitable for administration to any other mammal. Modification of compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the compositions is contemplated include, but are not limited to, humans, other primates, and other mammals, including commercially relevant mammals such as cattle, pigs, hoses, sheep, cats, dogs, mice, and/or rats.

A pharmaceutical composition including one or more lipid nanoparticles may be prepared by any method known or hereafter developed in the art of pharmacology. In general, such preparatory methods include bringing the active ingredient into association with an excipient and/or one or more other accessory ingredients, and then, if desirable or necessary, dividing, shaping, and/or packaging the product into a desired single- or multi-dose unit.

A pharmaceutical composition in accordance with the present disclosure may be prepared, packaged, and/or sold in bulk, as a single unit dose, and/or as a plurality of single unit doses. As used herein, a "unit dose" is discrete amount of the pharmaceutical composition comprising a predetermined amount of the active ingredient (e.g., lipid nanoparticle). The amount of the active ingredient is generally equal to the dosage of the active ingredient which would be administered to a subject and/or a convenient fraction of such a dosage such as, for example, one-half or one-third of such a dosage.

Pharmaceutical compositions may be prepared in a variety of forms suitable for a variety of routes and methods of administration. For example, pharmaceutical compositions may be prepared in liquid dosage forms (e.g., emulsions, microemulsions, nanoemulsions, solutions, suspensions, syrups, and elixirs), injectable forms, solid dosage forms (e.g., capsules, tablets, pills, powders, and granules), dosage forms for topical and/or transdermal administration (e.g., ointments, pastes, creams, lotions, gels, powders, solutions, sprays, inhalants, and patches), suspensions, powders, and other forms.

Liquid dosage forms for oral and parenteral administration include, but are not limited to, pharmaceutically acceptable emulsions, microemulsions, nanoemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include additional therapeutics and/or prophylactics, additional agents such as wetting agents, emulsifying and suspending agents, sweetening, flavoring, and/or perfuming agents. In some embodiments for parenteral administration, compositions are mixed with solubilizing agents such as Cremophor®, alcohols, oils, modified oils, glycols, polysorbates, cyclodextrins, polymers, and/or combinations thereof.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it is often desirable to slow the absorption of the active ingredient from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are prepared by entrapping the drug in liposomes or microemulsions which are compatible with body tissues.

Compositions for rectal or vaginal administration are typically suppositories which can be prepared by mixing compositions with suitable non-irritating excipients such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, films, powders, and granules. In such solid dosage forms, an active ingredient is mixed with at least one inert, pharmaceutically acceptable excipient such as sodium citrate or dicalcium phosphate and/or fillers or extenders (e.g., starches, lactose, sucrose, glucose, mannitol, and silicic acid), binders (e.g., carboxymethylcellulose, alginates, gelatin, polyvinylpyrrolidone, sucrose, and acacia), humectants (e.g., glycerol), disintegrating agents (e.g., agar, calcium carbonate, potato or tapioca starch, alginic acid, certain silicates, and sodium carbonate), solution retarding agents (e.g., paraffin), absorption accelerators (e.g., quaternary ammonium compounds), wetting agents (e.g., cetyl alcohol and glycerol monostearate), absorbents (e.g., kaolin and bentonite clay, silicates), and lubricants (e.g., talc, calcium stearate, magnesium stearate, solid polyethylene glycols, sodium lauryl sulfate), and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. Solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

Dosage forms for topical and/or transdermal administration of a composition may include ointments, pastes, creams, lotions, gels, powders, solutions, sprays, inhalants, and/or patches. Generally, an active ingredient is admixed under sterile conditions with a pharmaceutically acceptable excipient and/or any needed preservatives and/or buffers as may be required. Additionally, the present disclosure contemplates the use of transdermal patches, which often have the added advantage of providing controlled delivery of a compound to the body. Such dosage forms may be prepared, for example, by dissolving and/or dispensing the compound in the proper medium. Alternatively or additionally, rate may be controlled by either providing a rate controlling membrane and/or by dispersing the compound in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid compositions to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (wt/wt) active ingredient, although the concentration of active ingredient may be as high as the solubility limit of the active ingredient in the solvent. Formulations for topical administration may further comprise one or more of the additional ingredients described herein.

A pharmaceutical composition may be prepared, packaged, and/or sold in a formulation suitable for pulmonary administration via the buccal cavity. Such a formulation may comprise dry particles which comprise the active ingredient. Such compositions are conveniently in the form of dry powders for administration using a device comprising a dry powder reservoir to which a stream of propellant may be directed to disperse the powder and/or using a self-propelling solvent/powder dispensing container such as a device comprising the active ingredient dissolved and/or suspended in a low-boiling propellant in a sealed container. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50% to 99.9% (wt/wt) of the composition, and active ingredient may constitute 0.1% to 20% (wt/wt) of the composition. A propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide an active ingredient in the form of droplets of a solution and/or suspension. Such formulations may be prepared, packaged, and/or sold as aqueous and/or dilute alcoholic solutions and/or suspensions, optionally sterile, comprising active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. Droplets provided by this route of administration may have an average diameter in the range from about 1 nm to about 200 nm.

Formulations described herein as being useful for pulmonary delivery are useful for intranasal delivery of a pharmaceutical composition. Another formulation suitable for intranasal administration is a coarse powder comprising the active ingredient and having an average particle from about 0.2 m to 500 m. Such a formulation is administered in the manner in which snuff is taken, i.e. by rapid inhalation through the nasal passage from a container of the powder held close to the nose.

Formulations suitable for nasal administration may, for example, comprise from about as little as 0.1% (wt/wt) and as much as 100% (wt/wt) of active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, 0.1% to 20% (wt/wt) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising active ingredient. Such powdered, aerosolized, and/or aerosolized formulations, when dispersed, may have an average particle and/or droplet size in the range from about 0.1 nm to about 200 nm, and may further comprise one or more of any additional ingredients described herein.

A pharmaceutical composition may be prepared, packaged, and/or sold in a formulation suitable for ophthalmic administration. Such formulations may, for example, be in the form of eye drops including, for example, a 0.1/1.0% (wt/wt) solution and/or suspension of the active ingredient in an aqueous or oily liquid excipient. Such drops may further comprise buffering agents, salts, and/or one or more other of any additional ingredients described herein. Other ophthalmically-administrable formulations which are useful include those which comprise the active ingredient in microcrystalline form and/or in a liposomal preparation. Ear drops and/or eye drops are contemplated as being within the scope of this present disclosure.

Methods of Producing Polypeptides in Cells

The present disclosure provides methods of producing a polypeptide of interest in a mammalian cell. Methods of producing polypeptides involve contacting a cell with a formulation of the disclosure comprising a LNP including an mRNA encoding the polypeptide of interest. Upon contacting the cell with the lipid nanoparticle, the mRNA may be taken up and translated in the cell to produce the polypeptide of interest.

In general, the step of contacting a mammalian cell with a LNP including an mRNA encoding a polypeptide of interest may be performed in vivo, ex vivo, in culture, or in vitro. The amount of lipid nanoparticle contacted with a cell, and/or the amount of mRNA therein, may depend on the type of cell or tissue being contacted, the means of administration, the physiochemical characteristics of the lipid nanoparticle and the mRNA (e.g., size, charge, and chemical composition) therein, and other factors. In general, an effective amount of the lipid nanoparticle will allow for efficient polypeptide production in the cell. Metrics for efficiency may include polypeptide translation (indicated by polypeptide expression), level of mRNA degradation, and immune response indicators.

The step of contacting a LNP including an mRNA with a cell may involve or cause transfection. A phospholipid including in the lipid component of a LNP may facilitate transfection and/or increase transfection efficiency, for example, by interacting and/or fusing with a cellular or intracellular membrane. Transfection may allow for the translation of the mRNA within the cell.

In some embodiments, the lipid nanoparticles described herein may be used therapeutically. For example, an mRNA included in a LNP may encode a therapeutic polypeptide (e.g., in a translatable region) and produce the therapeutic polypeptide upon contacting and/or entry (e.g., transfection) into a cell. In other embodiments, an mRNA included in a LNP may encode a polypeptide that may improve or increase the immunity of a subject. For example, an mRNA may encode a granulocyte-colony stimulating factor or trastuzumab.

In some embodiments, an mRNA included in a LNP may encode a recombinant polypeptide that may replace one or more polypeptides that may be substantially absent in a cell contacted with the lipid nanoparticle. The one or more substantially absent polypeptides may be lacking due to a genetic mutation of the encoding gene or a regulatory pathway thereof. Alternatively, a recombinant polypeptide produced by translation of the mRNA may antagonize the activity of an endogenous protein present in, on the surface of, or secreted from the cell. An antagonistic recombinant polypeptide may be desirable to combat deleterious effects caused by activities of the endogenous protein, such as altered activities or localization caused by mutation. In another alternative, a recombinant polypeptide produced by translation of the mRNA may indirectly or directly antagonize the activity of a biological moiety present in, on the surface of, or secreted from the cell. Antagonized biological moieties may include, but are not limited to, lipids (e.g., cholesterol), lipoproteins (e.g., low density lipoprotein), nucleic acids, carbohydrates, and small molecule toxins. Recombinant polypeptides produced by translation of the mRNA may be engineered for localization within the cell, such as within a specific compartment such as the nucleus, or may be engineered for secretion from the cell or for translocation to the plasma membrane of the cell.

In some embodiments, contacting a cell with a LNP including an mRNA may reduce the innate immune response of a cell to an exogenous nucleic acid. A cell may be contacted with a first lipid nanoparticle including a first amount of a first exogenous mRNA including a translatable region and the level of the innate immune response of the cell to the first exogenous mRNA may be determined. Subsequently, the cell may be contacted with a second composition including a second amount of the first exogenous mRNA, the second amount being a lesser amount of the first exogenous mRNA compared to the first amount. Alternatively, the second composition may include a first amount of a second exogenous mRNA that is different from the first exogenous mRNA. The steps of contacting the cell with the first and second compositions may be repeated one or more times. Additionally, efficiency of polypeptide production (e.g., translation) in the cell may be optionally determined, and the cell may be re-contacted with the first and/or second composition repeatedly until a target protein production efficiency is achieved.

Methods of Delivering Therapeutic Agents to Cells and Organs

The present disclosure provides methods of delivering a therapeutic and/or prophylactic, such as a nucleic acid, to a mammalian cell or organ. Delivery of a therapeutic and/or prophylactic to a cell involves administering a formulation of the disclosure that comprises a LNP including the therapeutic and/or prophylactic, such as a nucleic acid, to a subject, where administration of the composition involves contacting the cell with the composition. For example, a protein, cytotoxic agent, radioactive ion, chemotherapeutic agent, or nucleic acid (such as an RNA, e.g., mRNA) may be delivered to a cell or organ. In the instance that a therapeutic and/or prophylactic is an mRNA, upon contacting a cell with the lipid nanoparticle, a translatable mRNA may be translated in the cell to produce a polypeptide of interest. However, mRNAs that are substantially not translatable may also be delivered to cells. Substantially non-translatable mRNAs may be useful as vaccines and/or may sequester translational components of a cell to reduce expression of other species in the cell.

In some embodiments, a LNP may target a particular type or class of cells (e.g., cells of a particular organ or system thereof). For example, a LNP including a therapeutic and/or prophylactic of interest may be specifically delivered to a mammalian liver, kidney, spleen, femur, or lung. Specific delivery to a particular class of cells, an organ, or a system or group thereof implies that a higher proportion of lipid nanoparticles including a therapeutic and/or prophylactic are delivered to the destination (e.g., tissue) of interest relative to other destinations, e.g., upon administration of a LNP to a mammal. In some embodiments, specific delivery may result in a greater than 2 fold, 5 fold, 10 fold, 15 fold, or 20 fold increase in the amount of therapeutic and/or prophylactic per 1 g of tissue of the targeted destination (e.g., tissue of interest, such as a liver) as compared to another destination (e.g., the spleen). In some embodiments, the tissue of interest is selected from the group consisting of a liver, kidney, a lung, a spleen, a femur, vascular endothelium in vessels (e.g., intra-coronary or intra-femoral) or kidney, and tumor tissue (e.g., via intratumoral injection).

As another example of targeted or specific delivery, an mRNA that encodes a protein-binding partner (e.g., an antibody or functional fragment thereof, a scaffold protein, or a peptide) or a receptor on a cell surface may be included in a LNP. An mRNA may additionally or instead be used to direct the synthesis and extracellular localization of lipids, carbohydrates, or other biological moieties. Alternatively, other therapeutics and/or prophylactics or elements (e.g., lipids or ligands) of a LNP may be selected based on their affinity for particular receptors (e.g., low density lipoprotein receptors) such that a LNP may more readily interact with a target cell population including the receptors. For example, ligands may include, but are not limited to, members of a specific binding pair, antibodies, monoclonal antibodies, Fv fragments, single chain Fv (scFv) fragments, Fab' fragments, F(ab')2 fragments, single domain antibodies, camelized antibodies and fragments thereof, humanized antibodies and fragments thereof, and multivalent versions thereof, multivalent binding reagents including mono- or bi-specific antibodies such as disulfide stabilized Fv fragments, scFv tandems, diabodies, tribodies, or tetrabodies; and aptamers, receptors, and fusion proteins.

In some embodiments, a ligand may be a surface-bound antibody, which can permit tuning of cell targeting specificity. This is especially useful since highly specific antibodies can be raised against an epitope of interest for the desired targeting site. In some embodiments, multiple antibodies are expressed on the surface of a cell, and each antibody can have a different specificity for a desired target. Such approaches can increase the avidity and specificity of targeting interactions.

A ligand can be selected, e.g., by a person skilled in the biological arts, based on the desired localization or function of the cell. For example an estrogen receptor ligand, such as tamoxifen, can target cells to estrogen-dependent breast cancer cells that have an increased number of estrogen receptors on the cell surface. Other non-limiting examples of ligand/receptor interactions include CCR1 (e.g., for treatment of inflamed joint tissues or brain in rheumatoid arthritis, and/or multiple sclerosis), CCR7, CCR8 (e.g., targeting to lymph node tissue), CCR6, CCR9, CCR10 (e.g., to target to intestinal tissue), CCR4, CCR10 (e.g., for targeting to skin), CXCR4 (e.g., for general enhanced transmigration), HCELL (e.g., for treatment of inflammation and inflammatory disorders, bone marrow), Alpha4beta7 (e.g., for intestinal mucosa targeting), and VLA-4NCAM-1 (e.g., targeting to endothelium). In general, any receptor involved in targeting (e.g., cancer metastasis) can be harnessed for use in the methods and compositions described herein.

Targeted cells may include, but are not limited to, hepatocytes, epithelial cells, hematopoietic cells, epithelial cells, endothelial cells, lung cells, bone cells, stem cells, mesenchymal cells, neural cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes, and tumor cells.

In some embodiments, a LNP may target hepatocytes. Apolipoproteins such as apolipoprotein E (apoE) have been shown to associate with neutral or near neutral lipid-containing lipid nanoparticles in the body, and are known to associate with receptors such as low-density lipoprotein receptors (LDLRs) found on the surface of hepatocytes. Thus, a LNP including a lipid component with a neutral or near neutral charge that is administered to a subject may acquire apoE in a subject's body and may subsequently deliver a therapeutic and/or prophylactic (e.g., an RNA) to hepatocytes including LDLRs in a targeted manner.

Methods of Treating Diseases and Disorders

Lipid nanoparticles may be useful for treating a disease, disorder, or condition. In particular, such compositions may be useful in treating a disease, disorder, or condition characterized by missing or aberrant protein or polypeptide activity. For example, a formulation of the disclosure that comprises a LNP including an mRNA encoding a missing or aberrant polypeptide may be administered or delivered to a cell. Subsequent translation of the mRNA may produce the polypeptide, thereby reducing or eliminating an issue caused by the absence of or aberrant activity caused by the polypeptide. Because translation may occur rapidly, the methods and compositions may be useful in the treatment of acute diseases, disorders, or conditions such as sepsis, stroke, and myocardial infarction. A therapeutic and/or prophylactic included in a LNP may also be capable of altering the rate of transcription of a given species, thereby affecting gene expression.

Diseases, disorders, and/or conditions characterized by dysfunctional or aberrant protein or polypeptide activity for which a composition may be administered include, but are not limited to, rare diseases, infectious diseases (as both vaccines and therapeutics), cancer and proliferative diseases, genetic diseases (e.g., cystic fibrosis), autoimmune diseases, diabetes, neurodegenerative diseases, cardio- and reno-vascular diseases, and metabolic diseases. Multiple diseases, disorders, and/or conditions may be characterized by missing (or substantially diminished such that proper protein function does not occur) protein activity. Such proteins may not be present, or they may be essentially non-functional. A specific example of a dysfunctional protein is the missense mutation variants of the cystic fibrosis transmembrane conductance regulator (CFTR) gene, which produce a dysfunctional protein variant of CFTR protein, which causes cystic fibrosis. The present disclosure provides a method for treating such diseases, disorders, and/or conditions in a subject by administering a LNP including an RNA and a lipid component including a lipid according to Formula (I), a phospholipid (optionally unsaturated), a PEG lipid, and a structural lipid, wherein the RNA may be an mRNA encoding a polypeptide that antagonizes or otherwise overcomes an aberrant protein activity present in the cell of the subject.

The disclosure provides methods involving administering lipid nanoparticles including one or more therapeutic and/or prophylactic agents, such as a nucleic acid, and pharmaceutical compositions including the same. The terms therapeutic and prophylactic can be used interchangeably herein with respect to features and embodiments of the present disclosure. Therapeutic compositions, or imaging, diagnostic, or prophylactic compositions thereof, may be administered to a subject using any reasonable amount and any route of administration effective for preventing, treating, diagnosing, or imaging a disease, disorder, and/or condition and/or any other purpose. The specific amount administered to a given subject may vary depending on the species, age, and general condition of the subject; the purpose of the administration; the particular composition; the mode of administration; and the like. Compositions in accordance with the present disclosure may be formulated in dosage unit form for ease of administration and uniformity of dosage. It will be understood, however, that the total daily usage of a composition of the present disclosure will be decided by an attending physician within the scope of sound medical judgment. The specific therapeutically effective, prophylactically effective, or otherwise appropriate dose level (e.g., for imaging) for any particular patient will depend upon a variety of factors including the severity and identify of a disorder being treated, if any; the one or more therapeutics and/or prophylactics employed; the specific composition employed; the age, body weight, general health, sex, and diet of the patient; the time of administration, route of administration, and rate of excretion of the specific pharmaceutical composition employed; the duration of the treatment; drugs used in combination or coincidental with the specific pharmaceutical composition employed; and like factors well known in the medical arts.

A LNP including one or more therapeutics and/or prophylactics, such as a nucleic acid, may be administered by any route. In some embodiments, compositions, including prophylactic, diagnostic, or imaging compositions including one or more lipid nanoparticles described herein, are administered by one or more of a variety of routes, including oral, intravenous, intramuscular, intra-arterial, intramedullary, intrathecal, subcutaneous, intraventricular, trans- or intradermal, interdermal, rectal, intravaginal, intraperitoneal, topical (e.g., by powders, ointments, creams, gels, lotions, and/or drops), mucosal, nasal, buccal, enteral, intravitreal, intratumoral, sublingual, intranasal; by intratracheal instillation, bronchial instillation, and/or inhalation; as an oral spray and/or powder, nasal spray, and/or aerosol, and/or through a portal vein catheter. In some embodiments, a composition may be administered intravenously, intramuscularly, intradermally, intra-arterially, intratumorally, subcutaneously, or by inhalation. However, the present disclosure encompasses the delivery or administration of compositions described herein by any appropriate route taking into consideration likely advances in the sciences of drug delivery. In general, the most appropriate route of administration will depend upon a variety of factors including the nature of the lipid nanoparticle including one or more therapeutics and/or prophylactics (e.g., its stability in various bodily environments such as the bloodstream and gastrointestinal tract), the condition of the patient (e.g., whether the patient is able to tolerate particular routes of administration), etc.

In some embodiments, compositions in accordance with the present disclosure may be administered at dosage levels sufficient to deliver from about 0.0001 mg/kg to about 10 mg/kg, from about 0.001 mg/kg to about 10 mg/kg, from about 0.005 mg/kg to about 10 mg/kg, from about 0.01 mg/kg to about 10 mg/kg, from about 0.05 mg/kg to about 10 mg/kg, from about 0.1 mg/kg to about 10 mg/kg, from about 1 mg/kg to about 10 mg/kg, from about 2 mg/kg to about 10 mg/kg, from about 5 mg/kg to about 10 mg/kg, from about 0.0001 mg/kg to about 5 mg/kg, from about 0.001 mg/kg to about 5 mg/kg, from about 0.005 mg/kg to about 5 mg/kg, from about 0.01 mg/kg to about 5 mg/kg, from about 0.05 mg/kg to about 5 mg/kg, from about 0.1 mg/kg to about 5 mg/kg, from about 1 mg/kg to about 5 mg/kg, from about 2 mg/kg to about 5 mg/kg, from about 0.0001 mg/kg to about 2.5 mg/kg, from about 0.001 mg/kg to about 2.5 mg/kg, from about 0.005 mg/kg to about 2.5 mg/kg, from about 0.01 mg/kg to about 2.5 mg/kg, from about 0.05 mg/kg to about 2.5 mg/kg, from about 0.1 mg/kg to about 2.5 mg/kg, from about 1 mg/kg to about 2.5 mg/kg, from about 2 mg/kg to about 2.5 mg/kg, from about 0.0001 mg/kg to about 1 mg/kg, from about 0.001 mg/kg to about 1 mg/kg, from about 0.005 mg/kg to about 1 mg/kg, from about 0.01 mg/kg to about 1 mg/kg, from about 0.05 mg/kg to about 1 mg/kg, from about 0.1 mg/kg to about 1 mg/kg, from about 0.0001 mg/kg to about 0.25 mg/kg, from about 0.001 mg/kg to about 0.25 mg/kg, from about 0.005 mg/kg to about 0.25 mg/kg, from about 0.01 mg/kg to about 0.25 mg/kg, from about 0.05 mg/kg to about 0.25 mg/kg, or from about 0.1 mg/kg to about 0.25 mg/kg of a therapeutic and/or prophylactic (e.g., an mRNA) in a given dose, where a dose of 1 mg/kg (mpk) provides 1 mg of a therapeutic and/or prophylactic per 1 kg of subject body weight. In some embodiments, a dose of about 0.001 mg/kg to about 10 mg/kg of a therapeutic and/or prophylactic (e.g., mRNA) of a LNP may be administered. In other embodiments, a dose of about 0.005 mg/kg to about 2.5 mg/kg of a therapeutic and/or prophylactic may be administered. In some embodiments, a dose of about 0.1 mg/kg to about 1 mg/kg may be administered. In other embodiments, a dose of about 0.05 mg/kg to about 0.25 mg/kg may be administered. A dose may be administered one or more times per day, in the same or a different amount, to obtain a desired level of mRNA expression and/or therapeutic, diagnostic, prophylactic, or imaging effect. The desired dosage may be delivered, for example, three times a day, two times a day, once a day, every other day, every third day, every week, every two weeks, every three weeks, or every four weeks. In some embodiments, the desired dosage may be delivered using multiple administrations (e.g., two, three, four, five, six, seven, eight, nine, ten, eleven, twelve, thirteen, fourteen, or more administrations). In some embodiments, a single dose may be administered, for example, prior to or after a surgical procedure or in the instance of an acute disease, disorder, or condition.

Lipid nanoparticles including one or more therapeutics and/or prophylactics, such as a nucleic acid, may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. For example, one or more lipid nanoparticles including one or more different therapeutics and/or prophylactics may be administered in combination. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of compositions, or imaging, diagnostic, or prophylactic compositions thereof in combination with agents that improve their bioavailability, reduce and/or modify their metabolism, inhibit their excretion, and/or modify their distribution within the body.

It will further be appreciated that therapeutically, prophylactically, diagnostically, or imaging active agents utilized in combination may be administered together in a single composition or administered separately in different compositions. In general, it is expected that agents utilized in combination will be utilized at levels that do not exceed the levels at which they are utilized individually. In some embodiments, the levels utilized in combination may be lower than those utilized individually.

The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a composition useful for treating cancer may be administered concurrently with a chemotherapeutic agent), or they may achieve different effects (e.g., control of any adverse effects, such as infusion related reactions).

A LNP may be used in combination with an agent to increase the effectiveness and/or therapeutic window of the composition. Such an agent may be, for example, an anti-inflammatory compound, a steroid (e.g., a corticosteroid), a statin, an estradiol, a BTK inhibitor, an S1P1 agonist, a glucocorticoid receptor modulator (GRM), or an anti-histamine. In some embodiments, a LNP may be used in combination with dexamethasone, methotrexate, acetaminophen, an H1 receptor blocker, or an H2 receptor blocker. In some embodiments, a method of treating a subject in need thereof or of delivering a therapeutic and/or prophylactic to a subject (e.g., a mammal) may involve pre-treating the subject with one or more agents prior to administering a LNP. For example, a subject may be pre-treated with a useful amount (e.g., 10 mg, 20 mg, 30 mg, 40 mg, 50 mg, 60 mg, 70 mg, 80 mg, 90 mg, 100 mg, or any other useful amount) of dexamethasone, methotrexate, acetaminophen, an H1 receptor blocker, or an H2 receptor blocker. Pre-treatment may occur 24 or fewer hours (e.g., 24 hours, 20 hours, 16 hours, 12 hours, 8 hours, 4 hours, 2 hours, 1 hour, 50 minutes, 40 minutes, 30 minutes, 20 minutes, or 10 minutes) before administration of the lipid nanoparticle and may occur one, two, or more times in, for example, increasing dosage amounts.

Those skilled in the art will recognize, or be able to ascertain using no more than routine experimentation, many equivalents to the specific embodiments in accordance with the disclosure described herein. The scope of the present disclosure is not intended to be limited to the above Description, but rather is as set forth in the appended claims.

Definitions

As used herein, the term "alkyl" or "alkyl group" means a linear or branched, saturated hydrocarbon including one or more carbon atoms (e.g., one, two, three, four, five, six, seven, eight, nine, ten, eleven, twelve, thirteen, fourteen, fifteen, sixteen, seventeen, eighteen, nineteen, twenty, or more carbon atoms), which is optionally substituted. The notation "$C_{1-14}$ alkyl" means an optionally substituted linear or branched, saturated hydrocarbon including 1-14 carbon atoms. Unless otherwise specified, an alkyl group described herein refers to both unsubstituted and substituted alkyl groups.

As used herein, the term "alkenyl" or "alkenyl group" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one double bond, which is optionally substituted. The notation "$C_{2-14}$ alkenyl" means an optionally substituted linear or branched hydrocarbon including 2-14 carbon atoms and at least one carbon-carbon double bond. An alkenyl group may include one, two, three, four, or more carbon-carbon double bonds. For example, $C_{18}$ alkenyl may include one or more double bonds. A $C_{18}$ alkenyl group including two double bonds may be a linoleyl group. Unless otherwise specified, an alkenyl group described herein refers to both unsubstituted and substituted alkenyl groups.

As used herein, the term "alkynyl" or "alkynyl group" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one carbon-carbon triple bond, which is optionally substituted. The notation "$C_{2-14}$ alkynyl" means an optionally substituted linear or branched hydrocarbon including 2-14 carbon atoms and at least one carbon-carbon triple bond. An alkynyl group may include one, two, three, four, or more carbon-carbon triple bonds. For example, $C_{18}$ alkynyl may include one or more carbon-carbon triple bonds. Unless otherwise specified, an alkynyl group described herein refers to both unsubstituted and substituted alkynyl groups.

As used herein, the term "carbocycle" or "carbocyclic group" means an optionally substituted mono- or multi-cyclic system including one or more rings of carbon atoms. Rings may be three, four, five, six, seven, eight, nine, ten, eleven, twelve, thirteen, fourteen, fifteen, sixteen, seventeen, eighteen, nineteen, or twenty membered rings. The notation "$C_{3-6}$ carbocycle" means a carbocycle including a single ring having 3-6 carbon atoms. Carbocycles may include one or more carbon-carbon double or triple bonds and may be non-aromatic or aromatic (e.g., cycloalkyl or aryl groups). Examples of carbocycles include cyclopropyl, cyclopentyl, cyclohexyl, phenyl, naphthyl, and 1,2-dihydronaphthyl groups. The term "cycloalkyl" as used herein means a non-aromatic carbocycle and may or may not include any double or triple bond. Unless otherwise specified, carbocycles described herein refers to both unsubstituted and substituted carbocycle groups, i.e., optionally substituted carbocycles.

As used herein, the term "heterocycle" or "heterocyclic group" means an optionally substituted mono- or multicyclic system including one or more rings, where at least one ring includes at least one heteroatom. Heteroatoms may be, for example, nitrogen, oxygen, or sulfur atoms. Rings may be three, four, five, six, seven, eight, nine, ten, eleven, twelve, thirteen, or fourteen membered rings. Heterocycles may include one or more double or triple bonds and may be non-aromatic or aromatic (e.g., heterocycloalkyl or heteroaryl groups). Examples of heterocycles include imidazolyl, imidazolidinyl, oxazolyl, oxazolidinyl, thiazolyl, thiazolidinyl, pyrazolidinyl, pyrazolyl, isoxazolidinyl, isoxazolyl, isothiazolidinyl, isothiazolyl, morpholinyl, pyrrolyl, pyrrolidinyl, furyl, tetrahydrofuryl, thiophenyl, pyridinyl, piperidinyl, quinolyl, and isoquinolyl groups. The term "heterocycloalkyl" as used herein means a non-aromatic heterocycle and may or may not include any double or triple bond. Unless otherwise specified, heterocycles described herein refers to both unsubstituted and substituted heterocycle groups, i.e., optionally substituted heterocycles.

As used herein, a "biodegradable group" is a group that may facilitate faster metabolism of a lipid in a mammalian entity. A biodegradable group may be selected from the group consisting of, but is not limited to, —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group. As used herein, an "aryl group" is an optionally substituted carbocyclic group including one or more aromatic rings. Examples of aryl groups include phenyl and naphthyl groups. As used herein, a "heteroaryl group" is an optionally substituted heterocyclic group including one or more aromatic rings. Examples of heteroaryl groups include pyrrolyl, furyl, thiophenyl, imidazolyl, oxazolyl, and thiazolyl. Both aryl and heteroaryl groups may be optionally substituted. For example, M and M' can be selected from the non-limiting group consisting of optionally substituted phenyl, oxazole, and thiazole. In the formulas herein, M and M' can be independently selected from the list of biodegradable groups above. Unless otherwise specified, aryl or heteroaryl groups described herein refers to both unsubstituted and substituted groups, i.e., optionally substituted aryl or heteroaryl groups.

Alkyl, alkenyl, and cyclyl (e.g., carbocyclyl and heterocyclyl) groups may be optionally substituted unless otherwise specified. Optional substituents may be selected from the group consisting of, but are not limited to, a halogen atom (e.g., a chloride, bromide, fluoride, or iodide group), a carboxylic acid (e.g., —C(O)OH), an alcohol (e.g., a hydroxyl, —OH), an ester (e.g., —C(O)OR or —OC(O)R), an aldehyde (e.g., —C(O)H), a carbonyl (e.g., —C(O)R, alternatively represented by C=O), an acyl halide (e.g., —C(O)X, in which X is a halide selected from bromide, fluoride, chloride, and iodide), a carbonate (e.g., —OC(O)OR), an alkoxy (e.g., —OR), an acetal (e.g., —C(OR)$_2$R''''), in which each OR are alkoxy groups that can be the same or different and R'''' is an alkyl or alkenyl group), a phosphate (e.g., P(O)$_4^{3-}$), a thiol (e.g., —SH), a sulfoxide (e.g., —S(O)R), a sulfinic acid (e.g., —S(O)OH), a sulfonic acid (e.g., —S(O)$_2$OH), a thial (e.g., —C(S)H), a sulfate (e.g., S(O)$_4^{2-}$), a sulfonyl (e.g., —S(O)$_2$—), an amide (e.g., —C(O)NR$_2$, or —N(R)C(O)R), an azido (e.g., —N$_3$), a nitro (e.g., —NO$_2$), a cyano (e.g., —CN), an isocyano (e.g., —NC), an acyloxy (e.g., —OC(O)R), an amino (e.g., —NR$_2$, —NRH, or —NH$_2$), a carbamoyl (e.g., —OC(O)NR$_2$, —OC(O)NRH, or —OC(O)NH$_2$), a sulfonamide (e.g., —S(O)$_2$NR$_2$, —S(O)$_2$NRH, —S(O)$_2$NH$_2$, —N(R)S(O)$_2$R, —N(H)S(O)$_2$R, —N(R)S(O)$_2$H, or —N(H)S(O)$_2$H), an alkyl group, an alkenyl group, and a cyclyl (e.g., carbocyclyl or heterocyclyl) group. In any of the preceding, R is an alkyl or alkenyl group, as defined herein. In some embodiments, the substituent groups themselves may be further substituted with, for example, one, two, three, four, five, or six substituents as defined herein. For example, a C$_{1-6}$ alkyl group may be further substituted with one, two, three, four, five, or six substituents as described herein.

About, Approximately: As used herein, the terms "approximately" and "about," as applied to one or more values of interest, refer to a value that is similar to a stated reference value. In some embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). For example, when used in the context of an amount of a given compound in a lipid component of a LNP, "about" may mean+/−10% of the recited value. For instance, a LNP including a lipid component having about 40% of a given compound may include 30-50% of the compound.

As used herein, the term "compound," is meant to include all isomers and isotopes of the structure depicted. "Isotopes" refers to atoms having the same atomic number but different mass numbers resulting from a different number of neutrons in the nuclei. For example, isotopes of hydrogen include tritium and deuterium. Further, a compound, salt, or complex of the present disclosure can be prepared in combination with solvent or water molecules to form solvates and hydrates by routine methods.

As used herein, the term "contacting" means establishing a physical connection between two or more entities. For example, contacting a mammalian cell with a LNP means that the mammalian cell and a nanoparticle are made to share a physical connection. Methods of contacting cells with external entities both in vivo and ex vivo are well known in the biological arts. For example, contacting a LNP and a mammalian cell disposed within a mammal may be performed by varied routes of administration (e.g., intravenous, intramuscular, intradermal, and subcutaneous) and may involve varied amounts of lipid nanoparticles. Moreover, more than one mammalian cell may be contacted by a LNP.

As used herein, the term "delivering" means providing an entity to a destination. For example, delivering a therapeutic and/or prophylactic to a subject may involve administering a LNP including the therapeutic and/or prophylactic to the subject (e.g., by an intravenous, intramuscular, intradermal, or subcutaneous route). Administration of a LNP to a mammal or mammalian cell may involve contacting one or more cells with the lipid nanoparticle.

As used herein, the term "enhanced delivery" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a therapeutic and/or prophylactic by a nanoparticle to a target tissue of interest (e.g., mammalian liver) compared to the level of delivery of a therapeutic and/or prophylactic by a control nanoparticle to a target tissue of interest (e.g., MC3, KC2, or DLinDMA). The level of delivery of a nanoparticle to a particular tissue may be measured by comparing the amount of protein produced in a tissue to the weight of said tissue, comparing the amount of therapeutic and/or prophylactic in a tissue to the weight of said tissue, comparing the amount of protein produced in a tissue to the amount of total protein in said tissue, or comparing the amount of therapeutic and/or prophylactic in a tissue to the amount of total therapeutic and/or prophylactic in said tissue. It will be understood that the enhanced delivery of a nanoparticle to a target tissue need not be determined in a subject being treated, it may be determined in a surrogate such as an animal model (e.g., a rat model).

As used herein, the term "specific delivery," "specifically deliver," or "specifically delivering" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a therapeutic and/or prophylactic by a nanoparticle to a target tissue of interest (e.g., mammalian liver) compared to an off-target tissue (e.g., mammalian spleen). The level of delivery of a nanoparticle to a particular tissue may be measured by comparing the amount of protein produced in a tissue to the weight of said tissue, comparing the amount of therapeutic and/or prophylactic in a tissue to the weight of said tissue, comparing the amount of protein produced in a tissue to the amount of total protein in said tissue, or comparing the amount of therapeutic and/or prophylactic in a tissue to the amount of total therapeutic and/or prophylactic in said tissue. For example, for renovascular targeting, a therapeutic and/or prophylactic is specifically provided to a mammalian kidney as compared to the liver and spleen if 1.5, 2-fold, 3-fold, 5-fold, 10-fold, 15 fold, or 20 fold more therapeutic and/or prophylactic per 1 g of tissue is delivered to a kidney compared to that delivered to the liver or spleen following systemic administration of the therapeutic and/or prophylactic. It will be understood that the ability of a nanoparticle to specifically deliver to a target tissue need not be determined in a subject being treated, it may be determined in a surrogate such as an animal model (e.g., a rat model).

As used herein, "encapsulation efficiency" refers to the amount of a therapeutic and/or prophylactic that becomes part of a LNP, relative to the initial total amount of therapeutic and/or prophylactic used in the preparation of a LNP. For example, if 97 mg of therapeutic and/or prophylactic are encapsulated in a LNP out of a total 100 mg of therapeutic and/or prophylactic initially provided to the composition, the encapsulation efficiency may be given as 97%. As used herein, "encapsulation" may refer to complete, substantial, or partial enclosure, confinement, surrounding, or encasement.

As used herein, "expression" of a nucleic acid sequence refers to translation of an mRNA into a polypeptide or protein and/or post-translational modification of a polypeptide or protein.

As used herein, the term "in vitro" refers to events that occur in an artificial environment, e.g., in a test tube or reaction vessel, in cell culture, in a Petri dish, etc., rather than within an organism (e.g., animal, plant, or microbe).

As used herein, the term "in vivo" refers to events that occur within an organism (e.g., animal, plant, or microbe or cell or tissue thereof).

As used herein, the term "ex vivo" refers to events that occur outside of an organism (e.g., animal, plant, or microbe or cell or tissue thereof). Ex vivo events may take place in an environment minimally altered from a natural (e.g., in vivo) environment.

As used herein, the term "isomer" means any geometric isomer, tautomer, zwitterion, stereoisomer, enantiomer, or diastereomer of a compound. Compounds may include one or more chiral centers and/or double bonds and may thus exist as stereoisomers, such as double-bond isomers (i.e., geometric E/Z isomers) or diastereomers (e.g., enantiomers (i.e., (+) or (−)) or cis/trans isomers). The present disclosure encompasses any and all isomers of the compounds described herein, including stereomerically pure forms (e.g., geometrically pure, enantiomerically pure, or diastereomerically pure) and enantiomeric and stereoisomeric mixtures, e.g., racemates. Enantiomeric and stereomeric mixtures of compounds and means of resolving them into their component enantiomers or stereoisomers are well-known.

As used herein, a "lipid component" is that component of a lipid nanoparticle that includes one or more lipids. For example, the lipid component may include one or more cationic/ionizable, PEGylated, structural, or other lipids, such as phospholipids.

As used herein, a "linker" is a moiety connecting two moieties, for example, the connection between two nucleosides of a cap species. A linker may include one or more groups including but not limited to phosphate groups (e.g., phosphates, boranophosphates, thiophosphates, selenophosphates, and phosphonates), alkyl groups, amidates, or glycerols. For example, two nucleosides of a cap analog may be linked at their 5' positions by a triphosphate group or by a chain including two phosphate moieties and a boranophosphate moiety.

As used herein, "methods of administration" may include intravenous, intramuscular, intradermal, subcutaneous, or other methods of delivering a composition to a subject. A method of administration may be selected to target delivery (e.g., to specifically deliver) to a specific region or system of a body.

As used herein, "modified" means non-natural. For example, an RNA may be a modified RNA. That is, an RNA may include one or more nucleobases, nucleosides, nucleotides, or linkers that are non-naturally occurring. A "modified" species may also be referred to herein as an "altered" species. Species may be modified or altered chemically, structurally, or functionally. For example, a modified nucleobase species may include one or more substitutions that are not naturally occurring.

As used herein, the "N:P ratio" is the molar ratio of ionizable (in the physiological pH range) nitrogen atoms in a lipid to phosphate groups in an RNA, e.g., in a LNP including a lipid component and an RNA.

As used herein, a "lipid nanoparticle" is a composition comprising one or more lipids. Lipid nanoparticles are typically sized on the order of micrometers or smaller and may include a lipid bilayer. Lipid nanoparticles, as used herein, unless otherwise specified, encompass lipid nanoparticles (LNPs), liposomes (e.g., lipid vesicles), and lipoplexes. For example, a LNP may be a liposome having a lipid bilayer with a diameter of 500 nm or less.

As used herein, "naturally occurring" means existing in nature without artificial aid.

As used herein, "patient" refers to a subject who may seek or be in need of treatment, requires treatment, is receiving treatment, will receive treatment, or a subject who is under care by a trained professional for a particular disease or condition.

As used herein, a "PEG lipid" or "PEGylated lipid" refers to a lipid comprising a polyethylene glycol component.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient," as used herein, refers to any ingredient other than the compounds described herein (for example, a vehicle capable of suspending, complexing, or dissolving the active compound) and having the properties of being substantially nontoxic and non-inflammatory in a patient. Excipients may include, for example: anti-adherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E (alpha-tocopherol), vitamin C, xylitol, and other species disclosed herein.

Compositions may also include salts of one or more compounds. Salts may be pharmaceutically acceptable salts. As used herein, "pharmaceutically acceptable salts" refers to derivatives of the disclosed compounds wherein the parent compound is altered by converting an existing acid or base moiety to its salt form (e.g., by reacting a free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17$^{th}$ ed., Mack Publishing Company, Easton, Pa., 1985, p. 1418, Pharmaceutical Salts: Properties, Selection, and Use, P. H. Stahl and C. G. Wermuth (eds.), Wiley-VCH, 2008, and Berge et al., Journal of Pharmaceutical Science, 66, 1-19 (1977), each of which is incorporated herein by reference in its entirety.

As used herein, a "phospholipid" is a lipid that includes a phosphate moiety and one or more carbon chains, such as unsaturated fatty acid chains. A phospholipid may include one or more multiple (e.g., double or triple) bonds (e.g., one or more unsaturations). A phospholipid or an analog or derivative thereof may include choline. A phospholipid or an analog or derivative thereof may not include choline. Particular phospholipids may facilitate fusion to a membrane. For example, a cationic phospholipid may interact with one or more negatively charged phospholipids of a membrane (e.g., a cellular or intracellular membrane). Fusion of a phospholipid to a membrane may allow one or more elements of a lipid-containing composition to pass through the membrane permitting, e.g., delivery of the one or more elements to a cell.

As used herein, the "polydispersity index" is a ratio that describes the homogeneity of the particle size distribution of a system. A small value, e.g., less than 0.3, indicates a narrow particle size distribution.

As used herein, an amphiphilic "polymer" is an amphiphilic compound that comprises an oligomer or a polymer. For example, an amphiphilic polymer can comprise an oligomer fragment, such as two or more PEG monomer units. For example, an amphiphilic polymer described herein can be PS 20.

As used herein, the term "polypeptide" or "polypeptide of interest" refers to a polymer of amino acid residues typically joined by peptide bonds that can be produced naturally (e.g., isolated or purified) or synthetically.

As used herein, an "RNA" refers to a ribonucleic acid that may be naturally or non-naturally occurring. For example, an RNA may include modified and/or non-naturally occurring components such as one or more nucleobases, nucleosides, nucleotides, or linkers. An RNA may include a cap structure, a chain terminating nucleoside, a stem loop, a polyA sequence, and/or a polyadenylation signal. An RNA may have a nucleotide sequence encoding a polypeptide of interest. For example, an RNA may be a messenger RNA (mRNA). Translation of an mRNA encoding a particular polypeptide, for example, in vivo translation of an mRNA inside a mammalian cell, may produce the encoded polypeptide. RNAs may be selected from the non-liming group consisting of small interfering RNA (siRNA), asymmetrical interfering RNA (aiRNA), microRNA (miRNA), Dicer-substrate RNA (dsRNA), small hairpin RNA (shRNA), mRNA, long non-coding RNA (lncRNA) and mixtures thereof.

As used herein, a "single unit dose" is a dose of any therapeutic administered in one dose/at one time/single route/single point of contact, i.e., single administration event.

As used herein, a "split dose" is the division of single unit dose or total daily dose into two or more doses.

As used herein, a "total daily dose" is an amount given or prescribed in 24 hour period. It may be administered as a single unit dose.

As used herein, "size" or "mean size" in the context of lipid nanoparticles refers to the mean diameter of a LNP.

As used herein, the term "subject" refers to any organism to which a composition or formulation in accordance with the disclosure may be administered, e.g., for experimental, diagnostic, prophylactic, and/or therapeutic purposes. Typical subjects include animals (e.g., mammals such as mice, rats, rabbits, non-human primates, and humans) and/or plants.

As used herein, "targeted cells" refers to any one or more cells of interest. The cells may be found in vitro, in vivo, in situ, or in the tissue or organ of an organism. The organism may be an animal, preferably a mammal, more preferably a human and most preferably a patient.

As used herein "target tissue" refers to any one or more tissue types of interest in which the delivery of a therapeutic and/or prophylactic would result in a desired biological and/or pharmacological effect. Examples of target tissues of interest include specific tissues, organs, and systems or groups thereof. In particular applications, a target tissue may be a kidney, a lung, a spleen, vascular endothelium in vessels (e.g., intra-coronary or intra-femoral), or tumor tissue (e.g., via intratumoral injection). An "off-target tissue" refers to any one or more tissue types in which the expression of the encoded protein does not result in a desired biological and/or pharmacological effect. In particular applications, off-target tissues may include the liver and the spleen.

The term "therapeutic agent" or "prophylactic agent" refers to any agent that, when administered to a subject, has a therapeutic, diagnostic, and/or prophylactic effect and/or elicits a desired biological and/or pharmacological effect. Therapeutic agents are also referred to as "actives" or "active agents." Such agents include, but are not limited to, cytotoxins, radioactive ions, chemotherapeutic agents, small molecule drugs, proteins, and nucleic acids.

As used herein, the term "therapeutically effective amount" means an amount of an agent to be delivered (e.g., nucleic acid, drug, composition, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

As used herein, "transfection" refers to the introduction of a species (e.g., an RNA) into a cell. Transfection may occur, for example, in vitro, ex vivo, or in vivo.

As used herein, the term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

As used herein, the "zeta potential" is the electrokinetic potential of a lipid, e.g., in a particle composition.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all, of the group members are present in, employed in, or otherwise relevant to a given product or process.

It is also noted that the term "comprising" is intended to be open and permits but does not require the inclusion of additional elements or steps. When the term "comprising" is used herein, the terms "consisting essentially of" and "consisting of" are thus also encompassed and disclosed. Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

Where ranges are given, endpoints are included. Furthermore, it is to be understood that unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

In addition, it is to be understood that any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein.

All cited sources, for example, references, publications, patent applications, databases, database entries, and art cited herein, are incorporated into this application by reference, even if not expressly stated in the citation. In case of conflicting statements of a cited source and the instant application, the statement in the instant application shall control.

EXAMPLES

Example 1: Varying how PEG is Added to Lipid Nanoparticles

To evaluate the effects of the manufacturing process of the disclosure on potency and stability of the lipid nanoparticles, five batches of nanoparticles were made as summarized in Table 1.

TABLE 1

Summary of lipid nanoparticle batches

| Batch No. | Batch Description | Core PEG (mol %) | Post Inserted PEG (mol %) | Post Addition PEG (mol %) | Total PEG (mol %) |
|---|---|---|---|---|---|
| 1 | Standard | 1.5 | 0.00 | 0.00 | 1.5 |
| 2 | Post Insertion-1.0 to 1.5 | 1.0 | 0.50 | 0.00 | 1.5 |
| 3 | Post addition-1.0 to 1.5 | 1.0 | 0.00 | 0.50 | 1.5 |
| 4 | Post Insertion-0.5 to 1.5 | 0.5 | 1.00 | 0.00 | 1.5 |
| 5 | Post addition-0.5 to 1.5 | 0.5 | 0.00 | 1.00 | 1.5 |

LNPs formed via three different methods were investigated. The LNPs only differed significantly in the particle formation process. In this example, the LNPs comprised 50 mol % cationic lipid, 10 mol % DSPC, 38.5 mol % cholesterol, and 1.5 mol % PEG-DMG. All LNPs were formed via a nanoprecipitation reaction using a T-mixer. However, three different procedures (i.e., standard, post-insertion, post addition) were used after the nanoprecipitation reaction. The standard procedure comprised (i) a nanoprecipitation reaction between the lipids dissolved in ethanol and the mRNA in aqueous solution, (ii) tangential flow filtration, and (iii) a final filtration step. The mol % of PEG-DMG used in the nanoprecipitation reaction was 1.5 mol % for the standard procedure.

The post-insertion procedure comprised (i) a nanoprecipitation reaction between the lipids dissolved in ethanol and the mRNA in aqueous solution, (ii) exposure of the resulting particles to a solution comprising a certain weight percentage of PEG-DMG, (iii) tangential flow filtration, and (iv) a final filtration step. The mol % of PEG-DMG used in the nanoprecipitation reaction varied depending on the amount of PEG-DMG used in the post-particle formation exposure step. 0.5 mol % of PEG-DMG was used when the resulting particles were exposed to 1.0 mol % PEG-DMG. The mol % of PEG-DMG used in the nanoprecipitation reaction was 1.0 mol % when the resulting particles were exposed to 0.5 mol % PEG-DMG.

The post addition procedure comprised (i) a nanoprecipitation reaction between the lipids dissolved in ethanol and the mRNA in aqueous solution, (ii) tangential flow filtration, (iii) exposure of the filtered particles to a solution comprising a certain weight percentage of PEG-DMG, and (iv) a final filtration step. The mol % of PEG-DMG used in the nanoprecipitation reaction varied depending on the amount of PEG-DMG used in the post-filtration exposure step. When the filtered particles were exposed to 1.0 mol % PEG-DMG, the mol % of PEG-DMG used in the nanoprecipitation reaction was 0.5 mol %. The mol % of PEG-DMG used in the nanoprecipitation reaction was 1.0 mol % when the filtered particles were exposed to 0.5 mol % PEG-DMG. The amount of PEG added for each procedure is shown in the table below.

The nanoparticles comprised ionizable lipid:DSPC:Chol:PEG-2 in a final mol ratio of 50:10:38.5:1.5. 1.5 mol % core PEG-2 (control); 1.0 mol % core; or 0.5 mol % core PEG were added during t-mix. In the nanoparticles made via the post-insertion process, the PEG level was adjusted to 1.5 mol % prior to tangential flow filtration. (TFF) In the nanoparticle made via the post addition process, PEG level was adjusted to 1.5 mol % prior to sterile filtration. 100 mM Tris pH 7.4 was used as diafiltration buffer and 93 mM tris 7.0 w % PG+1 mM DTPA pH 7.4 was used as final buffer. The final lipid composition is summarized in Table 2.

TABLE 2

Quantitative composition of final lipid

| Batch | mRNA (mg/mL) | Total lipids (mg/mL) | Lipid: RNA | Ionizable Lipid (Mol %) | DSPC (Mol %) | Chol (Mol %) | PEG (Mol %) |
|---|---|---|---|---|---|---|---|
| 1 | 0.507 | 9.53 | 18.8 | 50.37 | 9.66 | 38.51 | 1.45 |
| 2 | 0.459 | 8.69 | 18.9 | 49.68 | 10.04 | 38.85 | 1.41 |
| 3 | 0.544 | 10.21 | 18.8 | 50.32 | 9.90 | 38.52 | 1.25 |
| 4 | 0.493 | 9.07 | 18.4 | 49.85 | 10.26 | 38.44 | 1.44 |
| 5 | 0.485 | 9.52 | 19.6 | 49.96 | 10.18 | 38.48 | 1.38 |

In Vivo Study

For the in vivo study, Female Balb/C mice were dosed as summarized in Table 3. And analyzed by gB ELISA and Pentamer ELISA.

TABLE 3

In vivo experiment parameters

| Batch | Dose RNA (ug) | # of Female Balb/C mice | Injection Days | Bleed Days |
|---|---|---|---|---|
| 1 | 3 | 8 | 1, 22 | 21, 36 |
| 2 | 3 | 8 | 1, 22 | 21, 36 |
| 3 | 3 | 8 | 1, 22 | 21, 36 |
| 4 | 3 | 8 | 1, 22 | 21, 36 |
| 5 | 3 | 8 | 1, 22 | 21, 36 |

Evaluation of Particle Size

Figure 17:
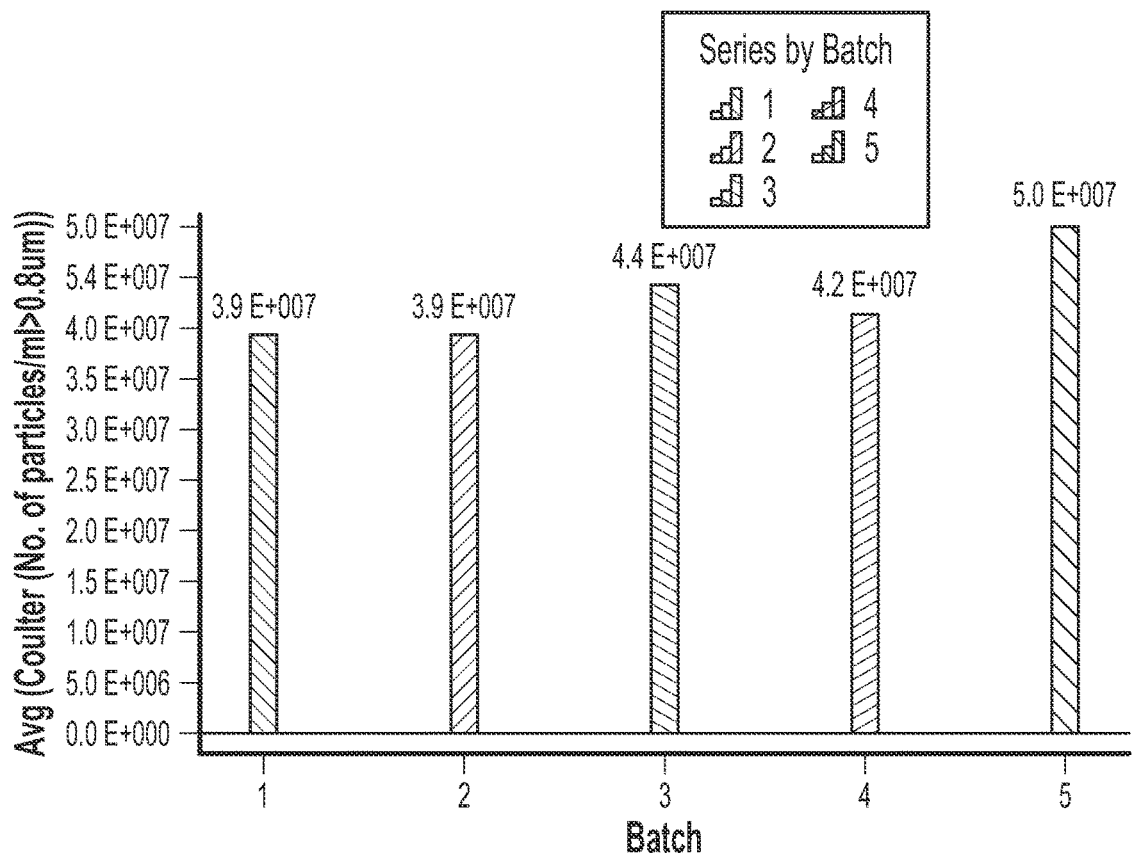
Figure 18:
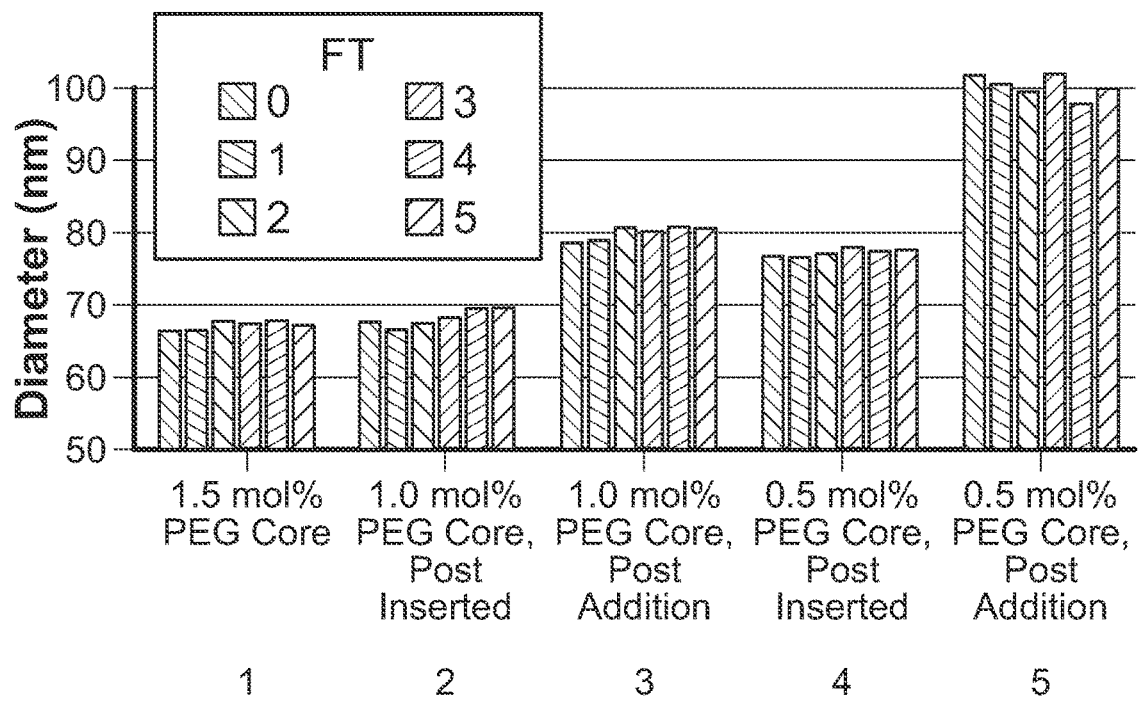
FIG. 18 is a histogram of particle size of nanoparticles made by the processes of the disclosure, determined by Dynamic Light Scattering (DLS) before freeze thaw and after up to 5 freeze thaw cycles.
Figure 19:
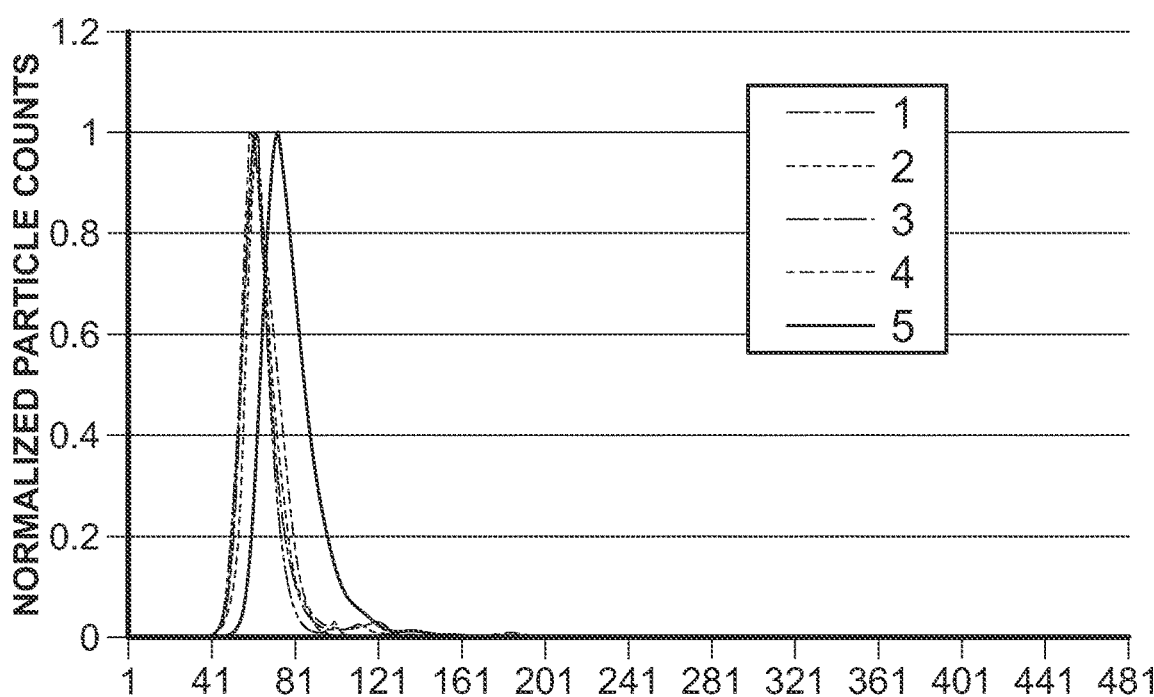
FIG. 19 is a graph summarizing the results of a nanoparticle tracking analysis of nanoparticles made by the processes of the disclosure.
Figure 21:
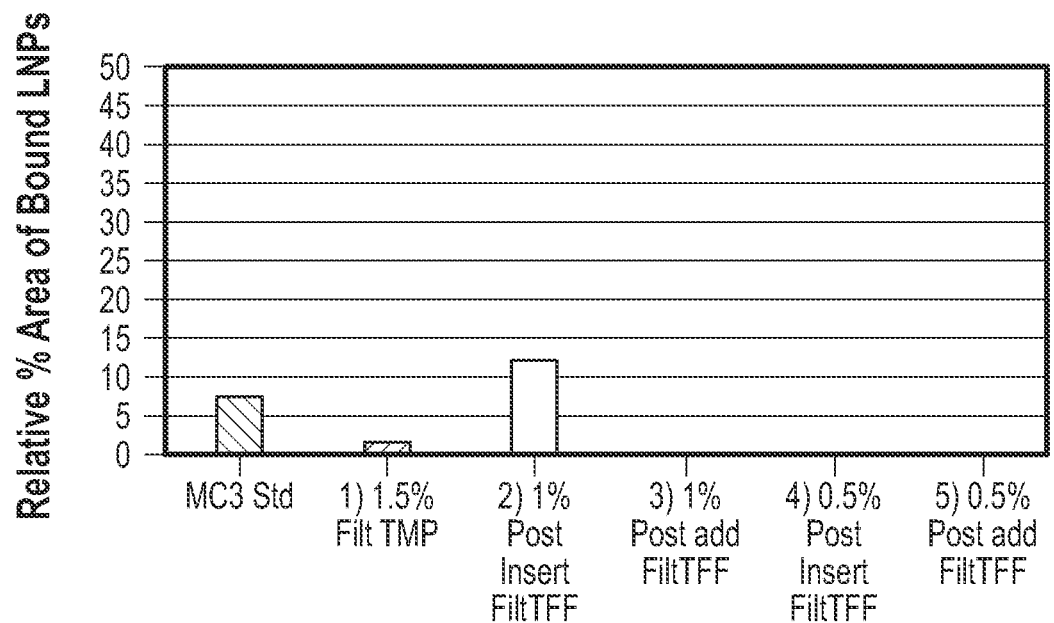
FIG. 21 is a histogram illustrating binding of the liquid nanoparticles to a Heparin Sepharose Column.
Figure 22:
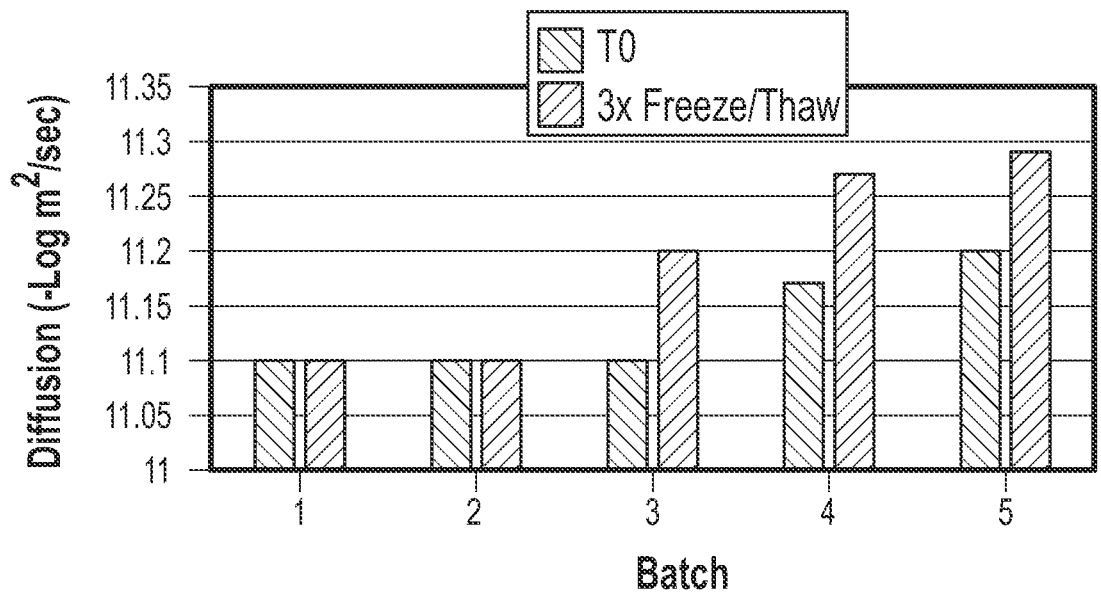
FIG. 22 is a histogram showing the results of freeze-thaw diffusion ordered spectroscopy (DOSY) of lipid nanoparticles formed via the processes of the disclosure. Batch 1 is made using the standard process, batches 2 and 4 are made by the post-insertion process, and batches 3 and 5 are made using the post addition process. The figure demonstrated that samples with more initial PEG were more stable. Given the small change in diffusion, the instability may be insignificant. While storage stability may be lower in batches 4 and 5, the higher instability may contribute to more RNA release/expression in vivo.
Figure 23:
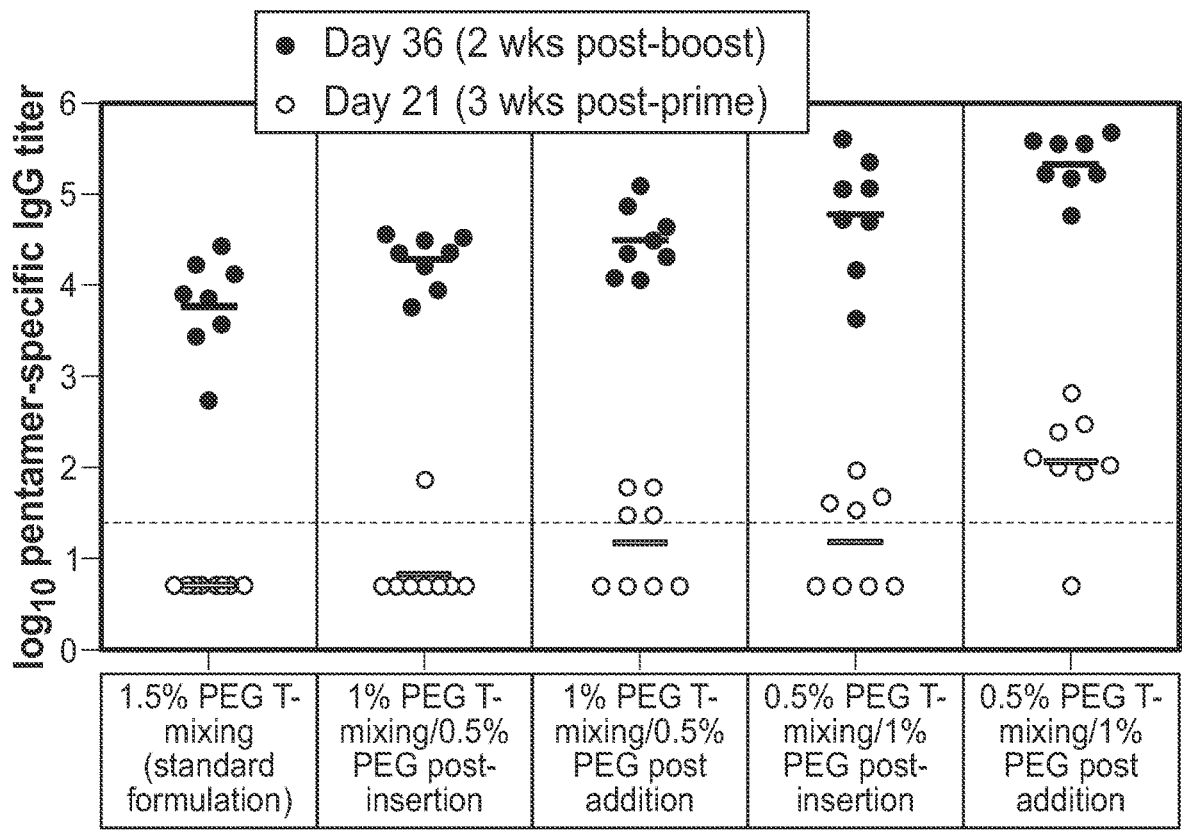
FIG. 23 is a graph of in vivo immunogenicity in mice (serum IgG titers) for lipid nanoparticles formed via the processes of the disclosure (assayed on pentamer coated plates).
Figure 24:
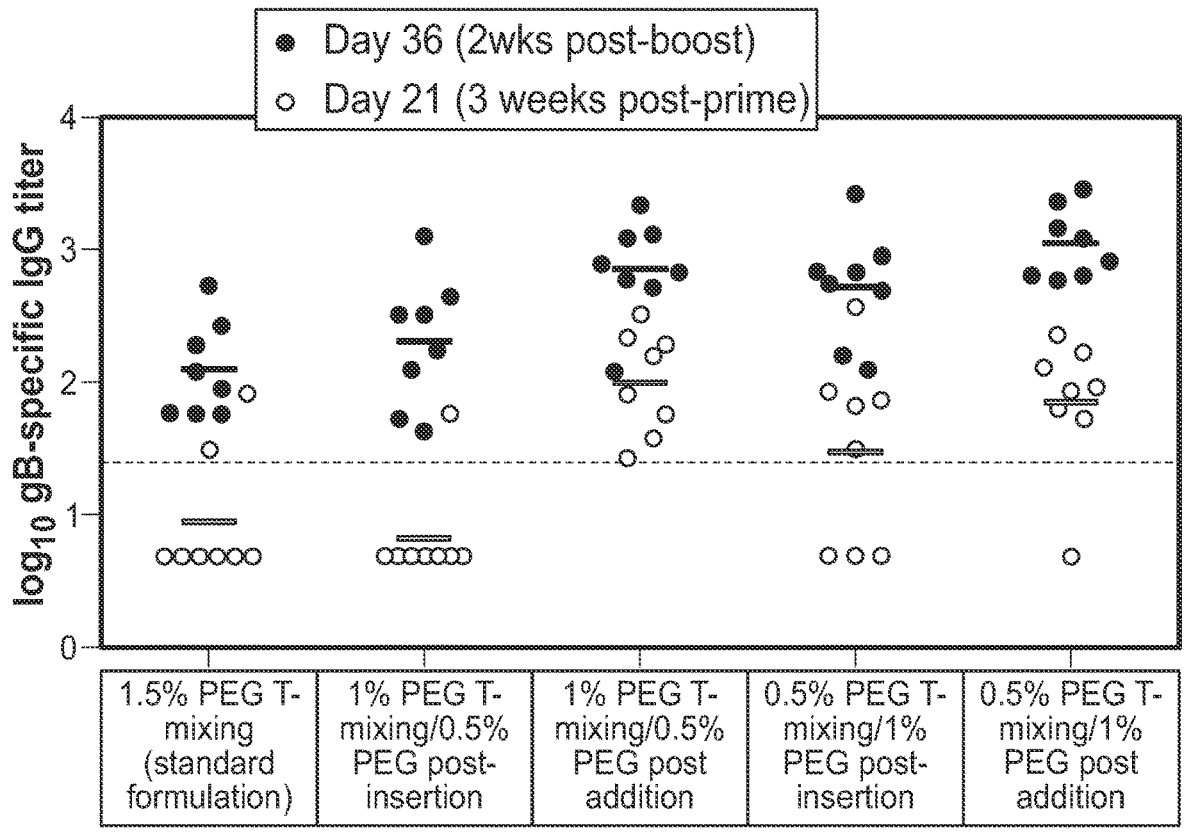
FIG. 24 is a graph of in vivo immunogenicity (serum IgG titers) for lipid nanoparticles formed via the processes of the disclosure (assayed on gB coated plates).
Figure 25:
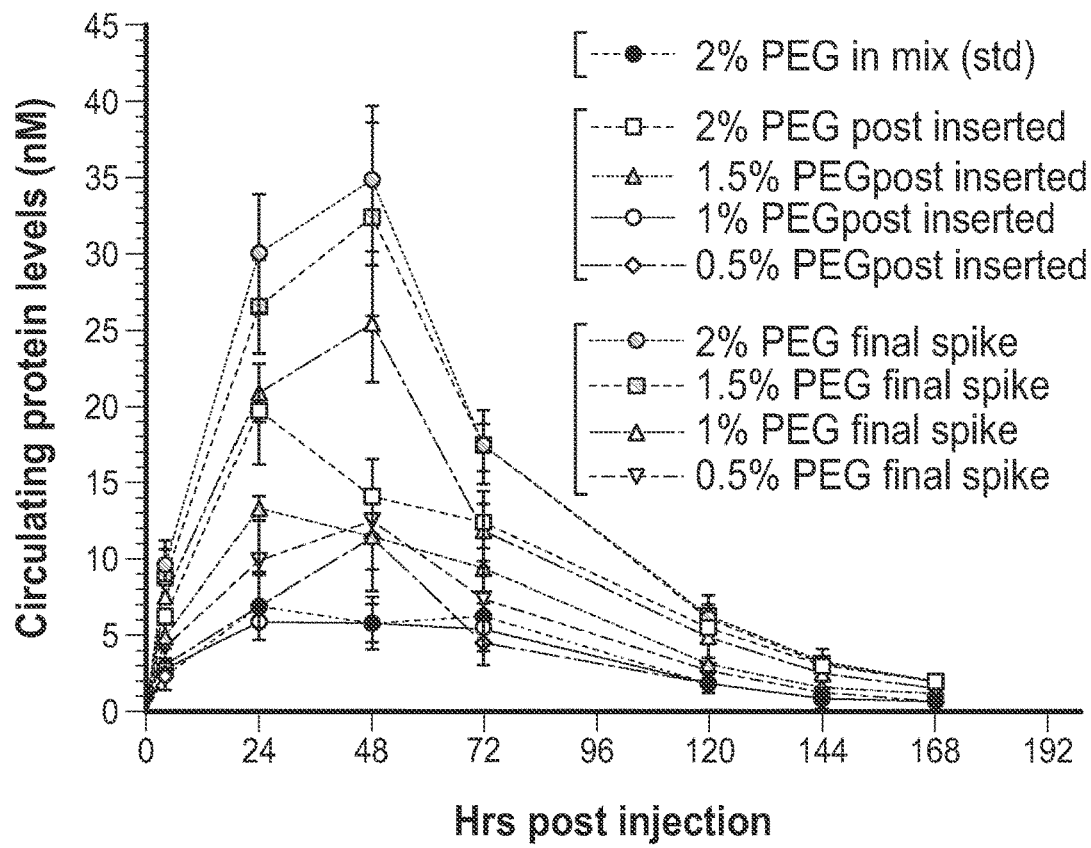
FIG. 25 is a graph illustrating protein pharmacokinetics in a WKY rat administered a formulation comprising compound 18 and PEG-1, assessed by circulating hormone protein levels.
Figure 26:
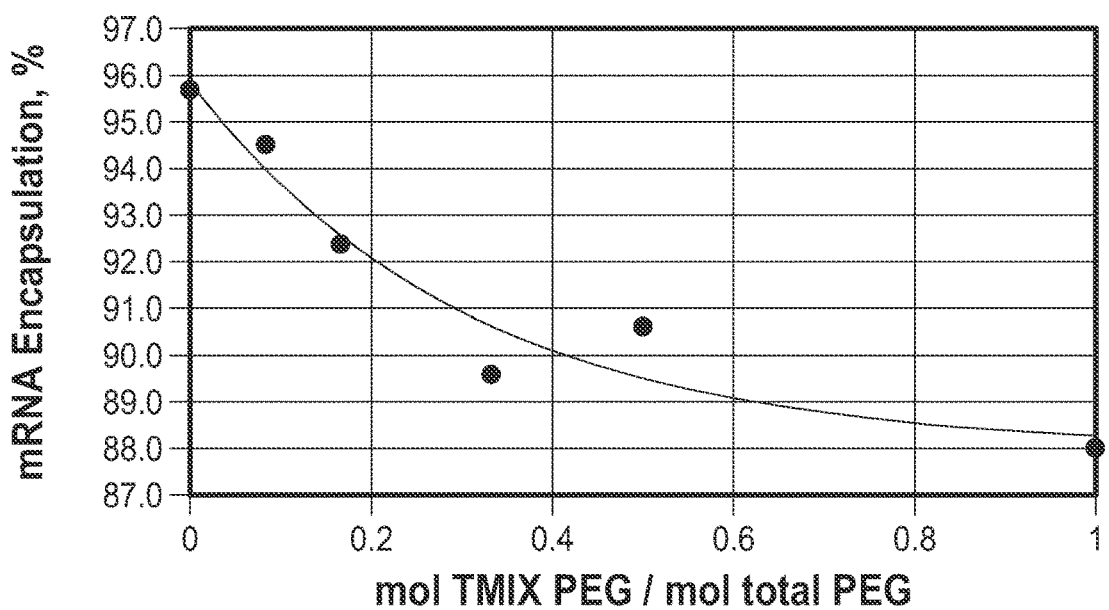
FIG. 26 is a diagram showing the encapsulation efficiency of LNPs (with a total amount of 3 mol % PEG lipid) prepared by process with post insertion (with the ratio between the PEG lipid added during the T-Mix stage and the PED lipid added during post insertion ranging from 0 to 1).
Figure 27A:
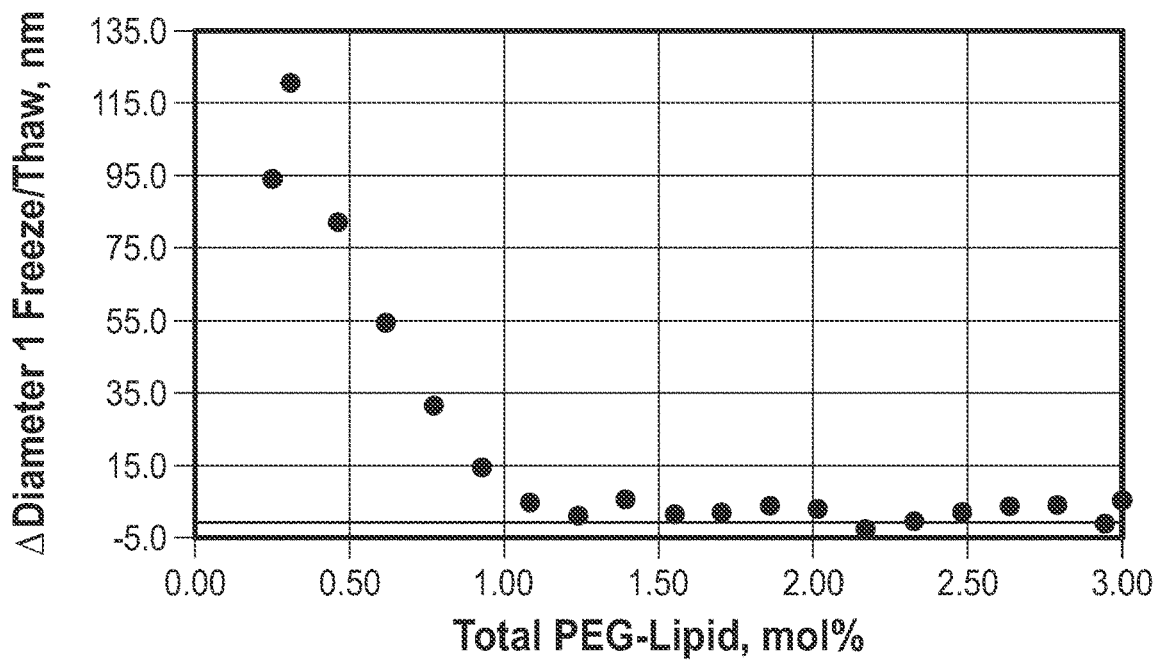
FIG. 27A-27B are diagrams showing effect of post addition with PEG-1 on stability and expression of LNP formulations (with a varied total amount of PEG lipid; and with 0.25 mol % PEG lipid added during T-Mix stage).
Figure 27B:
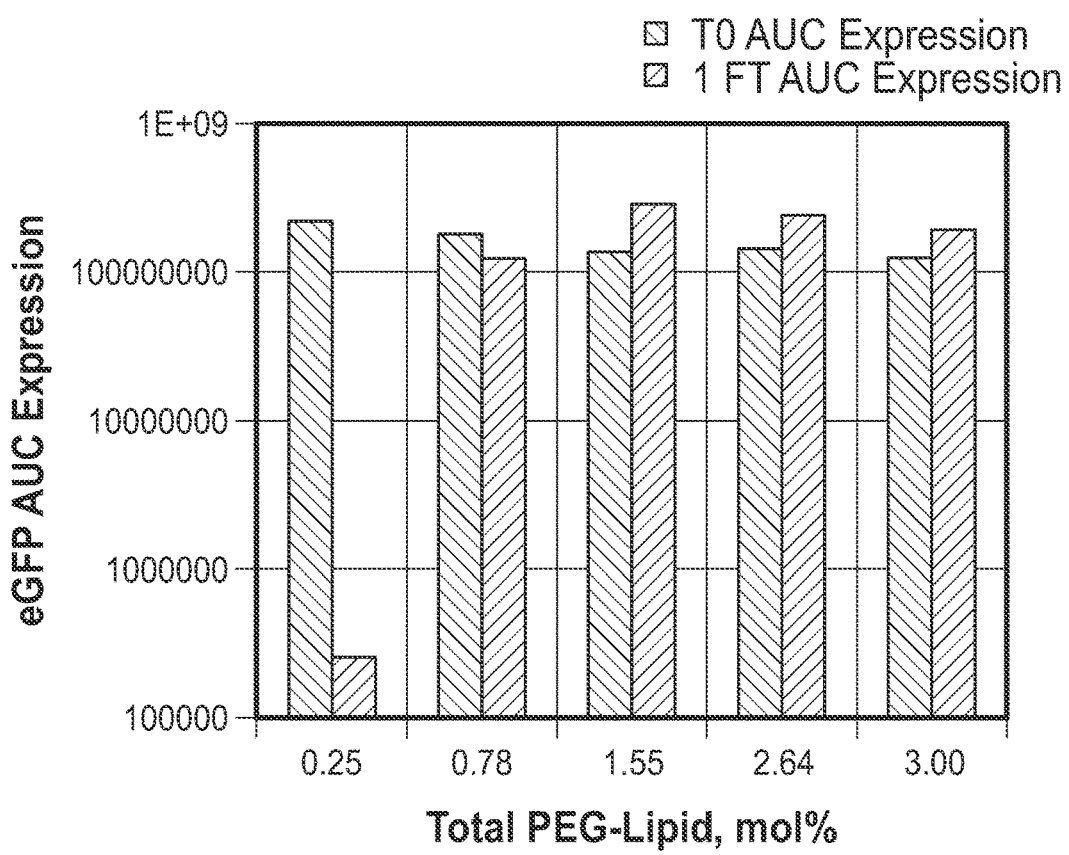
Figure 29A:
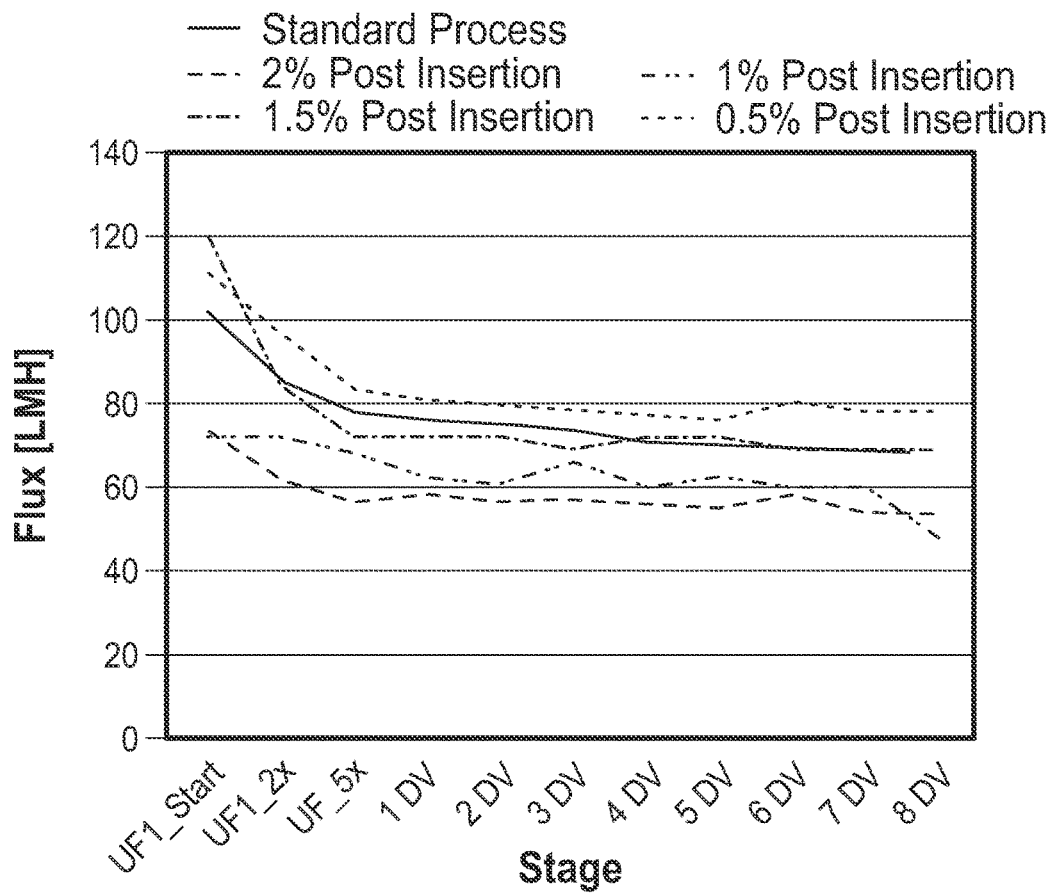
FIG. 29A-29B are diagrams showing the effect of post insertion with PEG lipid on membrane permeability of the LNP formulations.
Figure 29B:
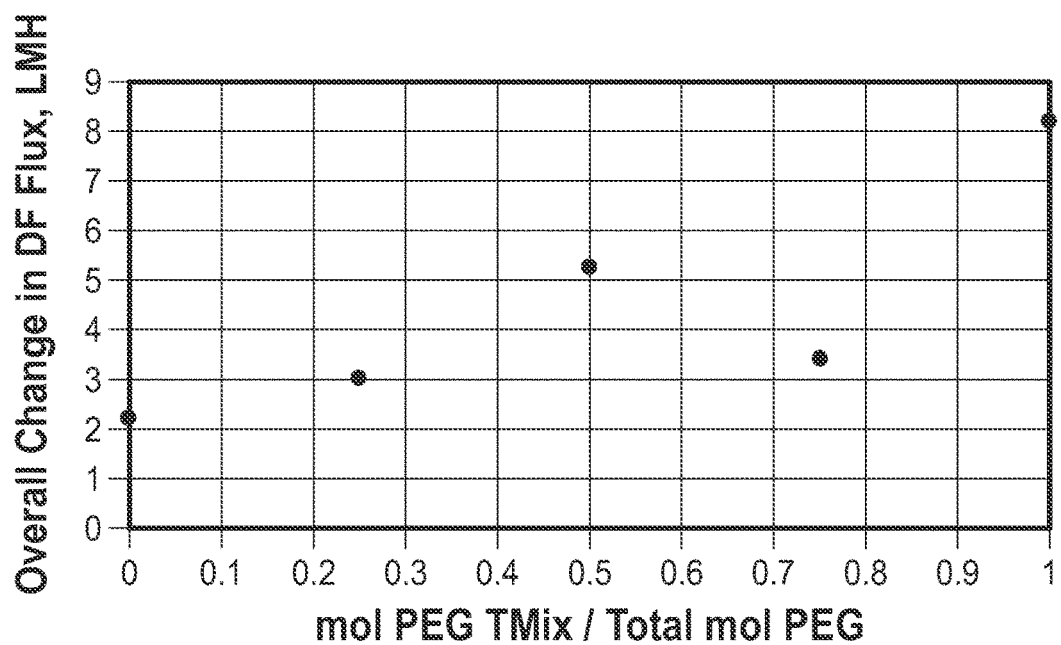
Figure 30A:
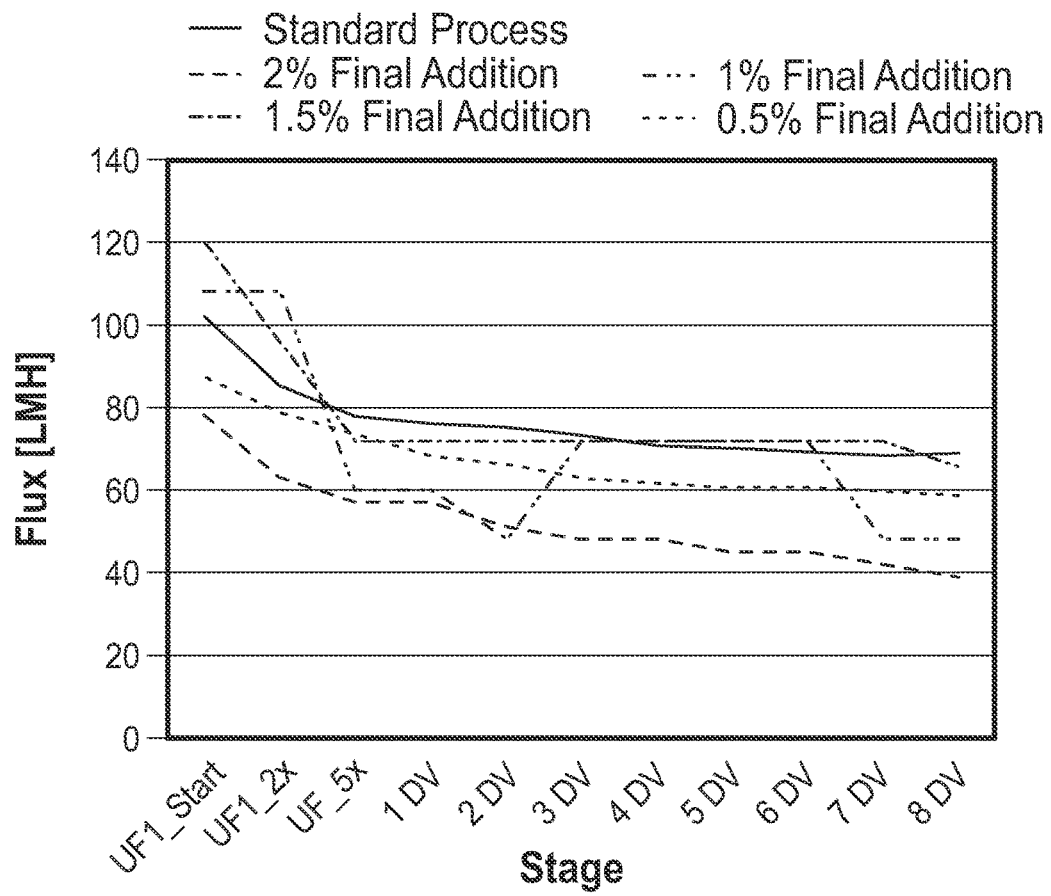
FIG. 30A-30B are diagrams showing the effect of post addition with PEG lipid on membrane permeability of the LNP formulations.
Figure 30B:
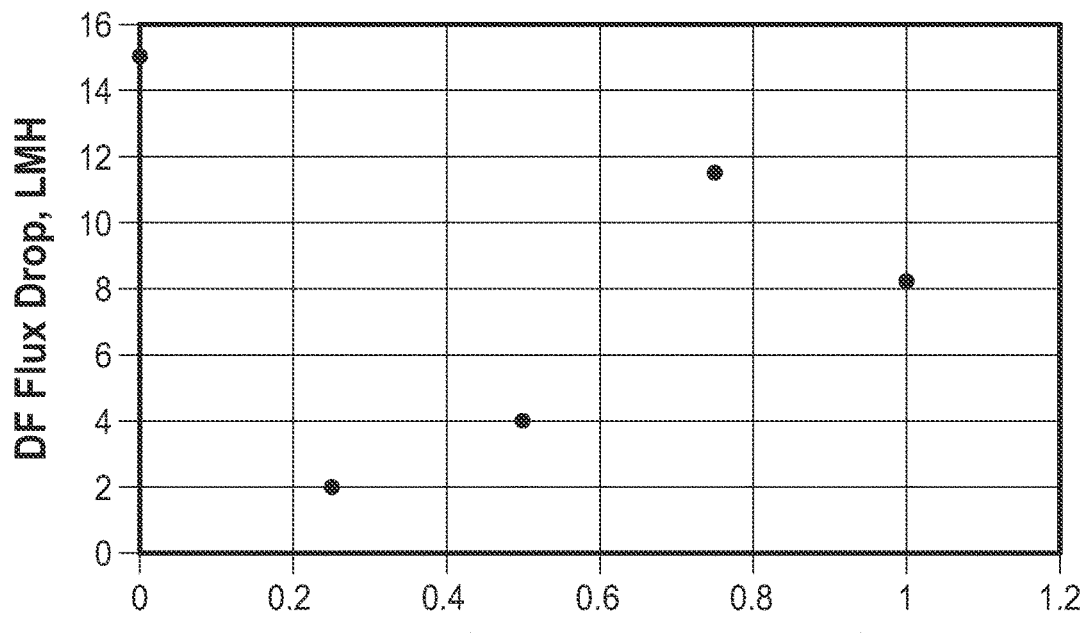
Figure 31A:
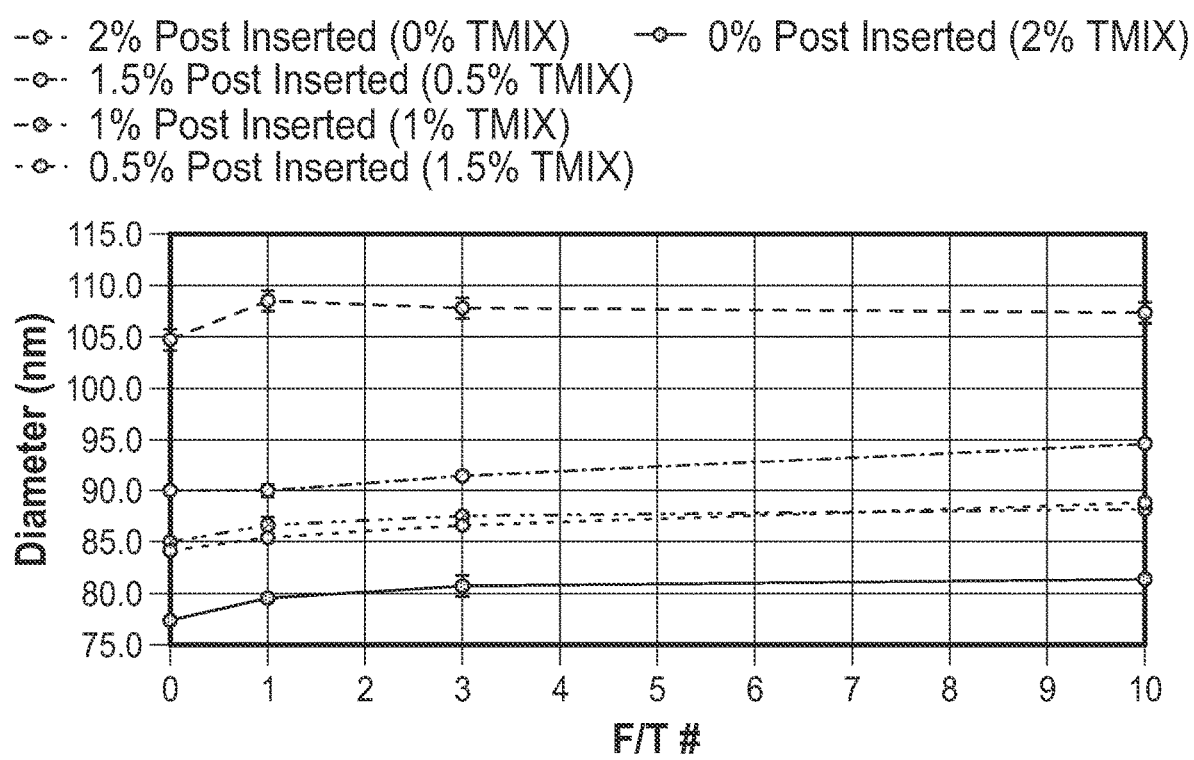
FIGS. 31A-31B are diagrams showing the effect of post insertion and post addition with PEG-1 on stability of the LNP formulations containing ionizable lipid.
Figure 31B:
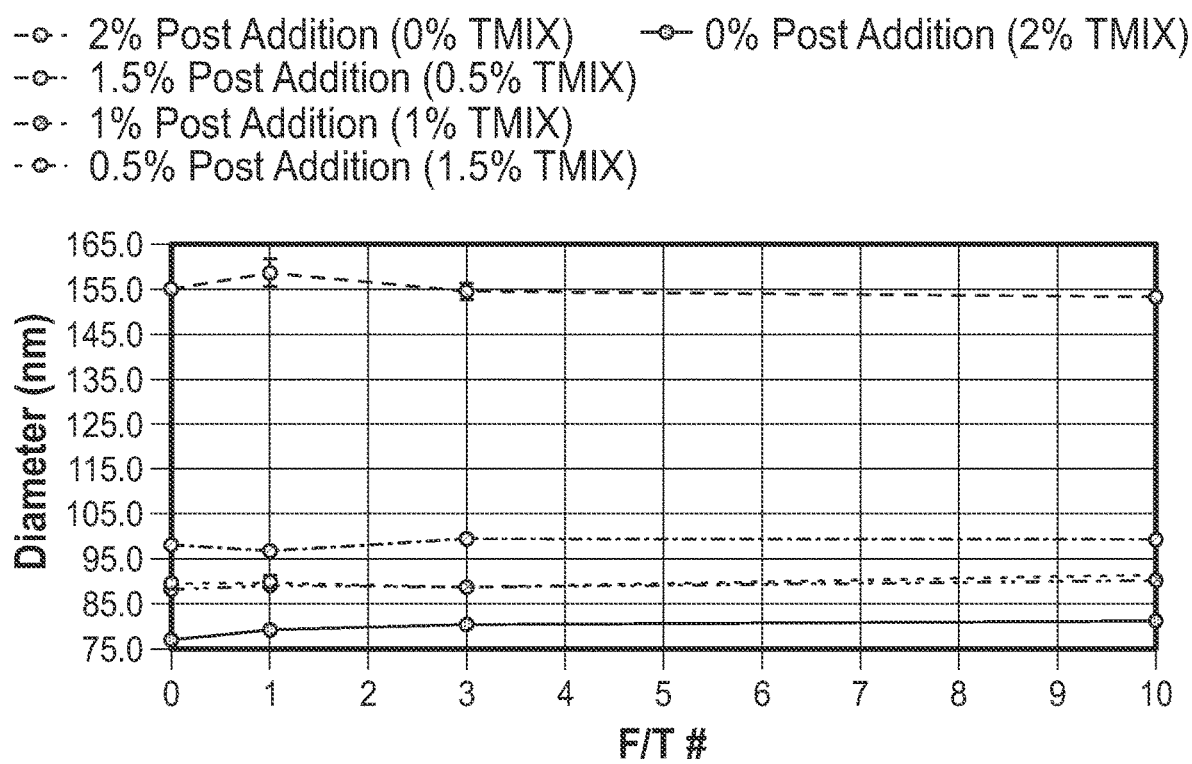
Figure 32A:
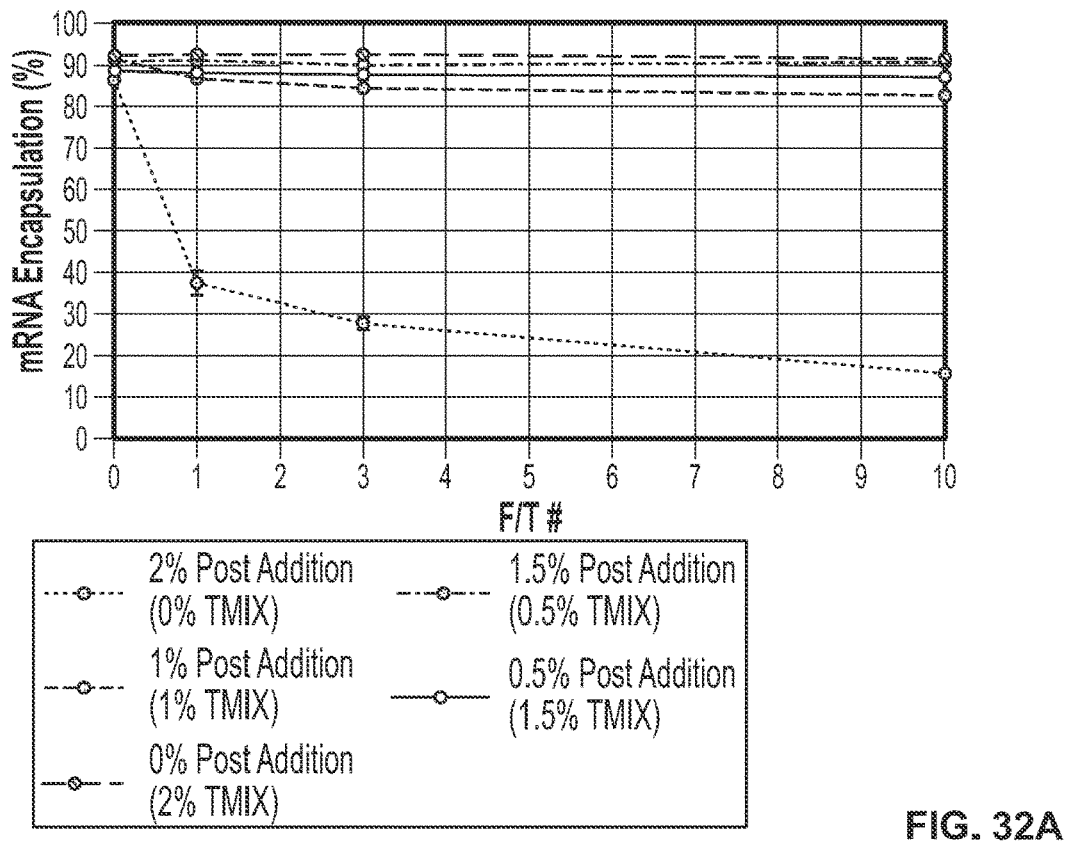
FIGS. 32A-32B are diagrams showing the effect of post insertion and post addition with PEG-1 on mRNA encapsulation efficiency of the LNP formulations containing ionizable lipid.
Figure 32B:
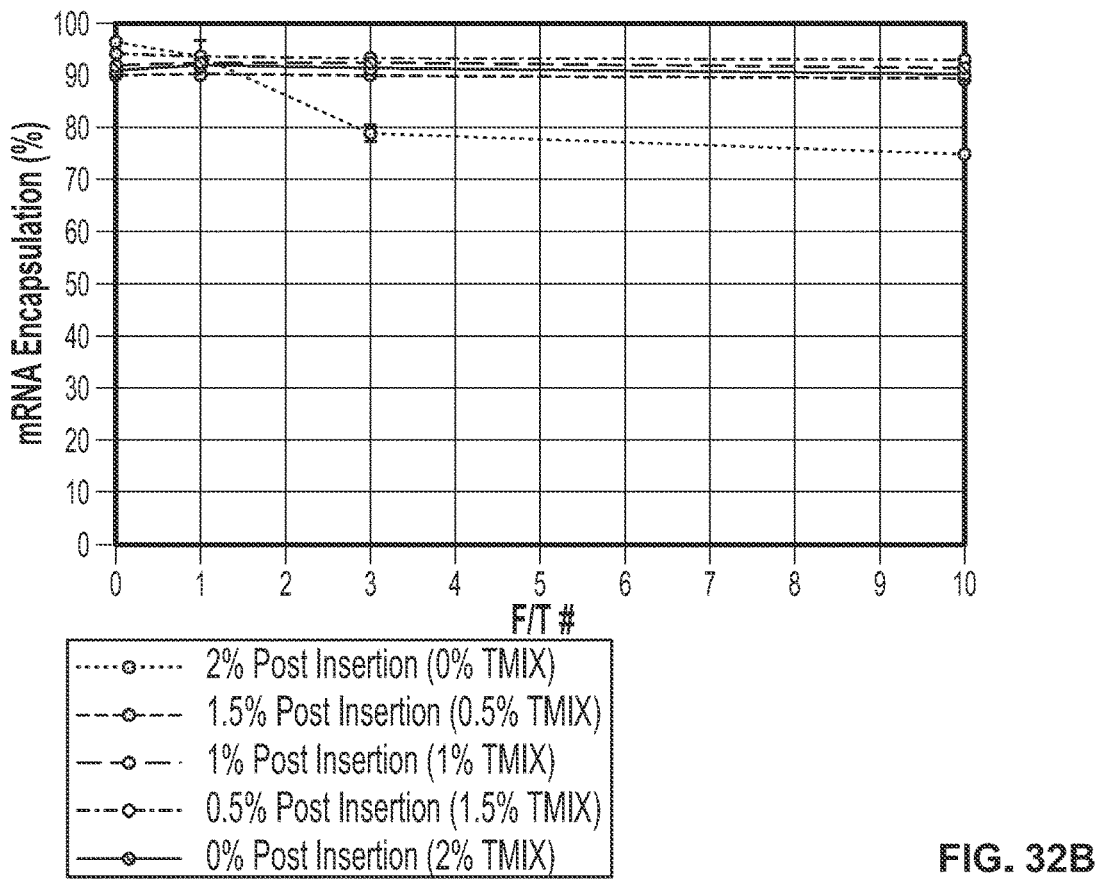
Figure 33A:
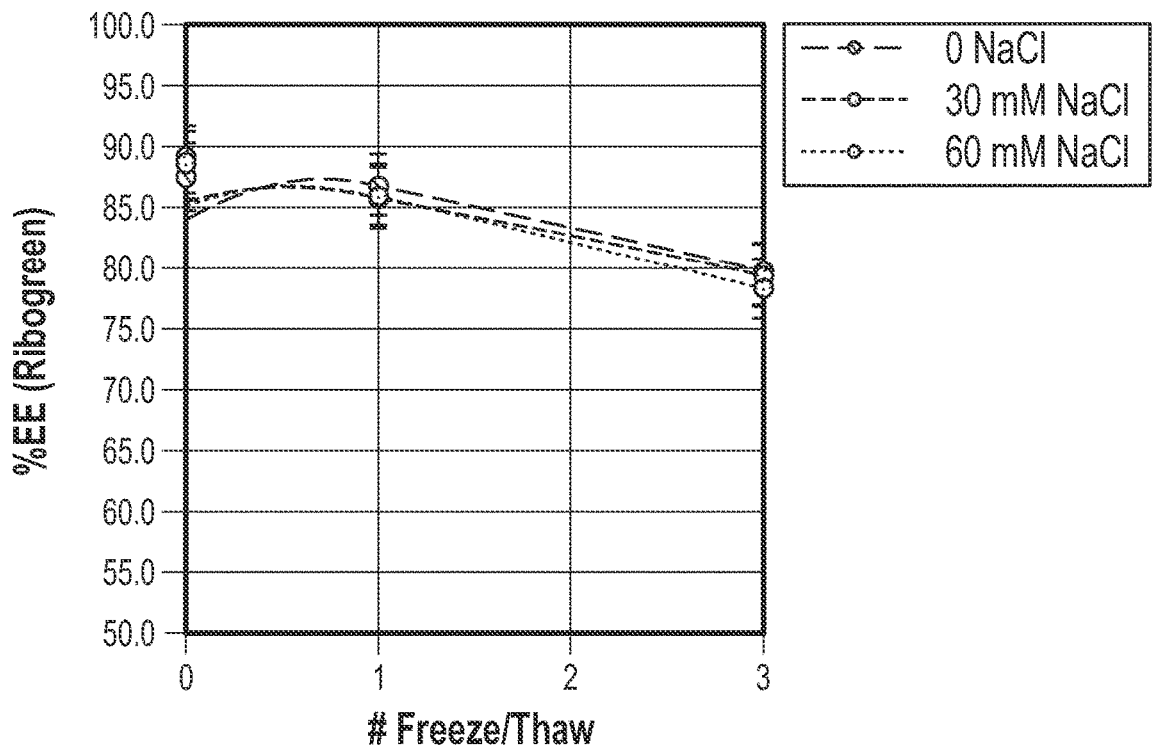
FIGS. 33A-33C are diagrams showing the effect of adding NaCl, DTPA, or Ethanol to the mRNA encapsulation efficiency of the LNP formulations containing ionizable lipid prepared by process with post addition of PEG-1.
Figure 33B:
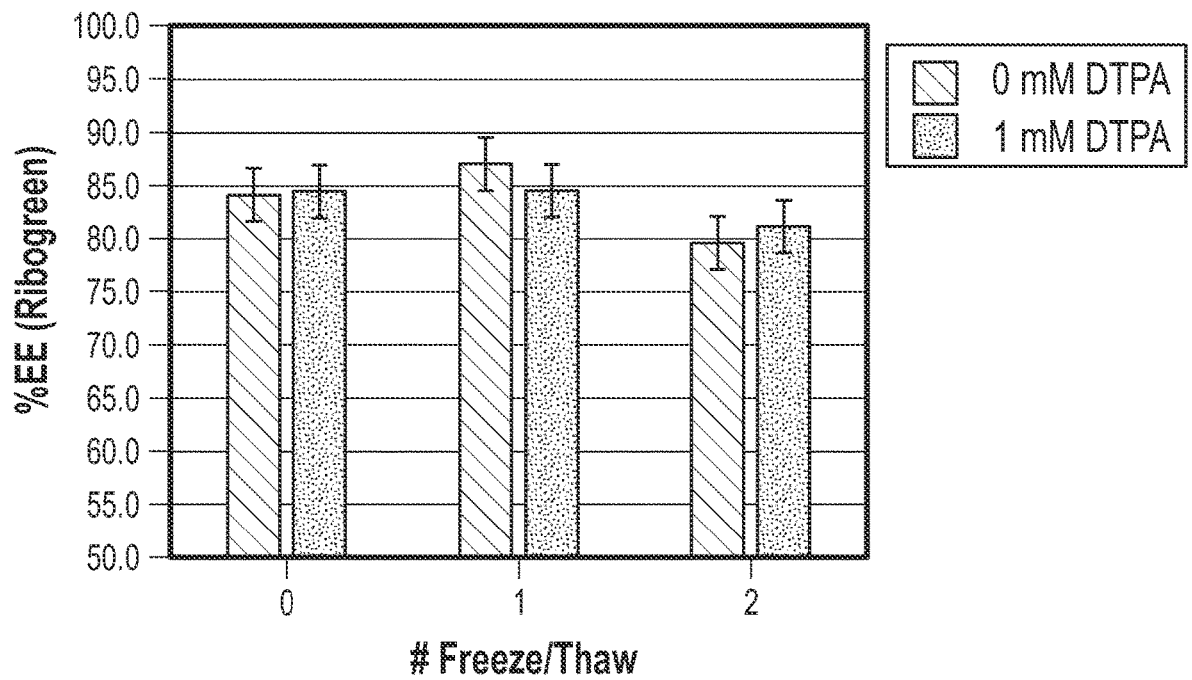
Figure 33C:
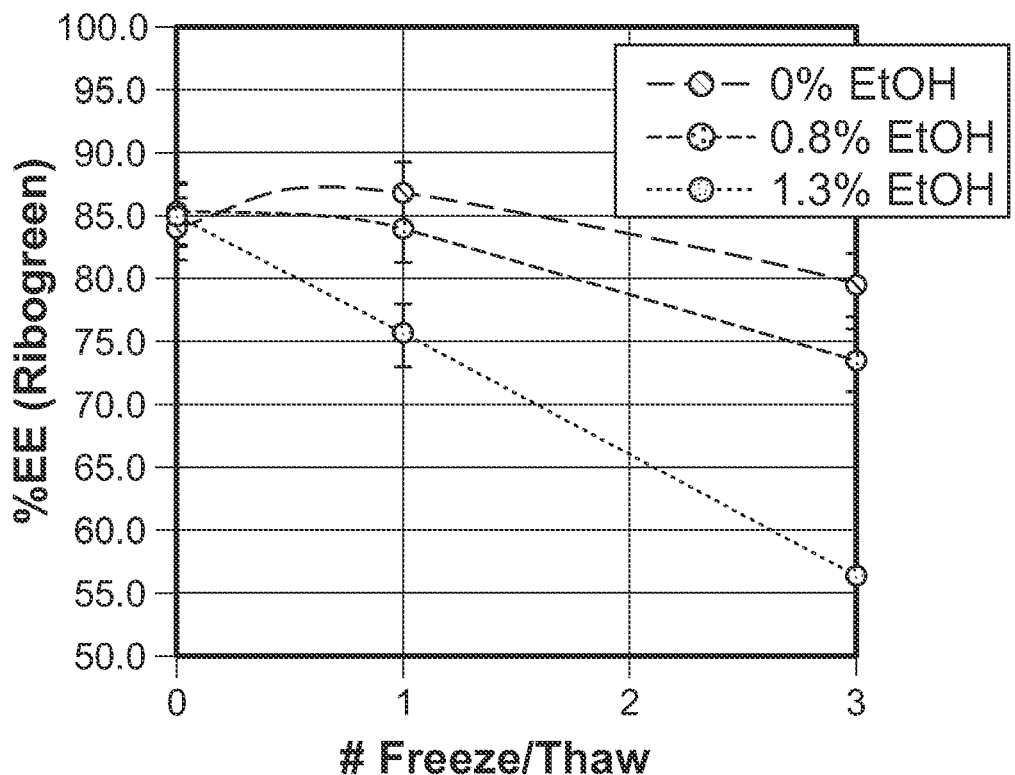
Figure 34A:
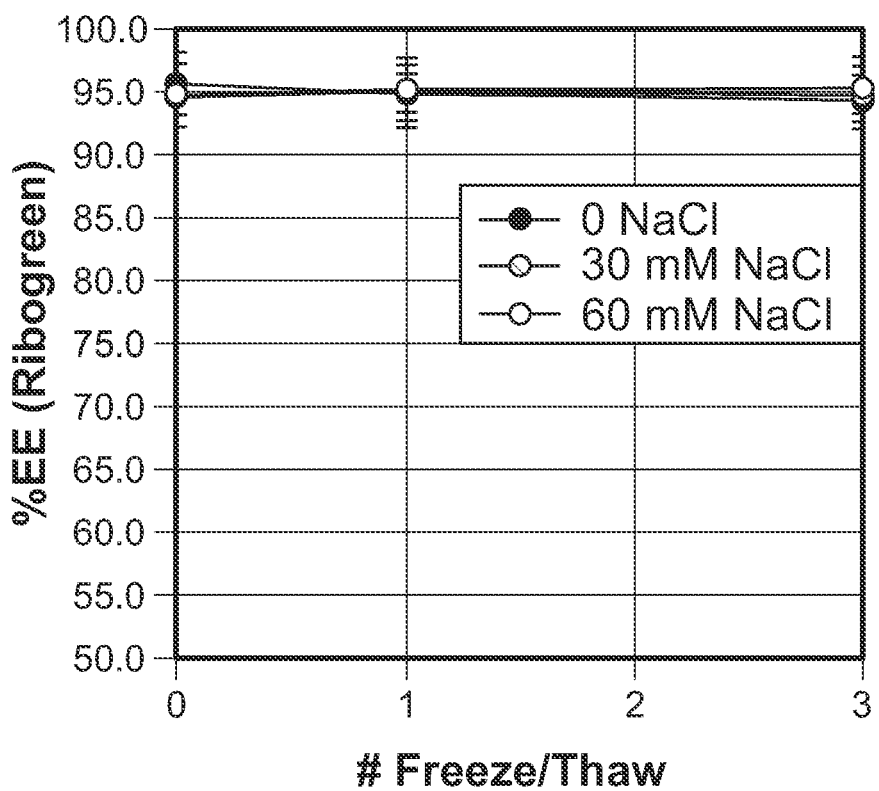
FIGS. 34A-34C are diagrams showing the effect of adding NaCl, DTPA, or Ethanol to the mRNA encapsulation efficiency of the LNP formulations containing ionizable lipid prepared by process with post insertion of PEG-1.
Figure 34B:
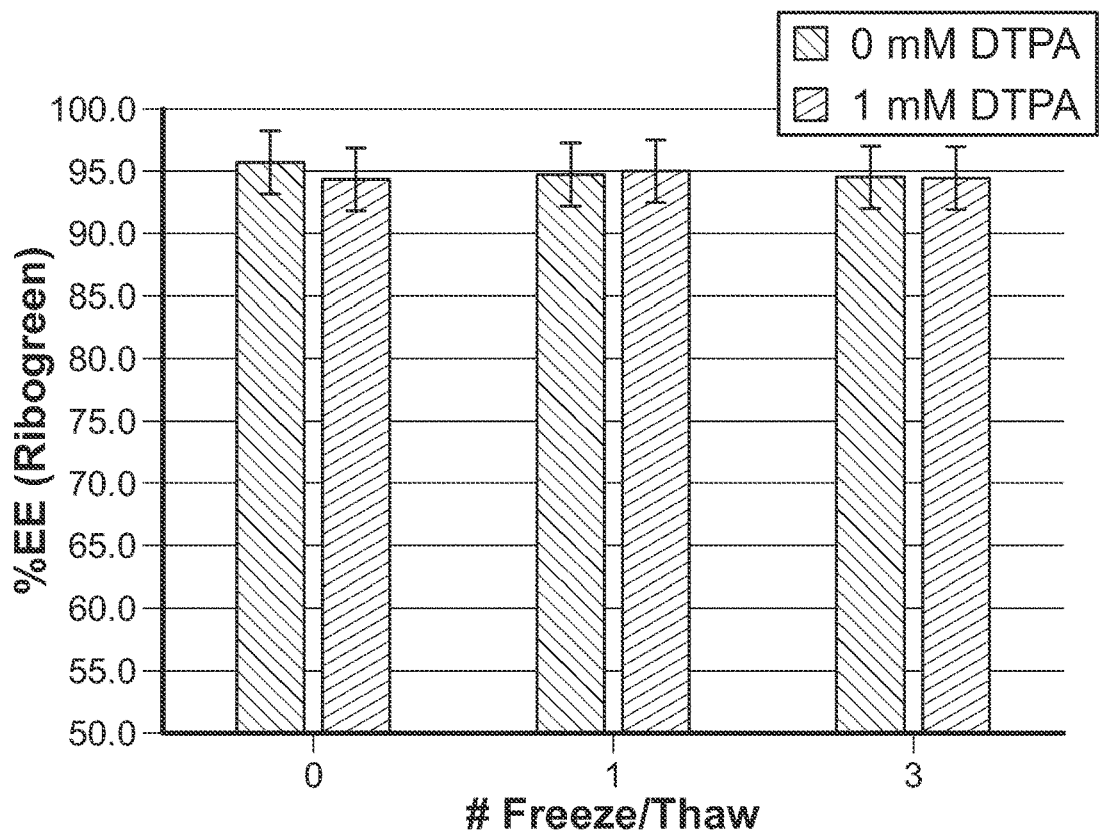
Figure 34C:
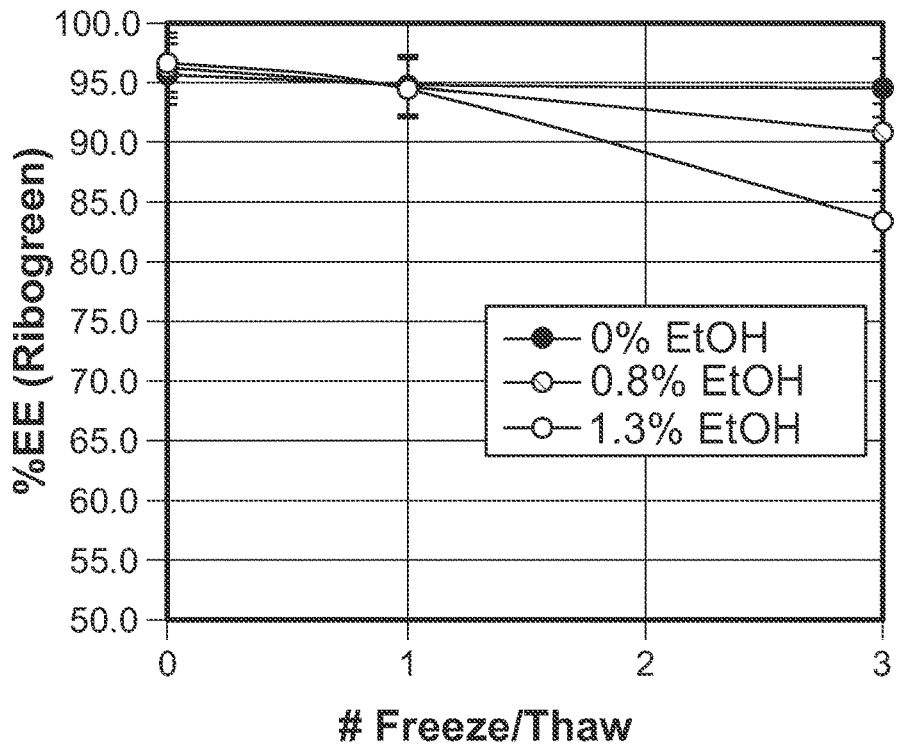
Figure 35:
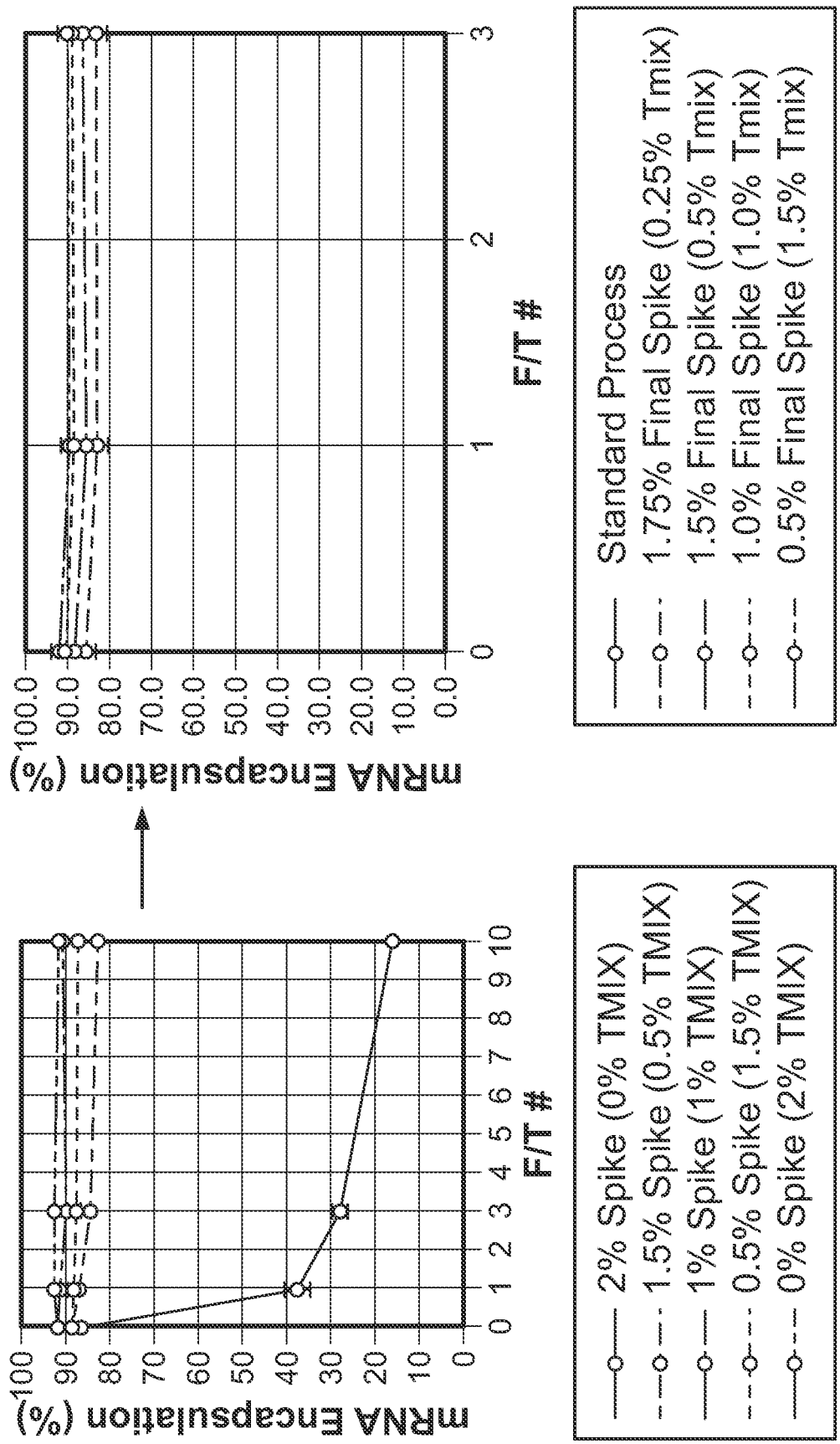
FIG. 35 illustrates the effect of different buffers on stability of nanoparticles. The elimination of ethanol from the frozen formulation buffer alleviated encapsulation sensitivity to freeze/thaw stress.
Figure 36:
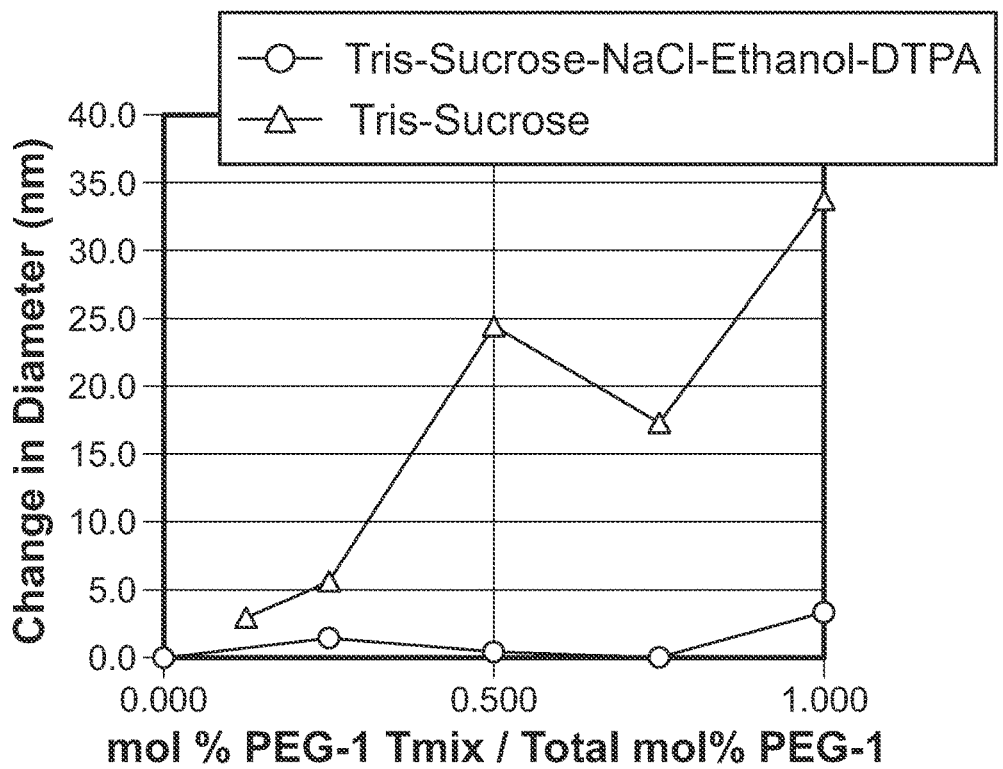
FIG. 36 illustrates the effect of different buffers on the size of nanoparticles. Tris-Sucrose-NaCl-Ethanol-DTPA buffer conferred protection of LNP diameter against freeze/thaw stress. Tris-Sucrose buffers show reduced diameter stability. Tris-Sucrose-based formulations are stabilized through PEG-1 post addition.

The effects of PEG addition on particle size was investigated in various ways, e.g. dynamic light scattering or via nanoparticle tracking analysis. See FIGS. 17 and 18. The lipids were also evaluated via small angle X-ray scattering (SAXS). It was found that none of the samples show obvious core-shell structure based on the scattering curves. The LNP size is different for different processes: Batch 1~ Batch 2<Batch 3~ Batch 4<Batch 5, which is also shown from the distance distribution function. Diameters were estimated to be about 35 nm for batches 1 and 2, about 40 nm for batches 3 and 4 and about 52 nm for batch 5. The SAXS spectra indicated a spherical structure. Endotoxin levels were determined and found to be low for all batches (Table 4).

TABLE 4

Endotoxin levels in nanoparticles of batches 1-5

| Batch | Endotoxin (EU/mL) |
|---|---|
| 1 | 1.4 |
| 2 | 1.2 |
| 3 | 0 |
| 4 | 0 |
| 5 | 0 |

Example 2: Hormone Protein Pharmacokinetic Study

Figure 37:
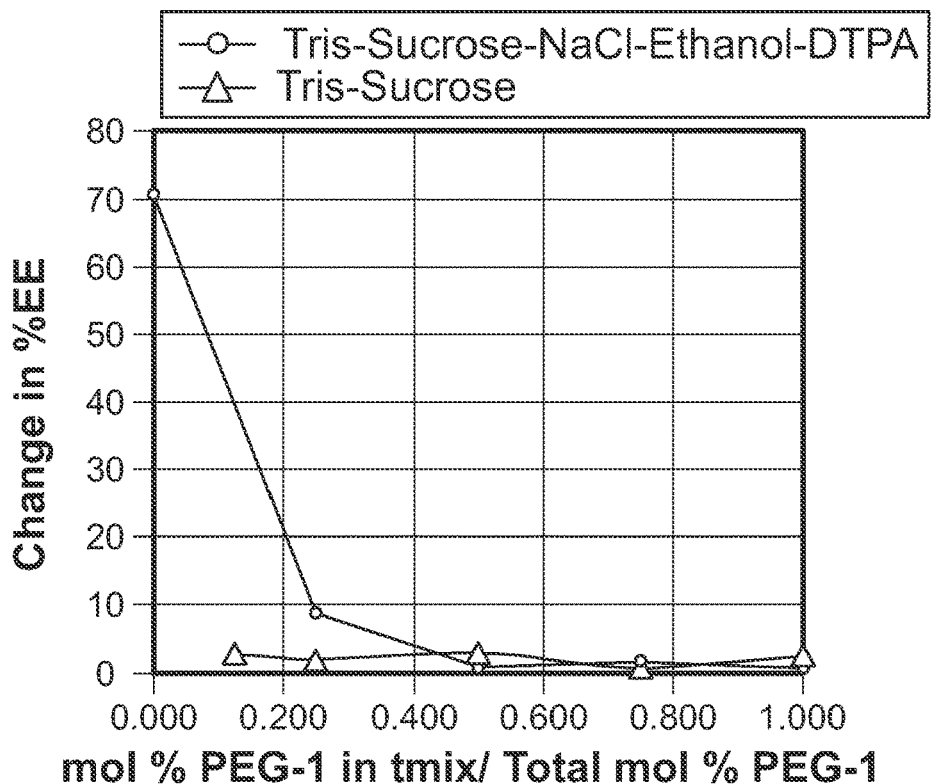
FIG. 37 illustrates the effect of different buffers on encapsulation efficiency of nanoparticles. Tris-Sucrose-NaCl-Ethanol-DTPA buffer results in sensitivity towards mRNA encapsulation. Tris-Sucrose show robust encapsulation values.
Figure 38:
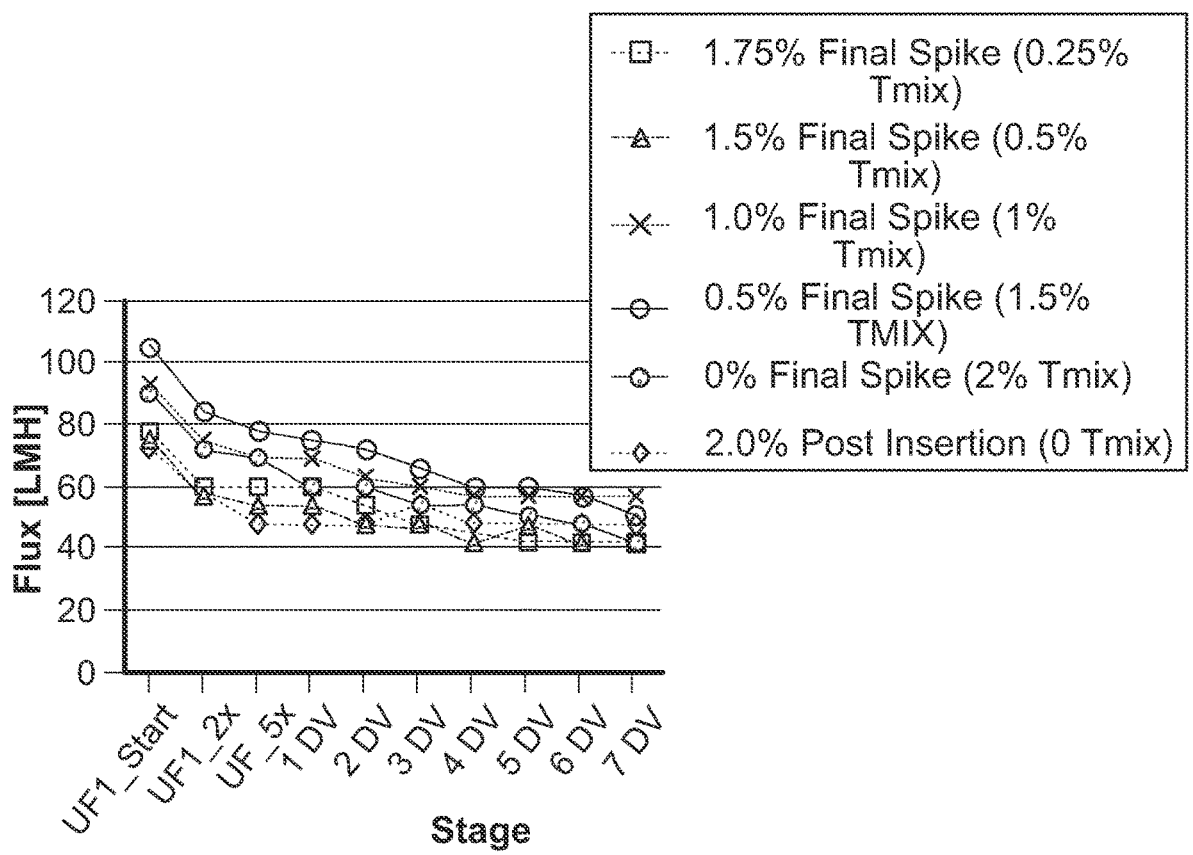
FIG. 38 illustrates the flux in tangential flow filtration (TFF) of particles made in the post addition process, compared to the post insertion process.
Figure 39:
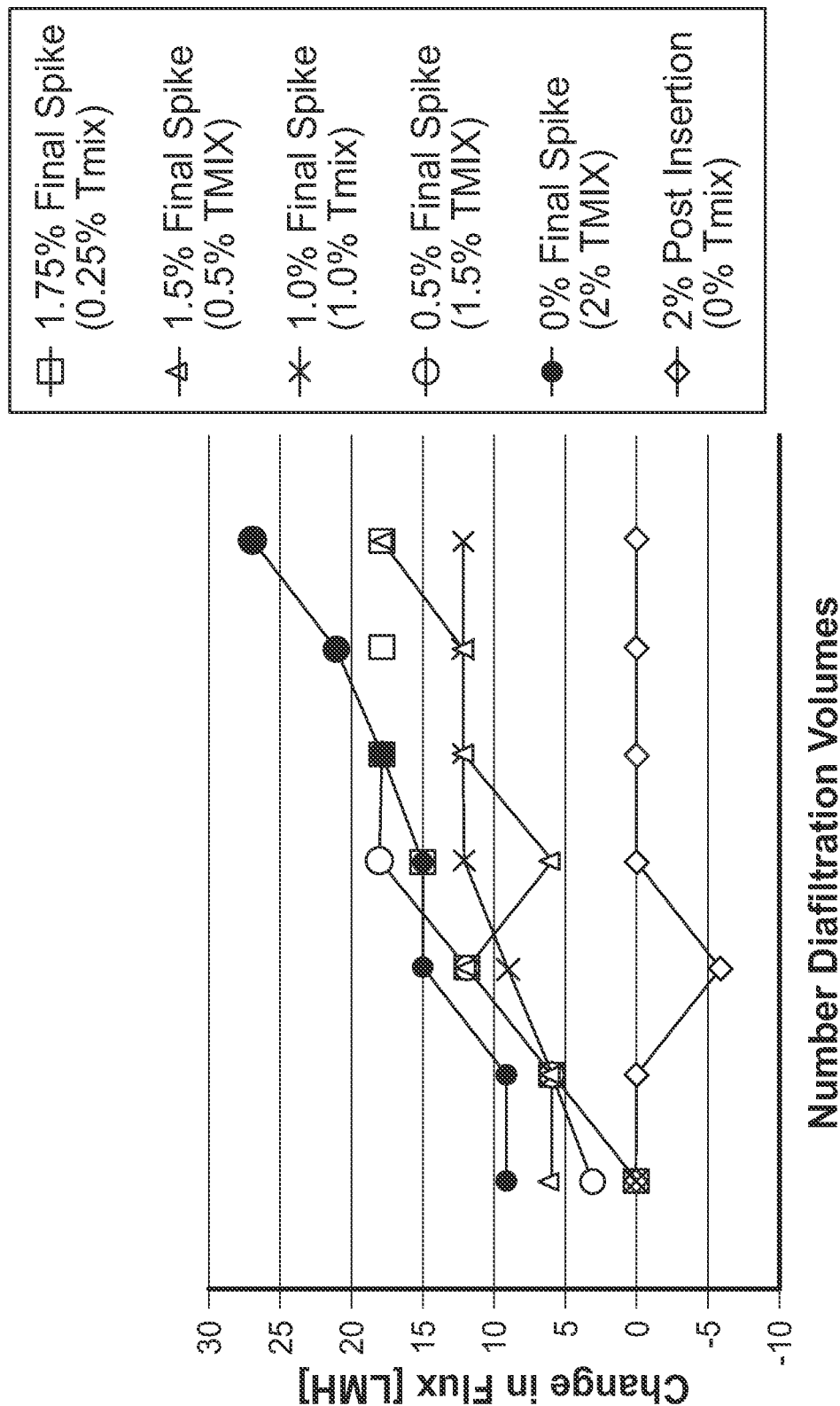
FIG. 39 summarizes the change in flux in tangential flow filtration (TFF) of particles made in the post addition process, compared to the post insertion process.
Figure 41:
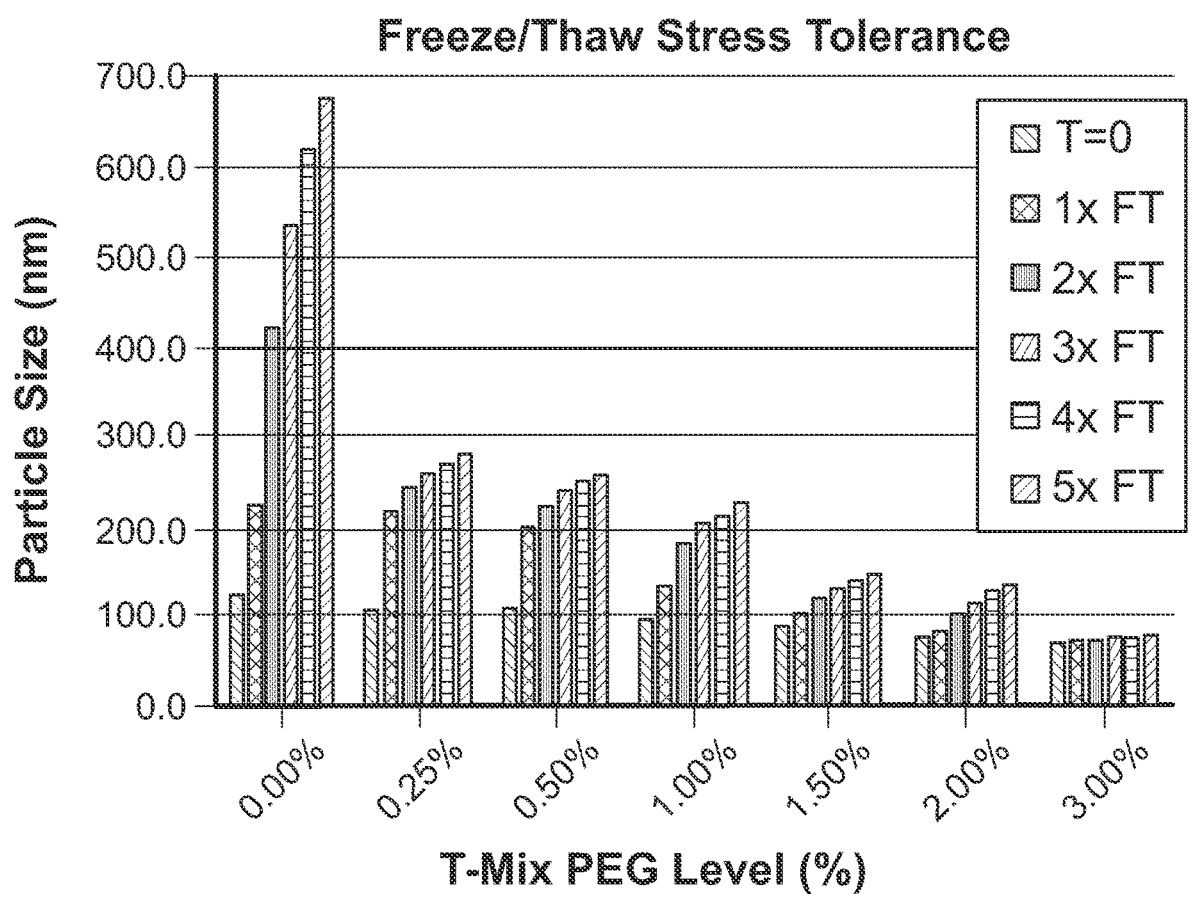
FIG. 41 is a graph depicting LNP particle size (nm) changes of various LNPs prepared by standard processing with varying amounts of PEG-lipid when subjected to 0-5 rounds of freeze/thaw (FT) events.
Figure 42:
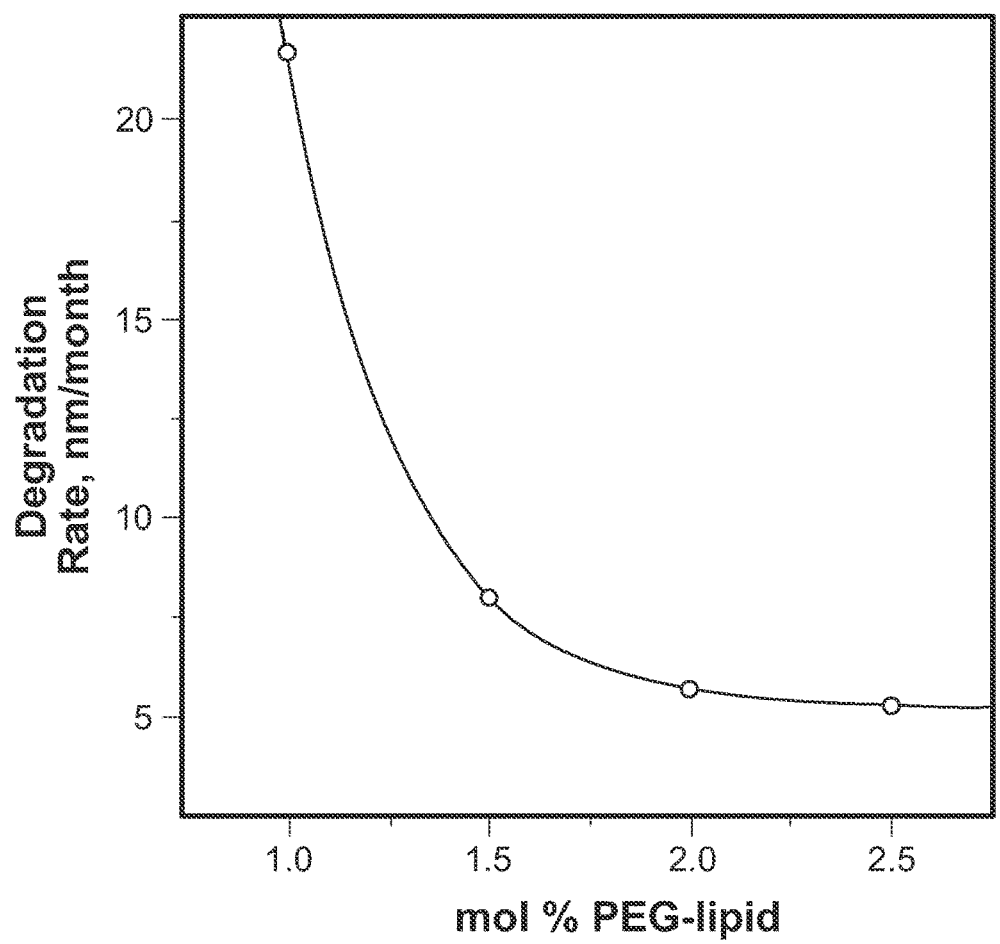
FIG. 42 is a graph depicting long-term storage, in terms of rate of degradation, of LNPs with varying amounts of PEG-lipid prepared by standard processing.
Figure 43:
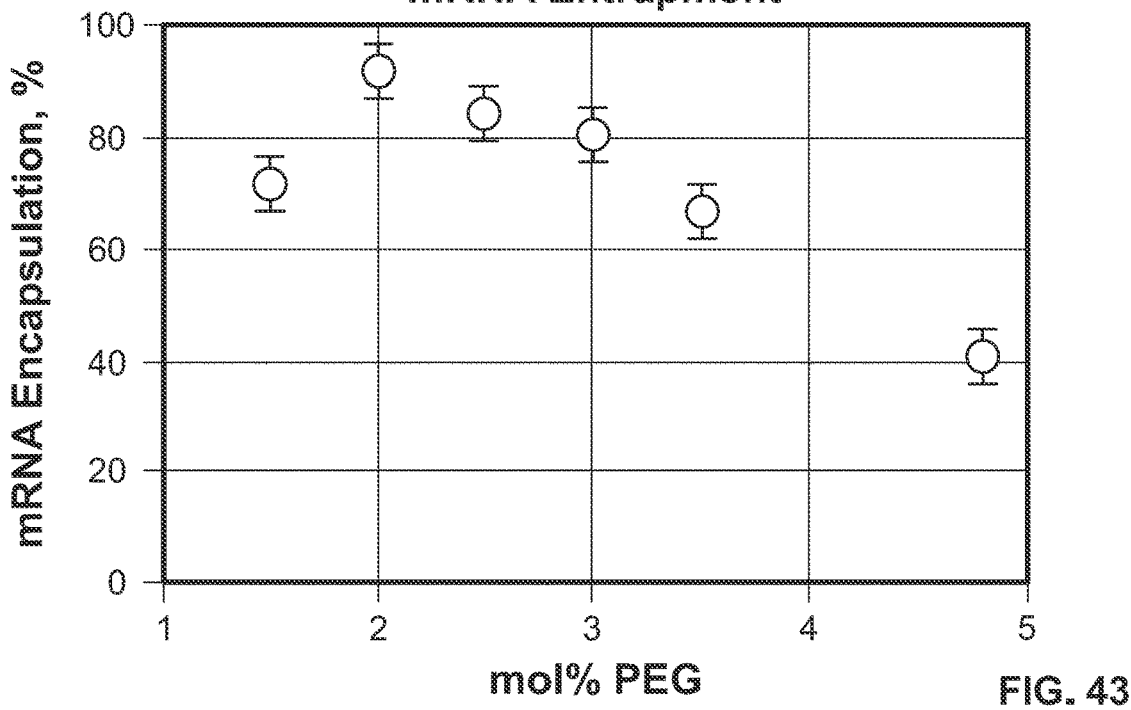
FIG. 43 is a graph depicting mRNA entrapment % of various LNPs prepared by standard processing with varying amounts of PEG-lipid.
Figure 44:
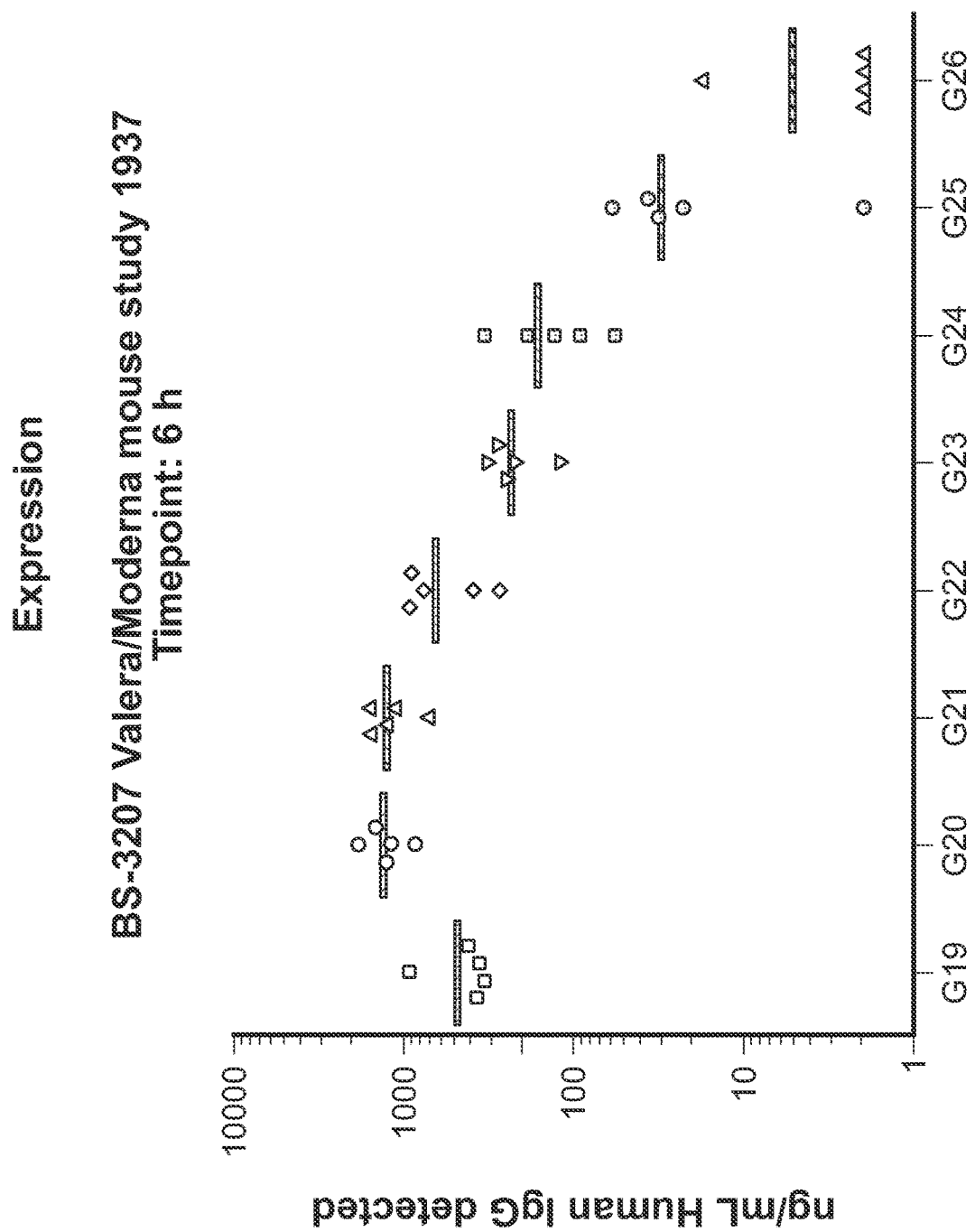
FIG. 44 is a graph depicting PEG-lipids adversely affecting expression of AUC eGFP, as measured in terms of Human IgG detection (ng/mL).
Figure 45:
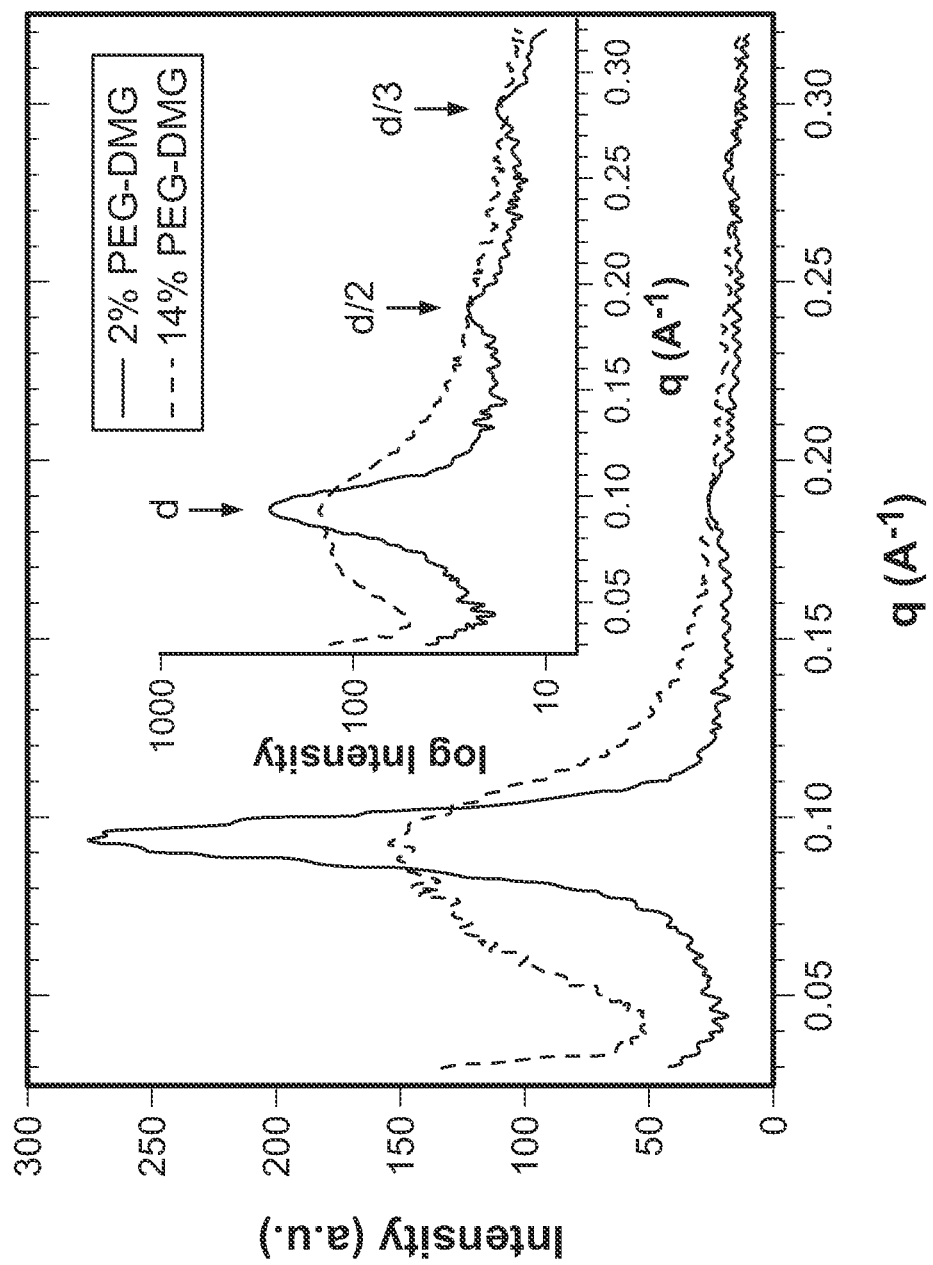
FIG. 45 is a graph depicting SAXS diffraction patterns, wherein lamellar structure lacks order with 14 mol % PEG-DMG and wherein the distinguished diffraction peak indicates an ordered lamellar structure at 2 mol % PEG-DMG.
Figure 46:
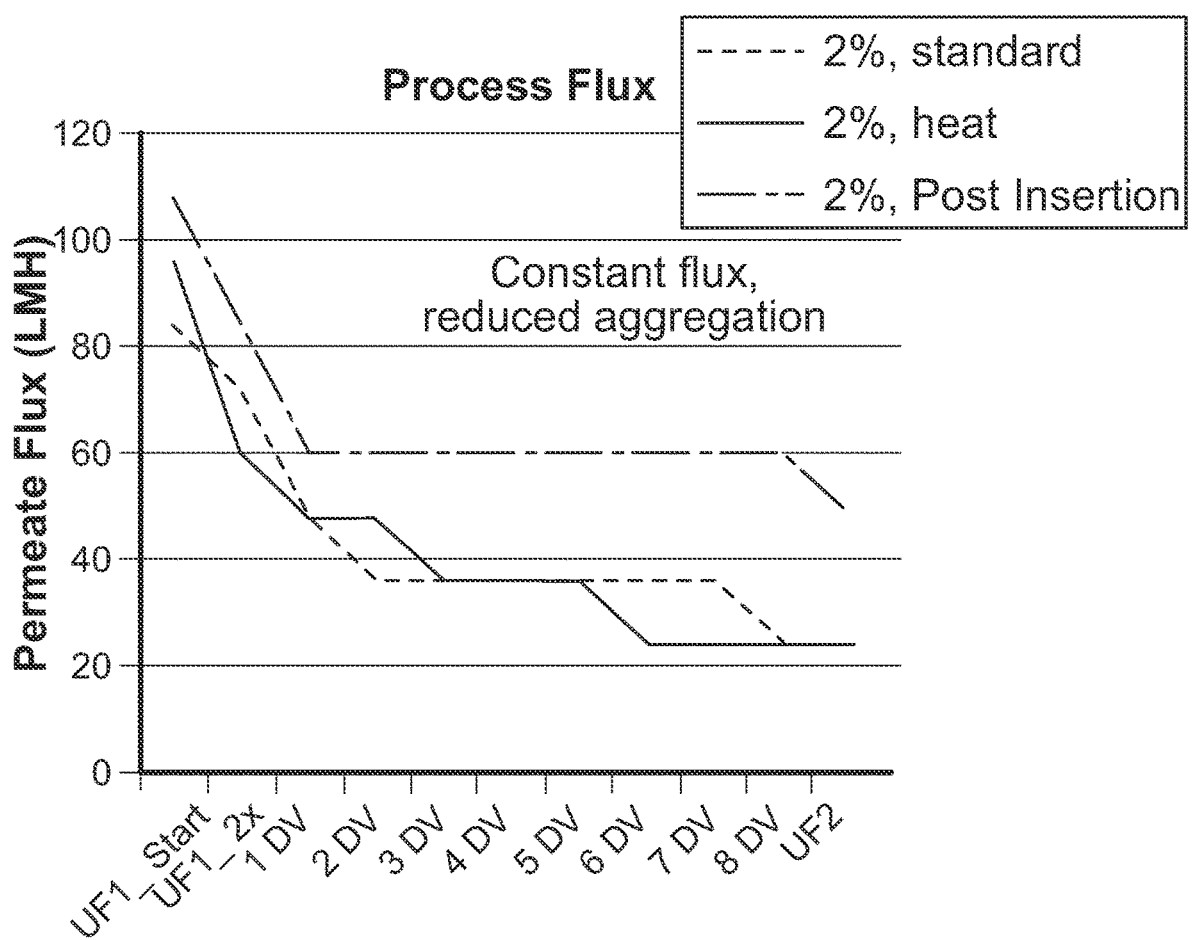
FIG. 46 is a graph depicting changes in process flux, which is defined as the volume flowing through a membrane per unit area per unit time. The drop in process flux may be indicative of biophysical changes, e.g., aggregation or diffusivity. Post-insertion consistently reduced/eliminated flux-loss over buffer exchange.
Figure 47A:
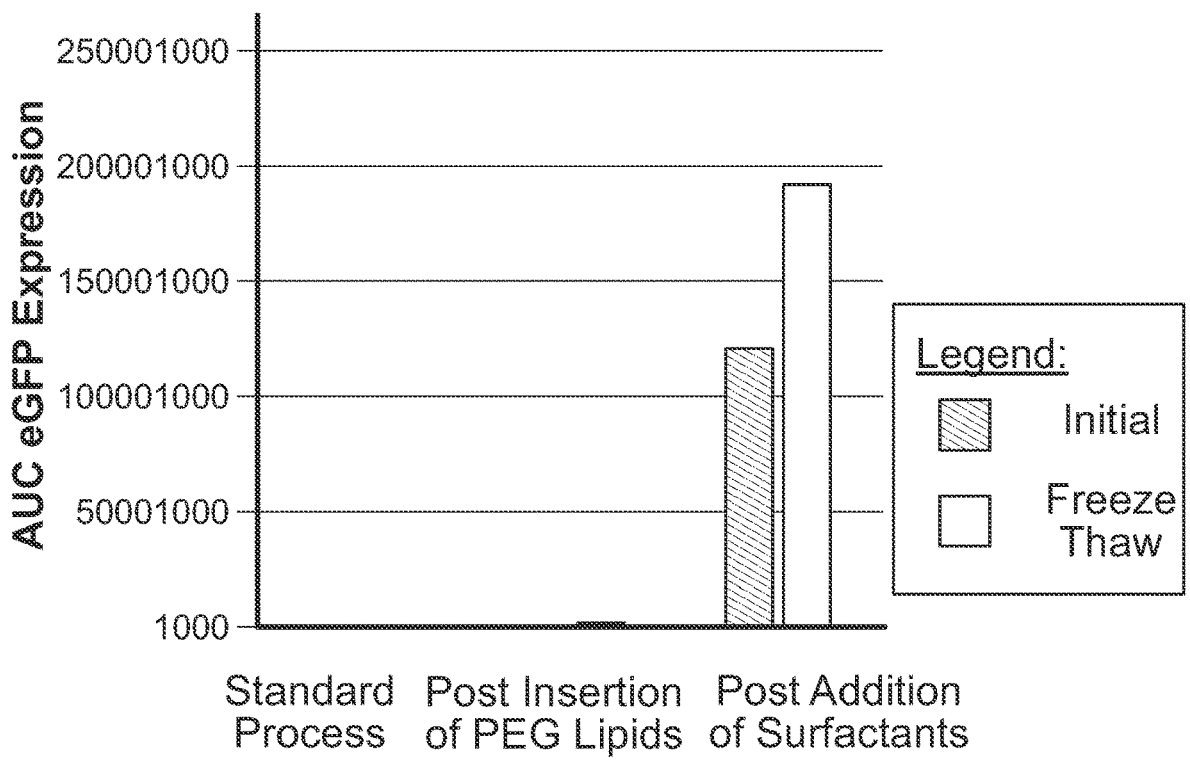
FIGS. 47A and 47B are graphs comparing AUC eGFP expression for LNPs prepared via standard processing, LNPs prepared via post insertion of PEG lipids, and LNPs prepared via post addition of surfactants.
Figure 47B:
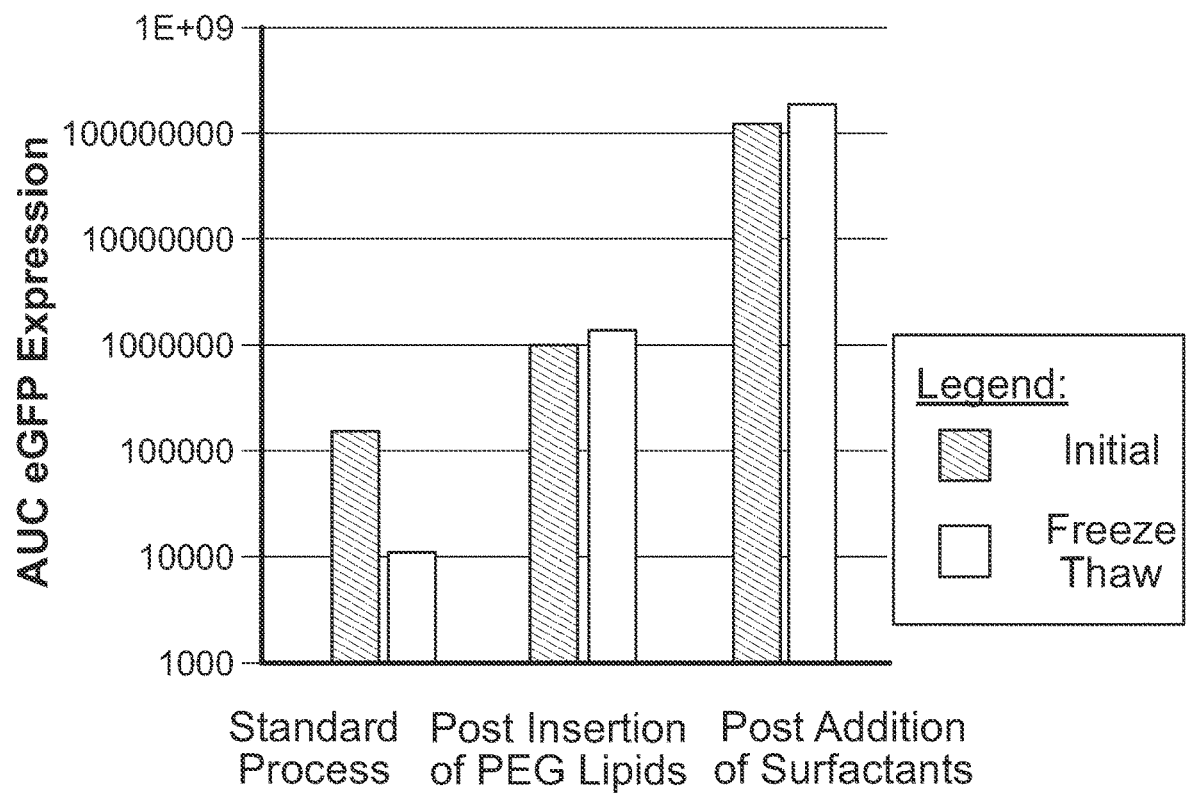
Figure 48:
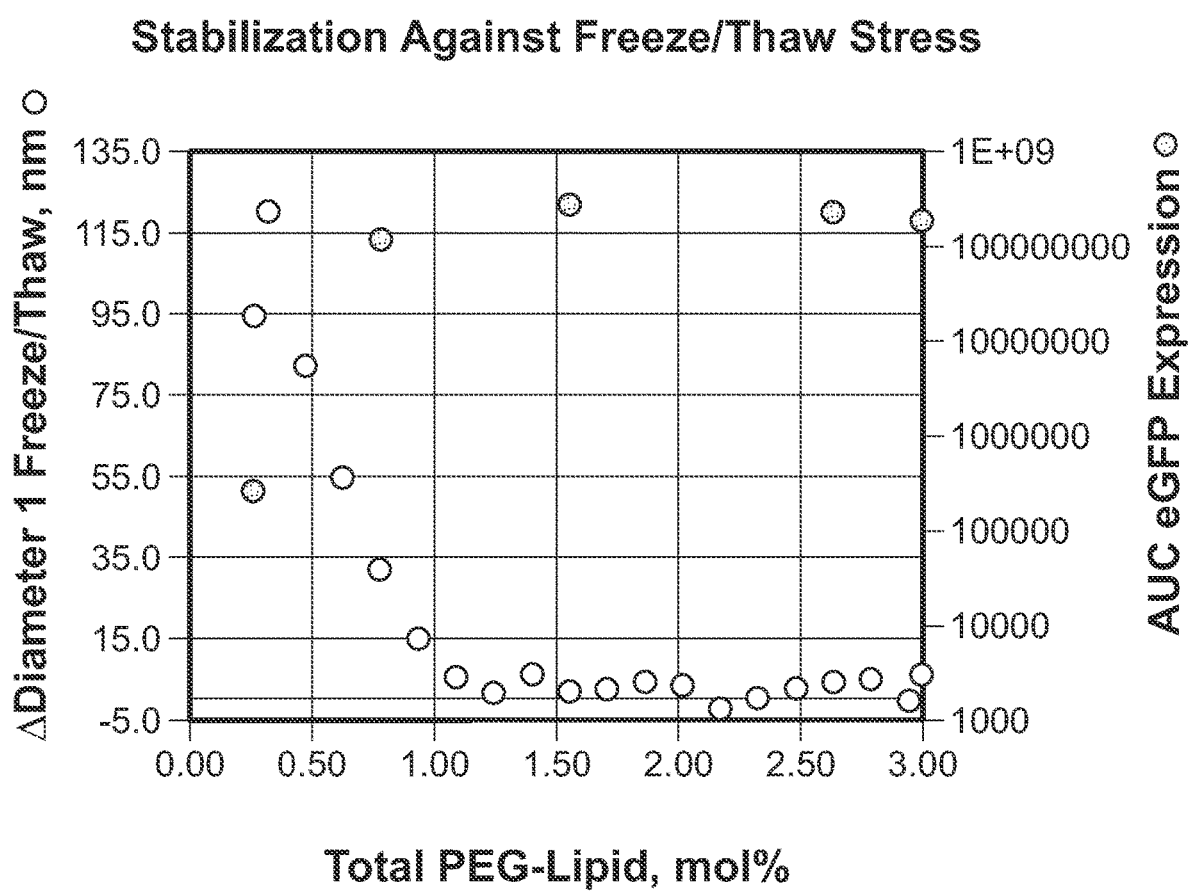
FIG. 48 is a graph depicting changes in LNP diameter upon Freeze/Thaw stress events and AUC eGFP expression of LNP compositions with various total amount of PEG lipid (PEG-1).

The effect of the processes summarized in Table 5 on the in vivo expression of an mRNA in a nanoparticle composition comprising ionizable lipid and PEG-1 were evaluated. Summarized study design: iv bolus, single dose, 0.5 mpk, N=4 Rats/arm, daily blood collection for protein PK (pre-dose as negative control). The hormone protein is a secreted protein, hence mRNA expression is tested through hormone protein quantification in the plasma. The results are shown in FIG. 37.

TABLE 5

Summary of production processes to make a composition comprising ionizable lipid and PEG-1

| PEG in Mix ("Core") | PEG Post-Inserted | PEG in Final Product Spike | Description |
|---|---|---|---|
| 2.0% | 0.0% | 0.0% | Standard Condition |
| 0.0% | 2.0% | 0.0% | Post-Insertion Series |
| 0.5% | 1.5% | 0.0% | |
| 1.0% | 1.0% | 0.0% | |
| 1.5% | 0.5% | 0.0% | |
| 0.0% | 0.0% | 2.0% | Post Addition Series |
| 0.5% | 0.0% | 1.5% | |
| 1.0% | 0.0% | 1.0% | |
| 1.5% | 0.0% | 0.5% | |

Example 3: Effect of Post Insertion and Post Addition on Potency and Stability of mRNA LNP Formulations To evaluate the effects of the manufacturing process of the disclosure on potency and stability of the lipid nanoparticles, additional LNP formulations were prepared with varied post insertion and/or post addition conditions. The membrane permeability, stability, update, and/or in vitro or in vivo expression of these LNP formulations were tested. See, e.g., FIGS. 1A-1C, 2A-2C, 3A-3B, 4A-4B, 5A-5B, 6A-6G, 7A-7C, 8-10, 11A-11B, 12A-12B, 13A-13B, 14-26, 27A-27B, 28, 29A-29B, 30A-30B, 31A-31B, 32A-32B, 33A-33C, 34A-34C, 35-39, 40, 41-46, 47A-47B, 48, 52A-52F, and 57-59.

Figure 49A:
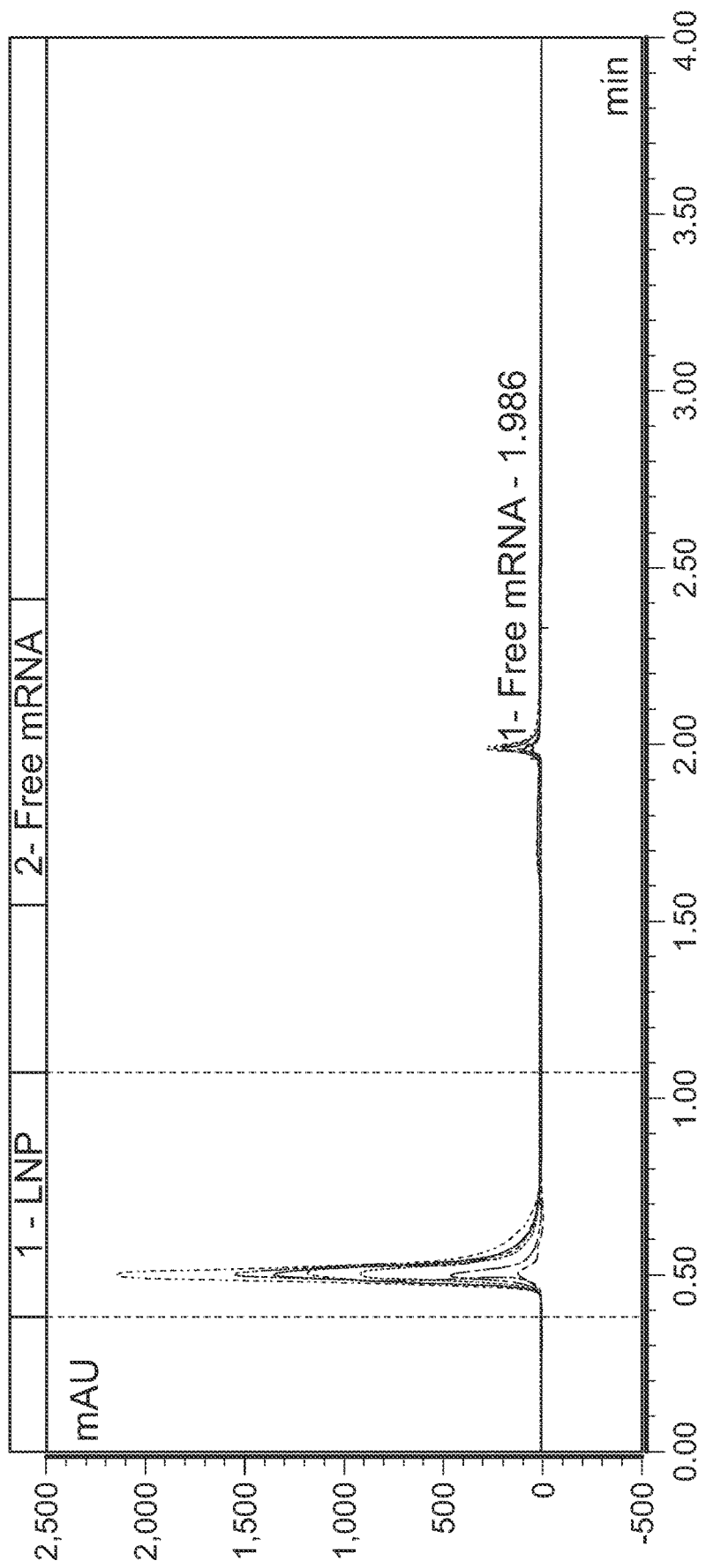
FIGS. 49A and 49B are a set of graphs depicting separation results demonstrating that LNP elutes in the void and mRNA elutes when gradient changes from low to high salt concentration.
Figure 49B:
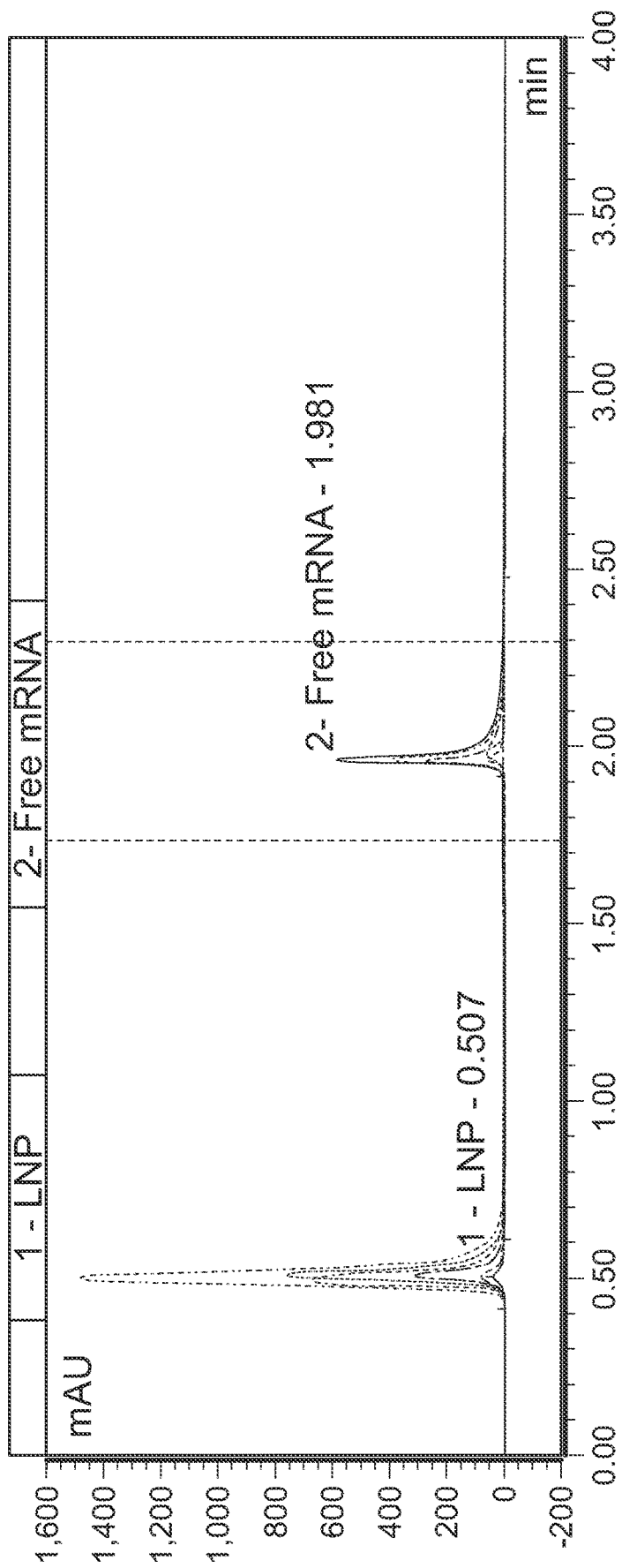

Example 4: Ion-Exchange Chromatography for Determining Encapsulation Efficiency IEX methodology was developed to separate free mRNA versus LNP-encapsulated mRNA. Using an exemplary process, LNP elutes in the void and mRNA elutes when gradient changes from low to high salt concentration. Representative separation is depicted in FIGS. 49A-49B. FIG. 49A depicts varying encapsulation efficiency based on mRNA formulation buffer conditions. FIG. 49B depicts varying encapsulation efficiency based on mRNA formulation salt concentrations.

The method conditions below were used to separate encapsulated from free mRNA encoding an infectious disease antigen.

| | |
|---|---|
| Buffer A | 25 mM NaOH/Glycine |
| Buffer B | 25 mM NaOH/Glycine with 750 mM NaCl |
| Column | Proswift WAX-1S |
| Flow rate | 0.7 mL/min |
| Run time | 4 minutes |

Gradient was as follows:

| No | Time | Flow mL/min | % B | Curve |
|---|---|---|---|---|
| 1 | 0.0 | 0.7 | 7 | 5 |
| 2 | 0.8 | 0.7 | 7 | 5 |
| 3 | 1.6 | 0.7 | 100 | 5 |
| 4 | 2.9 | 0.7 | 100 | 5 |
| 5 | 3.0 | 0.7 | 7 | 5 |
| 6 | 4.0 | 0.7 | 7 | 5 |

Example 5: Correlation of Encapsulation Efficiency as Determined by IEX with Biological Activity LNPs encapsulating an mRNA vaccine composition were fractionated according to SEC then subjected to second dimensional analysis (physiochemical analysis of the SEC fractions). Particle size was determined according to dynamic light scattering. % mass of mRNA across the peak on SEC was determined according to the following: % Mass of mRNA=Concentration of Fraction*Volume of Fraction collected/Yield.

Figure 50:
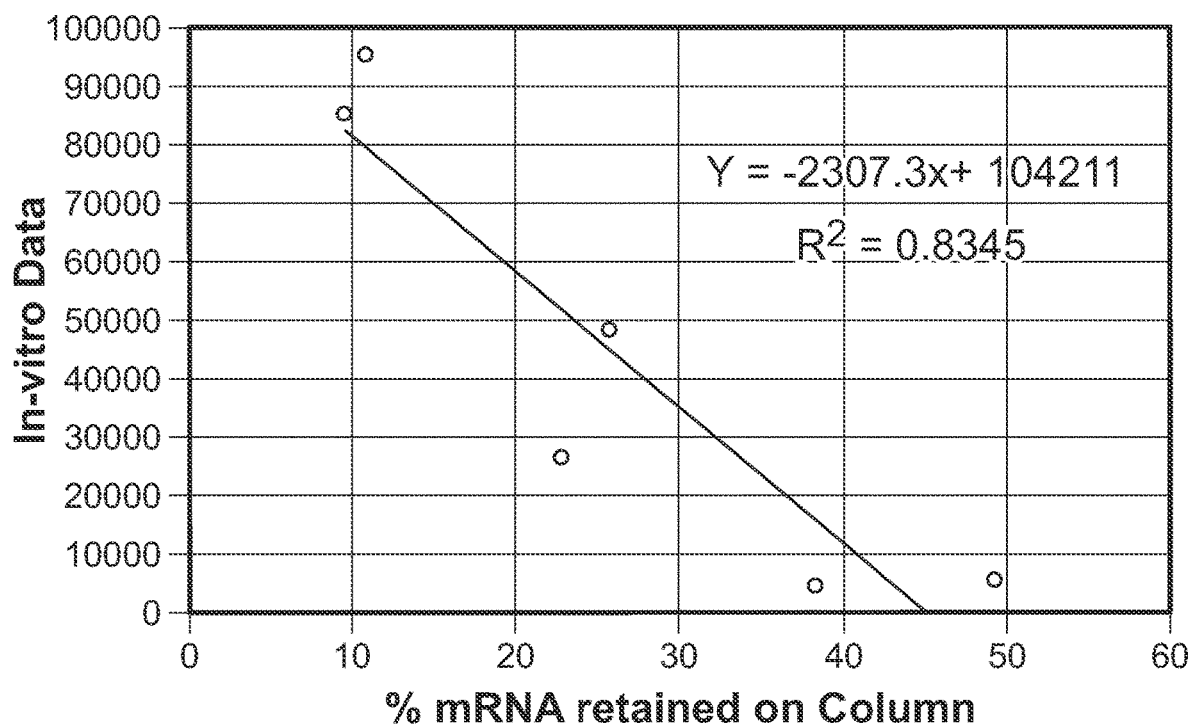
FIG. 50 is a graph showing correlation between the % mRNA retained on the column and in vitro expression of samples.

Fractions were subjected to both in vitro expression assay and encapsulation efficiency assay. The data in FIG. 50 show that % mRNA accessible or retention on IEX column correlates (inversely) with in vitro protein expression.

Example 6: Percent Encapsulation of mRNA

The encapsulation % of the mRNA in lipid nanoparticles is determined using a 4.6×50 mm Proswift WAX-1S weak anion exchange column in 25 mM Sodium Hydroxide and Glycine buffer with elution of accessible RNA using a sodium chloride salt gradient. Samples are diluted to a target concentration of 0.1 mg/mL RNA using 10 mM TRIS-HCL 1 mM EDTA buffer and the accessible RNA peaks is quantitated with an external reference standard. The methods are shown in the table.

| | |
|---|---|
| Instrument: | Thermofisher Vanquish UHPLC, Agilent 1260, or equivalent (Biocompatible System recommended by not required) |
| Column: | Thermofisher PROswift WAX-1S 4.6 × 50 mm Monolithic column |
| Mobile Phase A: | 25 mM NaOH/Glycine pH 10.09 |
| Mobile Phase B: | 25 mM NaOH/Glycine pH 10.09, 750 mM Sodium Chloride |
| Needle Wash: | 50% Ethanol: 50% Water |
| Seal Wash: | 0.1% Formic Acid in 25% Water: 75% IPA |
| Column Wash: | 1.80% 0.25N NaOH in water and 20% Ethanol |
| Acquisition/Run Time: | 4 minutes |
| Flow Rate: | 0.7 mL/min |
| Detection: | UV at 260 nm |
| Injection Volume: | 10 µL (except for standard curve in R&D analysis) |
| Column Temperature: | 25° C. |
| Auto sampler Temperature: | 20° C. |
| Injection/ Needle Wash: | After Draw or Both-20 seconds, 30 µL/sec (or wash vial for Agilent) |
| Sample Concentration: | Target 0.1 mg/mL |

| Time (min) | Mobile Phase A % | Mobile Phase B % |
|---|---|---|
| 0.0 | 93.0 | 7.0 |
| 0.8 | 93.0 | 7.0 |
| 1.6 | 0.0 | 100.0 |
| 2.9 | 0.0 | 100.0 |
| 3.0 | 93.0 | 7.0 |
| 4.0 | 93.0 | 7.0 |

Calculations:

$$\text{Accessible } RNA_{Conc} = \frac{(\text{Sample}_{Peak\,Area} * \text{Standard}_{Conc})}{\text{Mean Standard}_{peak\,area}} *$$

Dilution Factor Encapsulation % from Accessible $RNA =$ $$\left(\left[\frac{\text{Total } mRNA\ Conc - \text{Accessible } RNA_{Conc}}{\text{Total } mRNA\ Conc}\right] * 100\right)$$

$$\text{Accessible } RNA_{Conc} = \frac{(\text{Sample}_{Peak\,Area} * \text{Standard}_{Conc})}{\text{Mean Standard}_{peak\,area}} * \text{Dilution Factor}$$

Encapsulation % from Accessible $RNA =$ $$\left(\left[\frac{(\text{Total } mRNA\ Conc - \text{Accessible } RNA_{Conc})}{\text{Total } mRNA\ Conc}\right] * 100\right)$$

Accessible RNA—This is the concentration of RNA that can be quantitated when the formulations is diluted in non-denaturing conditions and assayed according to the method conditions. This RNA represents a combination of mRNA that is free or loosely associated with lipids.

Total RNA—This is the concentration of RNA that can be quantitated when the formulations is diluted in denaturing conditions. This RNA represents encapsulated, loosely associated, and free RNA.

Un-retained LNP—This is the un-retained material that elutes in the void of the column. Likely consists of mRNA in an encapsulation state that is strongly associated and lacks significant surface charge for retention.

Figure 51:
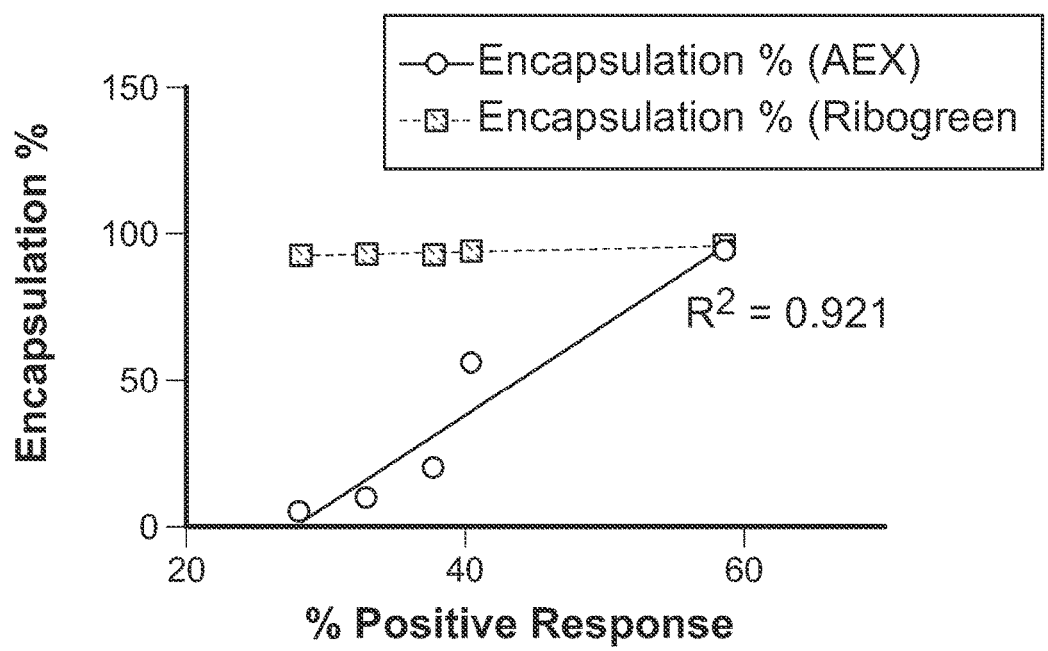
FIG. 51 is a graph of mRNA encapsulation percent as determined by Ribogreen and anion exchange chromatography versus in vitro expression.
Figure 52A:
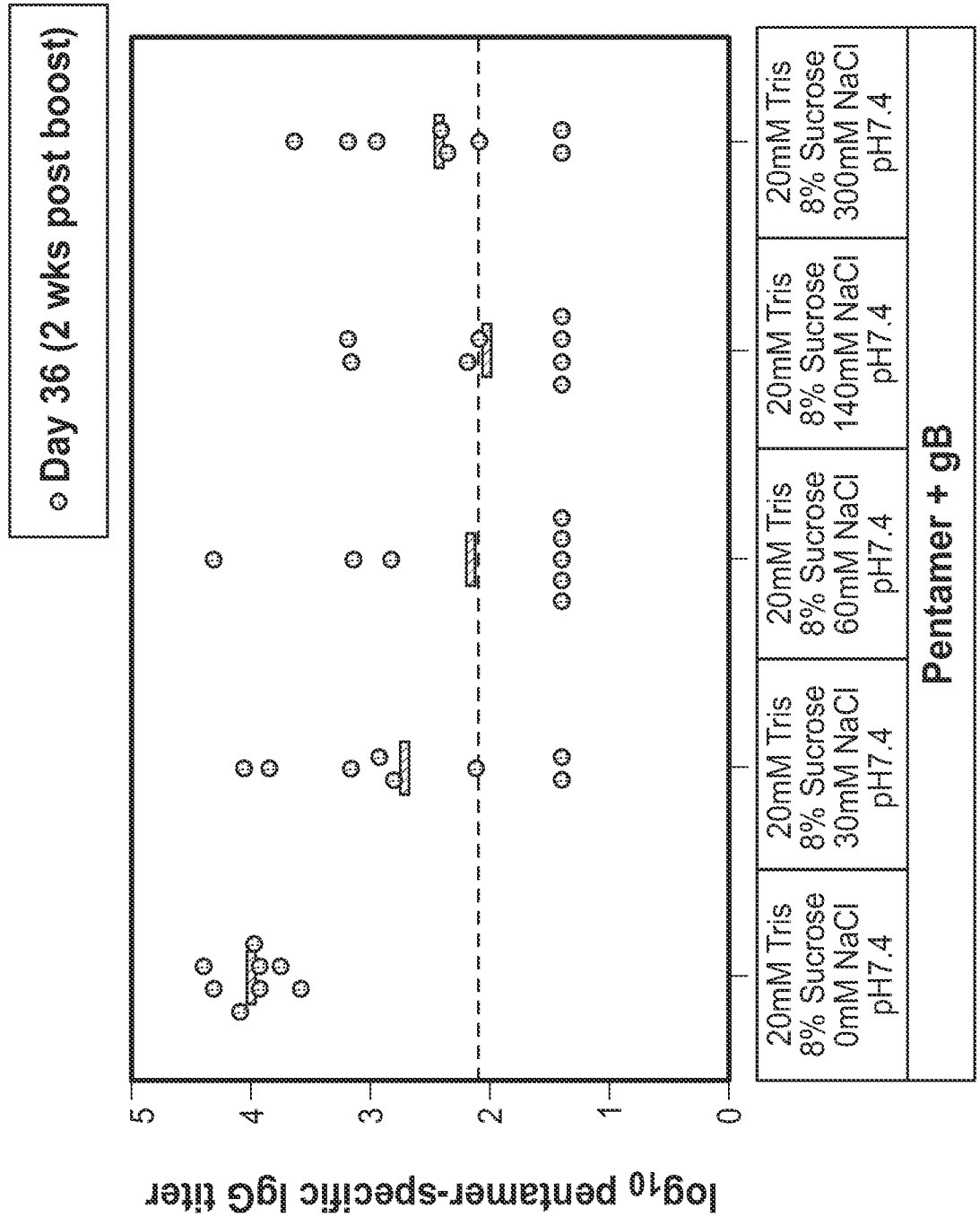
Figure 52C:
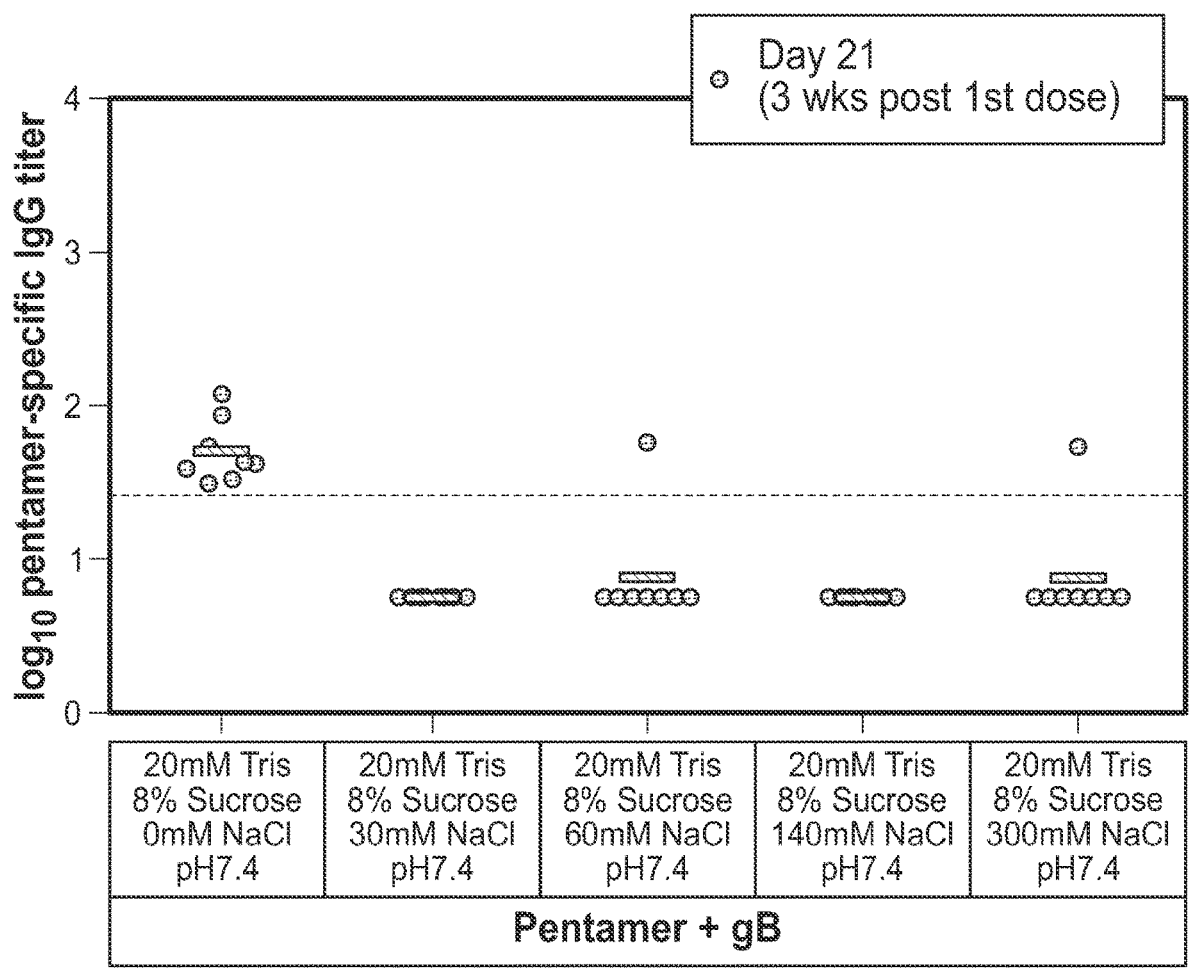
Figure 52D:
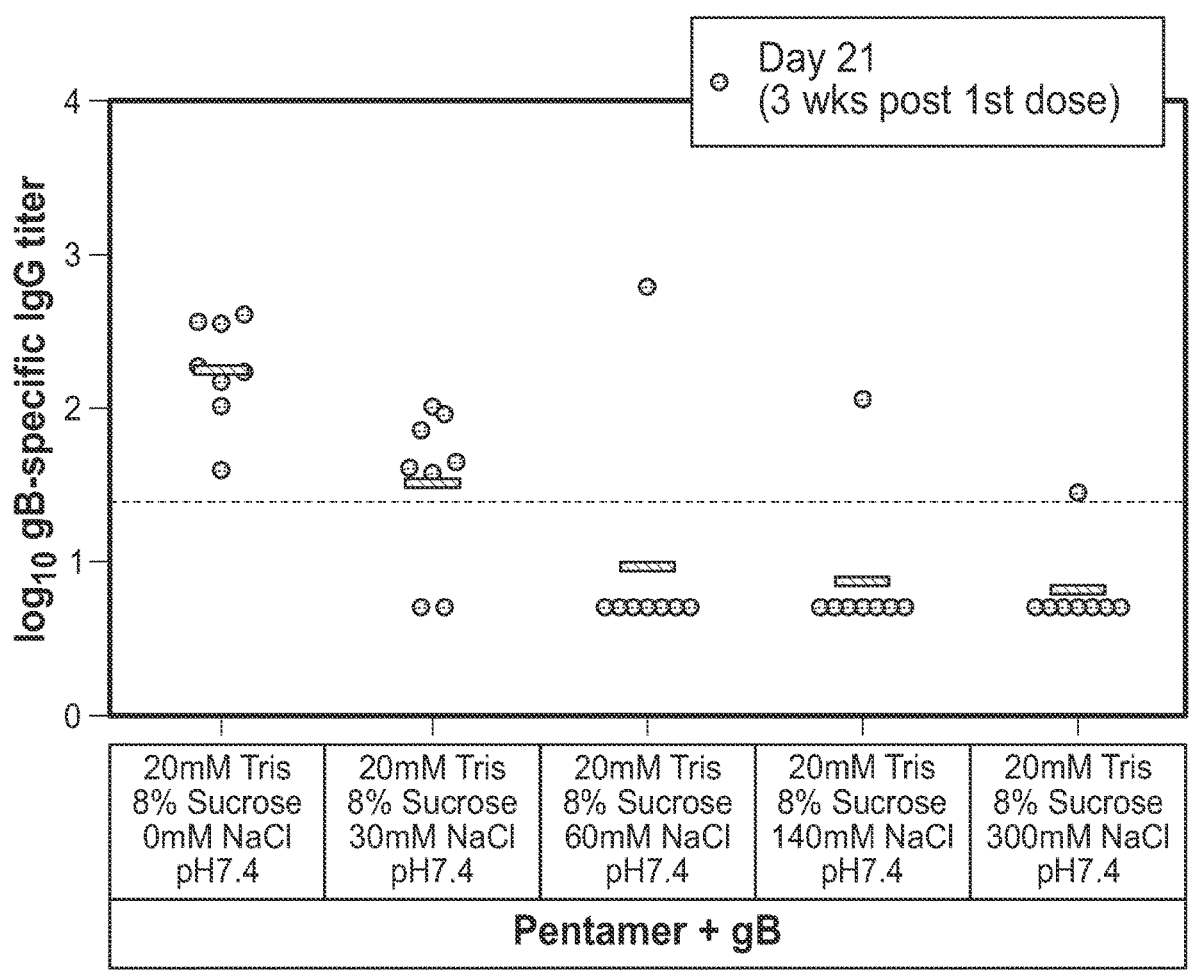
Figure 52E:
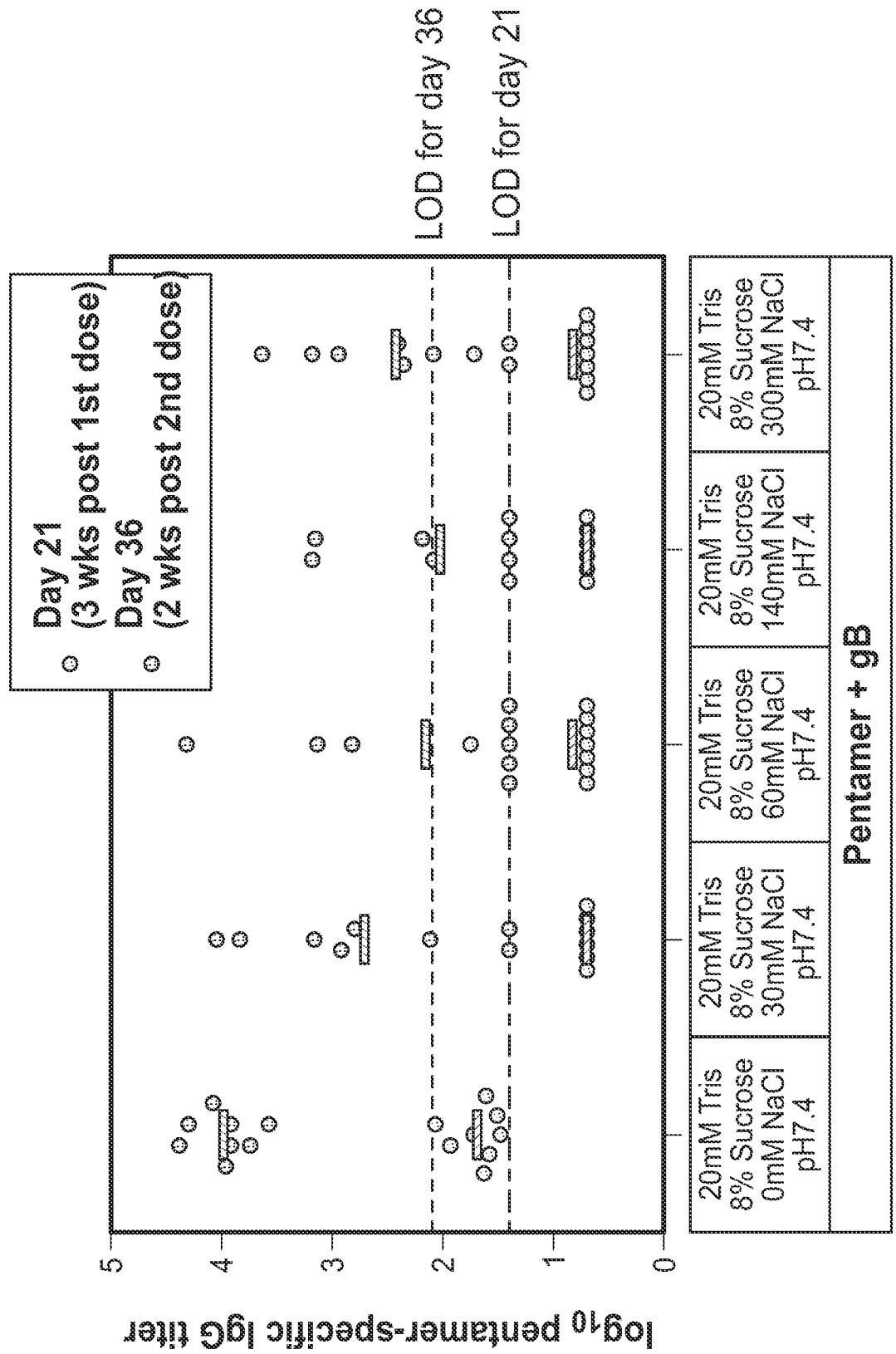
Figure 52F:
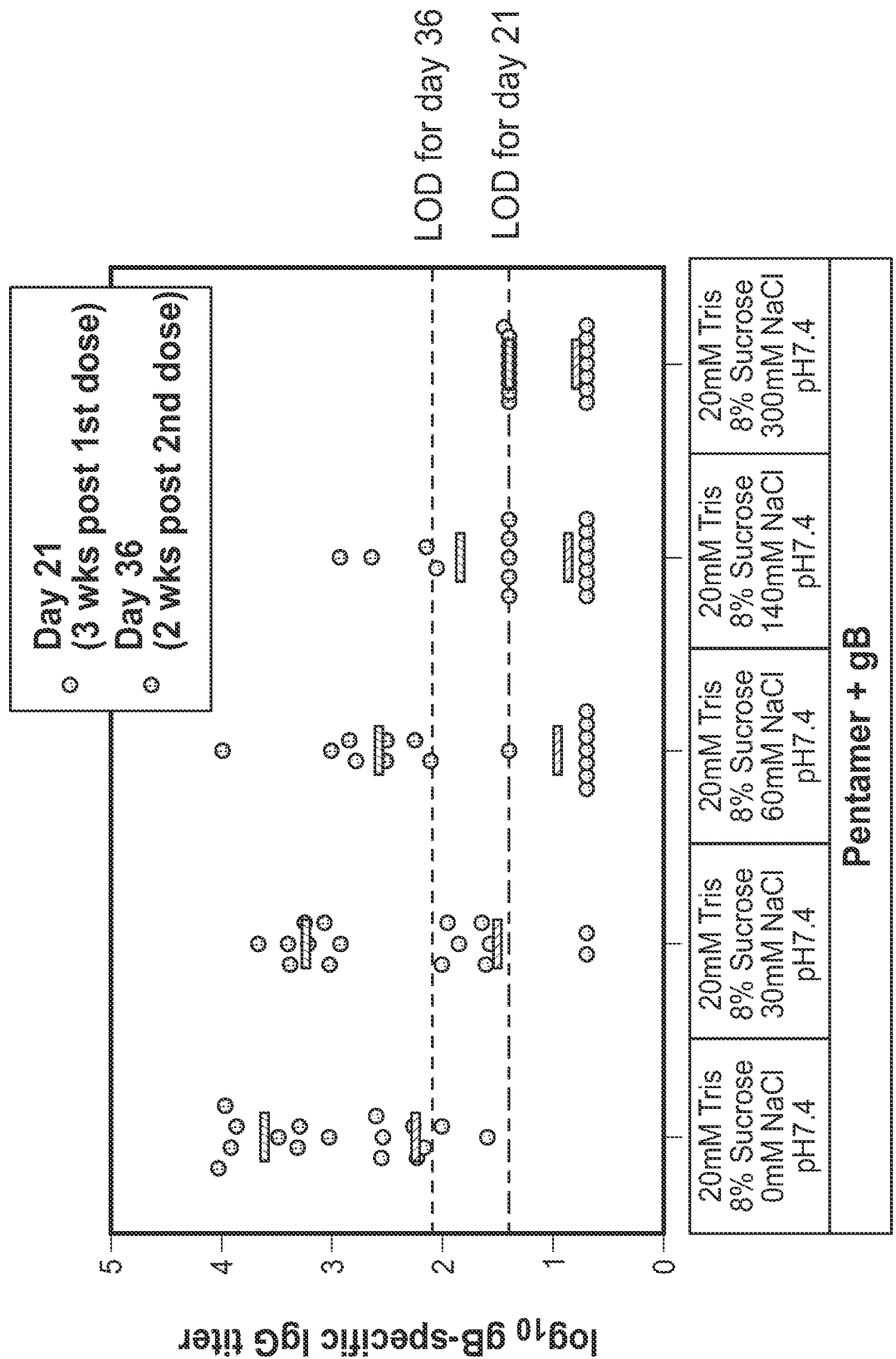

The Ribogreen assay cannot discriminate between the prototype formulations and shows them to be in the same encapsulation state, as illustrated by the graphs of in vitro expression in FIG. 51 and in vivo immunogenicity in FIG. 52. It is likely, that Ribogreen can only detect truly free RNA and does not discriminate between loose or poorly structured encapsulations states. Encapsulation by weak anion exchange chromatography can discriminate between the formulations and correlates reasonably well to the in-vitro expression data shown below. The table, below, shows the percent encapsulation using Ribogreen and using AEX for the compositions in FIG. 51.

| Prototype | Description | Encapsulation by Ribogreen (%) | Encapsulation by AEX (%) |
|---|---|---|---|
| 1 | 20 mM Tris 0 mM NaCl 8% Sucrose | 96 | 96 |
| 2 | 20 mM Tris 30 mM NaCl 8% Sucrose | 94 | 56 |
| 3 | 20 mM Tris 60 mM NaCl 8% Sucrose | 93 | 20 |
| 4 | 20 mM Tris 140 mM NaCl 8% Sucrose | 93 | 10 |
| 5 | 20 mM Tris 300 mM NaCl 8% Sucrose | 93 | 5 |

Figure 53:
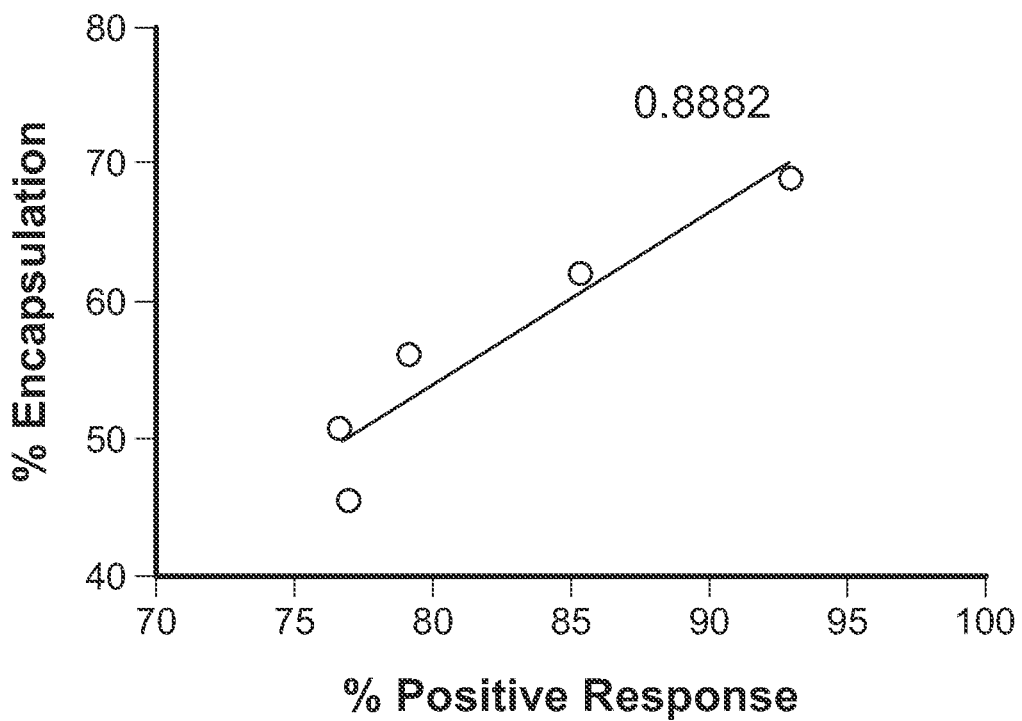
FIG. 53 is a graph of mRNA encapsulation percent as determined by anion exchange chromatography versus in vitro expression.
Figure 54:
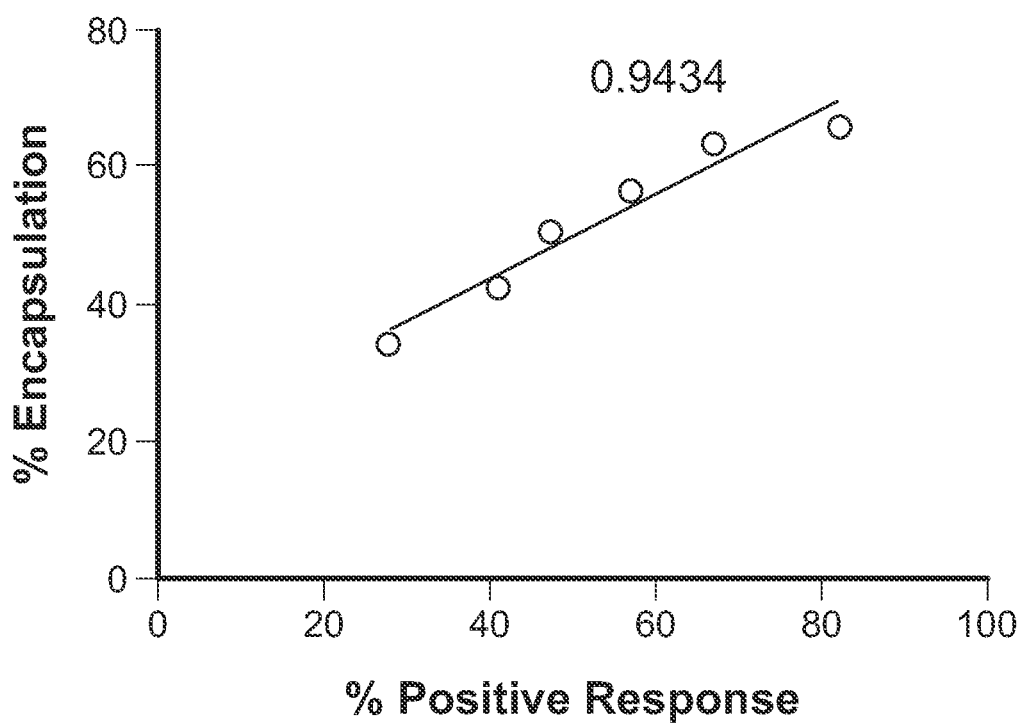
FIG. 54 is a graph of mRNA encapsulation percent as determined by anion exchange chromatography versus in vitro expression.

Exemplary Formulation SEC Fractions were assessed with varied encapsulation by anion exchange chromatography and in-vitro expression. Two batches were fractionated using size exclusion chromatography and characterized for physio-chemical characteristics and biological activity. SEC fractions varied in encapsulation state by weak ion exchange chromatography and correlated well with in-vitro expression as shown in FIGS. 53 and 54.

Figure 55:
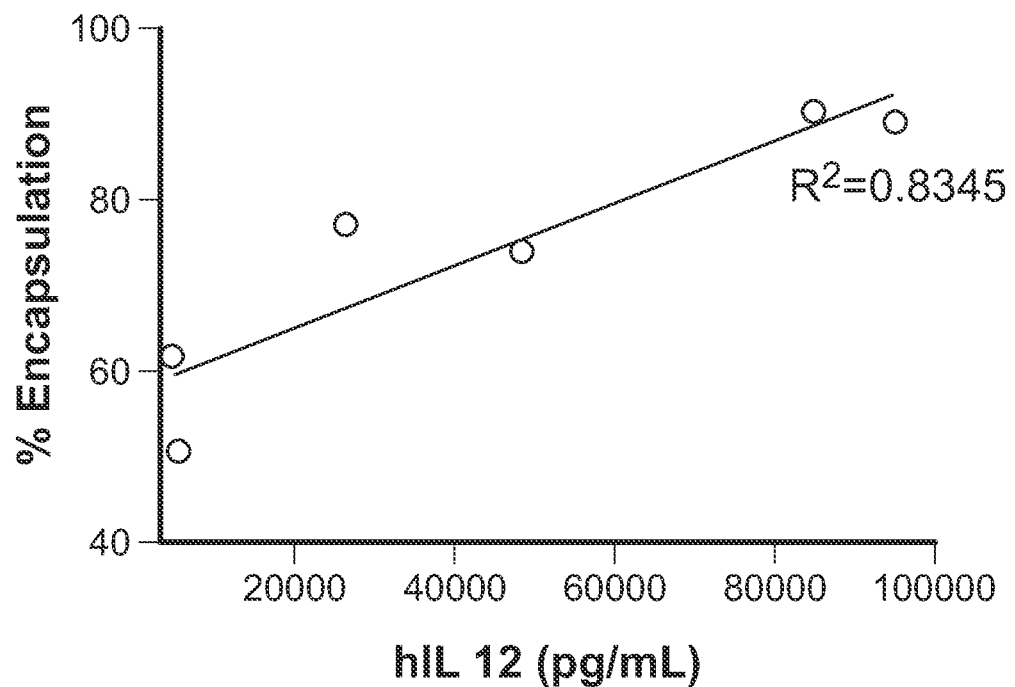
FIG. 55 is a graph of mRNA encapsulation percent as determined by anion exchange chromatography versus in vitro expression.

An exemplary cytokine prototype formulation was assessed with varied encapsulation by anion exchange chromatography and in-vitro expression. The data is shown in FIG. 55 (x-axis=cytokine expression in pg/ml).

Exemplary cytokine encoding RNA formulation-SEC Fractions with varied encapsulation by anion exchange chromatography and in-vitro expression.

Figure 56:
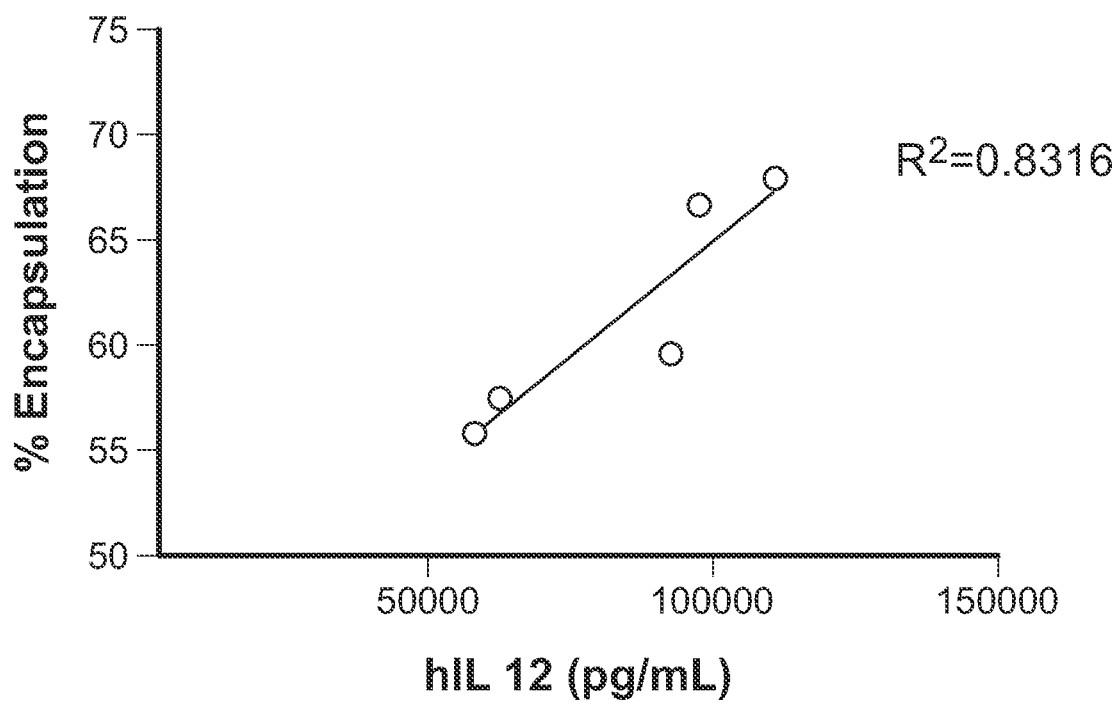
FIG. 56 is a graph of mRNA encapsulation percent as determined by anion exchange chromatography versus in vitro expression.
Figure 57:
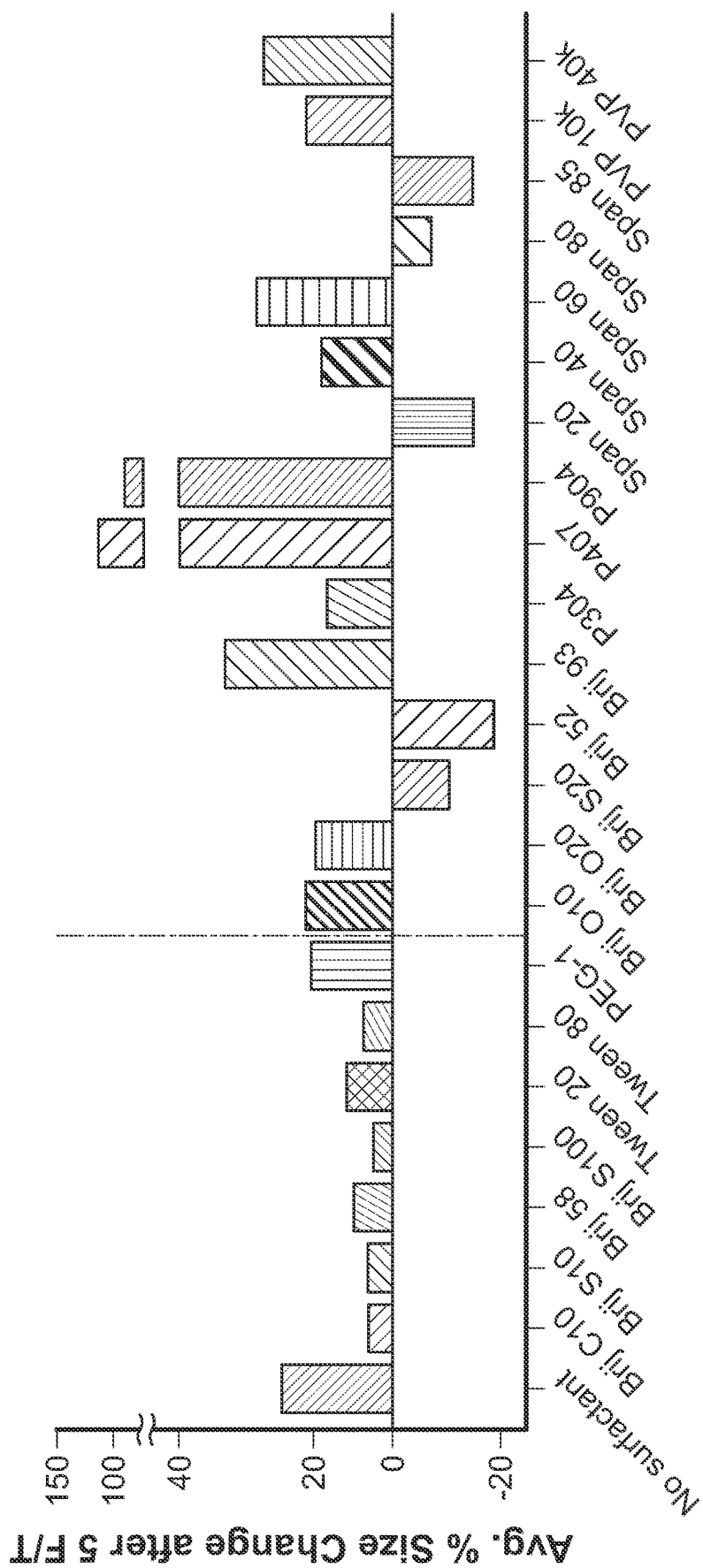
FIG. 57 is a graph of average percentage size change (%) of LNP formulations comprising 1% PEG prepared with a variety of surfactants and stored in 20 mM tris 8% sucrose after 5 cycles of freezing at −20° C. and thawing at room temperature.
Figure 58A:
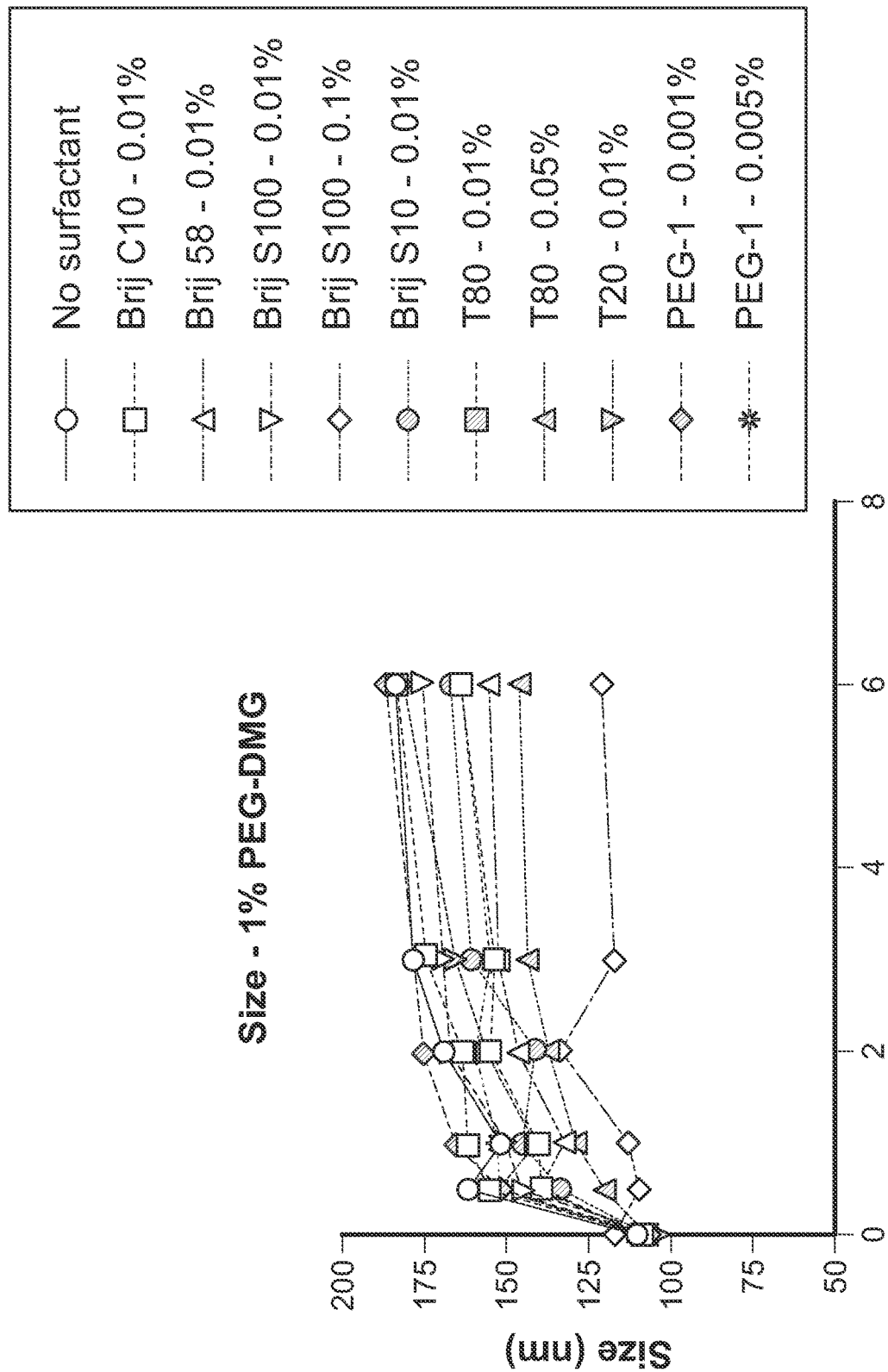
FIGS. 58A and 58B are graphs of size (nm) of LNP formulations comprising 1% PEG (A) and 1.5% PEG (B) with either no surfactant or various wt % of surfactant added stored at 0.5 mg/mL RNA in 20 mM tris 8% sucrose at −20° C. over a 6 month period of time.
Figure 58B:
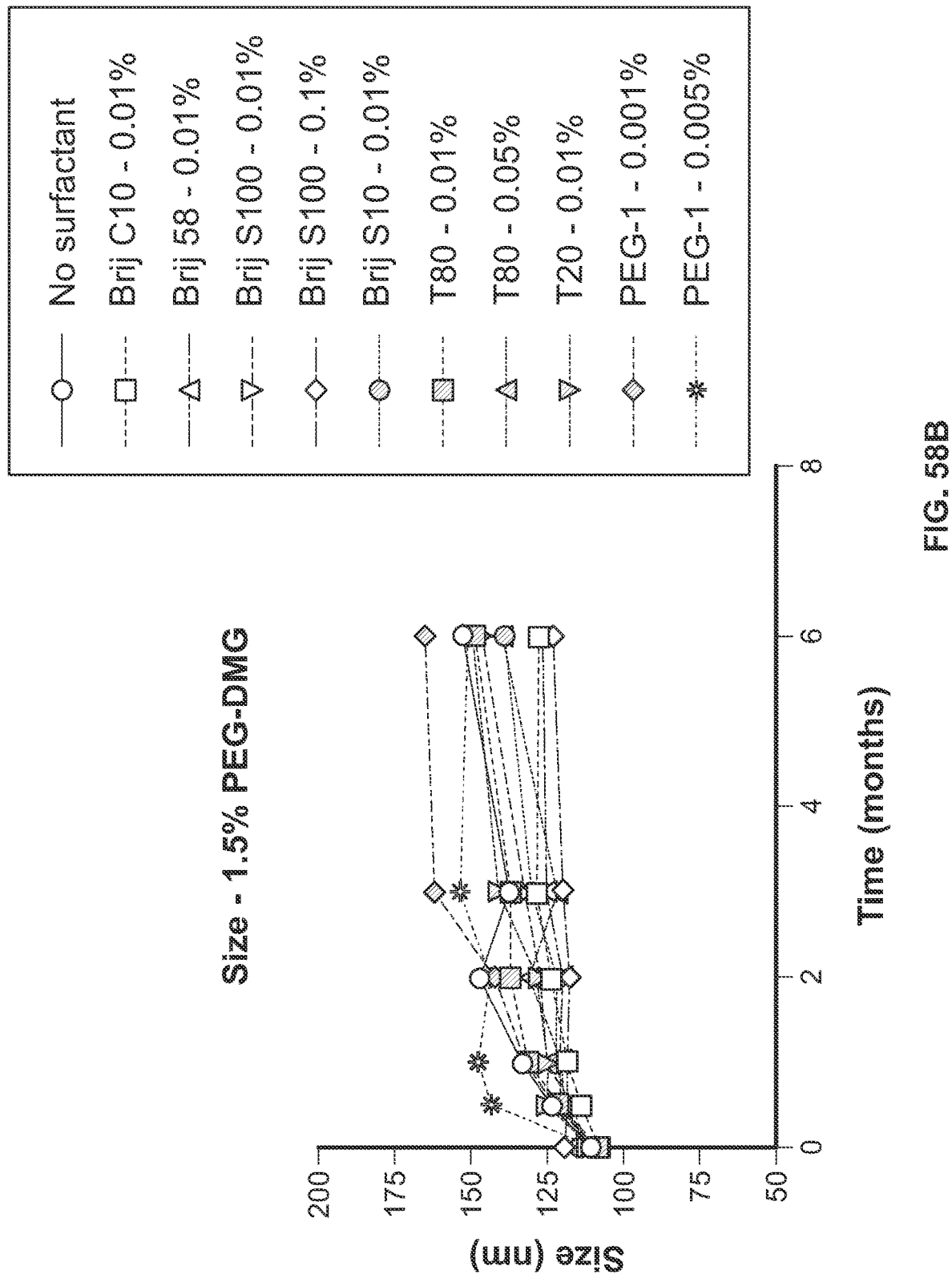
Figure 59:
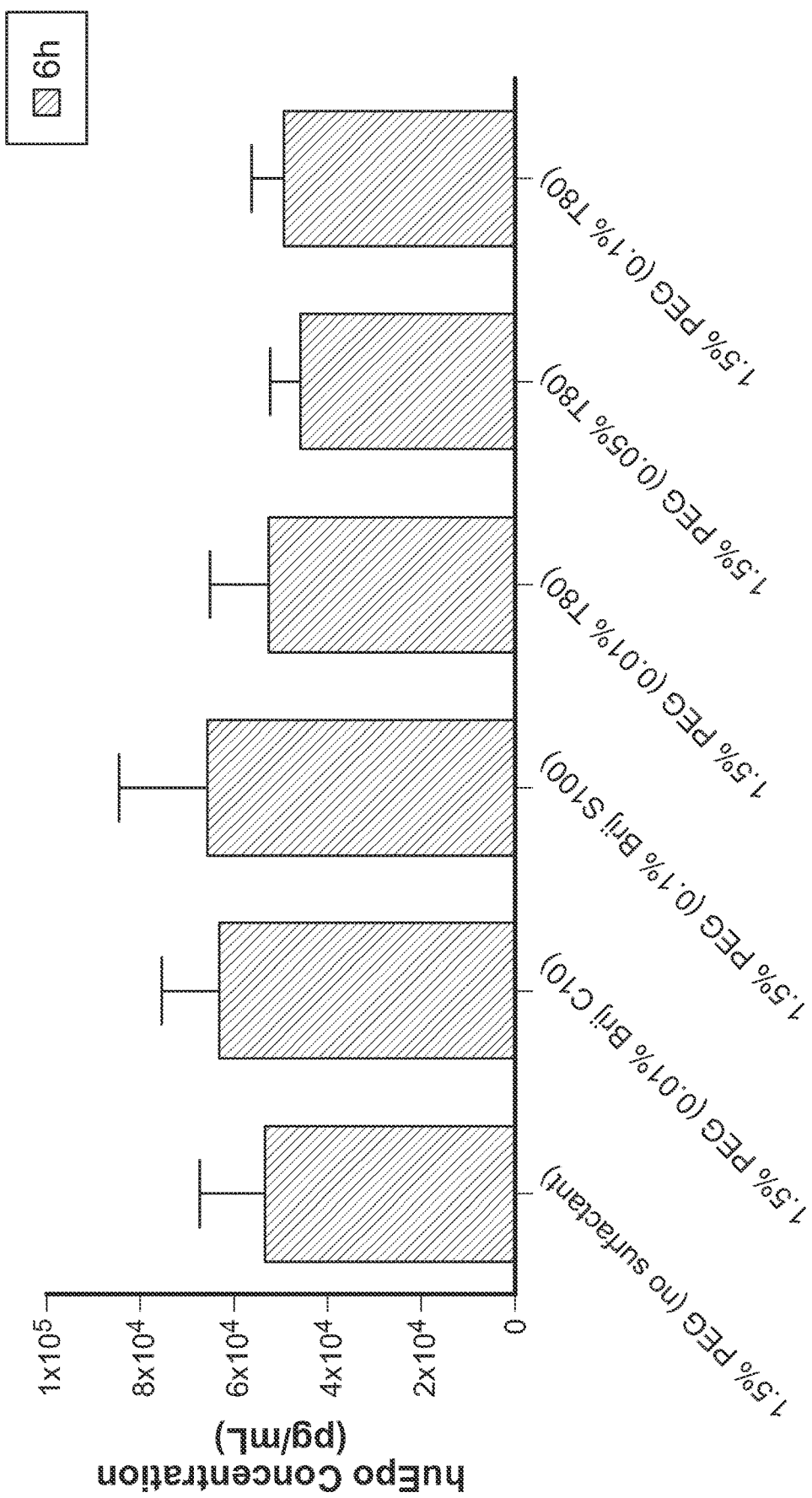
FIG. 59 is a graph of in vivo EPO expression for female CD-1 mice (n=5 mice per group) injected intramuscularly with 0.2 μg mRNA in LNPs containing 1.5% PEG and spiked with various wt % of various surfactants in 20 mM tris 8% sucrose and bled 6 hours after injection which demonstrates equivalent expression with the addition of surfactants.
Figure 60:
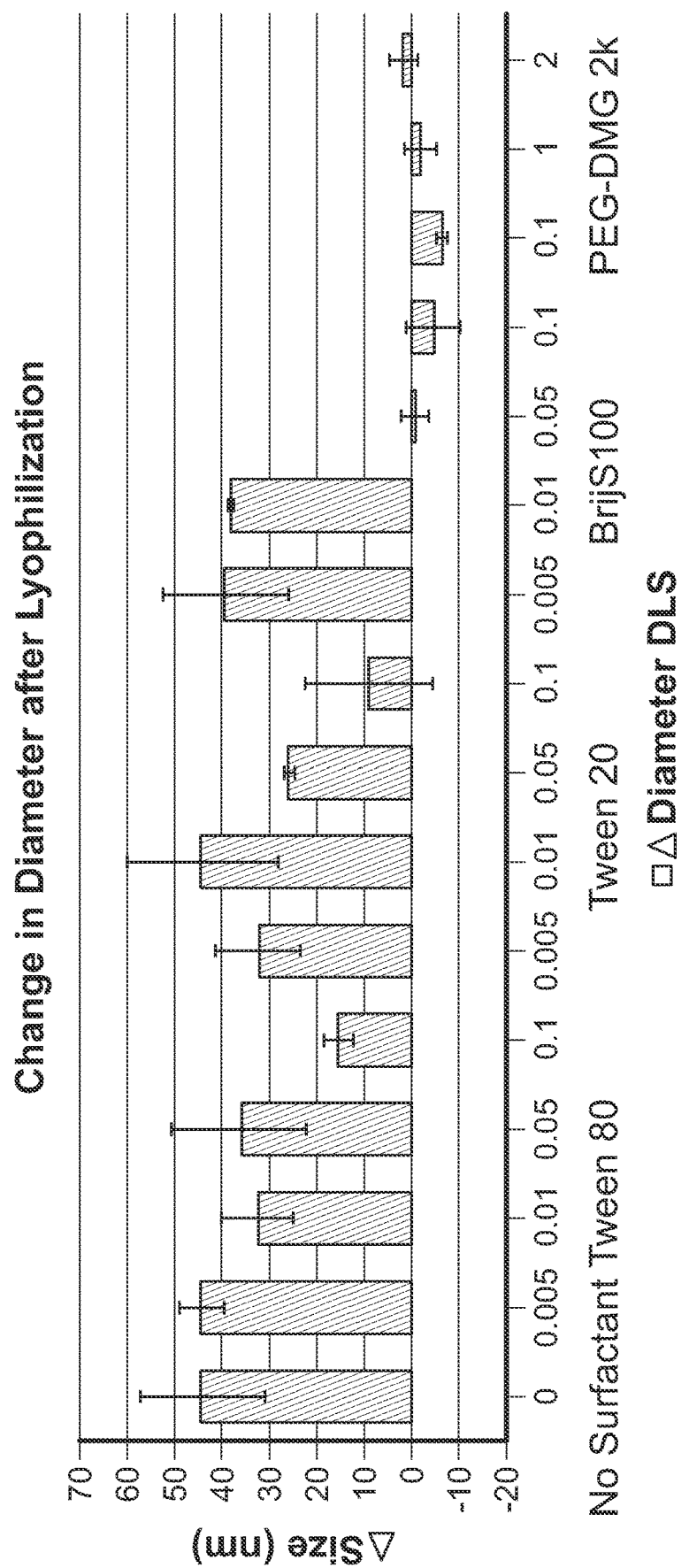
FIG. 60 is a graph of size change (nm) from before lyophilization to after lyophilzation at 0.2 mg/mL of RNA for LNPs formulated with 0.5% PEG in the core and 1% PEG added via post addition after dialysis into 20 mM tris (pH 7.4) and then addition of 10 wt % sucrose with surfactants of various wt % which demonstrates many surfactants reduce size growth during lyophilization.

A cytokine RNA batch was fractionated using size exclusion chromatography and characterized for physio-chemical characteristics and biological activity. SEC fractions varied in encapsulation state by weak ion exchange chromatography and correlated well with in-vitro expression. The data is shown in FIG. 56 (x-axis=cytokine expression in pg/ml).

EQUIVALENTS

It is to be understood that while the present disclosure has been described in conjunction with the detailed description thereof, the foregoing description is intended to illustrate and not limit the scope of the present disclosure, which is defined by the scope of the appended claims. Other aspects, advantages, and alterations are within the scope of the following claims.

ii) a compound of Formula (PL-II):

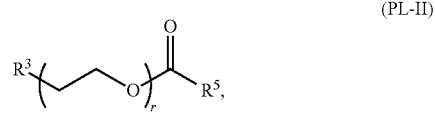

(PL-II)

or a salt thereof, wherein:

$R^3$ is —$OR^O$;

$R^O$ is hydrogen, optionally substituted alkyl, or an oxygen protecting group;

r is an integer between 1 and 100;

---

---

The invention claimed is:

1. A method of producing a nucleic acid lipid nanoparticle composition, the method comprising:

mixing a lipid solution comprising an ionizable lipid with a solution comprising a nucleic acid thereby forming a precursor nucleic acid lipid nanoparticle, wherein the precursor nucleic acid lipid nanoparticle comprises a first PEG lipid;

optionally processing the precursor nucleic acid lipid nanoparticle;

adding a second PEG lipid to the precursor nucleic acid lipid nanoparticle thereby forming a modified nucleic acid lipid nanoparticle; and processing the modified nucleic acid lipid nanoparticle, thereby forming the nucleic acid lipid nanoparticle composition, wherein:

the first PEG lipid and the second PEG lipid are independently i) a PEG-modified phosphatidylethanolamine, a PEG-modified phosphatidic acid, a PEG-modified ceramide, a PEG-modified dialkylamine, a PEG-modified diacylglycerol, or a PEG-modified dialkylglycerol;

$R^5$ is optionally substituted $C_{10-40}$ alkyl, optionally substituted $C_{10-40}$ alkenyl, or optionally substituted $C_{10-40}$ alkynyl; and optionally one or more methylene groups of $R^5$ are replaced with optionally substituted carbocyclylene, optionally substituted heterocyclylene, optionally substituted arylene, optionally substituted heteroarylene, $N(R^N)$, O, S, C(O), C(O) $N(R^N)$, $NR^NC(O)$, $NR^NC(O)N(R^N)$, C(O)O, OC(O), OC(O)O, OC(O)$N(R^N)$, $NR^NC(O)$O, C(O)S, SC(O), C(=$NR^N$), C(=$NR^N$)$N(R^N)$, $NR^NC$(=$NR^N$), $NR^NC$(=$NR^N$)$N(R^N)$, C(S), C(S)N($R^N$), $NR^NC(S)$, $NR^NC(S)N(R^N)$, S(O), OS(O), S(O)O, OS(O)O, $OS(O)_2$, $S(O)_2O$, $OS(O)_2O$, $N(R^N)S(O)$, $S(O)N(R^N)$, $N(R^N)S(O)N(R^N)$, $OS(O)N(R^N)$, $N(R^N)S(O)O$, $S(O)_2$, $N(R^N)S(O)_2$, $S(O)_2N(R^N)$, $N(R^N)S(O)_2N(R^N)$, $OS(O)_2N(R^N)$, or $N(R^N)S(O)_2O$; and each instance of $R^N$ is independently hydrogen, optionally substituted alkyl, or a nitrogen protecting group, or iii) a compound of Formula (PL-III):

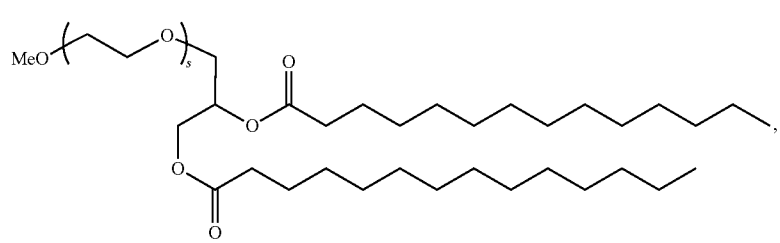

wherein s is an integer between 1 and 100.

2. The method of claim 1, wherein at least one of the first PEG lipid and the second PEG lipid is a compound of Formula (PL-II-OH):

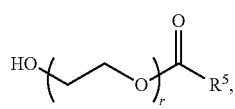

or a salt thereof, wherein:
r is an integer between 1 and 100;
$R^5$ is optionally substituted $C_{10-40}$ alkyl, optionally substituted $C_{10-40}$ alkenyl, or optionally substituted $C_{10-40}$ alkynyl; and optionally one or more methylene groups of $R^5$ are replaced with optionally substituted carbocyclylene, optionally substituted heterocyclylene, optionally substituted arylene, optionally substituted heteroarylene, $N(R^N)$, O, S, C(O), C(O)N($R^N$), $NR^N$C(O), $NR^N$C(O)N($R^N$), C(O)O, OC(O), OC(O)O, OC(O)N($R^N$), $NR^N$C(O)O, C(O)S, SC(O), C(=$NR^N$), C(=$NR^N$)N($R^N$), $NR^N$C(=$NR^N$), $NR^N$C(=$NR^N$)N($R^N$), C(S), C(S)N($R^N$), $NR^N$C(S), $NR^N$C(S)N($R^N$), S(O), OS(O), S(O)O, OS(O)O, S(O)$_2$, S(O)$_2$O, OS(O)$_2$O, N($R^N$)S(O), S(O)N($R^N$), N($R^N$)S(O)N($R^N$), OS(O)N($R^N$), N($R^N$)S(O)O, S(O)$_2$, N($R^N$)S(O)$_2$, S(O)$_2$N($R^N$), N($R^N$)S(O)$_2$N($R^N$), OS(O)$_2$N($R^N$), or N($R^N$)S(O)$_2$O; and
each instance of $R^N$ is independently hydrogen, optionally substituted alkyl, or a nitrogen protecting group.

3. The method of claim 1, wherein at least one of the first PEG lipid and the second PEG lipid is a compound of Formula (PL-II), wherein the compound of Formula (PL-II) is:

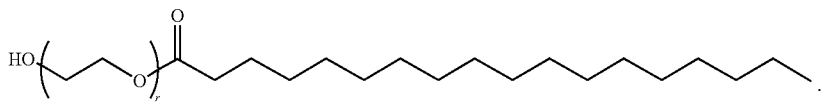

4. The method of claim 1, wherein at least one of the first PEG lipid and the second PEG lipid is a compound of Formula (PL-II), wherein the compound of Formula (PL-II) is:

(PEG-1)

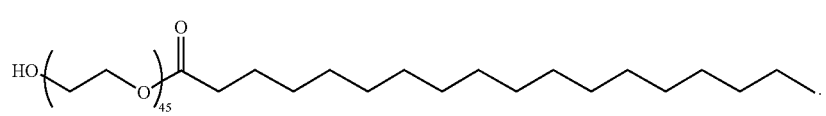

5. The method of claim 1, wherein at least one of the first PEG lipid and the second PEG lipid is a compound of following formula:

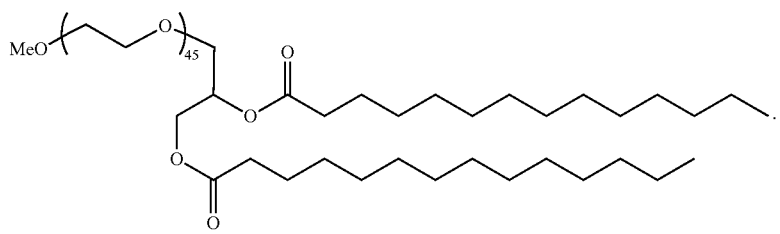

6. The method of claim 1, wherein the molar ratio of the first PEG lipid to the second PEG lipid is in a range of about 1:100 to about 1:1, about 1:50 to about 1:1, about 1:25 to about 1:1, or about 1:10 to about 1:1.

7. The method of claim 1, wherein the precursor nucleic acid lipid nanoparticle is processed prior to adding the second PEG lipid.

8. The method of claim 1, wherein the precursor nucleic acid lipid nanoparticle is not processed prior to adding the second PEG lipid.

9. The method of claim 1, wherein the mixing comprises turbulent mixing and/or microfluidic mixing.

10. The method of claim 1, wherein processing the modified nucleic acid lipid nanoparticle comprises filtration, freezing and/or lyophilizing, and/or packing.

11. The method of claim 1, wherein the precursor nucleic acid lipid nanoparticle further comprises a phospholipid and/or a structural lipid.

12. The method of claim 11, wherein the nucleic acid lipid nanoparticle composition comprises about 30-60 mol % of the ionizable lipid;
   about 0-30 mol % of the phospholipid;
   about 15-50 mol % of the structural lipid; and
   about 0.01-20 mol % total amount of the first PEG lipid and second PEG lipid.

13. The method of claim 1, wherein the nucleic acid is a messenger RNA (mRNA).

\* \* \* \* \*

SEQUENCE LISTING

```
Sequence total quantity: 2
SEQ ID NO: 1           moltype = DNA  length = 24
FEATURE                Location/Qualifiers
misc_feature           1..24
                       note = Synthetic sequence
source                 1..24
                       mol_type = other DNA
                       organism = synthetic construct
SEQUENCE: 1
caaaggctct tttcagagcc acca                                         24

SEQ ID NO: 2           moltype = RNA  length = 24
FEATURE                Location/Qualifiers
misc_feature           1..24
                       note = synthetic sequence
source                 1..24
                       mol_type = other RNA
                       organism = synthetic construct
SEQUENCE: 2
caaaggctct tttcagagcc acca                                         24
```